US012305189B2

(12) United States Patent
Sah et al.

(10) Patent No.: US 12,305,189 B2
(45) Date of Patent: May 20, 2025

(54) COMPOSITIONS AND METHODS FOR DELIVERY OF AAV

(71) Applicant: Voyager Therapeutics, Inc., Lexington, MA (US)

(72) Inventors: Dinah Wen-Yee Sah, Hopkinton, MA (US); Holger Patzke, Lexington, MA (US); Jinzhao Hou, Lexington, MA (US); Mathieu E. Nonnenmacher, Lexington, MA (US); Martin Goulet, Weston, MA (US); Todd Carter, Lexington, MA (US)

(73) Assignee: Voyager Therapeutics, Inc., Lexington, MA (US)

( * ) Notice: Subject to any disclaimer, the term of this patent is extended or adjusted under 35 U.S.C. 154(b) by 93 days.

(21) Appl. No.: 17/970,036

(22) Filed: Oct. 20, 2022

(65) Prior Publication Data
US 2023/0304032 A1 Sep. 28, 2023

Related U.S. Application Data

(63) Continuation of application No. 16/636,094, filed as application No. PCT/US2018/045088 on Aug. 3, 2018, now Pat. No. 11,512,327.

(60) Provisional application No. 62/572,706, filed on Oct. 16, 2017, provisional application No. 62/565,264, filed on Sep. 29, 2017, provisional application No. 62/540,776, filed on Aug. 3, 2017.

(51) Int. Cl.
*C12N 15/86* (2006.01)
*A61K 9/00* (2006.01)
*C07K 14/005* (2006.01)
*C12N 7/00* (2006.01)

(52) U.S. Cl.
CPC ............ *C12N 15/86* (2013.01); *A61K 9/0019* (2013.01); *C07K 14/005* (2013.01); *C12N 7/00* (2013.01); *C12N 2750/14121* (2013.01); *C12N 2750/14122* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | |
|---|---|---|
| 5,064,764 A | 11/1991 | Besnainon et al. |
| 5,474,935 A | 12/1995 | Chatterjee |
| 5,587,308 A | 12/1996 | Carter |
| 5,652,224 A | 7/1997 | Wilson et al. |
| 5,658,785 A | 8/1997 | Johnson |
| 5,688,676 A | 11/1997 | Zhou et al. |
| 5,691,176 A | 11/1997 | Lebkowski et al. |
| 5,693,531 A | 12/1997 | Chiorini et al. |
| 5,741,683 A | 4/1998 | Zhou et al. |
| 5,756,283 A | 5/1998 | Wilson et al. |
| 5,856,152 A | 1/1999 | Wilson |
| 5,858,351 A | 1/1999 | Podsakoff et al. |
| 5,858,775 A | 1/1999 | Johnson |
| 5,866,552 A | 2/1999 | Wilson et al. |
| 5,866,696 A | 2/1999 | Carter |
| 5,871,982 A | 2/1999 | Wilson |
| 5,952,221 A | 9/1999 | Kurtzman et al. |
| 5,962,313 A | 10/1999 | Podsakoff et al. |
| 5,989,540 A | 11/1999 | Carter |
| 6,083,716 A | 7/2000 | Wilson et al. |
| 6,143,548 A | 11/2000 | O'Riordan et al. |
| 6,143,567 A | 11/2000 | Van Agthoven et al. |
| 6,146,874 A | 11/2000 | Zolotukhin et al. |
| 6,156,303 A | 12/2000 | Russell et al. |
| 6,174,527 B1 | 1/2001 | Wilson et al. |
| 6,180,613 B1 | 1/2001 | Kaplitt et al. |
| 6,194,191 B1 | 2/2001 | Zhang et al. |
| 6,200,560 B1 | 3/2001 | Couto et al. |
| 6,204,059 B1 | 3/2001 | Samulski et al. |
| 6,211,163 B1 | 4/2001 | Podsakoff et al. |
| 6,251,677 B1 | 6/2001 | Wilson et al. |
| 6,258,595 B1 | 7/2001 | Gao et al. |
| 6,261,551 B1 | 7/2001 | Wilson et al. |
| 6,265,389 B1 | 7/2001 | Burke |
| 6,270,996 B1 | 8/2001 | Wilson et al. |
| 6,274,354 B1 | 8/2001 | Wilson et al. |
| 6,281,010 B1 | 8/2001 | Gao et al. |
| 6,325,998 B1 | 12/2001 | Podsakoff et al. |
| 6,335,011 B1 | 1/2002 | Podsakoff et al. |
| 6,365,394 B1 | 4/2002 | Gao et al. |
| 6,387,368 B1 | 5/2002 | Wilson et al. |

(Continued)

FOREIGN PATENT DOCUMENTS

| | | |
|---|---|---|
| EP | 1015619 A1 | 7/2000 |
| EP | 1046711 A2 | 10/2000 |

(Continued)

OTHER PUBLICATIONS

Types of Muscular Dystrophy, CDC, May 15, 2024, 4 pages, from www.cdc.gov/muscular-dystrophy/types/index.html, accessed Jul. 9, 2024 (Year: 2024).*

Duchenne Muscular Dystrophy from Muscular Dystrophy Association, www.mda.org/disease/duchenne-muscular-dystrophy, accessed Jul. 9, 2024, 5 pages (Year: 2024).*

Myotonic Dystrophy from Muscular Dystrophy Association, www.mda.org/disease/myotonic-dystrophy/causes-inheritance, accessed Jul. 9, 2024, 4 pages (Year: 2024).*

Limb-Girdle Muscular Dystrophy from Muscular Dystrophy Association, www.mda.org/disease/limb-girdle-muscular-dystrophy/causes-inheritance, accessed Jul. 9, 2024, 3 pages (Year: 2024).*

(Continued)

*Primary Examiner* — Stacy B Chen
(74) *Attorney, Agent, or Firm* — Finnegan, Henderson, Farabow, Garrett & Dunner, LLP

(57) ABSTRACT

The invention provides compositions and methods for the preparation, manufacture, formulation and therapeutic use of adeno-associated virus (AAV) particles for the prevention and/or treatment of diseases.

6 Claims, 1 Drawing Sheet

Specification includes a Sequence Listing.

(56) References Cited

U.S. PATENT DOCUMENTS

| | | |
|---|---|---|
| 6,399,385 B1 | 6/2002 | Croyle et al. |
| 6,410,300 B1 | 6/2002 | Samulski et al. |
| 6,416,992 B1 | 7/2002 | Mejza |
| 6,428,988 B1 | 8/2002 | Wilson et al. |
| 6,436,392 B1 | 8/2002 | Engelhardt et al. |
| 6,436,394 B1 | 8/2002 | Henderson et al. |
| 6,468,524 B1 | 10/2002 | Chiorini et al. |
| 6,468,771 B1 | 10/2002 | Einerhand et al. |
| 6,475,769 B1 | 11/2002 | Wilson |
| 6,482,634 B1 | 11/2002 | Wilson et al. |
| 6,485,966 B2 | 11/2002 | Gao et al. |
| 6,509,150 B1 | 1/2003 | Salvetti et al. |
| 6,521,426 B1 | 2/2003 | Ciliberto et al. |
| 6,555,525 B2 | 4/2003 | Burke |
| 6,566,118 B1 | 5/2003 | Atkinson et al. |
| 6,582,692 B1 | 6/2003 | Podsakoff et al. |
| 6,593,123 B1 | 7/2003 | Wright et al. |
| 6,610,290 B2 | 8/2003 | Podsakoff et al. |
| 6,642,051 B1 | 11/2003 | Lynch et al. |
| 6,660,514 B1 | 12/2003 | Zolotukhin et al. |
| 6,660,521 B2 | 12/2003 | Brough et al. |
| 6,670,176 B1 | 12/2003 | Samulski et al. |
| 6,676,935 B2 | 1/2004 | Henderson et al. |
| 6,699,706 B1 | 3/2004 | Brooks |
| 6,710,036 B2 | 3/2004 | Kurtzman et al. |
| 6,723,551 B2 | 4/2004 | Kotin et al. |
| 6,726,907 B2 | 4/2004 | Zhang |
| 6,753,419 B1 | 6/2004 | Toniatti et al. |
| 6,759,237 B1 | 7/2004 | Wilson et al. |
| 6,846,665 B1 | 1/2005 | Horer et al. |
| 6,855,314 B1 | 2/2005 | Chiorini et al. |
| 6,887,463 B2 | 5/2005 | Wilson et al. |
| 6,897,045 B2 | 5/2005 | Engelhardt et al. |
| 6,943,019 B2 | 9/2005 | Wilson et al. |
| 6,953,690 B1 | 10/2005 | Gao et al. |
| 6,984,517 B1 | 1/2006 | Chiorini et al. |
| 6,995,006 B2 | 2/2006 | Atkinson et al. |
| 7,015,026 B2 | 3/2006 | O'Riordan et al. |
| 7,022,519 B2 | 4/2006 | Gao et al. |
| 7,048,920 B2 | 5/2006 | Yu et al. |
| 7,056,502 B2 | 6/2006 | Hildinger et al. |
| 7,070,998 B2 | 7/2006 | Johnson, Jr. |
| 7,091,030 B2 | 8/2006 | Setiawan et al. |
| 7,094,604 B2 | 8/2006 | Snyder et al. |
| 7,105,345 B2 | 9/2006 | Wilson et al. |
| 7,112,321 B2 | 9/2006 | Wang et al. |
| 7,125,705 B2 | 10/2006 | Colosi |
| 7,125,706 B2 | 10/2006 | Zhang et al. |
| 7,169,612 B2 | 1/2007 | Kostenis et al. |
| 7,186,552 B2 | 3/2007 | Wilson et al. |
| 7,198,951 B2 | 4/2007 | Gao et al. |
| 7,223,585 B2 | 5/2007 | Coffey |
| 7,235,393 B2 | 6/2007 | Gao et al. |
| 7,238,526 B2 | 7/2007 | Wilson et al. |
| 7,241,447 B1 | 7/2007 | Engelhardt et al. |
| 7,247,472 B2 | 7/2007 | Wilson et al. |
| 7,271,002 B2 | 9/2007 | Kotin et al. |
| 7,282,199 B2 | 10/2007 | Gao et al. |
| 7,300,797 B2 | 11/2007 | van Agthoven et al. |
| 7,306,794 B2 | 12/2007 | Wilson et al. |
| 7,319,002 B2 | 1/2008 | Wilson et al. |
| 7,326,555 B2 | 2/2008 | Konz, Jr. et al. |
| 7,344,872 B2 | 3/2008 | Gao et al. |
| 7,419,817 B2 | 9/2008 | Chiorini et al. |
| 7,419,956 B2 | 9/2008 | Ohtaki et al. |
| 7,445,930 B2 | 11/2008 | Zhang et al. |
| 7,479,554 B2 | 1/2009 | Chiorini et al. |
| 7,510,872 B2 | 3/2009 | Clark et al. |
| 7,510,875 B2 | 3/2009 | Zhang et al. |
| 7,579,181 B2 | 8/2009 | O'Riordan et al. |
| 7,625,570 B1 | 12/2009 | Schaffer et al. |
| 7,638,120 B2 | 12/2009 | Liu et al. |
| 7,662,627 B2 | 2/2010 | Johnson, Jr. |
| 7,704,492 B2 | 4/2010 | Podsakoff et al. |
| 7,704,721 B2 | 4/2010 | Wright et al. |
| 7,732,129 B1 | 6/2010 | Zhang et al. |
| 7,790,449 B2 | 9/2010 | Gao et al. |
| 7,803,622 B2 | 9/2010 | Engelhardt et al. |
| 7,838,277 B2 | 11/2010 | Gao et al. |
| 7,888,096 B2 | 2/2011 | Wu et al. |
| 7,901,921 B2 | 3/2011 | Coffey |
| 7,906,111 B2 | 3/2011 | Wilson et al. |
| 8,105,574 B2 | 1/2012 | Wilson et al. |
| 8,110,351 B2 | 2/2012 | Bosnes |
| 8,137,948 B2 | 3/2012 | Qu et al. |
| 8,163,543 B2 | 4/2012 | Urabe et al. |
| 8,231,880 B2 | 7/2012 | Roy et al. |
| 8,236,495 B2 | 8/2012 | Nochumson et al. |
| 8,241,622 B2 | 8/2012 | Englehardt et al. |
| 8,273,344 B2 | 9/2012 | Wang et al. |
| 8,283,151 B2 | 10/2012 | Schmidt et al. |
| 8,318,480 B2 | 11/2012 | Gao et al. |
| 8,318,687 B2 | 11/2012 | Tabira et al. |
| 8,394,386 B2 | 3/2013 | Wilson |
| 8,409,842 B2 | 4/2013 | Clark et al. |
| 8,470,310 B2 | 6/2013 | Roy et al. |
| 8,512,981 B2 | 8/2013 | Hermens et al. |
| 8,524,219 B2 | 9/2013 | Roy et al. |
| 8,524,446 B2 | 9/2013 | Gao et al. |
| 8,603,459 B2 | 12/2013 | Wilson et al. |
| 8,614,101 B2 | 12/2013 | VanDine et al. |
| 8,637,255 B2 | 1/2014 | Wilson et al. |
| 8,642,314 B2 | 2/2014 | Bakker et al. |
| 8,685,734 B2 | 4/2014 | Coffey |
| 8,697,417 B2 | 4/2014 | Bakker et al. |
| 8,697,665 B2 | 4/2014 | Fontanellas Roma et al. |
| 8,834,863 B2 | 9/2014 | Roy et al. |
| 8,846,030 B2 | 9/2014 | Engelhardt |
| 8,846,389 B2 | 9/2014 | Chiorini et al. |
| 8,906,675 B2 | 12/2014 | Gao et al. |
| 8,927,514 B2 | 1/2015 | Chatterjee et al. |
| 8,962,330 B2 | 2/2015 | Gao et al. |
| 8,962,332 B2 | 2/2015 | Gao et al. |
| 8,999,678 B2 | 4/2015 | Vandenberghe et al. |
| 9,051,542 B2 | 6/2015 | Wright et al. |
| 9,056,892 B2 | 6/2015 | Pun et al. |
| 9,080,183 B2 | 7/2015 | Klein et al. |
| 9,089,667 B2 | 7/2015 | Bankiewicz |
| 9,102,943 B2 | 8/2015 | Shinmura et al. |
| 9,115,373 B2 | 8/2015 | Hermens et al. |
| 9,163,260 B2 | 10/2015 | Wilson et al. |
| 9,217,155 B2 | 12/2015 | Gao et al. |
| 9,217,159 B2 | 12/2015 | Roy et al. |
| 9,260,724 B2 | 2/2016 | Bakker et al. |
| 9,439,979 B2 | 9/2016 | Chiorini et al. |
| 9,441,206 B2 | 9/2016 | Grieger et al. |
| 9,464,119 B2 | 10/2016 | Sonntag et al. |
| 9,493,788 B2 | 11/2016 | Gao et al. |
| 9,506,083 B2 | 11/2016 | Arbetman et al. |
| 9,528,126 B2 | 12/2016 | Qu et al. |
| 9,546,112 B2 | 1/2017 | Voit et al. |
| 9,546,369 B2 | 1/2017 | Gao et al. |
| 9,567,607 B2 | 2/2017 | Wilson et al. |
| 9,580,691 B2 | 2/2017 | Bakker et al. |
| 9,587,250 B2 | 3/2017 | Gao et al. |
| 9,593,346 B2 | 3/2017 | Roy et al. |
| 9,596,835 B2 | 3/2017 | Gao et al. |
| 9,597,363 B2 | 3/2017 | Roy et al. |
| 9,598,703 B2 | 3/2017 | Garcia et al. |
| 9,617,561 B2 | 4/2017 | Roy et al. |
| 9,623,120 B2 | 4/2017 | Chatterjee et al. |
| 9,670,507 B2 | 6/2017 | Xiao et al. |
| 9,677,088 B2 | 6/2017 | Nakai et al. |
| 9,677,089 B2 | 6/2017 | Gao et al. |
| 9,765,338 B2 | 9/2017 | Bennett et al. |
| 9,976,138 B2 | 5/2018 | Prakash et al. |
| 11,512,327 B2 | 11/2022 | Sah et al. |
| 2013/0059902 A1 | 3/2013 | Corey et al. |
| 2013/0197061 A1 | 8/2013 | Hohjoh et al. |
| 2013/0237585 A1 | 9/2013 | Bennett et al. |
| 2015/0079038 A1* | 3/2015 | Deverman ............ C07K 7/06 506/10 |
| 2015/0238627 A1 | 8/2015 | Leger et al. |
| 2016/0304877 A1 | 10/2016 | Swayze et al. |

(56) References Cited

U.S. PATENT DOCUMENTS

| | | |
|---|---|---|
| 2017/0166926 A1 | 6/2017 | Deverman et al. |
| 2017/0182171 A1 | 6/2017 | Weeden et al. |
| 2017/0182182 A1 | 6/2017 | Seow et al. |
| 2017/0327825 A1 | 11/2017 | Karni |
| 2018/0112214 A1 | 4/2018 | De Kimpe et al. |
| 2021/0163985 A1 | 6/2021 | Sah et al. |

FOREIGN PATENT DOCUMENTS

| | | |
|---|---|---|
| EP | 1078096 A1 | 2/2001 |
| EP | 1164195 A2 | 12/2001 |
| EP | 1183380 A1 | 3/2002 |
| EP | 1218035 A2 | 7/2002 |
| EP | 1240345 A2 | 9/2002 |
| EP | 1279740 A1 | 1/2003 |
| EP | 1696036 A1 | 8/2006 |
| EP | 1847614 A1 | 10/2007 |
| EP | 1849872 A1 | 10/2007 |
| EP | 1857552 A1 | 11/2007 |
| EP | 1944043 A1 | 7/2008 |
| EP | 2292779 A3 | 3/2011 |
| EP | 2325298 A2 | 5/2011 |
| EP | 2359866 A1 | 8/2011 |
| EP | 2383346 A1 | 11/2011 |
| EP | 2660325 A2 | 11/2013 |
| EP | 2198016 B1 | 5/2015 |
| EP | 2871239 A9 | 6/2015 |
| EP | 2933336 A3 | 12/2015 |
| EP | 3058959 A1 | 8/2016 |
| EP | 1453547 B1 | 9/2016 |
| EP | 2220241 B1 | 9/2016 |
| EP | 2007795 B1 | 11/2016 |
| EP | 2176283 B1 | 11/2016 |
| EP | 3067417 A3 | 11/2016 |
| EP | 2220242 B1 | 12/2016 |
| EP | 3117005 A1 | 1/2017 |
| EP | 2737071 B1 | 3/2017 |
| EP | 2531604 B1 | 4/2017 |
| EP | 3168298 A1 | 5/2017 |
| EP | 2524037 B1 | 5/2018 |
| EP | 2879719 B1 | 7/2018 |
| EP | 2814958 B1 | 8/2019 |
| EP | 3108000 B1 | 8/2019 |
| EP | 3134431 B1 | 4/2021 |
| WO | 1993009239 A1 | 5/1993 |
| WO | 1995034670 A2 | 12/1995 |
| WO | 1996017947 A1 | 6/1996 |
| WO | 1996023810 A1 | 8/1996 |
| WO | 1996030540 A2 | 10/1996 |
| WO | 1998010088 A1 | 3/1998 |
| WO | 9915685 A1 | 4/1999 |
| WO | 1999027110 A1 | 6/1999 |
| WO | 1999043360 A1 | 9/1999 |
| WO | 1999058700 A1 | 11/1999 |
| WO | 1999061595 A2 | 12/1999 |
| WO | 1999060146 A9 | 5/2000 |
| WO | 2000024916 A1 | 5/2000 |
| WO | 2000066780 A2 | 11/2000 |
| WO | 2000075353 A1 | 12/2000 |
| WO | 2001023001 A2 | 4/2001 |
| WO | 2001025465 A1 | 4/2001 |
| WO | 2001036623 A2 | 5/2001 |
| WO | 2001042444 A2 | 6/2001 |
| WO | 2001014539 A3 | 9/2001 |
| WO | 2001068888 A2 | 9/2001 |
| WO | 2001032711 A3 | 12/2001 |
| WO | 2001096587 A2 | 12/2001 |
| WO | 2002012525 A2 | 2/2002 |
| WO | 2002014487 A2 | 2/2002 |
| WO | 2002020748 A2 | 3/2002 |
| WO | 2002070719 A2 | 9/2002 |
| WO | 2002071843 A1 | 9/2002 |
| WO | 2003010320 A2 | 2/2003 |
| WO | 2003042397 A2 | 5/2003 |
| WO | 2003087382 A1 | 10/2003 |
| WO | 2003087383 A1 | 10/2003 |
| WO | 2003024502 A3 | 11/2003 |
| WO | 2004044003 A3 | 6/2004 |
| WO | 2004083441 A2 | 9/2004 |
| WO | 2004108922 A2 | 12/2004 |
| WO | 2004111248 A2 | 12/2004 |
| WO | 2005012537 A3 | 6/2005 |
| WO | 2005111220 A2 | 11/2005 |
| WO | 2005005610 A3 | 12/2005 |
| WO | 2006102072 A3 | 11/2006 |
| WO | 2007130519 A2 | 11/2007 |
| WO | 2009030025 A1 | 3/2009 |
| WO | 2009073104 A2 | 6/2009 |
| WO | 2007148971 A8 | 7/2009 |
| WO | 2009134681 A2 | 11/2009 |
| WO | 2011038187 A1 | 3/2011 |
| WO | 2011054976 A3 | 7/2011 |
| WO | WO 2011/097614 A1 | 8/2011 |
| WO | 2011122950 A1 | 10/2011 |
| WO | 2011133890 A1 | 10/2011 |
| WO | 2010109053 A8 | 11/2011 |
| WO | 2012057363 A1 | 5/2012 |
| WO | 2012114090 A1 | 8/2012 |
| WO | 2012144446 A1 | 10/2012 |
| WO | 2013078199 A3 | 7/2013 |
| WO | 2013164793 A2 | 11/2013 |
| WO | 2013170078 A1 | 11/2013 |
| WO | 2014160092 A1 | 10/2014 |
| WO | 2014168953 A1 | 10/2014 |
| WO | 2014170470 A1 | 10/2014 |
| WO | 2014170480 A1 | 10/2014 |
| WO | 2014172669 A1 | 10/2014 |
| WO | WO 2014/167074 A1 | 10/2014 |
| WO | 2014186579 A1 | 11/2014 |
| WO | 2014194132 A1 | 12/2014 |
| WO | 2014201252 A2 | 12/2014 |
| WO | 2015018503 A1 | 2/2015 |
| WO | 2014186746 A9 | 3/2015 |
| WO | 2015012924 A3 | 3/2015 |
| WO | 2015038958 A1 | 3/2015 |
| WO | 2015031686 A9 | 4/2015 |
| WO | 2015044292 A1 | 4/2015 |
| WO | 2015060722 A1 | 4/2015 |
| WO | 2015108610 A1 | 7/2015 |
| WO | 2015114365 A1 | 8/2015 |
| WO | 2015121501 A1 | 8/2015 |
| WO | 2015124546 A1 | 8/2015 |
| WO | 2015137802 A1 | 9/2015 |
| WO | 2015127128 A9 | 11/2015 |
| WO | 2015196179 A1 | 12/2015 |
| WO | 2016019364 A1 | 2/2016 |
| WO | 2016054554 A1 | 4/2016 |
| WO | 2016054557 A1 | 4/2016 |
| WO | 2016065001 A1 | 4/2016 |
| WO | 2016081811 A1 | 5/2016 |
| WO | 2016115382 A1 | 7/2016 |
| WO | 2016115503 A1 | 7/2016 |
| WO | 2016081927 A3 | 8/2016 |
| WO | 2016122791 A1 | 8/2016 |
| WO | 2016126857 A1 | 8/2016 |
| WO | 2016154055 A1 | 9/2016 |
| WO | 2016154344 A1 | 9/2016 |
| WO | WO 2016/150964 A1 | 9/2016 |
| WO | 2016137949 A4 | 10/2016 |
| WO | 2016172008 A1 | 10/2016 |
| WO | 2016172155 A1 | 10/2016 |
| WO | 2016130591 A3 | 11/2016 |
| WO | 2016168728 A3 | 11/2016 |
| WO | 2016179496 A1 | 11/2016 |
| WO | 2016183297 A1 | 11/2016 |
| WO | 2016164609 A3 | 12/2016 |
| WO | 2016191418 A1 | 12/2016 |
| WO | 2016196507 A1 | 12/2016 |
| WO | 2017004514 A1 | 1/2017 |
| WO | 2017005806 A1 | 1/2017 |
| WO | 2017015102 A1 | 1/2017 |
| WO | 2017019876 A1 | 2/2017 |
| WO | 2017019994 A2 | 2/2017 |
| WO | WO 2017/053999 A1 | 3/2017 |

(56) References Cited

FOREIGN PATENT DOCUMENTS

| | | |
|---|---|---|
| WO | 2017070516 A1 | 4/2017 |
| WO | 2017070525 A1 | 4/2017 |
| WO | 2017070678 A1 | 4/2017 |
| WO | 2017058892 A3 | 5/2017 |
| WO | 2017075335 A1 | 5/2017 |
| WO | 2017083423 A1 | 5/2017 |
| WO | 2017070476 A3 | 6/2017 |
| WO | 2017075338 A3 | 6/2017 |
| WO | 2017093330 A1 | 6/2017 |
| WO | 2017096039 A1 | 6/2017 |
| WO | 2017100671 A1 | 6/2017 |
| WO | 2017100674 A1 | 6/2017 |
| WO | 2017100676 A1 | 6/2017 |
| WO | 2017100704 A1 | 6/2017 |
| WO | WO 2017/163076 A1 | 9/2017 |
| WO | WO 2017/176813 A1 | 10/2017 |
| WO | WO 2017/182581 A1 | 10/2017 |
| WO | WO 2018/050930 A1 | 3/2018 |
| WO | WO 2018/115477 A1 | 6/2018 |
| WO | WO 2018/129384 A1 | 7/2018 |
| WO | WO 2018/134301 A1 | 7/2018 |
| WO | 2019046069 A1 | 3/2019 |
| WO | 2019067840 A1 | 4/2019 |
| WO | 2019222329 A1 | 11/2019 |
| WO | 2020069461 A1 | 4/2020 |
| WO | 2020077165 A1 | 4/2020 |

OTHER PUBLICATIONS

Facioscapulohumeral Muscular Dystrophy from Muscular Dystrophy Association, www.mda.org/disease/facioscapulohumeral-muscular-dystrophy/causes-inheritance, accessed Jul. 9, 2024, 3 pages (Year: 2024).*

Congenital Muscular Dystrophy from Muscular Dystrophy Association, www.mda.org/disease/congenital-muscular-dystrophy/causes-inheritance, accessed Jul. 9, 2024, 9 pages (Year: 2024).*

Distal Myopathies from Muscular Dystrophy Association, www.mda.org/disease/distal-myopathies/causes-inheritance, accessed Jul. 9, 2024, 4 pages (Year: 2024).*

Oculopharyngeal Muscular Dystrophy from Muscular Dystrophy Association, www.mda.org/disease/oculopharyngeal-muscular-dystrophy/causes-inheritance, accessed Jul. 9, 2024, 2 pages (Year: 2024).*

Emery-Dreifuss Muscular Dystrophy from Muscular Dystrophy Association, www.mda.org/disease/emery-dreifuss-muscular-dystrophy/causes-inheritance, accessed Jul. 9, 2024, 3 pages (Year: 2024).*

Hastie E, et al. Recombinant adeno-associated virus vectors in the treatment of rare diseases. Expert Opin Orphan Drugs. 2015;3(6):675-689.

Heim et al., Wavelength mutations and posttranslational autoxidation of green fluorescent protein. Proc. Natl. Acad. Sci. USA (1994).

Heim R, et al. Engineering green fluorescent protein for improved brightness, longer wavelengths and fluorescence resonance energy transfer. Curr Biol. Feb. 1, 1996;6(2):178-82.

Heim R,et al. Improved green fluorescence Nature 373, 663-664 (Feb. 23, 1995); doi:10.1038/373663b0.

Heller KN, et al. Human alpha 7 integrin gene (ITGA7) delivered by adeno-associated virus extends survival of severely affected dystrophin/utrophin deficient mice. Oct. 2015;26(10):647-56.

Hinderer C et al. Delivery of an Adeno-Associated Virus Vector into CSF Attenuates Central Nervous System Disease in Mucopolysaccharidosis Type II Mice. Hum Gene Ther. Aug. 10, 2016.

Hinderer C, et al. Neonatal Systemic AAV Induces Tolerance to CNS Gene Therapy in MPS I Dogs and Nonhuman Primates. Mol Ther. Aug. 2015, 23(8)1298-307.

Hirsch ML, et al. Delivering Transgenic DNA Exceeding the Carrying Capacity of AAV Vectors. Methods Mol Biol. 2016;1382:21-39.

Hordeaux J, et al. The GPI-linked protein LY6A (SCA-1) drives AAV-PHP.B transport across the blood-brain barrier. Molecular Therapy. Feb. 20, 2019.

Hordeaux J., et al. Efficient central nervous system AAVrh10-mediated intrathecal gene transfers in adult and neonate rats. Gene Ther. Apr. 2015, 22(4):316-24.

Huang LY, et al. Characterization of the Adeno-Associated Virus 1 and 6 Sialic Acid Binding Site. J Virol. May 12, 2016;90(11):5219-30.

Huang LY, et al. Characterization of the adeno-associated virus 1 and 6 sialic acid binding site. J Virol. May 2016;90(11):5219-30.

Huang Q, et al. Delivering genes across the blood-brain barrier: LY6A, a novel cellular receptor for AAV-PHP.B capsids. bioRxiv. Feb. 1, 2019.

Hudry EM, et al. Exosome-associated AAV vector as a robust and convenient neuroscience tool. Gene Ther. Apr. 2016;23(4):380-92.

Ibrahim S, et al. Stable liver specific expression of human IDOL in humanized mice raises plasma cholesterol. Cardiovasc Res. May 2016;110(1):23-9.

International Search Report & Written Opinion dated Feb. 15, 2019 in co-pending application No. PCT/US2018/045088, entitled Compositions and Methods for Delivery of AAV.

Ishizu T, et al. Targeted Genome Replacement via Homolgy-directed Repair in Non-dividing Cardiomyocytes. Sci Rep. Aug. 24, 2017;7(1):9363.

Izpisua Belmonte et al., Brains, genes, and primates. Neuron. May 6, 2015;86(3):617-31.

Jackson KL, et al. Better Targeting, Better Efficiency for Wide-Scale Neuronal Transduction with the Synapsin Promoter and AAV-PHP. B. Front Mol Neurosci. Nov. 2016;6:116.

Jeong D, et al. Matricellular Protein CCN5 Reverses Established Cardiac Fibrosis. J Am Coll Cardiol. Apr. 5, 2016;67(13):1556-68.

Jin X, et al. Direct LC/MS Analysis for Complete Characterization of Recombinant Adeno-Associated Virus Capsid Proteins. Hum Gene Ther Methods. Jun. 18, 2017. Epub ahead of print.

Kailasan S, et al. Parvovirus Family Conundrum: What makes a killer? Annu Rev Virol. Nov. 2015;2(1):425-50.

Kailasan S, et al. Structure of an Enteric Pathogen, Bovine Parvovirus.J Virol. Mar. 2015, 89(5):2603-14.

Kajigaya S, et al. Self-assembled B19 parvovirus capsids, produced in a baculovirus system, are antigenically and Immunogenically similar to native virions. Proc Natl Acad Sci U S A. Jun. 1, 1991;88(11):4646-50.

Kanaan NM, et al. Rationally Engineered AAV Capsids Improve Transduction and Volumetric Spread in the CNS. Molecular Therapy—Nucleic Acids 8: 184-197 Sep. 15, 2017.

Kaplitt et al., Long-term gene expression and phenotypic correction using adeno-associated virus vectors in the mammalian brain. Nat Genet. Oct. 1994;8(2):148-54.

Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.

Katz ML, et al. AAV gene transfer delays disease onset in a TPP1-deficient canine model of the late infantile form of Batten Disease. Sci Transl Med. Nov. 2015;7(313):313ra180.

Ken Y Chan et al: "Engineered AAVs for efficient noninvasive gene delivery to the central and peripheral nervous systems", Nature Neuroscience, vol. 20, No. 8, Jun. 26, 2017 (Jun. 26, 2017), pp. 1172-1179.

Keravala A, et al. Evaluating AAV Hybrid Variants for Improved Tropism after Intravitreal Gene Delivery to the Retina. Molecular Therapy, vol. 23, Supplement 1, May 2015, pp. S127-S128.

Kevin D. Foust et al: "Therapeutic AAV9-mediated Suppression of Mutant SOD1 Slows Disease Progression and Extends Survivial in Models of Inherited ALS", Molecular Therapy: The Journal of the American Society of Gene Therapy, vol. 21, No. 12, Sep. 6, 2013 (Sep. 6, 2013), pp. 2148-2159.

Kirbauer R, et al. Virus-like particles of bovine papillomavirus type 4 in prophylactic and therapeutic immunization. Virology. May 1, 1996;219(1):37-44.

Knezevic T, et al. Adeno-associated Virus Serotype 9-Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.

(56) References Cited

OTHER PUBLICATIONS

Kohlbrenner E, et al. Production and Characterization of Vectors Based on the Cardiotropic AAV Serotype 9. Methods Mol Biol. 2017;1521:91-107.

Korbelin et al., Pulmonary targeting of adeno-associated viral vectors by next-generation sequencing-guided screening of random capsid displayed peptide libraries. Molecular Therapy. Jun. 1, 2016;24(6):1050-61.

Kothari P, et al. Iodine-124 Labeled Adeno-Associated Virus: A Promising Tool for Tracking Gene Therapy. Journal of Nuclear Medicine. May 2015, 56 (supplement 3), 494-494.

Kothari P, et al. Radioiodinated Capsids Facilitate In Vivo Non-Invasive Tracking of Adeno-Associated Gene Transfer Vectors. Sci Rep. Jan. 2017;7:39594.

Kotin RM, et al. Large-scale recombinant adeno-associated virus production. Hum Mol Genet. Apr. 15, 2011;20(R1):R2-6 doi: 10.1093/hmg/ddr141. Epub Apr. 29, 2011.

Kotin RM, et al. Manufacturing clinical grade recombinant adeno-associated virus using invertebrate cell lines. Hum Gene Ther. Mar. 28, 2017. Epub ahead of print.

Kotterman MA, et al. Enhanced cellular secretion of AAV2 by expression of foreign viral envelope proteins. Biochemical Engineering Journal, vol. 93, Jan. 15, 2015, pp. 108-114.

Kou Jinghong et al: "Catalytic Immunogobulin Gene Delivery in a Mouse Model of Alzheimer's Disease: Prophylactic and Therapeutic Applicat", Molecular Neurobiology, Humana Press, US, vol. 51, No. 1, Apr. 15, 2014 (Apr. 15, 2014), pp. 43-56.

Kozak M. Interpreting cDNA sequences: some insights from studies on translation. Mamm Genome. Aug. 1996;7(8):563-74.

Kozak M. Point mutations define a sequence flanking the AUG initiator codon that modulates translation by eukaryotic ribosomes. Cell. Jan. 31, 1986;44(2):283-92.

Kozak M. The scanning model for translation: an update. J Cell Biol. Feb. 1989;108(2):229-41.

Landegger LD, et al. A synthetic AAV vector enables safe and efficient gene transfer to the mammalian inner ear. Nat Biotechnol. Mar. 2017;35(3):280-284.

Lentz TB, et al. Insight into the Mechanism of Inhibition of Adeno-Associated Virus by the Mre11/Rad50/Nbs1 Complex. J Virol. Jan. 2015, 89(1):181-94.

Li BZ, et al. Site directed mutagenesis of surface-exposed lysine residues leads to improved transduction by AAV2 but hot AAV8 vectors in murine hepatocytes in vivo. Hum Gene Ther Methods. Dec. 2015;26(6):211-20.

Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.

Li SY, et al. Efficient and targeted transduction of nonhuman primate liver with systemically delivered optimized AAV3B vectors. Mol Ther. Dec. 2015;23(12):1867-76.

Iguore et al., AAV-PHP.B Administration Results in a Differential Pattern of CNS Biodistribution in Non-human Primates Compared with Mice. Molecular Therapy. Aug. 5, 2019. In press.

Adachi K, et al. Drawing a high-resolution functional map of adeno-associated virus capsid by massively parallel sequencing. Nat Commun. 2014;5:3075. doi: 10.1038/ncomms4075.

Adamson-Small L, et al. Sodium chloride enhances rAAV production in a serum-free suspension manufacturing platform using the Herpes Simplex Virus System. Hum Gene Ther Methods. Feb. 2017;28(1):1-14.

Afione S, et al. Identification and Mutagenesis of the Adeno-Associated Virus 5 Sialic Acid Binding Region.J Virol. Feb. 2015, 89(3):1660-72.

Ahmed SS, et al. rAAV gene therapy in a Canavan's disease mouse model reveals immune impairments and an extended pathology beyond the central nervous system. Mol Ther. Jun. 2016;24(6):1030-41.

Ai J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.

Ai J, et al. Adeno-associated virus serotype rh.10 displays strong muscle tropism following intraperitoneal delivery. Sci Rep. Jan. 2017;7:40336.

Alton EE, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.

Altschul SF, et al. Basic local alignment search tool. J Mol Biol. Oct. 5, 1990;215(3):403-10.

Alves S et al. Ultramicroscopy as a Novel Tool to Unravel the Tropism of AAV Gene Therapy Vectors in the Brain. Sci Rep. Jun. 20, 2016;6:28272.

Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.

Asokan et al., The AAV vector toolkit: poised at the clinical crossroads. Mol Ther. Apr. 2012;20(4):699-708.

Aubourg P. Gene therapy for rare central nervous system diseases comes to age. Endocr Dev. 2016;30:141-6.

Aydemir F, et al. Mutants at the 2-fold interface of AAV2 structural proteins suggest a role in viral transcription for AAV capsids. J Virol. Jul. 2016;90(16):7196-204.

Bankiewicz KS et al. AAV Viral Vector Delivery to the Brain by Shape-conforming MR-guided Infusions. J Control Release. Oct. 28, 2016;240:434-442.

Bantel-Schaal U, et al. Human adeno-associated virus type 5 is only distantly related to other known primate helper-dependent parvoviruses. J Virol. Feb. 1999;73(2):939-47.

Bartel et al., Directed evolution of novel adeno-associated viruses for therapeutic gene delivery. Gene Ther. Jun. 2012;19(6):694-700.

Batista et al., Ly6a differential expression in BBB is responsible for strain specific CNS transduction profile of AAV-PHP.B. Hum Gene Ther. Nov. 7, 2019. [Epub ahead of print].

Baum BJ, et al. Advances in salivary gland gene therapy—oral and systemic implications. Expert Opinion on Biological Therapy. 2015;15(10):1443-54.

Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.

Bedbrook CN, et al. Viral Strategies for Targeting the Central and Peripheral Nervous Systems. Annu Rev Neurosci. Jul. 8, 2018;41:323-348.

Bell P, et al. Effects of self-complementarity, codon optimization, transgene, and dose on liver transduction with AAV8. Hum Gene Ther Methods. Dec. 2016;27(6):228-237.

Benjamin E. Deverman et al: "Cre-dependent selction yields AAV variants for widespread gene tansfer tothe adult brain", Nature Biotechbnology, vol. 34, No. 2, Feb. 1, 2016, (Feb. 1, 2016), pp. 204-209.

Bennett A, et al. Understanding capsid assembly and genome packaging for adeno-associated viruses. Future Virology Jun. 2017; 12(6): 283-297.

Bensky MJ, et al. Targeted gene delivery to the enteric nervous system using AAV: a comparison across serotypes and capsid mutants. Mol Ther. Mar. 2015;23(3):488-500.

Berge SM Pharmaceutical salts. J Pharm Sci. Jan. 1977;66(1):1-19.

Berry GE, et al. Cellular transduction mechanisms of adeno-associated viral vectors. Curr Opin Virol. Dec. 2016;21:54-60.

Betley et al., Adeno-associated viral vectors for mapping, monitoring, and manipulating neural circuits. Hum Gene Ther. Jun. 2011;22(6):669-77.

Bevan AK et al., Systemic gene delivery in large species for targeting spinal cord, brain, and peripheral tissues for pediatric disorders. Mol Ther. Nov. 2011;19(11):1971-80.

Bey K, et al. Efficient CNS targeting in adult mice by intrathecal infusion of single-stranded AAV9-GFP for gene therapy of neurological disorders. Gene Ther. Apr. 20, 2017. Epub ahead of print.

(56) References Cited

OTHER PUBLICATIONS

Brulet R, et al. NEUROD1 Instructs Neuronal Conversion in Non-Reactive Astrocytes. Stem Cell Reports. May 11, 2017. Epub ahead of print.
Buclez PO, et al. Rapid, scalable, and low-cost purification of recombinant adeno-associated virus produced by paculovirus expression vector system. Mol Ther Methods Clin Dev. May 2016;3:16035.
Büning H, Srivastava A. Capsid Modifications for Targeting and Improving the Efficacy of AAV Vectors. Mol Ther Methods Clin Dev. Jan. 26, 2019;12:248-265.
Burnham B, et al. Analytical ultracentrifugation as an approach to characterize recombinant adeno-associated viral vectors. Hum Gene Ther Methods. Dec. 2015;26(6):228-42.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Callaway et al., Transneuronal circuit tracing with neurotropic viruses. Curr Opin Neurobiol. Dec. 2008;18(6):617-23.
Carillo H, et al. The Multiple Sequence Alignment Problem in Biology. SIAM J. Appl. Math. 48-5 (1988), pp. 1073-1082.
Carter BJ. Adeno-associated virus and the development of adeno-associated virus vectors: a historical perspective. Mol Ther. Dec. 2004;10(6):981-9.
Carter, AAV gene delivery of an anti-Tau antibody using a novel blood brain barrier penetrant capsid in wild type and P301S tauopathy mice. Congress of the European Society of Gene and Cell Therapy [poster presentation], Oct. 17, 2017. Berlin, Germany.
Castle MJ, et al. Controlling AAV Tropism in the Nervous System with Natural and Engineered Capsids. Methods Mol Biol. 2016;1382:133-49.
Catherine Gerard et al: "An AAV9 docing for frataxin clearly improved the symptoms and prolonged the life of Friedreich ataxia mouse models", Molecular Therapy—Methods & Clinical Development, vol. 1, Jan. 1, 2014 (Jan. 1, 2014), p. 14044.
Cearley et al., A single injection of an adeno-associated virus vector into nuclei with divergent connections results in widespread vector distribution in the brain and global correction of a neurogenetic disease. J Neurosci. Sep. 12, 2007;27(37):9928-40.
Challis et al., Systemic AAV vectors for widespread and targeted gene delivery in rodents. Nat Protoc. Feb. 2019;14(2):379-414.
Challis RC, et al. Systemic AAV vectors for widespread and targeted gene delivery in rodents. Nat Protoc. Jan. 9, 2019. [Epub ahead of print].
Chamberlain K, et al. Expressing transgenes that exceed the packaging capacity of AAV capsids. Hum Gene Ther Methods. Feb. 2016;27(1):1-12.
Chandler RJ, et al. rAAV integration and genotoxicity: insights from animal models. Hum Gene Ther. Apr. 2017;28(4):314-322.
Chandler RJ, et al. Systemic AAV9 gene therapy improves the lifespan of mice with Niemann-Pick disease, type C1. Hum Mol Genet. Jan. 2017;26(1):52-64.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Ling C, et al. Development of Optimized AAV Serotype Vectors for High-Efficiency Transduction at Further Reduced Doses. Hum Gene Ther Methods. Aug. 2016;27(4):143-9.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Ling C, et al. Strategies to generate high-titer, high-potency recombinant AAV3 serotype vectors. Mol Ther Methods Clin Dev. May 2016;3:16029.
Liu W, et al. Vectored Intracerebral Immunization with the Anti-Tau Monoclonal Antibody PHF1 Markedly Reduces Tau Pathology in Mutant Tau Transgenic Mice. J Neurosci. Dec. 2016;36(49):12425-12535.
Lu J, et al. A 5' Noncoding Exon Containing Engineered Intron Enhances Transgene Expression from Recombinant AAV Vectors in vivo. Hum Gene Ther. Jan. 2017;28(1):125-134.
Lukashcuk V et al. AAV9-mediated central nervous system-targeted gene delivery via cisterna magna route in mice. Mol Ther Methods Clin Dev. Feb. 17, 2016;3:15055.
Luo et al., Genetic dissection of neural circuits. Neuron. Mar. 13, 2008;57(5):634-60.
Maguire et al., Gene therapy for the nervous system: challenges and new strategies. Neurotherapeutics. Oct. 2014; 11(4):817-39.
Maniatis T. et al.,Molecular Cloning. CSH Laboratory, NY, N.Y. (1982).
Mao Y, et al. Single point mutation in adeno-associated viral vectors—DJ capsid leads to improvement for gene delivery in vivo BMC Biotechnol. Jan. 2016;16:1.
Marsic D et al. Altering Tropism of rAAV by Directed Evolution. Methods of Mol Biol. 2016;1382:151-73.
Mason JB, et al. Delivery and evaluation of recombinant adeno-associated viral vectors in the equine distal extremity tor the treatment of laminitis. Equine Vet J. Jan. 2017;49(1):79-86.
Matsuzaki Y, et al. Intravenous administration of the adeno-associated virus-PHP.B capsid fails to upregulate transduction efficiency in the marmoset brain.Neurosci Lett. Feb. 5, 2018,665:182-188.
Matsuzaki Y, Tanaka M, Hakoda S, Masuda T, Miyata R, Konno A, Hirai H. Neurotropic Properties of AAV-PHP.B Are Shared among Diverse Inbred Strains of Mice .Mol Ther. Feb. 28, 2019. [Epub ahead of print].
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Mendell JR, et al. Follistatin Gene Therapy for Sporadic Inclusion Body Myositis Improves Functional Outcomes. Mol Ther. Apr. 2017;25(4):870-879.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi:10.1111/jnc.13861.
Merten OW, et al. Viral vectors for gene therapy and gene modification approaches. Biochem Eng J. Apr. 2016;108:98-115.
Methods in Molecular Biology, ed. Richard, Humana Press, NJ (1995).
Michelfelder et al., Peptide ligands incorporated into the threefold spike capsid domain to re-direct gene transduction of AAV and AAV9 in vivo. PLoS One. 2011;6(8):e23101.
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Mingozzi F, et al. Adeno-associated viral vectors at the frontier between tolerance and immunity. Front Immunol. Mar. 2015, 6:120.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.

(56) References Cited

OTHER PUBLICATIONS

Mondo E, et al. Selective Neuronal Uptake and Distribution of AAVrh8, AAV9, and AAVrh10 in Sheep After Intra-Striatal Administration. Selective Neuronal Uptake and Distribution of AAVrh8, AAV9, and AAVrh10 in Sheep After Intra-StriatalAdministration. J Huntingtons Dis. 2018;7(4):309-319.
Morabito G, et al. Global-scale control of gene expression in the adult mouse nervous system by a single AAV-PHP.B systemic injection enables GBA1 gene therapy for complete protection from synucleinopathy Aug. 10, 2017.
Morgane Perdomini et al: Prevention and reversal of severe mitochondrial cardiomyopathy by gene therapy in a mouse model of Friedreich's ataxia, Nature Medicine, vol. 20, No. 5, Apr. 6, 2014 (Apr. 6, 2014), pp. 542-547.
Muralidharan G , et al. Unique glycan signatures regulate adeno-associated virus tropism in the developing brain. J Virol. Apr. 2015;89(7):3976-87.
Murlidharan G et al. Glymphatic Fluid Transport Controls Paravascular Clearance of AAV Vectors From the Brain. JCI Insight. Sep. 8, 2016;1(14).
Muzyczka N, et al. AAV's Golden Jubilee. Mol Ther. May 2015;23(5):807-8.
Myers EW, et al. Optimal alignments in linear space. Comput Appl Biosci. Mar. 1988;4(1):11-7.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Nery FC, et al. New methods for investigation of neuronal migration in embryonic brain explants J Meurosci Methods. Jan. 2015, 239:80-4.
Neuberger EWI, et al. Establishment of two quantitative nested qPCR assays targeting the human EPO transgene. Gene Ther. Apr. 2016;23(4):330-9.
Nicolson SC, et al. Identification and validation of small molecules that enhance recombinant Adeno-associated virus transduction following high throughput screen. J Virol. Jul. 2016;90(16):7019-31.
Nygaard S, et al. A universal system to select gene-modified hepatocytes in vivo. Sci Transl Med. Jun. 2016;8(342):342ra79.
Ojala DS, et al. Adeno-associated virus vectors and neurological gene therapy. Neuroscientist. Feb. 2015;21(1):84-98.
Oliva B, et al. An automated classification of the structure of protein loops. J Mol Biol. Mar. 7, 1997;266(4):814-30.
O'Reilly DR, et al. Baculovirus expression vectors: a laboratory manual. Oxford University Press, 1994.
Pacouret S, et al. AAV-ID: A Rapid and Robust Assay for Batch-to-Batch Consistency Evaluation of AAV Preparations. Mol Ther. Apr. 17, 2017. Epub ahead of print.
Parr MJ, et al. Tumor-selective transgene expression in vivo mediated by an E2F-responsive adenoviral vector. Nat Med. Oct. 1997;3(10):1145-9.
Patzke, Intravenous delivery of AAV gene therapy to cerebellum and peripheral tissues critical for the treatment of Friedreich's ataxia. International Ataxia Research Conference [oral presentation], Sep. 30, 2017. Pisa, Italy.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Petit L, et al. Rod Outer Segment Development Influences AAV-Mediated Photoreceptor Transduction After Subretinal Injection. Hum Gene Ther. May 16, 2017. Epub ahead of print.
Philiport, et al. Liposomes as tools in Basic Research and Industry. CRC Press, Ann Arbor, Mich. (1995).
Pierson EE, et al. Resolving adeno-associated viral particle diversity with charge detection mass spectrometry. Anal Chem. Jul. 2016;88(13):6718-25.
Pillay S, et al. An essential receptor for adeno-associated virus infection. Nature. Feb. 2016;530(7588):108-12.
Pillay S, et al. An essential receptor for adeno-associated virus infection. Nature. Nov. 17, 2016;539(7629):456.
Van Der Loo JCM, et al. Progress and challenges in viral vector manufacturing. Hum Mol Genet. Apr. 2016;25(R1):R42-52.
Vandendriessche et al., Efficacy and safety of adeno-associated viral vectors based on serotype 8 and 9 vs. lentiviral Vectors for hemophilia B gene therapy. J Thromb Haemost. Jan. 2007;5(1):16-24.
Vercauteren K, et al. Superior in vivo Transduction of Human Hepatocytes Using Engineered AAV3 Capsid. Mol Ther. Jun. 2016;24(6):1042-9.
Von Heinje G. Sequence Analysis in Molecular Biology. Academic Press, 1987.
Wang D, et al. A Rationally Engineered Capsid Variant of AAV9 for Systemic CNS-Directed and Peripheral Tissue-Detargeted Gene Delivery in Neonates. Mol Ther Methods Clin Dev. Mar. 16, 2018;9:234-246.
Wang et al., Noninvasive, neuron-specific gene therapy can be facilitated by focused ultrasound and recombinant adeno-associated virus. Gene Therapy. Nov. 22, 2014, 104-110.
Wang L, et al. Productive life cycle of adeno-associated virus serotype 2 in the complete absence of a conventional polyadenylation signal. J Gen Virol. Sep. 2015;96(9):2780-7.
Wang LL, et al. Comparative study of liver gene transfer with AAV vectors based on endogenous and engineered AAV capsids. Mol Ther. Dec. 2015;23(12):1877-87.
Wang M, et al. Direct interaction of human serum proteins with AAV virions to enhance AAV transduction: Immediate impact on clinical applications. Gene Ther. Jan. 2017;24(1):49-59.
Wang S, et al. Direct brain infusion can be enhanced with focused ultrasound and microbubbles. J Cereb Blood Flow Metab. Feb. 2017;37(2):706-714.
Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Watakabe A, et al. Comparative analyses of adeno-associated viral vector serotypes 1 2 5 8 and 9 in marmoset mouse and macaque cerebral cortex. Neurosci Res. Apr. 2015, 93:144-57.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Weber-Adrian D, et al. Gene delivery to the spinal cord using MRI-guided focused ultrasound. Gene Ther. Jul. 2015, 22(7):568-77.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016,90(21):9878-9888.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Wu P, et al. Mutational analysis of the adeno-associated virus type 2 (AAV2) capsid gene and construction of AAV2 vectors with altered tropism. J Virol. Sep. 2000;74(18):8635-47.
Xiao P, et al. Disruption of microtubules post virus entry enhances adeno-associated virus vector transduction. Hum Gene Ther. Apr. 2016;27(4):309-24.
Xie et al., MicroRNA-regulated, systemically delivered rAAV9: a step closer to CNS-restricted transgene expression. Mol Ther. Mar. 2011;19(3):526-35.
Xie J et al., Short DNA Hairpins Compromise Recombinant Adeno-Associated Virus Genome Homogeneity. Mol Ther. Jun. 7, 2017;25(6):1363-1374.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.

(56) References Cited

OTHER PUBLICATIONS

Yalvac ME, et al. AAV1.NT-3 gene therapy attenuates spontaneous autoimmune peripheral polyneuropathy. Gene Ther. Jan. 2016;23(1):95-102.
Yan ZY, et al. Optimization of recombinant adeno-associated virus mediated expression for large transgenes, using a synthetic promoter and tandem array enhancers. Hum Gene Ther. Jun. 2015;26(6):334-46.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Yla-Herttuala S, et al. Advances and Challenges in Cardiovascular gene therapy. Hum Gene Ther. Aug. 16, 2017.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zhang X, et al. Blood-brain barrier shuttle peptides enhance AAV transduction in the brain after systemic administration. Biomaterials Sep. 2018;176:71-83.
Zhang, Y, et al. Identification of adeno-associated virus capsid proteins using ZipChip CE/MS. Anal Biochem. Aug. 15, 2018;555:22-25.
Zhao KN, et al. BPV1 E2 protein enhances packaging of full-length plasmid DNA in BPV1 pseudovirions. Virology. Jul. 5, 2000;272(2):382-93.
Zhou et al., Comparative Analysis In Vitro of Regulatory Elements That Drive Targeted Gene Expression in Adenovirus-Associated Viral (AAV) Vectors (Abstract). Mol. Ther., vol. 23 (S1), S77-S78 (May 2015).
Zhou et al., Comparative Analysis In Vitro of Regulatory Elements That Drive Targeted Gene Expression in Adenovirus-Associated Viral (AAV) Vectors. Poster presented at: ASGCT 18th Annual Meeting; May 13-16, 2015; New Orleans, LA, USA.
Zhu W, et al. Soluble FLT1 Gene Therapy Alleviates Brain Arteriovenous Malformation Severity. Stroke. May 2017;48(5):1420-1423.
Zinn E, et al. In Silico Reconstruction of the Viral Evolutionary Lineage Yields a Potent Gene Therapy Vector. Cell Rep. Aug. 2015, 12(6):1056-68.
Zou W, et al. Nonstructural protein NP1 of human bocavirus 1 plays a critical role in the expression of viral capsid proteins. J Virol. Apr. 2016;90(9):4658-69.
Choi et al., AAV Hybrid Serotypes: Improved Vectors for Gene Delivery; Curr Gene Ther. Jun. 2005 ; 5(3): 299-310.
Choudhury et al. In Vivo Selection Yields AAV-B1 Capsid for Central Nervous System and Muscle Gene Therapy. Mol Ther. Aug. 2016;24(7):1247-57.
Choudhury SR, et al. Widespread CNS gene transfer and silencing after systemic delivery of novel AAV-AS vectors. Mol Ther. Apr. 2016;24(4):726-35.
Clement N, et al. Manufacturing of recombinant adeno-associated viral vectors for clinical trials. Mol Ther Methods Clin Dev. Mar. 2016;3:16002.
Dang CH, et al. In vivo dynamics of AAV-mediated gene delivery to sensory neurons of the trigeminal ganglia. Sci Rep. Apr. 19, 2017;7(1):927.
Dashkoff J, et al. Tailored transgene expression to specific cell types in the central nervous system after peripheral injection with AAV9. Mol Ther Methods Clin Dev. Dec. 2016;3:16081.
Database UniProt [Online] Jul. 15, 1999 (Jul. 15, 1999), EBI accession No. UNIPROT:Q16595 Database accession No. Q16595 All isoform sequence 13 pages.
Davidsson M, et al. A novel process of viral vector barcoding and library preparation enables high-diversity library generation and recombination-free paired-end sequencing. Sci Rep. Nov. 2016;6:3563.
Davis AS, et al. Rational design and engineering of a modified adeno-associated virus (AAV1)-based vector system for enhanced retrograde gene delivery. Neurosurgery. Feb. 2015;76(2):216-25.
Dayton RD, et al. More expansive gene transfer to the rat CNS: AAV PHP.EB vector dose—response and comparison to AAV PHP.B. Gene Ther. Jul. 16, 2018 Epub ahead of print.
D'Costa S, et al. Practical utilization of recombinant AAV vector reference standards: focus on vector genome titration by free ITR qPCR. Mol Ther Methods Clin Dev. Mar. 2016;5:16019.
De Leeuw CN et al. rAAV-compatible MiniPromoters for Restricted Expression in the Brain and Eye. Mol Brain. May 10, 2016;9(1):52.
Deng XF, et al. Replication of an autonomous human parvovirus in non-dividing human airway epithelium is facilitated through the DNA damage and repair pathways. PLoS Pathog. Jan. 2016;12(1):e1005399.
Devereux J A comprehensive set of sequence analysis programs for the VAX. Nucleic Acids Res. Jan. 11, 1984;12(1 Pt 1)387-95.
Deverman BE et al. Cre-dependent selection yields AAV variants for widespread gene transfer to the adult brain. Nat Biotechnol. Feb. 2016;34(2):204-9.
Deverman BE, et al. Gene therapy for neurological disorders: progress and prospects. Nat Rev Drug Discov. Aug. 10, 2018 Epub ahead of print.
Dimidschstein J, et al. A viral strategy for targeting and manipulating interneurons across vertebrate species. Nat Neurosci. Dec. 2016;19(12):1743-1749.
Ding C, et al., Biochemical Characterization of Junonia Coenia Densovirus Nonstructural Protein NS-1. J. Virol., 76(1):338-345 2002.
Donsante A et al. Intracerebroventricular delivery of self-complementary adeno-associated virus serotype 9 to the adult rat brain. Gene Ther. May 2016;23(5):401-7.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
El-Shamayleh Y, et al. Strategies for targeting primate neural circuits with viral vectors. J Neurophysiol. Jul. 2016;116(1):122-34.
Fargnoli AS, et al. Liquid jet delivery method featuring S100A1 gene therapy in the rodent model following acute myocardial infarction. Gene Ther. Feb. 2016;23(2):151-7.
Fenno et al., The development and application of optogenetics. Annu Rev Neurosci. 2011;34:389-412.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
G. S. Banker, Modern Pharmaceutics, Drugs and the Pharmaceutical Sciences, v. 72, Marcel Dekker, New York, Inc., 1996.
Gessler DJ et al. Gene Therapy for the Treatment of Neurological Disorders: Metabolic Disorders. Methods Mol Biol. 2016;1382:429-65.
Giles AR, et al. Mapping an adeno-associated virus 9-specific neutralizing epitope to develop next-generation gene delivery vectors. J Virol. Aug. 8, 2018 Epub ahead of print.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016; 1382:231-7.
Goulet et al., Comparison of CNS Transduction by Different AAV Capsids in Mouse and Non-Human Primate (Abstract). Mol. Ther., vol. 23 (S1), S37 (May 2015).
Goulet et al., Comparison of CNS Transduction by Different AAV Capsids in Mouse and Non-Human Primate. Poster presented at: ASGCT 18th Annual Meeting; May 13-16, 2015; New Orleans, LA, USA.

(56) References Cited

OTHER PUBLICATIONS

Greig JA, et al. Impact of intravenous infusion time on AAV8 vector pharmacokinetics, safety, and liver transduction in cynomolgus macaques. Mol Ther Methods Clin Dev. Dec. 2016;3:16079.
Greig JA, et al. Intramuscular administration of AAV overcomes pre-existing neutralizing antibodies in rhesus macaques. Vaccine. Dec. 2016;34(50):6323-6329.
Gribskov M, et al. Sequence Analysis Primer. M Stockton Press, New York, 1991.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Griffin AM, et al. Computer Analysis of Sequence Data, Part I. Humana Press, New Jersey, 1994.
Grimm D, et al. E Pluribus Unum: 50 years of research, millions of viruses and one goal—tailored acceleration of AAV evolution. Mol Ther. Dec. 2015;23(12):1819-1831.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Gruntman AM, et al. Delivery of Adeno-associated virus gene therapy by intravascular limb infusion methods. Hum Gene Ther Clin Dev Sep. 2015;26(3):159-64.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Gurda BL, et al. Evaluation of AAV-mediated gene therapy for central nervous system disease in canine mucopolysaccharidosis VII. Mol Ther. Feb. 2016;24(2):206-16.
Haery et al., Adeno-Associated Virus Technologies and Methods for Targeted Neuronal Manipulation. Front. Neuroanat., Nov. 26, 2019.
Hagg A, et al. Using AAV vectors expressing the beta 2-adrenoceptor or associated G alpha proteins to modulate skeletal muscle mass and muscle fiber size. Sci Rep. Mar. 2016;6:23042.
Hai B, et al. Long-term transduction of miniature pig parotid glands using serotype 2 adeno-associated viral vectors. J Gene Med. Jun. 2009;11(6):506-14.
Halder S, et al. Structure of neurotropic adeno-associated virus AAVrh.8. J Struct Biol. Oct. 2015;192(1):21-36.
Hastie E, et al. Adeno-Associated Virus at 50: A Golden Anniversary of Discovery, Research, and Gene Therapy Succes—A Personal Perspective. Hum Gene Ther. May 2015, 26(5):257-65.
Platt MP, et al. Embryonic disruption of the candidate dyslexia susceptibility gene homolog Kiaa0319-like results in neuronal migration disorders. Neuroscience. Sep. 17, 2013;248:585-93.
Pleger Sven T. et al: "Cardiac AAV9-S100A1 gene therapy rescues post-oschemic heart failure in a preclinical large animal model", Science Translational Medicine, vol. 3, No. 92 ra 64, Jul. 20, 2011 (Jul. 20, 2011), pp. 117-126.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.

Powell SK et al. Characterization of a novel adeno-associated viral vector with preferential oligodendrocyte tropism. Gene Ther. Sep. 15, 2016.
Powell SK, et al. Viral expression cassette elements to enhance transgene target specificity and expression in gene therapy. Discov Med. Jan. 2015;19(102):49-57.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ravindra et al., Multiplexed Cre-dependent selection yields systemic AAVs for targeting distinct brain cell types. Nat Methods. Apr. 20, 2020. [Epub ahead of print].
Reid CA, et al. miRNA mediated post-transcriptional silencing of transgenes leads to increased adeno-associated viral vector yield and targeting specificity. Gene Ther. Jun. 15, 2017. Epub ahead of print.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Rincon MY, et al. Widespread transduction of astrocytes and neurons in the mouse central nervous system after systemic delivery of a self-complementary AAV-PHP.B vector. Gene Ther. Apr. 2018;25(2):83-92.
Rosario AM et al. Microglia-specific Targeting by Novel Capsid-modified AAV6 Vectors. Mol Ther Methods Clin Dev. Apr. 13, 2016;3:16026.
Ruffing M, et al. Assembly of viruslike particles by recombinant structural proteins of adeno-associated virus type 2 in insect cells. J Virol. Dec. 1992;66(12):6922-30.
Rutledge EA, et al. Infectious clones and vectors derived from adeno-associated virus (AAV) serotypes other than AAV type 2. J Virol. Jan. 1998;72(1):309-19.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Samaranch L, et al. MR-guided parenchymal delivery of adeno-associated viral vector serotype 5 in non-human primate brain. Gene Ther. Apr. 2017;24(4):253-261.
Samulski RJ, et al. Helper-free stocks of recombinant adeno-associated viruses: normal integration does not require viral gene expression. J Virol. Sep. 1989;63(9):3822-8.
Saraiva J et al. Gene Therapy for the CNS Using AAVs: The Impact of Systemic Delivery by AAV9. J Control Release. Nov. 10, 2016;241:94-109.
Sawada Y et al. Inflammation-induced Reversible Switch of the Neuron-specific Enolase Promoter from Purkinje Neurons to Bergmann Glia. Sci Rep. Jun. 13, 2016;6:27758.
Schaffer et al., Molecular engineering of viral gene delivery vehicles. Annu Rev Biomed Eng. 2008;10:169-94.
Schnepp BC, et al. Recombinant adeno-associated virus vector genomes take the form of long-lived transcriptionally competent episomes in human muscle. Hum Gene Ther. Jan. 2016;27(1):32-42.
Shen F, et al. Inhibition of pathological brain angiogenesis through systemic delivery of AAV vector expressing soluble FLT1. Gene Therapy. Nov. 22, 2015(11):893-900.
Shen S, et al. Functional Analysis of the Putative Integrin Recognition Motif on Adeno-associated virus 9. J Biol Chem. Jan. 2015, 290(3):1496-504.
Shen W, et al. Analysis of the Cis and Trans Requirements for DNA Replication at the Right End Hairpin of the Human Bocavirus 1 Genome. J Virol. Aug. 2016;90(17):7761-77.
Shinohara Y, et al. Effects of Neutralizing Antibody Production on AAV-PHP.B-Mediated Transduction of the Mouse Central Nervous System.Mol Neurobiol. Oct. 5, 2018. Epub ahead of print.
Singer M. & Berg P. (1999). Genes & Genomes, A Changing Perspective. Mill Valley, CA: University Science Books.
Siu JJ, et al. Improved gene delivery to adult mouse spinal cord through the use of engineered hybrid adeno-associated viral serotypes. Gene Ther. Apr. 25, 2017. Epub ahead of print.
Smith DW, et al. Biocomputing: Informatics and Genome Projects. Academic Press, New York, 1993.

(56) References Cited

OTHER PUBLICATIONS

Smith RH, et al. A simplified baculovirus—AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.

Smith RH, et al. Germline viral "fossils" guide in silico reconstruction of a mid-Cenozoic era marsupial adeno-associated virus. Sci Rep. Jul. 2016;6:28965.

Sondhi D, et al. Genetic Modification of the Lung Directed Toward Treatment of Human Disease. Hum Gene Ther. Jan. 2017;28(1):3-84.

Srivastava A, et al. Nucleotide sequence and organization of the adeno-associated virus 2 genome. J Virol. Feb. 1983;45(2):555-64.

Srivastava A. Adeno-Associated Virus: The Naturally Occurring Virus Versus the Recombinant Vector. Hum Gene Ther. Jan. 2016;27(1):1-6.

Srivastava A. In Vivo Tissue-tropism of Adeno-associated Viral Vectors. Curr Opin Virol. Sep. 2, 2016;21:75-80.

Stahl PH, et al. Pharmaceutical Salts: Properties, Selection, and Use. Wiley-VCH, 2008.

Steines B, et al. CFTR gene transfer with AAV improves early cystic fibrosis pig phenotypes. JCI Insight. Sep. 2016;1(14):e88728.

Su W et al. Recombinant adeno-associated viral (rAAV) vectors mediate efficient gene transduction in cultured neonatal and adult microglia. J Neurochem. Jan. 2016;136 Suppl 1:49-62.

Summerford C, et al. AAVR: A multi-serotype receptor for AAV. Mol Ther. Apr. 2016;24(4):663-6.

Suzuki J, et al. Cochlear gene therapy with ancestral AAV in adult mice: complete transduction of inner hair cells without cochlear dysfunction. Apr. 3, 2017;7:45524.

Tadokoro T, et al. Subpial Adeno-associated Virus 9 (AAV9) Vector Delivery in Adult Mice. J Vis Exp. Jul. 13, 2017; (125). doi: 10.3791/55770.

Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.

Tervo et al. A Designer AAV Variant Permits Efficient Retrograde Access to Projection Neurons. Neuron. Oct. 19, 2016;92(2):372-382.

Thorne B, et al. Gene Therapy. Adv Biochem Eng Biotechnol. Mar. 14, 2017 Epub ahead of print.

Tordo J, et al. A novel adeno-associated virus capsid with enhanced neurotropism corrects a lysosomal transmembrane enzyme deficiency. Brain Jul. 1, 2018;141(7):2014-2031.

Tratschin JD, et al. Adeno-associated virus vector for high-frequency integration, expression, and rescue of genes in mammalian cells. Mol Cell Biol. Nov. 1985;5(11):3251-60.

Tse, LV, et al. Mapping and Engineering Functional Domains of the Assembly-Activating Protein of Adeno-associated Viruses . J Virol. Jun. 29, 2018;92(14).

Tu MY, et al. Role of capsid proteins in parvoviruses infection. Virol J. Aug. 4, 2015;12:114.

Urabe M, et al. Scalable generation of high-titer recombinant adeno-associated virus type 5 in insect cells. J Virol. Feb. 2006;80(4):1874-85.

GenBank accession No. AY530579.1: Adeno-associated virus 9 isolate hu.14 capsid protein VP1 (cap) gene, published Jun. 24, 2004.

* cited by examiner

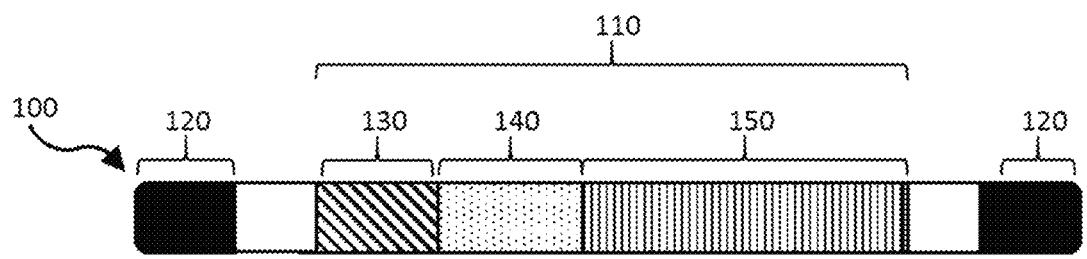

COMPOSITIONS AND METHODS FOR DELIVERY OF AAV

REFERENCE TO RELEVANT APPLICATIONS

This application is a continuation of U.S. application Ser. No. 16/636,094, filed Feb. 3, 2020, which is a 35 U.S.C. 371 national stage filing of International Application No. PCT/US2018/045088, filed Aug. 3, 2018, which claims the benefit of U.S. Provisional Patent Application No. 62/540,776, filed Aug. 3, 2017, U.S. Provisional Patent Application No. 62/565,264, filed Sep. 29, 2017, and U.S. Provisional Patent Application No. 62/572,706, filed Oct. 16, 2017. The contents of each of which are herein incorporated by reference in their entirety.

SEQUENCE LISTING

The instant application contains a Sequence Listing which has been submitted electronically in XML format and is hereby incorporated by reference in its entirety. Said XML copy, created on Jun. 9, 2023, is named VTJ-1050US-CN_SequenceListing.xml and is 4233 kilobytes in size.

FIELD OF THE INVENTION

The present invention relates to compositions, methods and processes for the design, preparation, manufacture, use and/or formulation of adeno-associated virus capsids for improved biodistribution.

BACKGROUND OF THE INVENTION

Adeno-associated viral (AAV) vectors are a promising candidate for therapeutic gene delivery and have proven safe and efficacious in clinical trial.

Delivery of AAV to some systems in the body has proven to be particularly challenging, requiring invasive surgeries for sufficient levels of gene transfer. For some body systems, intravenous delivery has historically resulted in limited gene transfer, in part due to inefficient transduction into cells. There remains a need in the art for AAV vectors that may be administered by intravenous delivery and yet are able to efficiently target regions critical for treating a multitude of diseases.

One example of a system where delivery is challenging is the central nervous system. Delivery of AAV to regions of the central nervous system (CNS) has proven to be particularly challenging, requiring invasive surgeries for sufficient levels of gene transfer (See e.g., Bevan et al. Mol Ther. 2011 November; 19(11): 1971-1980). Intravenous delivery has historically resulted in limited gene transfer to the CNS, in part due to the presence of the blood brain barrier (BBB). There remains a need in the art for AAV vectors that may be administered by intravenous delivery and yet are able to efficiently cross the blood brain barrier and target regions of the CNS critical for treating a multitude of CNS diseases.

Another example of a system where delivery is challenging is the cardiovascular system. Delivery of AAV to the cardiovascular system has proven to be particularly challenging, requiring invasive surgeries for sufficient levels of gene transfer. Intravenous delivery has historically resulted in limited gene transfer to the cardiovascular system, in part due to inefficient transduction into cardiomyocytes. There remains a need in the art for AAV vectors that may be administered by intravenous delivery and yet are able to efficiently target regions of the cardiovascular system critical for treating a multitude of diseases.

The present invention addresses this need by providing novel AAV particles with engineered capsid proteins that allow for efficient transduction of CNS tissues following intravenous delivery. Further, the viral genomes of these AAV particles may be altered to suit the needs of any number of CNS diseases, providing platform capsids for crossing the blood brain barrier and targeting of CNS tissues.

SUMMARY OF THE INVENTION

The invention provides an adeno-associated viral (AAV) particle comprising a capsid and a viral genome.

The AAV particle may comprise a capsid or a peptide insert such as, but not limited to, VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv-1, AAV Clv1-10, AAV CLv1-2, AAV CLv-12, AAV CLv1-3, AAV CLv-13, AAV Clv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof. In one aspect, the capsid of the AAV particle is VOY101. In one aspect, the capsid of the AAV particle is VOY201. In one aspect, the AAV particle comprises a peptide insert and the peptide insert is AAVPHP.N. In one aspect, the AAV particle comprises a peptide insert and the peptide insert is AAVPHP.B. In one aspect, the AAV particle comprises a peptide insert and the peptide insert is AAVPHP.A. In one aspect, the AAV particle comprises a peptide insert and the peptide insert is AAVPHP.S.

In one aspect, the AAV particle comprises a viral genome which comprises a nucleic acid sequence position between two inverted terminal repeats (ITRs).

In one aspect, the viral genome transduces cardiomyocytes upon delivery of the AAV particle. The delivery may be by any method known in the art, such as, but not limited to, intravenous administration or intracarotid artery delivery.

In one aspect, the capsid penetrates the blood brain barrier following delivery of the AAV particle. The delivery may be by any method known in the art, such as, but not limited to, intravenous administration or intracarotid artery delivery.

The AAV particles of the present invention may transduce CNS structures following administration. Non-limiting examples of CNS structures include brain, spinal cord, brainstem nuclei, cerebellum, cerebrum, motor cortex, caudate nucleus, thalamus, hypothalamus, cervical spinal cord, thoracic spinal cord, lumbar spinal cord, striatum, substantia nigra, hippocampus, amygdala and/or cerebral cortex.

In one aspect, the AAV particle comprises a viral genome which comprises a nucleic acid sequence that, when expressed, inhibits or suppresses the expression of a gene of interest (e.g., SOD1, HTT, APOE, and MAPT) in a cell. The nucleic acid sequence comprises a sense strand sequence and an antisense strand sequence which may be independently 30 nucleotides in length or less and, the sense and/or antisense strands may comprise a 3' overhang of at least 1 or at least 2 nucleotides. The sense sequence and antisense strand sequence may share a region of complementarity of at least four nucleotides in length (e.g., at least 17 nucleotides in length, between 19 and 21 nucleotides in length, or 19 nucleotides in length). The antisense strand may be excised from the AAV particle at a rate of at least 80%, 85%, 90%, 95%, or more than 95%, or more than 98%, or more than 99%. The antisense strand may be excised from the AAV particle at a rate greater than the excision of the sense strand (e.g., 2 times, 5 times, 10 times or more than 10 times greater).

Provided herein are compositions (e.g., pharmaceutical compositions) comprising AAV particles. The AAV particles may comprise a viral genome comprising a nucleic acid sequence encoding a protein of interest (e.g., an antibody, AADC, APOE2, Frataxin, ATP2A2, and/or S100A1). The AAV particles may comprise a viral genome comprising nucleic acid sequences that when expressed, inhibits or suppresses the expression of a gene of interest (e.g., SOD1, HTT, APOE, and/or MAPT) in a cell.

Provided herein are methods of using AAV particles.

In one aspect, provided are methods of inhibiting the expression of a target gene in a cell (e.g., mammalian cell, or mammalian cell of the CNS, or a cardiomyocyte).

In one aspect, provided are methods of increasing the expression of a target gene in a cell such as a mammalian cell (e.g., a mammalian cell of the CNS, or a cardiomyocyte)

In one aspect, provided are methods for treating and/or ameliorating a neurological disease in a subject by administering a therapeutically effective amount of a composition comprising the AAV particles described herein. The administration may be by intravenous or intracarotid artery delivery. The methods may be used to increase the expression of a protein of interest (e.g., an antibody, AADC, APOE2, and/or Frataxin). The methods may be used to decrease the amount of expression of a gene of interest (e.g., SOD1, HTT, APOE, and/or MAPT).

In one aspect, provided are methods for altering the level of a protein or gene of interest in a subject by administration of the AAV particles described herein. The administration may be by intravenous or intracarotid artery delivery. The methods may be used to increase the expression of a protein of interest (e.g., an antibody, AADC, APOE2, Frataxin, ATP2A2, and/or S100A1). The methods may be used to decrease the amount of expression of a gene of interest (e.g., SOD1, HTT, APOE, and/or MAPT).

Provided herein are methods for treating cardiovascular disease in a subject in need thereof by administering compositions of the AAV particles described herein. The delivery may be by any method known in the art, such as, but not limited to, intravenous administration or intracarotid artery delivery.

Provided herein are methods for treating heart failure in a subject in need thereof by administering compositions of the AAV particles described herein. The delivery may be by any method known in the art, such as, but not limited to, intravenous administration or intracarotid artery delivery.

The details of various embodiments of the invention are set forth in the description below. Other features, objects, and advantages of the invention will be apparent from the description, drawings, and the claims. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 1 is a schematic of a viral genome of the invention.

DETAILED DESCRIPTION OF THE INVENTION

The details of one or more embodiments of the invention are set forth in the accompanying description below.

Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

I. Compositions of the Invention

Adeno-Associated Viruses (AAVs) and AAV Particles

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

The Parvoviridae family comprises the Dependovirus genus which includes adeno-associated viruses (AAV) capable of replication in vertebrate hosts including, but not limited to, human, primate, bovine, canine, equine, and ovine species.

The AAV viral genome is a linear, single-stranded DNA (ssDNA) molecule approximately 5,000 nucleotides (nt) in length. The AAV viral genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV viral genome typically comprises two ITR sequences. The AAV vector genome comprises a characteristic T-shaped hairpin structure defined by the self-complementary terminal 145 nt of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In addition to the encoded heterologous payload, AAV particles may comprise the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997); Srivastava et al., J. Vir. 45:555-64 (1983); Chiorini et al., J. Vir. 73:1309-1319 (1999); Rutledge et al., J. Vir.

72:309-319 (1998); and Wu et al., J. Vir. 74: 8635-47 (2000), the contents of each of which are incorporated herein by reference in their entirety.

In one embodiment, AAV particles of the present invention are recombinant AAV viral vectors which are replication defective, lacking sequences encoding functional Rep and Cap proteins within their viral genome. These defective AAV particles may lack most or all parental coding sequences and essentially carry only one or two AAV ITR sequences and the nucleic acid of interest for delivery to a cell, a tissue, an organ or an organism.

In one embodiment, the viral genome of the AAV particles of the present invention comprise at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present invention, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV particles of the present invention may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV viral genomes (e.g., ssAAVs), the present invention also provides for self-complementary AAV (scAAVs) viral genomes. scAAV vector genomes contain DNA strands which anneal together to form double stranded DNA. By skipping second strand synthesis, scAAVs allow for rapid expression in the cell.

In one embodiment, the AAV particle of the present invention is an scAAV.

In one embodiment, the AAV particle of the present invention is an ssAAV.

Methods for producing and/or modifying AAV particles are disclosed in the art such as pseudotyped AAV particles (PCT Patent Publication Nos. WO200028004; WO200123001; WO2004112727; WO 2005005610 and WO 2005072364, the contents of each of which are incorporated herein by reference in their entirety).

AAV particles may be modified to enhance the efficiency of delivery. Such modified AAV particles can be packaged efficiently and be used to successfully infect the target cells at high frequency and with minimal toxicity. In some embodiments the capsids of the AAV particles are engineered according to the methods described in US Patent Application Publication NO. US 20130195801, the contents of which are incorporated herein by reference in their entirety.

In one embodiment, the AAV particles comprising a payload region encoding the polypeptides of the invention may be introduced into mammalian cells.

AAV Serotypes

AAV particles of the present invention may comprise or be derived from any natural or recombinant AAV serotype. According to the present invention, the AAV particles may utilize or be based on a serotype or include a peptide selected from any of the following VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv-1, AAV Clv1-10, AAV CLv1-2, AAV CLv1-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, the AAV serotype may be, or have, a sequence as described in U.S. Patent Application Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4

(US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in U.S. Patent Application Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6):1070-1078 (2011), the contents of which are herein incorporated by reference in their entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in U.S. Patent Application Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have, a sequence as described in U.S. Patent Application Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in U.S. Patent Application Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in U.S. Patent Application Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in U.S. Patent Application Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in U.S. Patent Application Publication No. US20160017005, the contents of which are herein incorporated by reference in its entirety.

In one embodiment, the AAV may be a serotype generated by the AAV9 capsid library with mutations in amino acids 390-627 (VP1 numbering) as described by Pulicherla et al. (Molecular Therapy 19(6):1070-1078 (2011); the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: X and X of U.S. Pat. No. 8,734,809), AAV CLv-R9 (SEQ ID NO: X and X of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734,809), or variants or derivatives thereof.

In some embodiments, the AAV serotype may be, or have, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In one embodiment, the AAV may be a serotype selected from any of those found in Table 1.

In one embodiment, the AAV may comprise a sequence, fragment or variant thereof, of the sequences in Table 1.

In one embodiment, the AAV may be encoded by a sequence, fragment or variant as described in Table 1.

TABLE 1

AAV Serotypes

| Serotype | SEQ ID NO | Reference Information |
|---|---|---|
| VOY101 | 1 or 1809 | — |
| VOY201 | 1810 | — |
| PHP.N/PHP.B-DGT | 2 | WO2017100671 SEQ ID NO: 46 |
| AAVPHP.B or G2B-26 | 3 | WO2015038958 SEQ ID NO: 8 and 13 |
| AAVPHP.B | 4 | WO2015038958 SEQ ID NO: 9 |
| AAVG2B-13 | 5 | WO2015038958 SEQ ID NO: 12 |
| AAVTH1.1-32 | 6 | WO2015038958 SEQ ID NO: 14 |
| AAVTH1.1-35 | 7 | WO2015038958 SEQ ID NO: 15 |
| PHP.S/G2A12 | 8 | WO2017100671 SEQ ID NO: 47 |
| AAV9/hu.14 K449R | 9 | WO2017100671 SEQ ID NO: 45 |
| AAV1 | 10 | US20150159173 SEQ ID NO: 11, US20150315612 SEQ ID NO: 202 |
| AAV1 | 11 | US20160017295 SEQ ID NO: 1, US20030138772 SEQ ID NO: 64, US20150159173 SEQ ID NO: 27, US20150315612 SEQ ID NO: 219, U.S. Pat. No. 7,198,951 SEQ ID NO: 5 |
| AAV1 | 12 | US20030138772 SEQ ID NO: 6 |
| AAV1.3 | 13 | US20030138772 SEQ ID NO: 14 |
| AAV10 | 14 | US20030138772 SEQ ID NO: 117 |
| AAV10 | 15 | WO2015121501 SEQ ID NO: 9 |
| AAV10 | 16 | WO2015121501 SEQ ID NO: 8 |
| AAV11 | 17 | US20030138772 SEQ ID NO: 118 |
| AAV12 | 18 | US20030138772 SEQ ID NO: 119 |
| AAV2 | 19 | US20150159173 SEQ ID NO: 7, US20150315612 SEQ ID NO: 211 |
| AAV2 | 20 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 21 | U.S. Pat. No. 6,156,303 SEQ ID NO: 8 |
| AAV2 | 22 | US20030138772 SEQ ID NO: 7 |
| AAV2 | 23 | U.S. Pat. No. 6,156,303 SEQ ID NO: 3 |
| AAV2.5T | 24 | U.S. Pat. No. 9,233,131 SEQ ID NO: 42 |
| AAV223.10 | 25 | US20030138772 SEQ ID NO: 75 |
| AAV223.2 | 26 | US20030138772 SEQ ID NO: 49 |
| AAV223.2 | 27 | US20030138772 SEQ ID NO: 76 |
| AAV223.4 | 28 | US20030138772 SEQ ID NO: 50 |
| AAV223.4 | 29 | US20030138772 SEQ ID NO: 73 |
| AAV223.5 | 30 | US20030138772 SEQ ID NO: 51 |
| AAV223.5 | 31 | US20030138772 SEQ ID NO: 74 |
| AAV223.6 | 32 | US20030138772 SEQ ID NO: 52 |
| AAV223.6 | 33 | US20030138772 SEQ ID NO: 78 |
| AAV223.7 | 34 | US20030138772 SEQ ID NO: 53 |
| AAV223.7 | 35 | US20030138772 SEQ ID NO: 77 |
| AAV29.3 | 36 | US20030138772 SEQ ID NO: 82 |
| AAV29.4 | 37 | US20030138772 SEQ ID NO: 12 |
| AAV29.5 | 38 | US20030138772 SEQ ID NO: 83 |
| AAV29.5 (AAVbb.2) | 39 | US20030138772 SEQ ID NO: 13 |
| AAV3 | 40 | US20150159173 SEQ ID NO: 12 |
| AAV3 | 41 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 42 | US20030138772 SEQ ID NO: 8 |
| AAV3.3b | 43 | US20030138772 SEQ ID NO: 72 |
| AAV3-3 | 44 | US20150315612 SEQ ID NO: 200 |
| AAV3-3 | 45 | US20150315612 SEQ ID NO: 217 |
| AAV3a | 46 | U.S. Pat. No. 6,156,303 SEQ ID NO: 5 |
| AAV3a | 47 | U.S. Pat. No. 6,156,303 SEQ ID NO: 9 |
| AAV3b | 48 | U.S. Pat. No. 6,156,303 SEQ ID NO: 6 |
| AAV3b | 49 | U.S. Pat. No. 6,156,303 SEQ ID NO: 10 |
| AAV3b | 50 | U.S. Pat. No. 6,156,303 SEQ ID NO: 1 |
| AAV4 | 51 | US20140348794 SEQ ID NO: 17 |
| AAV4 | 52 | US20140348794 SEQ ID NO: 5 |
| AAV4 | 53 | US20140348794 SEQ ID NO: 3 |
| AAV4 | 54 | US20140348794 SEQ ID NO: 14 |
| AAV4 | 55 | US20140348794 SEQ ID NO: 15 |
| AAV4 | 56 | US20140348794 SEQ ID NO: 19 |
| AAV4 | 57 | US20140348794 SEQ ID NO: 12 |
| AAV4 | 58 | US20140348794 SEQ ID NO: 13 |
| AAV4 | 59 | US20140348794 SEQ ID NO: 7 |
| AAV4 | 60 | US20140348794 SEQ ID NO: 8 |
| AAV4 | 61 | US20140348794 SEQ ID NO: 9 |
| AAV4 | 62 | US20140348794 SEQ ID NO: 2 |
| AAV4 | 63 | US20140348794 SEQ ID NO: 10 |
| AAV4 | 64 | US20140348794 SEQ ID NO: 11 |
| AAV4 | 65 | US20140348794 SEQ ID NO: 18 |

TABLE 1-continued

AAV Serotypes

| Serotype | SEQ ID NO | Reference Information |
|---|---|---|
| AAV4 | 66 | US20030138772 SEQ ID NO: 63, US20160017295 SEQ ID NO: 4, US20140348794 SEQ ID NO: 4 |
| AAV4 | 67 | US20140348794 SEQ ID NO: 16 |
| AAV4 | 68 | US20140348794 SEQ ID NO: 20 |
| AAV4 | 69 | US20140348794 SEQ ID NO: 6 |
| AAV4 | 70 | US20140348794 SEQ ID NO: 1 |
| AAV42.2 | 71 | US20030138772 SEQ ID NO: 9 |
| AAV42.2 | 72 | US20030138772 SEQ ID NO: 102 |
| AAV42.3b | 73 | US20030138772 SEQ ID NO: 36 |
| AAV42.3B | 74 | US20030138772 SEQ ID NO: 107 |
| AAV42.4 | 75 | US20030138772 SEQ ID NO: 33 |
| AAV42.4 | 76 | US20030138772 SEQ ID NO: 88 |
| AAV42.8 | 77 | US20030138772 SEQ ID NO: 27 |
| AAV42.8 | 78 | US20030138772 SEQ ID NO: 85 |
| AAV43.1 | 79 | US20030138772 SEQ ID NO: 39 |
| AAV43.1 | 80 | US20030138772 SEQ ID NO: 92 |
| AAV43.12 | 81 | US20030138772 SEQ ID NO: 41 |
| AAV43.12 | 82 | US20030138772 SEQ ID NO: 93 |
| AAV43.20 | 83 | US20030138772 SEQ ID NO: 42 |
| AAV43.20 | 84 | US20030138772 SEQ ID NO: 99 |
| AAV43.21 | 85 | US20030138772 SEQ ID NO: 43 |
| AAV43.21 | 86 | US20030138772 SEQ ID NO: 96 |
| AAV43.23 | 87 | US20030138772 SEQ ID NO: 44 |
| AAV43.23 | 88 | US20030138772 SEQ ID NO: 98 |
| AAV43.25 | 89 | US20030138772 SEQ ID NO: 45 |
| AAV43.25 | 90 | US20030138772 SEQ ID NO: 97 |
| AAV43.5 | 91 | US20030138772 SEQ ID NO: 40 |
| AAV43.5 | 92 | US20030138772 SEQ ID NO: 94 |
| AAV4-4 | 93 | US20150315612 SEQ ID NO: 201 |
| AAV4-4 | 94 | US20150315612 SEQ ID NO: 218 |
| AAV44.1 | 95 | US20030138772 SEQ ID NO: 46 |
| AAV44.1 | 96 | US20030138772 SEQ ID NO: 79 |
| AAV44.5 | 97 | US20030138772 SEQ ID NO: 47 |
| AAV44.5 | 98 | US20030138772 SEQ ID NO: 80 |
| AAV4407 | 99 | US20150315612 SEQ ID NO: 90 |
| AAV5 | 100 | U.S. Pat. No. 7,427,396 SEQ ID NO: 1 |
| AAV5 | 101 | US20030138772 SEQ ID NO: 114 |
| AAV5 | 102 | US20160017295 SEQ ID NO: 5, U.S. Pat. No. 7,427,396 SEQ ID NO: 2, US20150315612 SEQ ID NO: 216 |
| AAV5 | 103 | US20150315612 SEQ ID NO: 199 |
| AAV6 | 104 | US20150159173 SEQ ID NO: 13 |
| AAV6 | 105 | US20030138772 SEQ ID NO: 65, US20150159173 SEQ ID NO: 29, US20160017295 SEQ ID NO: 6, U.S. Pat. No. 6,156,303 SEQ ID NO: 7 |
| AAV6 | 106 | U.S. Pat. No. 6,156,303 SEQ ID NO: 11 |
| AAV6 | 107 | U.S. Pat. No. 6,156,303 SEQ ID NO: 2 |
| AAV6 | 108 | US20150315612 SEQ ID NO: 203 |
| AAV6 | 109 | US20150315612 SEQ ID NO: 220 |
| AAV6.1 | 110 | US20150159173 |
| AAV6.12 | 111 | US20150159173 |
| AAV6.2 | 112 | US20150159173 |
| AAV7 | 113 | US20150159173 SEQ ID NO: 14 |
| AAV7 | 114 | US20150315612 SEQ ID NO: 183 |
| AAV7 | 115 | US20030138772 SEQ ID NO: 2, US20150159173 SEQ ID NO: 30, US20150315612 SEQ ID NO: 181, US20160017295 SEQ ID NO: 7 |
| AAV7 | 116 | US20030138772 SEQ ID NO: 3 |
| AAV7 | 117 | US20030138772 SEQ ID NO: 1, US20150315612 SEQ ID NO: 180 |
| AAV7 | 118 | US20150315612 SEQ ID NO: 213 |
| AAV7 | 119 | US20150315612 SEQ ID NO: 222 |
| AAV8 | 120 | US20150159173 SEQ ID NO: 15 |
| AAV8 | 121 | US20150376240 SEQ ID NO: 7 |
| AAV8 | 122 | US20030138772 SEQ ID NO: 4, US20150315612 SEQ ID NO: 182 |
| AAV8 | 123 | US20030138772 SEQ ID NO: 95, US20140359799 SEQ ID NO: 1, US20150159173 SEQ ID NO: 31, US20160017295 SEQ ID NO: 8, U.S. Pat. No. 7,198,951 SEQ ID NO: 7, US20150315612 SEQ ID NO: 223 |
| AAV8 | 124 | US20150376240 SEQ ID NO: 8 |
| AAV8 | 125 | US20150315612 SEQ ID NO: 214 |
| AAV-8b | 126 | US20150376240 SEQ ID NO: 5 |
| AAV-8b | 127 | US20150376240 SEQ ID NO: 3 |
| AAV-8h | 128 | US20150376240 SEQ ID NO: 6 |
| AAV-8h | 129 | US20150376240 SEQ ID NO: 4 |
| AAV9 | 130 | US20030138772 SEQ ID NO: 5 |
| AAV9 | 131 | U.S. Pat. No. 7,198,951 SEQ ID NO: 1 |
| AAV9 | 132 | US20160017295 SEQ ID NO: 9 |
| AAV9 | 133 | US20030138772 SEQ ID NO: 100, U.S. Pat. No. 7,198,951 SEQ ID NO: 2 |
| AAV9 | 134 | U.S. Pat. No. 7,198,951 SEQ ID NO: 3 |
| AAV9 (AAVhu.14) | 135 | U.S. Pat. No. 7,906,111 SEQ ID NO: 3; WO2015038958 SEQ ID NO: 11 |

TABLE 1-continued

AAV Serotypes

| Serotype | SEQ ID NO | Reference Information |
|---|---|---|
| AAV9 (AAVhu.14) | 136 | U.S. Pat. No. 7,906,111 SEQ ID NO: 123; WO2015038958 SEQ ID NO: 2 |
| AAVA3.1 | 137 | US20030138772 SEQ ID NO: 120 |
| AAVA3.3 | 138 | US20030138772 SEQ ID NO: 57 |
| AAVA3.3 | 139 | US20030138772 SEQ ID NO: 66 |
| AAVA3.4 | 140 | US20030138772 SEQ ID NO: 54 |
| AAVA3.4 | 141 | US20030138772 SEQ ID NO: 68 |
| AAVA3.5 | 142 | US20030138772 SEQ ID NO: 55 |
| AAVA3.5 | 143 | US20030138772 SEQ ID NO: 69 |
| AAVA3.7 | 144 | US20030138772 SEQ ID NO: 56 |
| AAVA3.7 | 145 | US20030138772 SEQ ID NO: 67 |
| AAV29.3 (AAVbb.1) | 146 | US20030138772 SEQ ID NO: 11 |
| AAVC2 | 147 | US20030138772 SEQ ID NO: 61 |
| AAVCh.5 | 148 | US20150159173 SEQ ID NO: 46, US20150315612 SEQ ID NO: 234 |
| AAVcy.2 (AAV13.3) | 149 | US20030138772 SEQ ID NO: 15 |
| AAV24.1 | 150 | US20030138772 SEQ ID NO: 101 |
| AAVcy.3 (AAV24.1) | 151 | US20030138772 SEQ ID NO: 16 |
| AAV27.3 | 152 | US20030138772 SEQ ID NO: 104 |
| AAVcy.4 (AAV27.3) | 153 | US20030138772 SEQ ID NO: 17 |
| AAVcy.5 | 154 | US20150315612 SEQ ID NO: 227 |
| AAV7.2 | 155 | US20030138772 SEQ ID NO: 103 |
| AAVcy.5 (AAV7.2) | 156 | US20030138772 SEQ ID NO: 18 |
| AAV16.3 | 157 | US20030138772 SEQ ID NO: 105 |
| AAVcy.6 (AAV16.3) | 158 | US20030138772 SEQ ID NO: 10 |
| AAVcy.5 | 159 | US20150159173 SEQ ID NO: 8 |
| AAVcy.5 | 160 | US20150159173 SEQ ID NO: 24 |
| AAVCy.5R1 | 161 | US20150159173 |
| AAVCy.5R2 | 162 | US20150159173 |
| AAVCy.5R3 | 163 | US20150159173 |
| AAVCy.5R4 | 164 | US20150159173 |
| AAVDJ | 165 | US20140359799 SEQ ID NO: 3, U.S. Pat. No. 7,588,772 SEQ ID NO: 2 |
| AAVDJ | 166 | US20140359799 SEQ ID NO: 2, U.S. Pat. No. 7,588,772 SEQ ID NO: 1 |
| AAVDJ-8 | 167 | U.S. Pat. No. 7,588,772; Grimm et al 2008 |
| AAVDJ-8 | 168 | U.S. Pat. No. 7,588,772; Grimm et al 2008 |
| AAVF5 | 169 | US20030138772 SEQ ID NO: 110 |
| AAVH2 | 170 | US20030138772 SEQ ID NO: 26 |
| AAVH6 | 171 | US20030138772 SEQ ID NO: 25 |
| AAVhE1.1 | 172 | U.S. Pat. No. 9,233,131 SEQ ID NO: 44 |
| AAVhEr1.14 | 173 | U.S. Pat. No. 9,233,131 SEQ ID NO: 46 |
| AAVhEr1.16 | 174 | U.S. Pat. No. 9,233,131 SEQ ID NO: 48 |
| AAVhEr1.18 | 175 | U.S. Pat. No. 9,233,131 SEQ ID NO: 49 |
| AAVhEr1.23 (AAVhEr2.29) | 176 | U.S. Pat. No. 9,233,131 SEQ ID NO: 53 |
| AAVhEr1.35 | 177 | U.S. Pat. No. 9,233,131 SEQ ID NO: 50 |
| AAVhEr1.36 | 178 | U.S. Pat. No. 9,233,131 SEQ ID NO: 52 |
| AAVhEr1.5 | 179 | U.S. Pat. No. 9,233,131 SEQ ID NO: 45 |
| AAVhEr1.7 | 180 | U.S. Pat. No. 9,233,131 SEQ ID NO: 51 |
| AAVhEr1.8 | 181 | U.S. Pat. No. 9,233,131 SEQ ID NO: 47 |
| AAVhEr2.16 | 182 | U.S. Pat. No. 9,233,131 SEQ ID NO: 55 |
| AAVhEr2.30 | 183 | U.S. Pat. No. 9,233,131 SEQ ID NO: 56 |
| AAVhEr2.31 | 184 | U.S. Pat. No. 9,233,131 SEQ ID NO: 58 |
| AAVhEr2.36 | 185 | U.S. Pat. No. 9,233,131 SEQ ID NO: 57 |
| AAVhEr2.4 | 186 | U.S. Pat. No. 9,233,131 SEQ ID NO: 54 |
| AAVhEr3.1 | 187 | U.S. Pat. No. 9,233,131 SEQ ID NO: 59 |
| AAVhu.1 | 188 | US20150315612 SEQ ID NO: 46 |
| AAVhu.1 | 189 | US20150315612 SEQ ID NO: 144 |
| AAVhu.10 (AAV16.8) | 190 | US20150315612 SEQ ID NO: 56 |
| AAVhu.10 (AAV16.8) | 191 | US20150315612 SEQ ID NO: 156 |
| AAVhu.11 (AAV16.12) | 192 | US20150315612 SEQ ID NO: 57 |
| AAVhu.11 (AAV16.12) | 193 | US20150315612 SEQ ID NO: 153 |
| AAVhu.12 | 194 | US20150315612 SEQ ID NO: 59 |
| AAVhu.12 | 195 | US20150315612 SEQ ID NO: 154 |
| AAVhu.13 | 196 | US20150159173 SEQ ID NO: 16, US20150315612 SEQ ID NO: 71 |
| AAVhu.13 | 197 | US20150159173 SEQ ID NO: 32, US20150315612 SEQ ID NO: 129 |
| AAVhu.136.1 | 198 | US20150315612 SEQ ID NO: 165 |
| AAVhu.140.1 | 199 | US20150315612 SEQ ID NO: 166 |
| AAVhu.140.2 | 200 | US20150315612 SEQ ID NO: 167 |
| AAVhu.145.6 | 201 | US20150315612 SEQ ID No: 178 |
| AAVhu.15 | 202 | US20150315612 SEQ ID NO: 147 |
| AAVhu.15 (AAV33.4) | 203 | US20150315612 SEQ ID NO: 50 |
| AAVhu.156.1 | 204 | US20150315612 SEQ ID No: 179 |
| AAVhu.16 | 205 | US20150315612 SEQ ID NO: 148 |
| AAVhu.16 (AAV33.8) | 206 | US20150315612 SEQ ID NO: 51 |
| AAVhu.17 | 207 | US20150315612 SEQ ID NO: 83 |
| AAVhu.17 (AAV33.12) | 208 | US20150315612 SEQ ID NO: 4 |
| AAVhu.172.1 | 209 | US20150315612 SEQ ID NO: 171 |
| AAVhu.172.2 | 210 | US20150315612 SEQ ID NO: 172 |
| AAVhu.173.4 | 211 | US20150315612 SEQ ID NO: 173 |

TABLE 1-continued

AAV Serotypes

| Serotype | SEQ ID NO | Reference Information |
|---|---|---|
| AAVhu.173.8 | 212 | US20150315612 SEQ ID NO: 175 |
| AAVhu.18 | 213 | US20150315612 SEQ ID NO: 52 |
| AAVhu.18 | 214 | US20150315612 SEQ ID NO: 149 |
| AAVhu.19 | 215 | US20150315612 SEQ ID NO: 62 |
| AAVhu.19 | 216 | US20150315612 SEQ ID NO: 133 |
| AAVhu.2 | 217 | US20150315612 SEQ ID NO: 48 |
| AAVhu.2 | 218 | US20150315612 SEQ ID NO: 143 |
| AAVhu.20 | 219 | US20150315612 SEQ ID NO: 63 |
| AAVhu.20 | 220 | US20150315612 SEQ ID NO: 134 |
| AAVhu.21 | 221 | US20150315612 SEQ ID NO: 65 |
| AAVhu.21 | 222 | US20150315612 SEQ ID NO: 135 |
| AAVhu.22 | 223 | US20150315612 SEQ ID NO: 67 |
| AAVhu.22 | 224 | US20150315612 SEQ ID NO: 138 |
| AAVhu.23 | 225 | US20150315612 SEQ ID NO: 60 |
| AAVhu.23.2 | 226 | US20150315612 SEQ ID NO: 137 |
| AAVhu.24 | 227 | US20150315612 SEQ ID NO: 66 |
| AAVhu.24 | 228 | US20150315612 SEQ ID NO: 136 |
| AAVhu.25 | 229 | US20150315612 SEQ ID NO: 49 |
| AAVhu.25 | 230 | US20150315612 SEQ ID NO: 146 |
| AAVhu.26 | 231 | US20150159173 SEQ ID NO: 17, US20150315612 SEQ ID NO: 61 |
| AAVhu.26 | 232 | US20150159173 SEQ ID NO: 33, US20150315612 SEQ ID NO: 139 |
| AAVhu.27 | 233 | US20150315612 SEQ ID NO: 64 |
| AAVhu.27 | 234 | US20150315612 SEQ ID NO: 140 |
| AAVhu.28 | 235 | US20150315612 SEQ ID NO: 68 |
| AAVhu.28 | 236 | US20150315612 SEQ ID NO: 130 |
| AAVhu.29 | 237 | US20150315612 SEQ ID NO: 69 |
| AAVhu.29 | 238 | US20150159173 SEQ ID NO: 42, US20150315612 SEQ ID NO: 132 |
| AAVhu.29 | 239 | US20150315612 SEQ ID NO: 225 |
| AAVhu.29R | 240 | US20150159173 |
| AAVhu.3 | 241 | US20150315612 SEQ ID NO: 44 |
| AAVhu.3 | 242 | US20150315612 SEQ ID NO: 145 |
| AAVhu.30 | 243 | US20150315612 SEQ ID NO: 70 |
| AAVhu.30 | 244 | US20150315612 SEQ ID NO: 131 |
| AAVhu.31 | 245 | US20150315612 SEQ ID NO: 1 |
| AAVhu.31 | 246 | US20150315612 SEQ ID NO: 121 |
| AAVhu.32 | 247 | US20150315612 SEQ ID NO: 2 |
| AAVhu.32 | 248 | US20150315612 SEQ ID NO: 122 |
| AAVhu.33 | 249 | US20150315612 SEQ ID NO: 75 |
| AAVhu.33 | 250 | US20150315612 SEQ ID NO: 124 |
| AAVhu.34 | 251 | US20150315612 SEQ ID NO: 72 |
| AAVhu.34 | 252 | US20150315612 SEQ ID NO: 125 |
| AAVhu.35 | 253 | US20150315612 SEQ ID NO: 73 |
| AAVhu.35 | 254 | US20150315612 SEQ ID NO: 164 |
| AAVhu.36 | 255 | US20150315612 SEQ ID NO: 74 |
| AAVhu.36 | 256 | US20150315612 SEQ ID NO: 126 |
| AAVhu.37 | 257 | US20150159173 SEQ ID NO: 34, US20150315612 SEQ ID NO: 88 |
| AAVhu.37 (AAV106.1) | 258 | US20150315612 SEQ ID NO: 10, US20150159173 SEQ ID NO: 18 |
| AAVhu.38 | 259 | US20150315612 SEQ ID NO: 161 |
| AAVhu.39 | 260 | US20150315612 SEQ ID NO: 102 |
| AAVhu.39 (AAVLG-9) | 261 | US20150315612 SEQ ID NO: 24 |
| AAVhu.4 | 262 | US20150315612 SEQ ID NO: 47 |
| AAVhu.4 | 263 | US20150315612 SEQ ID NO: 141 |
| AAVhu.40 | 264 | US20150315612 SEQ ID NO: 87 |
| AAVhu.40 (AAV114.3) | 265 | US20150315612 SEQ ID No: 11 |
| AAVhu.41 | 266 | US20150315612 SEQ ID NO: 91 |
| AAVhu.41 (AAV127.2) | 267 | US20150315612 SEQ ID NO: 6 |
| AAVhu.42 | 268 | US20150315612 SEQ ID NO: 85 |
| AAVhu.42 (AAV127.5) | 269 | US20150315612 SEQ ID NO: 8 |
| AAVhu.43 | 270 | US20150315612 SEQ ID NO: 160 |
| AAVhu.43 | 271 | US20150315612 SEQ ID NO: 236 |
| AAVhu.43 (AAV128.1) | 272 | US20150315612 SEQ ID NO: 80 |
| AAVhu.44 | 273 | US20150159173 SEQ ID NO: 45, US20150315612 SEQ ID NO: 158 |
| AAVhu.44 (AAV128.3) | 274 | US20150315612 SEQ ID NO: 81 |
| AAVhu.44R1 | 275 | US20150159173 |
| AAVhu.44R2 | 276 | US20150159173 |
| AAVhu.44R3 | 277 | US20150159173 |
| AAVhu.45 | 278 | US20150315612 SEQ ID NO: 76 |
| AAVhu.45 | 279 | US20150315612 SEQ ID NO: 127 |
| AAVhu.46 | 280 | US20150315612 SEQ ID NO: 82 |
| AAVhu.46 | 281 | US20150315612 SEQ ID NO: 159 |
| AAVhu.46 | 282 | US20150315612 SEQ ID NO: 224 |
| AAVhu.47 | 283 | US20150315612 SEQ ID NO: 77 |
| AAVhu.47 | 284 | US20150315612 SEQ ID NO: 128 |
| AAVhu.48 | 285 | US20150159173 SEQ ID NO: 38 |
| AAVhu.48 | 286 | US20150315612 SEQ ID NO: 157 |
| AAVhu.48 (AAV130.4) | 287 | US20150315612 SEQ ID NO: 78 |

TABLE 1-continued

AAV Serotypes

| Serotype | SEQ ID NO | Reference Information |
|---|---|---|
| AAVhu.48R1 | 288 | US20150159173 |
| AAVhu.48R2 | 289 | US20150159173 |
| AAVhu.48R3 | 290 | US20150159173 |
| AAVhu.49 | 291 | US20150315612 SEQ ID NO: 209 |
| AAVhu.49 | 292 | US20150315612 SEQ ID NO: 189 |
| AAVhu.5 | 293 | US20150315612 SEQ ID NO: 45 |
| AAVhu.5 | 294 | US20150315612 SEQ ID NO: 142 |
| AAVhu.51 | 295 | US20150315612 SEQ ID NO: 208 |
| AAVhu.51 | 296 | US20150315612 SEQ ID NO: 190 |
| AAVhu.52 | 297 | US20150315612 SEQ ID NO: 210 |
| AAVhu.52 | 298 | US20150315612 SEQ ID NO: 191 |
| AAVhu.53 | 299 | US20150159173 SEQ ID NO: 19 |
| AAVhu.53 | 300 | US20150159173 SEQ ID NO: 35 |
| AAVhu.53 (AAV145.1) | 301 | US20150315612 SEQ ID NO: 176 |
| AAVhu.54 | 302 | US20150315612 SEQ ID NO: 188 |
| AAVhu.54 (AAV145.5) | 303 | US20150315612 SEQ ID No: 177 |
| AAVhu.55 | 304 | US20150315612 SEQ ID NO: 187 |
| AAVhu.56 | 305 | US20150315612 SEQ ID NO: 205 |
| AAVhu.56 (AAV145.6) | 306 | US20150315612 SEQ ID NO: 168 |
| AAVhu.56 (AAV145.6) | 307 | US20150315612 SEQ ID NO: 192 |
| AAVhu.57 | 308 | US20150315612 SEQ ID NO: 206 |
| AAVhu.57 | 309 | US20150315612 SEQ ID NO: 169 |
| AAVhu.57 | 310 | US20150315612 SEQ ID NO: 193 |
| AAVhu.58 | 311 | US20150315612 SEQ ID NO: 207 |
| AAVhu.58 | 312 | US20150315612 SEQ ID NO: 194 |
| AAVhu.6 (AAV3.1) | 313 | US20150315612 SEQ ID NO: 5 |
| AAVhu.6 (AAV3.1) | 314 | US20150315612 SEQ ID NO: 84 |
| AAVhu.60 | 315 | US20150315612 SEQ ID NO: 184 |
| AAVhu.60 (AAV161.10) | 316 | US20150315612 SEQ ID NO: 170 |
| AAVhu.61 | 317 | US20150315612 SEQ ID NO: 185 |
| AAVhu.61 (AAV161.6) | 318 | US20150315612 SEQ ID NO: 174 |
| AAVhu.63 | 319 | US20150315612 SEQ ID NO: 204 |
| AAVhu.63 | 320 | US20150315612 SEQ ID NO: 195 |
| AAVhu.64 | 321 | US20150315612 SEQ ID NO: 212 |
| AAVhu.64 | 322 | US20150315612 SEQ ID NO: 196 |
| AAVhu.66 | 323 | US20150315612 SEQ ID NO: 197 |
| AAVhu.67 | 324 | US20150315612 SEQ ID NO: 215 |
| AAVhu.67 | 325 | US20150315612 SEQ ID NO: 198 |
| AAVhu.7 | 326 | US20150315612 SEQ ID NO: 226 |
| AAVhu.7 | 327 | US20150315612 SEQ ID NO: 150 |
| AAVhu.7 (AAV7.3) | 328 | US20150315612 SEQ ID NO: 55 |
| AAVhu.71 | 329 | US20150315612 SEQ ID NO: 79 |
| AAVhu.8 | 330 | US20150315612 SEQ ID NO: 53 |
| AAVhu.8 | 331 | US20150315612 SEQ ID NO: 12 |
| AAVhu.8 | 332 | US20150315612 SEQ ID NO: 151 |
| AAVhu.9 (AAV3.1) | 333 | US20150315612 SEQ ID NO: 58 |
| AAVhu.9 (AAV3.1) | 334 | US20150315612 SEQ ID NO: 155 |
| AAV-LK01 | 335 | US20150376607 SEQ ID NO: 2 |
| AAV-LK01 | 336 | US20150376607 SEQ ID NO: 29 |
| AAV-LK02 | 337 | US20150376607 SEQ ID NO: 3 |
| AAV-LK02 | 338 | US20150376607 SEQ ID NO: 30 |
| AAV-LK03 | 339 | US20150376607 SEQ ID NO: 4 |
| AAV-LK03 | 340 | WO2015121501 SEQ ID NO: 12, US20150376607 SEQ ID NO: 31 |
| AAV-LK04 | 341 | US20150376607 SEQ ID NO: 5 |
| AAV-LK04 | 342 | US20150376607 SEQ ID NO: 32 |
| AAV-LK05 | 343 | US20150376607 SEQ ID NO: 6 |
| AAV-LK05 | 344 | US20150376607 SEQ ID NO: 33 |
| AAV-LK06 | 345 | US20150376607 SEQ ID NO: 7 |
| AAV-LK06 | 346 | US20150376607 SEQ ID NO: 34 |
| AAV-LK07 | 347 | US20150376607 SEQ ID NO: 8 |
| AAV-LK07 | 348 | US20150376607 SEQ ID NO: 35 |
| AAV-LK08 | 349 | US20150376607 SEQ ID NO: 9 |
| AAV-LK08 | 350 | US20150376607 SEQ ID NO: 36 |
| AAV-LK09 | 351 | US20150376607 SEQ ID NO: 10 |
| AAV-LK09 | 352 | US20150376607 SEQ ID NO: 37 |
| AAV-LK10 | 353 | US20150376607 SEQ ID NO: 11 |
| AAV-LK10 | 354 | US20150376607 SEQ ID NO: 38 |
| AAV-LK11 | 355 | US20150376607 SEQ ID NO: 12 |
| AAV-LK11 | 356 | US20150376607 SEQ ID NO: 39 |
| AAV-LK12 | 357 | US20150376607 SEQ ID NO: 13 |
| AAV-LK12 | 358 | US20150376607 SEQ ID NO: 40 |
| AAV-LK13 | 359 | US20150376607 SEQ ID NO: 14 |
| AAV-LK13 | 360 | US20150376607 SEQ ID NO: 41 |
| AAV-LK14 | 361 | US20150376607 SEQ ID NO: 15 |
| AAV-LK14 | 362 | US20150376607 SEQ ID NO: 42 |
| AAV-LK15 | 363 | US20150376607 SEQ ID NO: 16 |

TABLE 1-continued

AAV Serotypes

| Serotype | SEQ ID NO | Reference Information |
|---|---|---|
| AAV-LK15 | 364 | US20150376607 SEQ ID NO: 43 |
| AAV-LK16 | 365 | US20150376607 SEQ ID NO: 17 |
| AAV-LK16 | 366 | US20150376607 SEQ ID NO: 44 |
| AAV-LK17 | 367 | US20150376607 SEQ ID NO: 18 |
| AAV-LK17 | 368 | US20150376607 SEQ ID NO: 45 |
| AAV-LK18 | 369 | US20150376607 SEQ ID NO: 19 |
| AAV-LK18 | 370 | US20150376607 SEQ ID NO: 46 |
| AAV-LK19 | 371 | US20150376607 SEQ ID NO: 20 |
| AAV-LK19 | 372 | US20150376607 SEQ ID NO: 47 |
| AAV-PAEC | 373 | US20150376607 SEQ ID NO: 1 |
| AAV-PAEC | 374 | US20150376607 SEQ ID NO: 48 |
| AAV-PAEC11 | 375 | US20150376607 SEQ ID NO: 26 |
| AAV-PAEC11 | 376 | US20150376607 SEQ ID NO: 54 |
| AAV-PAEC12 | 377 | US20150376607 SEQ ID NO: 27 |
| AAV-PAEC12 | 378 | US20150376607 SEQ ID NO: 51 |
| AAV-PAEC13 | 379 | US20150376607 SEQ ID NO: 28 |
| AAV-PAEC13 | 380 | US20150376607 SEQ ID NO: 49 |
| AAV-PAEC2 | 381 | US20150376607 SEQ ID NO: 21 |
| AAV-PAEC2 | 382 | US20150376607 SEQ ID NO: 56 |
| AAV-PAEC4 | 383 | US20150376607 SEQ ID NO: 22 |
| AAV-PAEC4 | 384 | US20150376607 SEQ ID NO: 55 |
| AAV-PAEC6 | 385 | US20150376607 SEQ ID NO: 23 |
| AAV-PAEC6 | 386 | US20150376607 SEQ ID NO: 52 |
| AAV-PAEC7 | 387 | US20150376607 SEQ ID NO: 24 |
| AAV-PAEC7 | 388 | US20150376607 SEQ ID NO: 53 |
| AAV-PAEC8 | 389 | US20150376607 SEQ ID NO: 25 |
| AAV-PAEC8 | 390 | US20150376607 SEQ ID NO: 50 |
| AAVpi.1 | 391 | US20150315612 SEQ ID NO: 28 |
| AAVpi.1 | 392 | US20150315612 SEQ ID NO: 93 |
| AAVpi.2 | 393 | US20150315612 SEQ ID NO: 30 |
| AAVpi.2 | 394 | US20150315612 SEQ ID NO: 95 |
| AAVpi.3 | 395 | US20150315612 SEQ ID NO: 29 |
| AAVpi.3 | 396 | US20150315612 SEQ ID NO: 94 |
| AAVrh.10 | 397 | US20150159173 SEQ ID NO: 9 |
| AAVrh.10 | 398 | US20150159173 SEQ ID NO: 25 |
| AAV44.2 | 399 | US20030138772 SEQ ID NO: 59 |
| AAVrh.10 (AAV44.2) | 400 | US20030138772 SEQ ID NO: 81 |
| AAV42.1B | 401 | US20030138772 SEQ ID NO: 90 |
| AAVrh.12 (AAV42.1b) | 402 | US20030138772 SEQ ID NO: 30 |
| AAVrh.13 | 403 | US20150159173 SEQ ID NO: 10 |
| AAVrh.13 | 404 | US20150159173 SEQ ID NO: 26 |
| AAVrh.13 | 405 | US20150315612 SEQ ID NO: 228 |
| AAVrh.13R | 406 | US20150159173 |
| AAV42.3A | 407 | US20030138772 SEQ ID NO: 87 |
| AAVrh.14 (AAV42.3a) | 408 | US20030138772 SEQ ID NO: 32 |
| AAV42.5A | 409 | US20030138772 SEQ ID NO: 89 |
| AAVrh.17 (AAV42.5a) | 410 | US20030138772 SEQ ID NO: 34 |
| AAV42.5B | 411 | US20030138772 SEQ ID NO: 91 |
| AAVrh.18 (AAV42.5b) | 412 | US20030138772 SEQ ID NO: 29 |
| AAV42.6B | 413 | US20030138772 SEQ ID NO: 112 |
| AAVrh.19 (AAV42.6b) | 414 | US20030138772 SEQ ID NO: 38 |
| AAVrh.2 | 415 | US20150159173 SEQ ID NO: 39 |
| AAVrh.2 | 416 | US20150315612 SEQ ID NO: 231 |
| AAVrh.20 | 417 | US20150159173 SEQ ID NO: 1 |
| AAV42.10 | 418 | US20030138772 SEQ ID NO: 106 |
| AAVrh.21 (AAV42.10) | 419 | US20030138772 SEQ ID NO: 35 |
| AAV42.11 | 420 | US20030138772 SEQ ID NO: 108 |
| AAVrh.22 (AAV42.11) | 421 | US20030138772 SEQ ID NO: 37 |
| AAV42.12 | 422 | US20030138772 SEQ ID NO: 113 |
| AAVrh.23 (AAV42.12) | 423 | US20030138772 SEQ ID NO: 58 |
| AAV42.13 | 424 | US20030138772 SEQ ID NO: 86 |
| AAVrh.24 (AAV42.13) | 425 | US20030138772 SEQ ID NO: 31 |
| AAV42.15 | 426 | US20030138772 SEQ ID NO: 84 |
| AAVrh.25 (AAV42.15) | 427 | US20030138772 SEQ ID NO: 28 |
| AAVrh.2R | 428 | US20150159173 |
| AAVrh.31 (AAV223.1) | 429 | US20030138772 SEQ ID NO: 48 |
| AAVC1 | 430 | US20030138772 SEQ ID NO: 60 |
| AAVrh.32 (AAVC1) | 431 | US20030138772 SEQ ID NO: 19 |
| AAVrh.32/33 | 432 | US20150159173 SEQ ID NO: 2 |
| AAVrh.33 (AAVC3) | 433 | US20030138772 SEQ ID NO: 20 |
| AAVC5 | 434 | US20030138772 SEQ ID NO: 62 |
| AAVrh.34 (AAVC5) | 435 | US20030138772 SEQ ID NO: 21 |
| AAVF1 | 436 | US20030138772 SEQ ID NO: 109 |
| AAVrh.35 (AAVF1) | 437 | US20030138772 SEQ ID NO: 22 |
| AAVF3 | 438 | US20030138772 SEQ ID NO: 111 |
| AAVrh.36 (AAVF3) | 439 | US20030138772 SEQ ID NO: 23 |

TABLE 1-continued

AAV Serotypes

| Serotype | SEQ ID NO | Reference Information |
|---|---|---|
| AAVrh.37 | 440 | US20030138772 SEQ ID NO: 24 |
| AAVrh.37 | 441 | US20150159173 SEQ ID NO: 40 |
| AAVrh.37 | 442 | US20150315612 SEQ ID NO: 229 |
| AAVrh.37R2 | 443 | US20150159173 |
| AAVrh.38 (AAVLG-4) | 444 | US20150315612 SEQ ID NO: 7 |
| AAVrh.38 (AAVLG-4) | 445 | US20150315612 SEQ ID NO: 86 |
| AAVrh.39 | 446 | US20150159173 SEQ ID NO: 20, US20150315612 SEQ ID NO: 13 |
| AAVrh.39 | 447 | US20150159173 SEQ ID NO: 3, US20150159173 SEQ ID NO: 36, US20150315612 SEQ ID NO: 89 |
| AAVrh.40 | 448 | US20150315612 SEQ ID NO: 92 |
| AAVrh.40 (AAVLG-10) | 449 | US20150315612 SEQ ID No: 14 |
| AAVrh.43 (AAVN721-8) | 450 | US20150315612 SEQ ID NO: 43, US20150159173 SEQ ID NO: 21 |
| AAVrh.43 (AAVN721-8) | 451 | US20150315612 SEQ ID NO: 163, US20150159173 SEQ ID NO: 37 |
| AAVrh.44 | 452 | US20150315612 SEQ ID NO: 34 |
| AAVrh.44 | 453 | US20150315612 SEQ ID NO: 111 |
| AAVrh.45 | 454 | US20150315612 SEQ ID NO: 41 |
| AAVrh.45 | 455 | US20150315612 SEQ ID NO: 109 |
| AAVrh.46 | 456 | US20150159173 SEQ ID NO: 22, US20150315612 SEQ ID NO: 19 |
| AAVrh.46 | 457 | US20150159173 SEQ ID NO: 4, US20150315612 SEQ ID NO: 101 |
| AAVrh.47 | 458 | US20150315612 SEQ ID NO: 38 |
| AAVrh.47 | 459 | US20150315612 SEQ ID NO: 118 |
| AAVrh.48 | 460 | US20150159173 SEQ ID NO: 44, US20150315612 SEQ ID NO: 115 |
| AAVrh.48.1 | 461 | US20150159173 |
| AAVrh.48.1.2 | 462 | US20150159173 |
| AAVrh.48.2 | 463 | US20150159173 |
| AAVrh.48 (AAV1-7) | 464 | US20150315612 SEQ ID NO: 32 |
| AAVrh.49 (AAV1-8) | 465 | US20150315612 SEQ ID NO: 25 |
| AAVrh.49 (AAV1-8) | 466 | US20150315612 SEQ ID NO: 103 |
| AAVrh.50 (AAV2-4) | 467 | US20150315612 SEQ ID NO: 23 |
| AAVrh.50 (AAV2-4) | 468 | US20150315612 SEQ ID NO: 108 |
| AAVrh.51 (AAV2-5) | 469 | US20150315612 SEQ ID No: 22 |
| AAVrh.51 (AAV2-5) | 470 | US20150315612 SEQ ID NO: 104 |
| AAVrh.52 (AAV3-9) | 471 | US20150315612 SEQ ID NO: 18 |
| AAVrh.52 (AAV3-9) | 472 | US20150315612 SEQ ID NO: 96 |
| AAVrh.53 | 473 | US20150315612 SEQ ID NO: 97 |
| AAVrh.53 (AAV3-11) | 474 | US20150315612 SEQ ID NO: 17 |
| AAVrh.53 (AAV3-11) | 475 | US20150315612 SEQ ID NO: 186 |
| AAVrh.54 | 476 | US20150315612 SEQ ID NO: 40 |
| AAVrh.54 | 477 | US20150159173 SEQ ID NO: 49, US20150315612 SEQ ID NO: 116 |
| AAVrh.55 | 478 | US20150315612 SEQ ID NO: 37 |
| AAVrh.55 (AAV4-19) | 479 | US20150315612 SEQ ID NO: 117 |
| AAVrh.56 | 480 | US20150315612 SEQ ID NO: 54 |
| AAVrh.56 | 481 | US20150315612 SEQ ID NO: 152 |
| AAVrh.57 | 482 | US20150315612 SEQ ID NO: 26 |
| AAVrh.57 | 483 | US20150315612 SEQ ID NO: 105 |
| AAVrh.58 | 484 | US20150315612 SEQ ID NO: 27 |
| AAVrh.58 | 485 | US20150159173 SEQ ID NO: 48, US20150315612 SEQ ID NO: 106 |
| AAVrh.58 | 486 | US20150315612 SEQ ID NO: 232 |
| AAVrh.59 | 487 | US20150315612 SEQ ID NO: 42 |
| AAVrh.59 | 488 | US20150315612 SEQ ID NO: 110 |
| AAVrh.60 | 489 | US20150315612 SEQ ID NO: 31 |
| AAVrh.60 | 490 | US20150315612 SEQ ID NO: 120 |
| AAVrh.61 | 491 | US20150315612 SEQ ID NO: 107 |
| AAVrh.61 (AAV2-3) | 492 | US20150315612 SEQ ID NO: 21 |
| AAVrh.62 (AAV2-15) | 493 | US20150315612 SEQ ID No: 33 |
| AAVrh.62 (AAV2-15) | 494 | US20150315612 SEQ ID NO: 114 |
| AAVrh.64 | 495 | US20150315612 SEQ ID No: 15 |
| AAVrh.64 | 496 | US20150159173 SEQ ID NO: 43, US20150315612 SEQ ID NO: 99 |
| AAVrh.64 | 497 | US20150315612 SEQ ID NO: 233 |
| AAVRh.64R1 | 498 | US20150159173 |
| AAVRh.64R2 | 499 | US20150159173 |
| AAVrh.65 | 500 | US20150315612 SEQ ID NO: 35 |
| AAVrh.65 | 501 | US20150315612 SEQ ID NO: 112 |
| AAVrh.67 | 502 | US20150315612 SEQ ID NO: 36 |
| AAVrh.67 | 503 | US20150315612 SEQ ID NO: 230 |
| AAVrh.67 | 504 | US20150159173 SEQ ID NO: 47, US20150315612 SEQ ID NO: 113 |
| AAVrh.68 | 505 | US20150315612 SEQ ID NO: 16 |
| AAVrh.68 | 506 | US20150315612 SEQ ID NO: 100 |
| AAVrh.69 | 507 | US20150315612 SEQ ID NO: 39 |
| AAVrh.69 | 508 | US20150315612 SEQ ID NO: 119 |
| AAVrh.70 | 509 | US20150315612 SEQ ID NO: 20 |
| AAVrh.70 | 510 | US20150315612 SEQ ID NO: 98 |
| AAVrh.71 | 511 | US20150315612 SEQ ID NO: 162 |
| AAVrh.72 | 512 | US20150315612 SEQ ID NO: 9 |
| AAVrh.73 | 513 | US20150159173 SEQ ID NO: 5 |
| AAVrh.74 | 514 | US20150159173 SEQ ID NO: 6 |

TABLE 1-continued

AAV Serotypes

| Serotype | SEQ ID NO | Reference Information |
|---|---|---|
| AAVrh.8 | 515 | US20150159173 SEQ ID NO: 41 |
| AAVrh.8 | 516 | US20150315612 SEQ ID NO: 235 |
| AAVrh.8R | 517 | US20150159173, WO2015168666 SEQ ID NO: 9 |
| AAVrh.8R A586R mutant | 518 | WO2015168666 SEQ ID NO: 10 |
| AAVrh.8R R533A mutant | 519 | WO2015168666 SEQ ID NO: 11 |
| BAAV (bovine AAV) | 520 | U.S. Pat. No. 9,193,769 SEQ ID NO: 8 |
| BAAV (bovine AAV) | 521 | U.S. Pat. No. 9,193,769 SEQ ID NO: 10 |
| BAAV (bovine AAV) | 522 | U.S. Pat. No. 9,193,769 SEQ ID NO: 4 |
| BAAV (bovine AAV) | 523 | U.S. Pat. No. 9,193,769 SEQ ID NO: 2 |
| BAAV (bovine AAV) | 524 | U.S. Pat. No. 9,193,769 SEQ ID NO: 6 |
| BAAV (bovine AAV) | 525 | U.S. Pat. No. 9,193,769 SEQ ID NO: 1 |
| BAAV (bovine AAV) | 526 | U.S. Pat. No. 9,193,769 SEQ ID NO: 5 |
| BAAV (bovine AAV) | 527 | U.S. Pat. No. 9,193,769 SEQ ID NO: 3 |
| BAAV (bovine AAV) | 528 | U.S. Pat. No. 9,193,769 SEQ ID NO: 11 |
| BAAV (bovine AAV) | 529 | U.S. Pat. No. 7,427,396 SEQ ID NO: 5 |
| BAAV (bovine AAV) | 530 | U.S. Pat. No. 7,427,396 SEQ ID NO: 6 |
| BAAV (bovine AAV) | 531 | U.S. Pat. No. 9,193,769 SEQ ID NO: 7 |
| BAAV (bovine AAV) | 532 | U.S. Pat. No. 9,193,769 SEQ ID NO: 9 |
| BNP61 AAV | 533 | US20150238550 SEQ ID NO: 1 |
| BNP61 AAV | 534 | US20150238550 SEQ ID NO: 2 |
| BNP62 AAV | 535 | US20150238550 SEQ ID NO: 3 |
| BNP63 AAV | 536 | US20150238550 SEQ ID NO: 4 |
| caprine AAV | 537 | U.S. Pat. No. 7,427,396 SEQ ID NO: 3 |
| caprine AAV | 538 | U.S. Pat. No. 7,427,396 SEQ ID NO: 4 |
| true type AAV (ttAAV) | 539 | WO2015121501 SEQ ID NO: 2 |
| AAAV (Avian AAV) | 540 | U.S. Pat. No. 9,238,800 SEQ ID NO: 12 |
| AAAV (Avian AAV) | 541 | U.S. Pat. No. 9,238,800 SEQ ID NO: 2 |
| AAAV (Avian AAV) | 542 | U.S. Pat. No. 9,238,800 SEQ ID NO: 6 |
| AAAV (Avian AAV) | 543 | U.S. Pat. No. 9,238,800 SEQ ID NO: 4 |
| AAAV (Avian AAV) | 544 | U.S. Pat. No. 9,238,800 SEQ ID NO: 8 |
| AAAV (Avian AAV) | 545 | U.S. Pat. No. 9,238,800 SEQ ID NO: 14 |
| AAAV (Avian AAV) | 546 | U.S. Pat. No. 9,238,800 SEQ ID NO: 10 |
| AAAV (Avian AAV) | 547 | U.S. Pat. No. 9,238,800 SEQ ID NO: 15 |
| AAAV (Avian AAV) | 548 | U.S. Pat. No. 9,238,800 SEQ ID NO: 5 |
| AAAV (Avian AAV) | 549 | U.S. Pat. No. 9,238,800 SEQ ID NO: 9 |
| AAAV (Avian AAV) | 550 | U.S. Pat. No. 9,238,800 SEQ ID NO: 3 |
| AAAV (Avian AAV) | 551 | U.S. Pat. No. 9,238,800 SEQ ID NO: 7 |
| AAAV (Avian AAV) | 552 | U.S. Pat. No. 9,238,800 SEQ ID NO: 11 |
| AAAV (Avian AAV) | 553 | U.S. Pat. No. 9,238,800 SEQ ID NO: 13 |
| AAAV (Avian AAV) | 554 | U.S. Pat. No. 9,238,800 SEQ ID NO: 1 |
| AAV Shuffle 100-1 | 555 | US20160017295 SEQ ID NO: 23 |
| AAV Shuffle 100-1 | 556 | US20160017295 SEQ ID NO: 11 |
| AAV Shuffle 100-2 | 557 | US20160017295 SEQ ID NO: 37 |
| AAV Shuffle 100-2 | 558 | US20160017295 SEQ ID NO: 29 |
| AAV Shuffle 100-3 | 559 | US20160017295 SEQ ID NO: 24 |
| AAV Shuffle 100-3 | 560 | US20160017295 SEQ ID NO: 12 |
| AAV Shuffle 100-7 | 561 | US20160017295 SEQ ID NO: 25 |
| AAV Shuffle 100-7 | 562 | US20160017295 SEQ ID NO: 13 |
| AAV Shuffle 10-2 | 563 | US20160017295 SEQ ID NO: 34 |
| AAV Shuffle 10-2 | 564 | US20160017295 SEQ ID NO: 26 |
| AAV Shuffle 10-6 | 565 | US20160017295 SEQ ID NO: 35 |
| AAV Shuffle 10-6 | 566 | US20160017295 SEQ ID NO: 27 |
| AAV Shuffle 10-8 | 567 | US20160017295 SEQ ID NO: 36 |
| AAV Shuffle 10-8 | 568 | US20160017295 SEQ ID NO: 28 |
| AAV SM 100-10 | 569 | US20160017295 SEQ ID NO: 41 |
| AAV SM 100-10 | 570 | US20160017295 SEQ ID NO: 33 |
| AAV SM 100-3 | 571 | US20160017295 SEQ ID NO: 40 |
| AAV SM 100-3 | 572 | US20160017295 SEQ ID NO: 32 |
| AAV SM 10-1 | 573 | US20160017295 SEQ ID NO: 38 |
| AAV SM 10-1 | 574 | US20160017295 SEQ ID NO: 30 |
| AAV SM 10-2 | 575 | US20160017295 SEQ ID NO: 10 |
| AAV SM 10-2 | 576 | US20160017295 SEQ ID NO: 22 |
| AAV SM 10-8 | 577 | US20160017295 SEQ ID NO: 39 |
| AAV SM 10-8 | 578 | US20160017295 SEQ ID NO: 31 |
| AAVF1/HSC1 | 579 | WO2016049230 SEQ ID NO: 20 |
| AAVF2/HSC2 | 580 | WO2016049230 SEQ ID NO: 21 |
| AAVF3/HSC3 | 581 | WO2016049230 SEQ ID NO: 22 |
| AAVF4/HSC4 | 582 | WO2016049230 SEQ ID NO: 23 |
| AAVF5/HSC5 | 583 | WO2016049230 SEQ ID NO: 25 |
| AAVF6/HSC6 | 584 | WO2016049230 SEQ ID NO: 24 |
| AAVF7/HSC7 | 585 | WO2016049230 SEQ ID NO: 27 |
| AAVF8/HSC8 | 586 | WO2016049230 SEQ ID NO: 28 |
| AAVF9/HSC9 | 587 | WO2016049230 SEQ ID NO: 29 |
| AAVF11/HSC11 | 588 | WO2016049230 SEQ ID NO: 26 |
| AAVF12/HSC12 | 589 | WO2016049230 SEQ ID NO: 30 |
| AAVF13/HSC13 | 590 | WO2016049230 SEQ ID NO: 31 |

TABLE 1-continued

AAV Serotypes

| Serotype | SEQ ID NO | Reference Information |
|---|---|---|
| AAVF14/HSC14 | 591 | WO2016049230 SEQ ID NO: 32 |
| AAVF15/HSC15 | 592 | WO2016049230 SEQ ID NO: 33 |
| AAVF16/HSC16 | 593 | WO2016049230 SEQ ID NO: 34 |
| AAVF17/HSC17 | 594 | WO2016049230 SEQ ID NO: 35 |
| AAVF1/HSC1 | 595 | WO2016049230 SEQ ID NO: 2 |
| AAVF2/HSC2 | 596 | WO2016049230 SEQ ID NO: 3 |
| AAVF3/HSC3 | 597 | WO2016049230 SEQ ID NO: 5 |
| AAVF4/HSC4 | 598 | WO2016049230 SEQ ID NO: 6 |
| AAVF5/HSC5 | 599 | WO2016049230 SEQ ID NO: 11 |
| AAVF6/HSC6 | 600 | WO2016049230 SEQ ID NO: 7 |
| AAVF7/HSC7 | 601 | WO2016049230 SEQ ID NO: 8 |
| AAVF8/HSC8 | 602 | WO2016049230 SEQ ID NO: 9 |
| AAVF9/HSC9 | 603 | WO2016049230 SEQ ID NO: 10 |
| AAVF11/HSC11 | 604 | WO2016049230 SEQ ID NO: 4 |
| AAVF12/HSC12 | 605 | WO2016049230 SEQ ID NO: 12 |
| AAVF13/HSC13 | 606 | WO2016049230 SEQ ID NO: 14 |
| AAVF14/HSC14 | 607 | WO2016049230 SEQ ID NO: 15 |
| AAVF15/HSC15 | 608 | WO2016049230 SEQ ID NO: 16 |
| AAVF16/HSC16 | 609 | WO2016049230 SEQ ID NO: 17 |
| AAVF17/HSC17 | 610 | WO2016049230 SEQ ID NO: 13 |
| AAV CBr-E1 | 611 | U.S. Pat. No. 8,734,809 SEQ ID NO: 13 |
| AAV CBr-E2 | 612 | U.S. Pat. No. 8,734,809 SEQ ID NO: 14 |
| AAV CBr-E3 | 613 | U.S. Pat. No. 8,734,809 SEQ ID NO: 15 |
| AAV CBr-E4 | 614 | U.S. Pat. No. 8,734,809 SEQ ID NO: 16 |
| AAV CBr-E5 | 615 | U.S. Pat. No. 8,734,809 SEQ ID NO: 17 |
| AAV CBr-e5 | 616 | U.S. Pat. No. 8,734,809 SEQ ID NO: 18 |
| AAV CBr-E6 | 617 | U.S. Pat. No. 8,734,809 SEQ ID NO: 19 |
| AAV CBr-E7 | 618 | U.S. Pat. No. 8,734,809 SEQ ID NO: 20 |
| AAV CBr-E8 | 619 | U.S. Pat. No. 8,734,809 SEQ ID NO: 21 |
| AAV CLv-D1 | 620 | U.S. Pat. No. 8,734,809 SEQ ID NO: 22 |
| AAV CLv-D2 | 621 | U.S. Pat. No. 8,734,809 SEQ ID NO: 23 |
| AAV CLv-D3 | 622 | U.S. Pat. No. 8,734,809 SEQ ID NO: 24 |
| AAV CLv-D4 | 623 | U.S. Pat. No. 8,734,809 SEQ ID NO: 25 |
| AAV CLv-D5 | 624 | U.S. Pat. No. 8,734,809 SEQ ID NO: 26 |
| AAV CLv-D6 | 625 | U.S. Pat. No. 8,734,809 SEQ ID NO: 27 |
| AAV CLv-D7 | 626 | U.S. Pat. No. 8,734,809 SEQ ID NO: 28 |
| AAV CLv-D8 | 627 | U.S. Pat. No. 8,734,809 SEQ ID NO: 29 |
| AAV CLv-E1 | 628 | U.S. Pat. No. 8,734,809 SEQ ID NO: 13 |
| AAV CLv-R1 | 629 | U.S. Pat. No. 8,734,809 SEQ ID NO: 30 |
| AAV CLv-R2 | 630 | U.S. Pat. No. 8,734,809 SEQ ID NO: 31 |
| AAV CLv-R3 | 631 | U.S. Pat. No. 8,734,809 SEQ ID NO: 32 |
| AAV CLv-R4 | 632 | U.S. Pat. No. 8,734,809 SEQ ID NO: 33 |
| AAV CLv-R5 | 633 | U.S. Pat. No. 8,734,809 SEQ ID NO: 34 |
| AAV CLv-R6 | 634 | U.S. Pat. No. 8,734,809 SEQ ID NO: 35 |
| AAV CLv-R7 | 635 | U.S. Pat. No. 8,734,809 SEQ ID NO: 36 |
| AAV CLv-R8 | 636 | U.S. Pat. No. 8,734,809 SEQ ID NO: 37 |
| AAV CLv-R9 | 637 | U.S. Pat. No. 8,734,809 SEQ ID NO: 38 |
| AAV CLg-F1 | 638 | U.S. Pat. No. 8,734,809 SEQ ID NO: 39 |
| AAV CLg-F2 | 639 | U.S. Pat. No. 8,734,809 SEQ ID NO: 40 |
| AAV CLg-F3 | 640 | U.S. Pat. No. 8,734,809 SEQ ID NO: 41 |
| AAV CLg-F4 | 641 | U.S. Pat. No. 8,734,809 SEQ ID NO: 42 |
| AAV CLg-F5 | 642 | U.S. Pat. No. 8,734,809 SEQ ID NO: 43 |
| AAV CLg-F6 | 643 | U.S. Pat. No. 8,734,809 SEQ ID NO: 43 |
| AAV CLg-F7 | 644 | U.S. Pat. No. 8,734,809 SEQ ID NO: 44 |
| AAV CLg-F8 | 645 | U.S. Pat. No. 8,734,809 SEQ ID NO: 43 |
| AAV CSp-1 | 646 | U.S. Pat. No. 8,734,809 SEQ ID NO: 45 |
| AAV CSp-10 | 647 | U.S. Pat. No. 8,734,809 SEQ ID NO: 46 |
| AAV CSp-11 | 648 | U.S. Pat. No. 8,734,809 SEQ ID NO: 47 |
| AAV CSp-2 | 649 | U.S. Pat. No. 8,734,809 SEQ ID NO: 48 |
| AAV CSp-3 | 650 | U.S. Pat. No. 8,734,809 SEQ ID NO: 49 |
| AAV CSp-4 | 651 | U.S. Pat. No. 8,734,809 SEQ ID NO: 50 |
| AAV CSp-6 | 652 | U.S. Pat. No. 8,734,809 SEQ ID NO: 51 |
| AAV CSp-7 | 653 | U.S. Pat. No. 8,734,809 SEQ ID NO: 52 |
| AAV CSp-8 | 654 | U.S. Pat. No. 8,734,809 SEQ ID NO: 53 |
| AAV CSp-9 | 655 | U.S. Pat. No. 8,734,809 SEQ ID NO: 54 |
| AAV CHt-2 | 656 | U.S. Pat. No. 8,734,809 SEQ ID NO: 55 |
| AAV CHt-3 | 657 | U.S. Pat. No. 8,734,809 SEQ ID NO: 56 |
| AAV CKd-1 | 658 | U.S. Pat. No. 8,734,809 SEQ ID NO: 57 |
| AAV CKd-10 | 659 | U.S. Pat. No. 8,734,809 SEQ ID NO: 58 |
| AAV CKd-2 | 660 | U.S. Pat. No. 8,734,809 SEQ ID NO: 59 |
| AAV CKd-3 | 661 | U.S. Pat. No. 8,734,809 SEQ ID NO: 60 |
| AAV CKd-4 | 662 | U.S. Pat. No. 8,734,809 SEQ ID NO: 61 |
| AAV CKd-6 | 663 | U.S. Pat. No. 8,734,809 SEQ ID NO: 62 |
| AAV CKd-7 | 664 | U.S. Pat. No. 8,734,809 SEQ ID NO: 63 |
| AAV CKd-8 | 665 | U.S. Pat. No. 8,734,809 SEQ ID NO: 64 |
| AAV CLv-1 | 666 | U.S. Pat. No. 8,734,809 SEQ ID NO: 65 |

TABLE 1-continued

AAV Serotypes

| Serotype | SEQ ID NO | Reference Information |
|---|---|---|
| AAV CLv-12 | 667 | U.S. Pat. No. 8,734,809 SEQ ID NO: 66 |
| AAV CLv-13 | 668 | U.S. Pat. No. 8,734,809 SEQ ID NO: 67 |
| AAV CLv-2 | 669 | U.S. Pat. No. 8,734,809 SEQ ID NO: 68 |
| AAV CLv-3 | 670 | U.S. Pat. No. 8,734,809 SEQ ID NO: 69 |
| AAV CLv-4 | 671 | U.S. Pat. No. 8,734,809 SEQ ID NO: 70 |
| AAV CLv-6 | 672 | U.S. Pat. No. 8,734,809 SEQ ID NO: 71 |
| AAV CLv-8 | 673 | U.S. Pat. No. 8,734,809 SEQ ID NO: 72 |
| AAV CKd-B1 | 674 | U.S. Pat. No. 8,734,809 SEQ ID NO: 73 |
| AAV CKd-B2 | 675 | U.S. Pat. No. 8,734,809 SEQ ID NO: 74 |
| AAV CKd-B3 | 676 | U.S. Pat. No. 8,734,809 SEQ ID NO: 75 |
| AAV CKd-B4 | 677 | U.S. Pat. No. 8,734,809 SEQ ID NO: 76 |
| AAV CKd-B5 | 678 | U.S. Pat. No. 8,734,809 SEQ ID NO: 77 |
| AAV CKd-B6 | 679 | U.S. Pat. No. 8,734,809 SEQ ID NO: 78 |
| AAV CKd-B7 | 680 | U.S. Pat. No. 8,734,809 SEQ ID NO: 79 |
| AAV CKd-B8 | 681 | U.S. Pat. No. 8,734,809 SEQ ID NO: 80 |
| AAV CKd-H1 | 682 | U.S. Pat. No. 8,734,809 SEQ ID NO: 81 |
| AAV CKd-H2 | 683 | U.S. Pat. No. 8,734,809 SEQ ID NO: 82 |
| AAV CKd-H3 | 684 | U.S. Pat. No. 8,734,809 SEQ ID NO: 83 |
| AAV CKd-H4 | 685 | U.S. Pat. No. 8,734,809 SEQ ID NO: 84 |
| AAV CKd-H5 | 686 | U.S. Pat. No. 8,734,809 SEQ ID NO: 85 |
| AAV CKd-H6 | 687 | U.S. Pat. No. 8,734,809 SEQ ID NO: 77 |
| AAV CHt-1 | 688 | U.S. Pat. No. 8,734,809 SEQ ID NO: 86 |
| AAV CLvl-1 | 689 | U.S. Pat. No. 8,734,809 SEQ ID NO: 171 |
| AAV CLv1-2 | 690 | U.S. Pat. No. 8,734,809 SEQ ID NO: 172 |
| AAV CLv1-3 | 691 | U.S. Pat. No. 8,734,809 SEQ ID NO: 173 |
| AAV CLv1-4 | 692 | U.S. Pat. No. 8,734,809 SEQ ID NO: 174 |
| AAV Clv1-7 | 693 | U.S. Pat. No. 8,734,809 SEQ ID NO: 175 |
| AAV Clv1-8 | 694 | U.S. Pat. No. 8,734,809 SEQ ID NO: 176 |
| AAV Clv1-9 | 695 | U.S. Pat. No. 8,734,809 SEQ ID NO: 177 |
| AAV Clv1-10 | 696 | U.S. Pat. No. 8,734,809 SEQ ID NO: 178 |
| AAV.VR-355 | 697 | U.S. Pat. No. 8,734,809 SEQ ID NO: 181 |
| AAV.hu.48R3 | 698 | U.S. Pat. No. 8,734,809 SEQ ID NO: 183 |
| AAV CBr-E1 | 699 | U.S. Pat. No. 8,734,809 SEQ ID NO: 87 |
| AAV CBr-E2 | 700 | U.S. Pat. No. 8,734,809 SEQ ID NO: 88 |
| AAV CBr-E3 | 701 | U.S. Pat. No. 8,734,809 SEQ ID NO: 89 |
| AAV CBr-E4 | 702 | U.S. Pat. No. 8,734,809 SEQ ID NO: 90 |
| AAV CBr-E5 | 703 | U.S. Pat. No. 8,734,809 SEQ ID NO: 91 |
| AAV CBr-e5 | 704 | U.S. Pat. No. 8,734,809 SEQ ID NO: 92 |
| AAV CBr-E6 | 705 | U.S. Pat. No. 8,734,809 SEQ ID NO: 93 |
| AAV CBr-E7 | 706 | U.S. Pat. No. 8,734,809 SEQ ID NO: 94 |
| AAV CBr-E8 | 707 | U.S. Pat. No. 8,734,809 SEQ ID NO: 95 |
| AAV CLv-D1 | 708 | U.S. Pat. No. 8,734,809 SEQ ID NO: 96 |
| AAV CLv-D2 | 709 | U.S. Pat. No. 8,734,809 SEQ ID NO: 97 |
| AAV CLv-D3 | 710 | U.S. Pat. No. 8,734,809 SEQ ID NO: 98 |
| AAV CLv-D4 | 711 | U.S. Pat. No. 8,734,809 SEQ ID NO: 99 |
| AAV CLv-D5 | 712 | U.S. Pat. No. 8,734,809 SEQ ID NO: 100 |
| AAV CLv-D6 | 713 | U.S. Pat. No. 8,734,809 SEQ ID NO: 101 |
| AAV CLv-D7 | 714 | U.S. Pat. No. 8,734,809 SEQ ID NO: 102 |
| AAV CLv-D8 | 715 | U.S. Pat. No. 8,734,809 SEQ ID NO: 103 |
| AAV CLv-E1 | 716 | U.S. Pat. No. 8,734,809 SEQ ID NO: 87 |
| AAV CLv-R1 | 717 | U.S. Pat. No. 8,734,809 SEQ ID NO: 104 |
| AAV CLv-R2 | 718 | U.S. Pat. No. 8,734,809 SEQ ID NO: 105 |
| AAV CLv-R3 | 719 | U.S. Pat. No. 8,734,809 SEQ ID NO: 106 |
| AAV CLv-R4 | 720 | U.S. Pat. No. 8,734,809 SEQ ID NO: 107 |
| AAV CLv-R5 | 721 | U.S. Pat. No. 8,734,809 SEQ ID NO: 108 |
| AAV CLv-R6 | 722 | U.S. Pat. No. 8,734,809 SEQ ID NO: 109 |
| AAV CLv-R7 | 723 | U.S. Pat. No. 8,734,809 SEQ ID NO: 110 |
| AAV CLv-R8 | 724 | U.S. Pat. No. 8,734,809 SEQ ID NO: 111 |
| AAV CLv-R9 | 725 | U.S. Pat. No. 8,734,809 SEQ ID NO: 112 |
| AAV CLg-F1 | 726 | U.S. Pat. No. 8,734,809 SEQ ID NO: 113 |
| AAV CLg-F2 | 727 | U.S. Pat. No. 8,734,809 SEQ ID NO: 114 |
| AAV CLg-F3 | 728 | U.S. Pat. No. 8,734,809 SEQ ID NO: 115 |
| AAV CLg-F4 | 729 | U.S. Pat. No. 8,734,809 SEQ ID NO: 116 |
| AAV CLg-F5 | 730 | U.S. Pat. No. 8,734,809 SEQ ID NO: 117 |
| AAV CLg-F6 | 731 | U.S. Pat. No. 8,734,809 SEQ ID NO: 117 |
| AAV CLg-F7 | 732 | U.S. Pat. No. 8,734,809 SEQ ID NO: 118 |
| AAV CLg-F8 | 733 | U.S. Pat. No. 8,734,809 SEQ ID NO: 117 |
| AAV CSp-1 | 734 | U.S. Pat. No. 8,734,809 SEQ ID NO: 119 |
| AAV CSp-10 | 735 | U.S. Pat. No. 8,734,809 SEQ ID NO: 120 |
| AAV CSp-11 | 736 | U.S. Pat. No. 8,734,809 SEQ ID NO: 121 |
| AAV CSp-2 | 737 | U.S. Pat. No. 8,734,809 SEQ ID NO: 122 |
| AAV CSp-3 | 738 | U.S. Pat. No. 8,734,809 SEQ ID NO: 123 |
| AAV CSp-4 | 739 | U.S. Pat. No. 8,734,809 SEQ ID NO: 124 |
| AAV CSp-6 | 740 | U.S. Pat. No. 8,734,809 SEQ ID NO: 125 |
| AAV CSp-7 | 741 | U.S. Pat. No. 8,734,809 SEQ ID NO: 126 |
| AAV CSp-8 | 742 | U.S. Pat. No. 8,734,809 SEQ ID NO: 127 |

TABLE 1-continued

AAV Serotypes

| Serotype | SEQ ID NO | Reference Information |
|---|---|---|
| AAV CSp-9 | 743 | U.S. Pat. No. 8,734,809 SEQ ID NO: 128 |
| AAV CHt-2 | 744 | U.S. Pat. No. 8,734,809 SEQ ID NO: 129 |
| AAV CHt-3 | 745 | U.S. Pat. No. 8,734,809 SEQ ID NO: 130 |
| AAV CKd-1 | 746 | U.S. Pat. No. 8,734,809 SEQ ID NO: 131 |
| AAV CKd-10 | 747 | U.S. Pat. No. 8,734,809 SEQ ID NO: 132 |
| AAV CKd-2 | 748 | U.S. Pat. No. 8,734,809 SEQ ID NO: 133 |
| AAV CKd-3 | 749 | U.S. Pat. No. 8,734,809 SEQ ID NO: 134 |
| AAV CKd-4 | 750 | U.S. Pat. No. 8,734,809 SEQ ID NO: 135 |
| AAV CKd-6 | 751 | U.S. Pat. No. 8,734,809 SEQ ID NO: 136 |
| AAV CKd-7 | 752 | U.S. Pat. No. 8,734,809 SEQ ID NO: 137 |
| AAV CKd-8 | 753 | U.S. Pat. No. 8,734,809 SEQ ID NO: 138 |
| AAV CLv-1 | 754 | U.S. Pat. No. 8,734,809 SEQ ID NO: 139 |
| AAV CLv-12 | 755 | U.S. Pat. No. 8,734,809 SEQ ID NO: 140 |
| AAV CLv-13 | 756 | U.S. Pat. No. 8,734,809 SEQ ID NO: 141 |
| AAV CLv-2 | 757 | U.S. Pat. No. 8,734,809 SEQ ID NO: 142 |
| AAV CLv-3 | 758 | U.S. Pat. No. 8,734,809 SEQ ID NO: 143 |
| AAV CLv-4 | 759 | U.S. Pat. No. 8,734,809 SEQ ID NO: 144 |
| AAV CLv-6 | 760 | U.S. Pat. No. 8,734,809 SEQ ID NO: 145 |
| AAV CLv-8 | 761 | U.S. Pat. No. 8,734,809 SEQ ID NO: 146 |
| AAV CKd-B1 | 762 | U.S. Pat. No. 8,734,809 SEQ ID NO: 147 |
| AAV CKd-B2 | 763 | U.S. Pat. No. 8,734,809 SEQ ID NO: 148 |
| AAV CKd-B3 | 764 | U.S. Pat. No. 8,734,809 SEQ ID NO: 149 |
| AAV CKd-B4 | 765 | U.S. Pat. No. 8,734,809 SEQ ID NO: 150 |
| AAV CKd-B5 | 766 | U.S. Pat. No. 8,734,809 SEQ ID NO: 151 |
| AAV CKd-B6 | 767 | U.S. Pat. No. 8,734,809 SEQ ID NO: 152 |
| AAV CKd-B7 | 768 | U.S. Pat. No. 8,734,809 SEQ ID NO: 153 |
| AAV CKd-B8 | 769 | U.S. Pat. No. 8,734,809 SEQ ID NO: 154 |
| AAV CKd-H1 | 770 | U.S. Pat. No. 8,734,809 SEQ ID NO: 155 |
| AAV CKd-H2 | 771 | U.S. Pat. No. 8,734,809 SEQ ID NO: 156 |
| AAV CKd-H3 | 772 | U.S. Pat. No. 8,734,809 SEQ ID NO: 157 |
| AAV CKd-H4 | 773 | U.S. Pat. No. 8,734,809 SEQ ID NO: 158 |
| AAV CKd-H5 | 774 | U.S. Pat. No. 8,734,809 SEQ ID NO: 159 |
| AAV CKd-H6 | 775 | U.S. Pat. No. 8,734,809 SEQ ID NO: 151 |
| AAV CHt-1 | 776 | U.S. Pat. No. 8,734,809 SEQ ID NO: 160 |
| AAV CHt-P2 | 777 | WO2016065001 SEQ ID NO: 1 |
| AAV CHt-P5 | 778 | WO2016065001 SEQ ID NO: 2 |
| AAV CHt-P9 | 779 | WO2016065001 SEQ ID NO: 3 |
| AAV CBr-7.1 | 780 | WO2016065001 SEQ ID NO: 4 |
| AAV CBr-7.2 | 781 | WO2016065001 SEQ ID NO: 5 |
| AAV CBr-7.3 | 782 | WO2016065001 SEQ ID NO: 6 |
| AAV CBr-7.4 | 783 | WO2016065001 SEQ ID NO: 7 |
| AAV CBr-7.5 | 784 | WO2016065001 SEQ ID NO: 8 |
| AAV CBr-7.7 | 785 | WO2016065001 SEQ ID NO: 9 |
| AAV CBr-7.8 | 786 | WO2016065001 SEQ ID NO: 10 |
| AAV CBr-7.10 | 787 | WO2016065001 SEQ ID NO: 11 |
| AAV CKd-N3 | 788 | WO2016065001 SEQ ID NO: 12 |
| AAV CKd-N4 | 789 | WO2016065001 SEQ ID NO: 13 |
| AAV CKd-N9 | 790 | WO2016065001 SEQ ID NO: 14 |
| AAV CLv-L4 | 791 | WO2016065001 SEQ ID NO: 15 |
| AAV CLv-L5 | 792 | WO2016065001 SEQ ID NO: 16 |
| AAV CLv-L6 | 793 | WO2016065001 SEQ ID NO: 17 |
| AAV CLv-K1 | 794 | WO2016065001 SEQ ID NO: 18 |
| AAV CLv-K3 | 795 | WO2016065001 SEQ ID NO: 19 |
| AAV CLv-K6 | 796 | WO2016065001 SEQ ID NO: 20 |
| AAV CLv-M1 | 797 | WO2016065001 SEQ ID NO: 21 |
| AAV CLv-M11 | 798 | WO2016065001 SEQ ID NO: 22 |
| AAV CLv-M2 | 799 | WO2016065001 SEQ ID NO: 23 |
| AAV CLv-M5 | 800 | WO2016065001 SEQ ID NO: 24 |
| AAV CLv-M6 | 801 | WO2016065001 SEQ ID NO: 25 |
| AAV CLv-M7 | 802 | WO2016065001 SEQ ID NO: 26 |
| AAV CLv-M8 | 803 | WO2016065001 SEQ ID NO: 27 |
| AAV CLv-M9 | 804 | WO2016065001 SEQ ID NO: 28 |
| AAV CHt-P1 | 805 | WO2016065001 SEQ ID NO: 29 |
| AAV CHt-P6 | 806 | WO2016065001 SEQ ID NO: 30 |
| AAV CHt-P8 | 807 | WO2016065001 SEQ ID NO: 31 |
| AAV CHt-6.1 | 808 | WO2016065001 SEQ ID NO: 32 |
| AAV CHt-6.10 | 809 | WO2016065001 SEQ ID NO: 33 |
| AAV CHt-6.5 | 810 | WO2016065001 SEQ ID NO: 34 |
| AAV CHt-6.6 | 811 | WO2016065001 SEQ ID NO: 35 |
| AAV CHt-6.7 | 812 | WO2016065001 SEQ ID NO: 36 |
| AAV CHt-6.8 | 813 | WO2016065001 SEQ ID NO: 37 |
| AAV CSp-8.10 | 814 | WO2016065001 SEQ ID NO: 38 |
| AAV CSp-8.2 | 815 | WO2016065001 SEQ ID NO: 39 |
| AAV CSp-8.4 | 816 | WO2016065001 SEQ ID NO: 40 |
| AAV CSp-8.5 | 817 | WO2016065001 SEQ ID NO: 41 |
| AAV CSp-8.6 | 818 | WO2016065001 SEQ ID NO: 42 |

TABLE 1-continued

AAV Serotypes

| Serotype | SEQ ID NO | Reference Information |
|---|---|---|
| AAV CSp-8.7 | 819 | WO2016065001 SEQ ID NO: 43 |
| AAV CSp-8.8 | 820 | WO2016065001 SEQ ID NO: 44 |
| AAV CSp-8.9 | 821 | WO2016065001 SEQ ID NO: 45 |
| AAV CBr-B7.3 | 822 | WO2016065001 SEQ ID NO: 46 |
| AAV CBr-B7.4 | 823 | WO2016065001 SEQ ID NO: 47 |
| AAV3B | 824 | WO2016065001 SEQ ID NO: 48 |
| AAV4 | 825 | WO2016065001 SEQ ID NO: 49 |
| AAV5 | 826 | WO2016065001 SEQ ID NO: 50 |
| AAV CHt-P2 | 827 | WO2016065001 SEQ ID NO: 51 |
| AAV CHt-P5 | 828 | WO2016065001 SEQ ID NO: 52 |
| AAV CHt-P9 | 829 | WO2016065001 SEQ ID NO: 53 |
| AAV CBr-7.1 | 830 | WO2016065001 SEQ ID NO: 54 |
| AAV CBr-7.2 | 831 | WO2016065001 SEQ ID NO: 55 |
| AAV CBr-7.3 | 832 | WO2016065001 SEQ ID NO: 56 |
| AAV CBr-7.4 | 833 | WO2016065001 SEQ ID NO: 57 |
| AAV CBr-7.5 | 834 | WO2016065001 SEQ ID NO: 58 |
| AAV CBr-7.7 | 835 | WO2016065001 SEQ ID NO: 59 |
| AAV CBr-7.8 | 836 | WO2016065001 SEQ ID NO: 60 |
| AAV CBr-7.10 | 837 | WO2016065001 SEQ ID NO: 61 |
| AAV CKd-N3 | 838 | WO2016065001 SEQ ID NO: 62 |
| AAV CKd-N4 | 839 | WO2016065001 SEQ ID NO: 63 |
| AAV CKd-N9 | 840 | WO2016065001 SEQ ID NO: 64 |
| AAV CLv-L4 | 841 | WO2016065001 SEQ ID NO: 65 |
| AAV CLv-L5 | 842 | WO2016065001 SEQ ID NO: 66 |
| AAV CLv-L6 | 843 | WO2016065001 SEQ ID NO: 67 |
| AAV CLv-K1 | 844 | WO2016065001 SEQ ID NO: 68 |
| AAV CLv-K3 | 845 | WO2016065001 SEQ ID NO: 69 |
| AAV CLv-K6 | 846 | WO2016065001 SEQ ID NO: 70 |
| AAV CLv-M1 | 847 | WO2016065001 SEQ ID NO: 71 |
| AAV CLv-M11 | 848 | WO2016065001 SEQ ID NO: 72 |
| AAV CLv-M2 | 849 | WO2016065001 SEQ ID NO: 73 |
| AAV CLv-M5 | 850 | WO2016065001 SEQ ID NO: 74 |
| AAV CLv-M6 | 851 | WO2016065001 SEQ ID NO: 75 |
| AAV CLv-M7 | 852 | WO2016065001 SEQ ID NO: 76 |
| AAV CLv-M8 | 853 | WO2016065001 SEQ ID NO: 77 |
| AAV CLv-M9 | 854 | WO2016065001 SEQ ID NO: 78 |
| AAV CHt-P1 | 855 | WO2016065001 SEQ ID NO: 79 |
| AAV CHt-P6 | 856 | WO2016065001 SEQ ID NO: 80 |
| AAV CHt-P8 | 857 | WO2016065001 SEQ ID NO: 81 |
| AAV CHt-6.1 | 858 | WO2016065001 SEQ ID NO: 82 |
| AAV CHt-6.10 | 859 | WO2016065001 SEQ ID NO: 83 |
| AAV CHt-6.5 | 860 | WO2016065001 SEQ ID NO: 84 |
| AAV CHt-6.6 | 861 | WO2016065001 SEQ ID NO: 85 |
| AAV CHt-6.7 | 862 | WO2016065001 SEQ ID NO: 86 |
| AAV CHt-6.8 | 863 | WO2016065001 SEQ ID NO: 87 |
| AAV CSp-8.10 | 864 | WO2016065001 SEQ ID NO: 88 |
| AAV CSp-8.2 | 865 | WO2016065001 SEQ ID NO: 89 |
| AAV CSp-8.4 | 866 | WO2016065001 SEQ ID NO: 90 |
| AAV CSp-8.5 | 867 | WO2016065001 SEQ ID NO: 91 |
| AAV CSp-8.6 | 868 | WO2016065001 SEQ ID NO: 92 |
| AAV CSp-8.7 | 869 | WO2016065001 SEQ ID NO: 93 |
| AAV CSp-8.8 | 870 | WO2016065001 SEQ ID NO: 94 |
| AAV CSp-8.9 | 871 | WO2016065001 SEQ ID NO: 95 |
| AAV CBr-B7.3 | 872 | WO2016065001 SEQ ID NO: 96 |
| AAV CBr-B7.4 | 873 | WO2016065001 SEQ ID NO: 97 |
| AAV3B | 874 | WO2016065001 SEQ ID NO: 98 |
| AAV4 | 875 | WO2016065001 SEQ ID NO: 99 |
| AAV5 | 876 | WO2016065001 SEQ ID NO: 100 |
| GPV | 877 | U.S. Pat. No. 9,624,274B2 SEQ ID NO: 192 |
| B19 | 878 | U.S. Pat. No. 9,624,274B2 SEQ ID NO: 193 |
| MVM | 879 | U.S. Pat. No. 9,624,274B2 SEQ ID NO: 194 |
| FPV | 880 | U.S. Pat. No. 9,624,274B2 SEQ ID NO: 195 |
| CPV | 881 | U.S. Pat. No. 9,624,274B2 SEQ ID NO: 196 |
| AAV6 | 882 | U.S. Pat. No. 9,546,112B2 SEQ ID NO: 5 |
| AAV6 | 883 | U.S. Pat. No. 9,457,103B2 SEQ ID NO: 1 |
| AAV2 | 884 | U.S. Pat. No. 9,457,103B2 SEQ ID NO: 2 |
| ShH10 | 885 | U.S. Pat. No. 9,457,103B2 SEQ ID NO: 3 |
| ShH13 | 886 | U.S. Pat. No. 9,457,103B2 SEQ ID NO: 4 |
| ShH10 | 887 | U.S. Pat. No. 9,457,103B2 SEQ ID NO: 5 |
| ShH10 | 888 | U.S. Pat. No. 9,457,103B2 SEQ ID NO: 6 |
| ShH10 | 889 | U.S. Pat. No. 9,457,103B2 SEQ ID NO: 7 |
| ShH10 | 890 | U.S. Pat. No. 9,457,103B2 SEQ ID NO: 8 |
| ShH10 | 891 | U.S. Pat. No. 9,457,103B2 SEQ ID NO: 9 |
| rh74 | 892 | U.S. Pat. No. 9,434,928B2 SEQ ID NO: 1, US2015023924A1 SEQ ID NO: 2 |
| rh74 | 893 | U.S. Pat. No. 9,434,928B2 SEQ ID NO: 2, US2015023924A1 SEQ ID NO: 1 |
| AAV8 | 894 | U.S. Pat. No. 9,434,928B2 SEQ ID NO: 4 |

TABLE 1-continued

AAV Serotypes

| Serotype | SEQ ID NO | Reference Information |
|---|---|---|
| rh74 | 895 | U.S. Pat. No. 9,434,928B2 SEQ ID NO: 5 |
| rh74 (RHM4-1) | 896 | US2015023924A1 SEQ ID NO: 5, US20160375110A1 SEQ ID NO: 4 |
| rh74 (RHM15-1) | 897 | US2015023924A1 SEQ ID NO: 6, US20160375110A1 SEQ ID NO: 5 |
| rh74 (RHM15-2) | 898 | US2015023924A1 SEQ ID NO: 7, US20160375110A1 SEQ ID NO: 6 |
| rh74 (RHM15-3/RHM15-5) | 899 | US2015023924A1 SEQ ID NO: 8, US20160375110A1 SEQ ID NO: 7 |
| rh74 (RHM15-4) | 900 | US2015023924A1 SEQ ID NO: 9, US20160375110A1 SEQ ID NO: 8 |
| rh74 (RHM15-6) | 901 | US2015023924A1 SEQ ID NO: 10, US20160375110A1 SEQ ID NO: 9 |
| rh74 (RHM4-1) | 902 | US2015023924A1 SEQ ID NO: 11 |
| rh74 (RHM15-1) | 903 | US2015023924A1 SEQ ID NO: 12 |
| rh74 (RHM15-2) | 904 | US2015023924A1 SEQ ID NO: 13 |
| rh74 (RHM15-3/RHM15-5) | 905 | US2015023924A1 SEQ ID NO: 14 |
| rh74 (RHM15-4) | 906 | US2015023924A1 SEQ ID NO: 15 |
| rh74 (RHM15-6) | 907 | US2015023924A1 SEQ ID NO: 16 |
| AAV2 (comprising lung specific polypeptide) | 908 | US20160175389A1 SEQ ID NO: 9 |
| AAV2 (comprising lung specific polypeptide) | 909 | US20160175389A1 SEQ ID NO: 10 |
| Anc80 | 910 | US20170051257A1 SEQ ID NO: 1 |
| Anc80 | 911 | US20170051257A1 SEQ ID NO: 2 |
| Anc81 | 912 | US20170051257A1 SEQ ID NO: 3 |
| Anc80 | 913 | US20170051257A1 SEQ ID NO: 4 |
| Anc82 | 914 | US20170051257A1 SEQ ID NO: 5 |
| Anc82 | 915 | US20170051257A1 SEQ ID NO: 6 |
| Anc83 | 916 | US20170051257A1 SEQ ID NO: 7 |
| Anc83 | 917 | US20170051257A1 SEQ ID NO: 8 |
| Anc84 | 918 | US20170051257A1 SEQ ID NO: 9 |
| Anc84 | 919 | US20170051257A1 SEQ ID NO: 10 |
| Anc94 | 920 | US20170051257A1 SEQ ID NO: 11 |
| Anc94 | 921 | US20170051257A1 SEQ ID NO: 12 |
| Anc113 | 922 | US20170051257A1 SEQ ID NO: 13 |
| Anc113 | 923 | US20170051257A1 SEQ ID NO: 14 |
| Anc126 | 924 | US20170051257A1 SEQ ID NO: 15 |
| Anc126 | 925 | US20170051257A1 SEQ ID NO: 16 |
| Anc127 | 926 | US20170051257A1 SEQ ID NO: 17 |
| Anc127 | 927 | US20170051257A1 SEQ ID NO: 18 |
| Anc80L27 | 928 | US20170051257A1 SEQ ID NO: 19 |
| Anc80L59 | 929 | US20170051257A1 SEQ ID NO: 20 |
| Anc80L60 | 930 | US20170051257A1 SEQ ID NO: 21 |
| Anc80L62 | 931 | US20170051257A1 SEQ ID NO: 22 |
| Anc80L65 | 932 | US20170051257A1 SEQ ID NO: 23 |
| Anc80L33 | 933 | US20170051257A1 SEQ ID NO: 24 |
| Anc80L36 | 934 | US20170051257A1 SEQ ID NO: 25 |
| Anc80L44 | 935 | US20170051257A1 SEQ ID NO: 26 |
| Anc80L1 | 936 | US20170051257A1 SEQ ID NO: 35 |
| Anc80L1 | 937 | US20170051257A1 SEQ ID NO: 36 |
| AAV-X1 | 938 | U.S. Pat. No. 8,283,151B2 SEQ ID NO: 11 |
| AAV-X1b | 939 | U.S. Pat. No. 8,283,151B2 SEQ ID NO: 12 |
| AAV-X5 | 940 | U.S. Pat. No. 8,283,151B2 SEQ ID NO: 13 |
| AAV-X19 | 941 | U.S. Pat. No. 8,283,151B2 SEQ ID NO: 14 |
| AAV-X21 | 942 | U.S. Pat. No. 8,283,151B2 SEQ ID NO: 15 |
| AAV-X22 | 943 | U.S. Pat. No. 8,283,151B2 SEQ ID NO: 16 |
| AAV-X23 | 944 | U.S. Pat. No. 8,283,151B2 SEQ ID NO: 17 |
| AAV-X24 | 945 | U.S. Pat. No. 8,283,151B2 SEQ ID NO: 18 |
| AAV-X25 | 946 | U.S. Pat. No. 8,283,151B2 SEQ ID NO: 19 |
| AAV-X26 | 947 | U.S. Pat. No. 8,283,151B2 SEQ ID NO: 20 |
| AAV-X1 | 948 | U.S. Pat. No. 8,283,151B2 SEQ ID NO: 21 |
| AAV-X1b | 949 | U.S. Pat. No. 8,283,151B2 SEQ ID NO: 22 |
| AAV-X5 | 950 | U.S. Pat. No. 8,283,151B2 SEQ ID NO: 23 |
| AAV-X19 | 951 | U.S. Pat. No. 8,283,151B2 SEQ ID NO: 24 |
| AAV-X21 | 952 | U.S. Pat. No. 8,283,151B2 SEQ ID NO: 25 |
| AAV-X22 | 953 | U.S. Pat. No. 8,283,151B2 SEQ ID NO: 26 |
| AAV-X23 | 954 | U.S. Pat. No. 8,283,151B2 SEQ ID NO: 27 |
| AAV-X24 | 955 | U.S. Pat. No. 8,283,151B2 SEQ ID NO: 28 |
| AAV-X25 | 956 | U.S. Pat. No. 8,283,151B2 SEQ ID NO: 29 |
| AAV-X26 | 957 | U.S. Pat. No. 8,283,151B2 SEQ ID NO: 30 |
| AAVrh8 | 958 | WO2016054554A1 SEQ ID NO: 8 |
| AAVrh8VP2FC5 | 959 | WO2016054554A1 SEQ ID NO: 9 |
| AAVrh8VP2FC44 | 960 | WO2016054554A1 SEQ ID NO: 10 |
| AAVrh8VP2ApoB100 | 961 | WO2016054554A1 SEQ ID NO: 11 |
| AAVrh8VP2RVG | 962 | WO2016054554A1 SEQ ID NO: 12 |
| AA Vrh8VP2Angiopep-2 VP2 | 963 | WO2016054554A1 SEQ ID NO: 13 |
| AAV9.47VP1.3 | 964 | WO2016054554A1 SEQ ID NO: 14 |
| AAV9.47VP2ICAMg3 | 965 | WO2016054554A1 SEQ ID NO: 15 |
| AAV9.47VP2RVG | 966 | WO2016054554A1 SEQ ID NO: 16 |
| AAV9.47VP2Angiopep-2 | 967 | WO2016054554A1 SEQ ID NO: 17 |
| AAV9.47VP2A-string | 968 | WO2016054554A1 SEQ ID NO: 18 |
| AAVrh8VP2FC5 VP2 | 969 | WO2016054554A1 SEQ ID NO: 19 |
| AAVrh8VP2FC44 VP2 | 970 | WO2016054554A1 SEQ ID NO: 20 |

TABLE 1-continued

| AAV Serotypes | | |
|---|---|---|
| Serotype | SEQ ID NO | Reference Information |
| AAVrh8VP2ApoB100 VP2 | 971 | WO2016054554A1 SEQ ID NO: 21 |
| AAVrh8VP2RVG VP2 | 972 | WO2016054554A1 SEQ ID NO: 22 |
| AAVrh8VP2Angiopep-2 VP2 | 973 | WO2016054554A1 SEQ ID NO: 23 |
| AAV9.47VP2ICAMg3 VP2 | 974 | WO2016054554A1 SEQ ID NO: 24 |
| AAV9.47VP2RVG VP2 | 975 | WO2016054554A1 SEQ ID NO: 25 |
| AAV9.47VP2Angiopep-2 VP2 | 976 | WO2016054554A1 SEQ ID NO: 26 |
| AAV9.47VP2A-string VP2 | 977 | WO2016054554A1 SEQ ID NO: 27 |
| rAAV-B1 | 978 | WO2016054557A1 SEQ ID NO: 1 |
| rAAV-B2 | 979 | WO2016054557A1 SEQ ID NO: 2 |
| rAAV-B3 | 980 | WO2016054557A1 SEQ ID NO: 3 |
| rAAV-B4 | 981 | WO2016054557A1 SEQ ID NO: 4 |
| rAAV-B1 | 982 | WO2016054557A1 SEQ ID NO: 5 |
| rAAV-B2 | 983 | WO2016054557A1 SEQ ID NO: 6 |
| rAAV-B3 | 984 | WO2016054557A1 SEQ ID NO: 7 |
| rAAV-B4 | 985 | WO2016054557A1 SEQ ID NO: 8 |
| rAAV-L1 | 986 | WO2016054557A1 SEQ ID NO: 9 |
| rAAV-L2 | 987 | WO2016054557A1 SEQ ID NO: 10 |
| rAAV-L3 | 988 | WO2016054557A1 SEQ ID NO: 11 |
| rAAV-L4 | 989 | WO2016054557A1 SEQ ID NO: 12 |
| rAAV-L1 | 990 | WO2016054557A1 SEQ ID NO: 13 |
| rAAV-L2 | 991 | WO2016054557A1 SEQ ID NO: 14 |
| rAAV-L3 | 992 | WO2016054557A1 SEQ ID NO: 15 |
| rAAV-L4 | 993 | WO2016054557A1 SEQ ID NO: 16 |
| AAV9 | 994 | WO2016073739A1 SEQ ID NO: 3 |
| rAAV | 995 | WO2016081811A1 SEQ ID NO: 1 |
| rAAV | 996 | WO2016081811A1 SEQ ID NO: 2 |
| rAAV | 997 | WO2016081811A1 SEQ ID NO: 3 |
| rAAV | 998 | WO2016081811A1 SEQ ID NO: 4 |
| rAAV | 999 | WO2016081811A1 SEQ ID NO: 5 |
| rAAV | 1000 | WO2016081811A1 SEQ ID NO: 6 |
| rAAV | 1001 | WO2016081811A1 SEQ ID NO: 7 |
| rAAV | 1002 | WO2016081811A1 SEQ ID NO: 8 |
| rAAV | 1003 | WO2016081811A1 SEQ ID NO: 9 |
| rAAV | 1004 | WO2016081811A1 SEQ ID NO: 10 |
| rAAV | 1005 | WO2016081811A1 SEQ ID NO: 11 |
| rAAV | 1006 | WO2016081811A1 SEQ ID NO: 12 |
| rAAV | 1007 | WO2016081811A1 SEQ ID NO: 13 |
| rAAV | 1008 | WO2016081811A1 SEQ ID NO: 14 |
| rAAV | 1009 | WO2016081811A1 SEQ ID NO: 15 |
| rAAV | 1010 | WO2016081811A1 SEQ ID NO: 16 |
| rAAV | 1011 | WO2016081811A1 SEQ ID NO: 17 |
| rAAV | 1012 | WO2016081811A1 SEQ ID NO: 18 |
| rAAV | 1013 | WO2016081811A1 SEQ ID NO: 19 |
| rAAV | 1014 | WO2016081811A1 SEQ ID NO: 20 |
| rAAV | 1015 | WO2016081811A1 SEQ ID NO: 21 |
| rAAV | 1016 | WO2016081811A1 SEQ ID NO: 22 |
| rAAV | 1017 | WO2016081811A1 SEQ ID NO: 23 |
| rAAV | 1018 | WO2016081811A1 SEQ ID NO: 24 |
| rAAV | 1019 | WO2016081811A1 SEQ ID NO: 25 |
| rAAV | 1020 | WO2016081811A1 SEQ ID NO: 26 |
| rAAV | 1021 | WO2016081811A1 SEQ ID NO: 27 |
| rAAV | 1022 | WO2016081811A1 SEQ ID NO: 28 |
| rAAV | 1023 | WO2016081811A1 SEQ ID NO: 29 |
| rAAV | 1024 | WO2016081811A1 SEQ ID NO: 30 |
| rAAV | 1025 | WO2016081811A1 SEQ ID NO: 31 |
| rAAV | 1026 | WO2016081811A1 SEQ ID NO: 32 |
| rAAV | 1027 | WO2016081811A1 SEQ ID NO: 33 |
| rAAV | 1028 | WO2016081811A1 SEQ ID NO: 34 |
| rAAV | 1029 | WO2016081811A1 SEQ ID NO: 35 |
| rAAV | 1030 | WO2016081811A1 SEQ ID NO: 36 |
| rAAV | 1031 | WO2016081811A1 SEQ ID NO: 37 |
| rAAV | 1032 | WO2016081811A1 SEQ ID NO: 38 |
| rAAV | 1033 | WO2016081811A1 SEQ ID NO: 39 |
| rAAV | 1034 | WO2016081811A1 SEQ ID NO: 40 |
| rAAV | 1035 | WO2016081811A1 SEQ ID NO: 41 |
| rAAV | 1036 | WO2016081811A1 SEQ ID NO: 42 |
| rAAV | 1037 | WO2016081811A1 SEQ ID NO: 43 |
| rAAV | 1038 | WO2016081811A1 SEQ ID NO: 44 |
| rAAV | 1039 | WO2016081811A1 SEQ ID NO: 45 |
| rAAV | 1040 | WO2016081811A1 SEQ ID NO: 46 |
| rAAV | 1041 | WO2016081811A1 SEQ ID NO: 47 |
| rAAV | 1042 | WO2016081811A1 SEQ ID NO: 48 |
| rAAV | 1043 | WO2016081811A1 SEQ ID NO: 49 |
| rAAV | 1044 | WO2016081811A1 SEQ ID NO: 50 |
| rAAV | 1045 | WO2016081811A1 SEQ ID NO: 51 |
| rAAV | 1046 | WO2016081811A1 SEQ ID NO: 52 |

TABLE 1-continued

AAV Serotypes

| Serotype | SEQ ID NO | Reference Information |
|---|---|---|
| rAAV | 1047 | WO2016081811A1 SEQ ID NO: 53 |
| rAAV | 1048 | WO2016081811A1 SEQ ID NO: 54 |
| rAAV | 1049 | WO2016081811A1 SEQ ID NO: 55 |
| rAAV | 1050 | WO2016081811A1 SEQ ID NO: 56 |
| rAAV | 1051 | WO2016081811A1 SEQ ID NO: 57 |
| rAAV | 1052 | WO2016081811A1 SEQ ID NO: 58 |
| rAAV | 1053 | WO2016081811A1 SEQ ID NO: 59 |
| rAAV | 1054 | WO2016081811A1 SEQ ID NO: 60 |
| rAAV | 1055 | WO2016081811A1 SEQ ID NO: 61 |
| rAAV | 1056 | WO2016081811A1 SEQ ID NO: 62 |
| rAAV | 1057 | WO2016081811A1 SEQ ID NO: 63 |
| rAAV | 1058 | WO2016081811A1 SEQ ID NO: 64 |
| rAAV | 1059 | WO2016081811A1 SEQ ID NO: 65 |
| rAAV | 1060 | WO2016081811A1 SEQ ID NO: 66 |
| rAAV | 1061 | WO2016081811A1 SEQ ID NO: 67 |
| rAAV | 1062 | WO2016081811A1 SEQ ID NO: 68 |
| rAAV | 1063 | WO2016081811A1 SEQ ID NO: 69 |
| rAAV | 1064 | WO2016081811A1 SEQ ID NO: 70 |
| rAAV | 1065 | WO2016081811A1 SEQ ID NO: 71 |
| rAAV | 1066 | WO2016081811A1 SEQ ID NO: 72 |
| rAAV | 1067 | WO2016081811A1 SEQ ID NO: 73 |
| rAAV | 1068 | WO2016081811A1 SEQ ID NO: 74 |
| rAAV | 1069 | WO2016081811A1 SEQ ID NO: 75 |
| rAAV | 1070 | WO2016081811A1 SEQ ID NO: 76 |
| rAAV | 1071 | WO2016081811A1 SEQ ID NO: 77 |
| rAAV | 1072 | WO2016081811A1 SEQ ID NO: 78 |
| rAAV | 1073 | WO2016081811A1 SEQ ID NO: 79 |
| rAAV | 1074 | WO2016081811A1 SEQ ID NO: 80 |
| rAAV | 1075 | WO2016081811A1 SEQ ID NO: 81 |
| rAAV | 1076 | WO2016081811A1 SEQ ID NO: 82 |
| rAAV | 1077 | WO2016081811A1 SEQ ID NO: 83 |
| rAAV | 1078 | WO2016081811A1 SEQ ID NO: 84 |
| rAAV | 1079 | WO2016081811A1 SEQ ID NO: 85 |
| rAAV | 1080 | WO2016081811A1 SEQ ID NO: 86 |
| rAAV | 1081 | WO2016081811A1 SEQ ID NO: 87 |
| rAAV | 1082 | WO2016081811A1 SEQ ID NO: 88 |
| rAAV | 1083 | WO2016081811A1 SEQ ID NO: 89 |
| rAAV | 1084 | WO2016081811A1 SEQ ID NO: 90 |
| rAAV | 1085 | WO2016081811A1 SEQ ID NO: 91 |
| rAAV | 1086 | WO2016081811A1 SEQ ID NO: 92 |
| rAAV | 1087 | WO2016081811A1 SEQ ID NO: 93 |
| rAAV | 1088 | WO2016081811A1 SEQ ID NO: 94 |
| rAAV | 1089 | WO2016081811A1 SEQ ID NO: 95 |
| rAAV | 1090 | WO2016081811A1 SEQ ID NO: 96 |
| rAAV | 1091 | WO2016081811A1 SEQ ID NO: 97 |
| rAAV | 1092 | WO2016081811A1 SEQ ID NO: 98 |
| rAAV | 1093 | WO2016081811A1 SEQ ID NO: 99 |
| rAAV | 1094 | WO2016081811A1 SEQ ID NO: 100 |
| rAAV | 1095 | WO2016081811A1 SEQ ID NO: 101 |
| rAAV | 1096 | WO2016081811A1 SEQ ID NO: 102 |
| rAAV | 1097 | WO2016081811A1 SEQ ID NO: 103 |
| rAAV | 1098 | WO2016081811A1 SEQ ID NO: 104 |
| rAAV | 1099 | WO2016081811A1 SEQ ID NO: 105 |
| rAAV | 1100 | WO2016081811A1 SEQ ID NO: 106 |
| rAAV | 1101 | WO2016081811A1 SEQ ID NO: 107 |
| rAAV | 1102 | WO2016081811A1 SEQ ID NO: 108 |
| rAAV | 1103 | WO2016081811A1 SEQ ID NO: 109 |
| rAAV | 1104 | WO2016081811A1 SEQ ID NO: 110 |
| rAAV | 1105 | WO2016081811A1 SEQ ID NO: 111 |
| rAAV | 1106 | WO2016081811A1 SEQ ID NO: 112 |
| rAAV | 1107 | WO2016081811A1 SEQ ID NO: 113 |
| rAAV | 1108 | WO2016081811A1 SEQ ID NO: 114 |
| rAAV | 1109 | WO2016081811A1 SEQ ID NO: 115 |
| rAAV | 1110 | WO2016081811A1 SEQ ID NO: 116 |
| rAAV | 1111 | WO2016081811A1 SEQ ID NO: 117 |
| rAAV | 1112 | WO2016081811A1 SEQ ID NO: 118 |
| rAAV | 1113 | WO2016081811A1 SEQ ID NO: 119 |
| rAAV | 1114 | WO2016081811A1 SEQ ID NO: 120 |
| rAAV | 1115 | WO2016081811A1 SEQ ID NO: 121 |
| rAAV | 1116 | WO2016081811A1 SEQ ID NO: 122 |
| rAAV | 1117 | WO2016081811A1 SEQ ID NO: 123 |
| rAAV | 1118 | WO2016081811A1 SEQ ID NO: 124 |
| rAAV | 1119 | WO2016081811A1 SEQ ID NO: 125 |
| rAAV | 1120 | WO2016081811A1 SEQ ID NO: 126 |
| rAAV | 1121 | WO2016081811A1 SEQ ID NO: 127 |
| rAAV | 1122 | WO2016081811A1 SEQ ID NO: 128 |

TABLE 1-continued

AAV Serotypes

| Serotype | SEQ ID NO | Reference Information |
|---|---|---|
| AAV8 E532K | 1123 | WO2016081811A1 SEQ ID NO: 133 |
| AAV8 E532K | 1124 | WO2016081811A1 SEQ ID NO: 134 |
| rAAV4 | 1125 | WO2016115382A1 SEQ ID NO: 2 |
| rAAV4 | 1126 | WO2016115382A1 SEQ ID NO: 3 |
| rAAV4 | 1127 | WO2016115382A1 SEQ ID NO: 4 |
| rAAV4 | 1128 | WO2016115382A1 SEQ ID NO: 5 |
| rAAV4 | 1129 | WO2016115382A1 SEQ ID NO: 6 |
| rAAV4 | 1130 | WO2016115382A1 SEQ ID NO: 7 |
| rAAV4 | 1131 | WO2016115382A1 SEQ ID NO: 8 |
| rAAV4 | 1132 | WO2016115382A1 SEQ ID NO: 9 |
| rAAV4 | 1133 | WO2016115382A1 SEQ ID NO: 10 |
| rAAV4 | 1134 | WO2016115382A1 SEQ ID NO: 11 |
| rAAV4 | 1135 | WO2016115382A1 SEQ ID NO: 12 |
| rAAV4 | 1136 | WO2016115382A1 SEQ ID NO: 13 |
| rAAV4 | 1137 | WO2016115382A1 SEQ ID NO: 14 |
| rAAV4 | 1138 | WO2016115382A1 SEQ ID NO: 15 |
| rAAV4 | 1139 | WO2016115382A1 SEQ ID NO: 16 |
| rAAV4 | 1140 | WO2016115382A1 SEQ ID NO: 17 |
| rAAV4 | 1141 | WO2016115382A1 SEQ ID NO: 18 |
| rAAV4 | 1142 | WO2016115382A1 SEQ ID NO: 19 |
| rAAV4 | 1143 | WO2016115382A1 SEQ ID NO: 20 |
| rAAV4 | 1144 | WO2016115382A1 SEQ ID NO: 21 |
| AAV11 | 1145 | WO2016115382A1 SEQ ID NO: 22 |
| AAV12 | 1146 | WO2016115382A1 SEQ ID NO: 23 |
| rh32 | 1147 | WO2016115382A1 SEQ ID NO: 25 |
| rh33 | 1148 | WO2016115382A1 SEQ ID NO: 26 |
| rh34 | 1149 | WO2016115382A1 SEQ ID NO: 27 |
| rAAV4 | 1150 | WO2016115382A1 SEQ ID NO: 28 |
| rAAV4 | 1151 | WO2016115382A1 SEQ ID NO: 29 |
| rAAV4 | 1152 | WO2016115382A1 SEQ ID NO: 30 |
| rAAV4 | 1153 | WO2016115382A1 SEQ ID NO: 31 |
| rAAV4 | 1154 | WO2016115382A1 SEQ ID NO: 32 |
| rAAV4 | 1155 | WO2016115382A1 SEQ ID NO: 33 |
| AAV2/8 | 1156 | WO2016131981A1 SEQ ID NO: 47 |
| AAV2/8 | 1157 | WO2016131981A1 SEQ ID NO: 48 |
| ancestral AAV | 1158 | WO2016154344A1 SEQ ID NO: 7 |
| ancestral AAV variant C4 | 1159 | WO2016154344A1 SEQ ID NO: 13 |
| ancestral AAV variant C7 | 1160 | WO2016154344A1 SEQ ID NO: 14 |
| ancestral AAV variant G4 | 1161 | WO2016154344A1 SEQ ID NO: 15 |
| consensus amino acid sequence of ancestral AAV variants, C4, C7 and G4 | 1162 | WO2016154344A1 SEQ ID NO: 16 |
| consensus amino acid sequence of ancestral AAV variants, C4 and C7 | 1163 | WO2016154344A1 SEQ ID NO: 17 |
| AAV8 (with an AAV2 phospholipase domain) | 1164 | WO2016150403A1 SEQ ID NO: 13 |
| AAV VR-942n | 1165 | US20160289275A1 SEQ ID NO: 10 |
| AAV5-A (M569V) | 1166 | US20160289275A1 SEQ ID NO: 13 |
| AAV5-A (M569V) | 1167 | US20160289275A1 SEQ ID NO: 14 |
| AAV5-A (Y585V) | 1168 | US20160289275A1 SEQ ID NO: 16 |
| AAV5-A (Y585V) | 1169 | US20160289275A1 SEQ ID NO: 17 |
| AAV5-A (L587T) | 1170 | US20160289275A1 SEQ ID NO: 19 |
| AAV5-A (L587T) | 1171 | US20160289275A1 SEQ ID NO: 20 |
| AAV5-A (Y585V/L587T) | 1172 | US20160289275A1 SEQ ID NO: 22 |
| AAV5-A (Y585V/L587T) | 1173 | US20160289275A1 SEQ ID NO: 23 |
| AAV5-B (D652A) | 1174 | US20160289275A1 SEQ ID NO: 25 |
| AAV5-B (D652A) | 1175 | US20160289275A1 SEQ ID NO: 26 |
| AAV5-B (T362M) | 1176 | US20160289275A1 SEQ ID NO: 28 |
| AAV5-B (T362M) | 1177 | US20160289275A1 SEQ ID NO: 29 |
| AAV5-B (Q359D) | 1178 | US20160289275A1 SEQ ID NO: 31 |
| AAV5-B (Q359D) | 1179 | US20160289275A1 SEQ ID NO: 32 |
| AAV5-B (E350Q) | 1180 | US20160289275A1 SEQ ID NO: 34 |
| AAV5-B (E350Q) | 1181 | US20160289275A1 SEQ ID NO: 35 |
| AAV5-B (P533S) | 1182 | US20160289275A1 SEQ ID NO: 37 |
| AAV5-B (P533S) | 1183 | US20160289275A1 SEQ ID NO: 38 |
| AAV5-B (P533G) | 1184 | US20160289275A1 SEQ ID NO: 40 |
| AAV5-B (P533G) | 1185 | US20160289275A1 SEQ ID NO: 41 |
| AAV5-mutation in loop VII | 1186 | US20160289275A1 SEQ ID NO: 43 |
| AAV5-mutation in loop VII | 1187 | US20160289275A1 SEQ ID NO: 44 |
| AAV8 | 1188 | US20160289275A1 SEQ ID NO: 47 |
| Mut A (LK03/AAV8) | 1189 | WO2016181123A1 SEQ ID NO: 1 |
| Mut B (LK03/AAV5) | 1190 | WO2016181123A1 SEQ ID NO: 2 |
| Mut C (AAV8/AAV3B) | 1191 | WO2016181123A1 SEQ ID NO: 3 |
| Mut D (AAV5/AAV3B) | 1192 | WO2016181123A1 SEQ ID NO: 4 |
| Mut E (AAV8/AAV3B) | 1193 | WO2016181123A1 SEQ ID NO: 5 |
| Mut F (AAV3B/AAV8) | 1194 | WO2016181123A1 SEQ ID NO: 6 |
| AAV44.9 | 1195 | WO2016183297A1 SEQ ID NO: 4 |
| AAV44.9 | 1196 | WO2016183297A1 SEQ ID NO: 5 |

TABLE 1-continued

AAV Serotypes

| Serotype | SEQ ID NO | Reference Information |
|---|---|---|
| AAVrh8 | 1197 | WO2016183297A1 SEQ ID NO: 6 |
| AAV44.9 (S470N) | 1198 | WO2016183297A1 SEQ ID NO: 9 |
| rh74 VP1 | 1199 | US20160375110A1 SEQ ID NO: 1 |
| AAV-LK03 (L125I) | 1200 | WO2017015102A1 SEQ ID NO: 5 |
| AAV3B (S663V + T492V) | 1201 | WO2017015102A1 SEQ ID NO: 6 |
| Anc80 | 1202 | WO2017019994A2 SEQ ID NO: 1 |
| Anc80 | 1203 | WO2017019994A2 SEQ ID NO: 2 |
| Anc81 | 1204 | WO2017019994A2 SEQ ID NO: 3 |
| Anc81 | 1205 | WO2017019994A2 SEQ ID NO: 4 |
| Anc82 | 1206 | WO2017019994A2 SEQ ID NO: 5 |
| Anc82 | 1207 | WO2017019994A2 SEQ ID NO: 6 |
| Anc83 | 1208 | WO2017019994A2 SEQ ID NO: 7 |
| Anc83 | 1209 | WO2017019994A2 SEQ ID NO: 8 |
| Anc84 | 1210 | WO2017019994A2 SEQ ID NO: 9 |
| Anc84 | 1211 | WO2017019994A2 SEQ ID NO: 10 |
| Anc94 | 1212 | WO2017019994A2 SEQ ID NO: 11 |
| Anc94 | 1213 | WO2017019994A2 SEQ ID NO: 12 |
| Anc113 | 1214 | WO2017019994A2 SEQ ID NO: 13 |
| Anc113 | 1215 | WO2017019994A2 SEQ ID NO: 14 |
| Anc126 | 1216 | WO2017019994A2 SEQ ID NO: 15 |
| Anc126 | 1217 | WO2017019994A2 SEQ ID NO: 16 |
| Anc127 | 1218 | WO2017019994A2 SEQ ID NO: 17 |
| Anc127 | 1219 | WO2017019994A2 SEQ ID NO: 18 |
| Anc80L27 | 1220 | WO2017019994A2 SEQ ID NO: 19 |
| Anc80L59 | 1221 | WO2017019994A2 SEQ ID NO: 20 |
| Anc80L60 | 1222 | WO2017019994A2 SEQ ID NO: 21 |
| Anc80L62 | 1223 | WO2017019994A2 SEQ ID NO: 22 |
| Anc80L65 | 1224 | WO2017019994A2 SEQ ID NO: 23 |
| Anc80L33 | 1225 | WO2017019994A2 SEQ ID NO: 24 |
| Anc80L36 | 1226 | WO2017019994A2 SEQ ID NO: 25 |
| Anc80L44 | 1227 | WO2017019994A2 SEQ ID NO: 26 |
| Anc80L1 | 1228 | WO2017019994A2 SEQ ID NO: 35 |
| Anc80L1 | 1229 | WO2017019994A2 SEQ ID NO: 36 |
| AAVrh10 | 1230 | WO2017019994A2 SEQ ID NO: 41 |
| Anc110 | 1231 | WO2017019994A2 SEQ ID NO: 42 |
| Anc110 | 1232 | WO2017019994A2 SEQ ID NO: 43 |
| AAVrh32.33 | 1233 | WO2017019994A2 SEQ ID NO: 45 |
| AAVrh74 | 1234 | WO2017049031A1 SEQ ID NO: 1 |
| AAV2 | 1235 | WO2017053629A2 SEQ ID NO: 49 |
| AAV2 | 1236 | WO2017053629A2 SEQ ID NO: 50 |
| AAV2 | 1237 | WO2017053629A2 SEQ ID NO: 82 |
| Parvo-like virus | 1238 | WO2017070476A2 SEQ ID NO: 1 |
| Parvo-like virus | 1239 | WO2017070476A2 SEQ ID NO: 2 |
| Parvo-like virus | 1240 | WO2017070476A2 SEQ ID NO: 3 |
| Parvo-like virus | 1241 | WO2017070476A2 SEQ ID NO: 4 |
| Parvo-like virus | 1242 | WO2017070476A2 SEQ ID NO: 5 |
| Parvo-like virus | 1243 | WO2017070476A2 SEQ ID NO: 6 |
| AAVrh.10 | 1244 | WO2017070516A1 SEQ ID NO: 7 |
| AAVrh.10 | 1245 | WO2017070516A1 SEQ ID NO: 14 |
| AAV2tYF | 1246 | WO2017070491A1 SEQ ID NO: 1 |
| AAV-SPK | 1247 | WO2017075619A1 SEQ ID NO: 28 |
| AAV2.5 | 1248 | US20170128528A1 SEQ ID NO: 13 |
| AAV1.1 | 1249 | US20170128528A1 SEQ ID NO: 15 |
| AAV6.1 | 1250 | US20170128528A1 SEQ ID NO: 17 |
| AAV6.3.1 | 1251 | US20170128528A1 SEQ ID NO: 18 |
| AAV2i8 | 1252 | US20170128528A1 SEQ ID NO: 28 |
| AAV2i8 | 1253 | US20170128528A1 SEQ ID NO: 29 |
| ttAAV | 1254 | US20170128528A1 SEQ ID NO: 30 |
| ttAAV-S312N | 1255 | US20170128528A1 SEQ ID NO: 32 |
| ttAAV-S312N | 1256 | US20170128528A1 SEQ ID NO: 33 |
| AAV6 (Y705, Y731, and T492) | 1257 | WO2016134337A1 SEQ ID NO: 24 |
| AAV2 | 1258 | WO2016134375A1 SEQ ID NO: 9 |
| AAV2 | 1259 | WO2016134375A1 SEQ ID NO: 10 |

In one embodiment, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 135 and 136 respectively herein), PHP.B (SEQ ID NO: 8 and 9 of WO2015038958, herein SEQ ID NO: 3 and 4), G2B-13 (SEQ ID NO: 12 of WO2015038958, herein SEQ ID NO: 5), G2B-26 (SEQ ID NO: 13 of WO2015038958, herein SEQ ID NO: 3), TH1.1-32 (SEQ ID NO: 14 of WO2015038958, herein SEQ ID NO: 6), TH1.1-35 (SEQ ID NO: 15 of WO2015038958, herein SEQ ID NO: 7) or variants thereof. Further, any of the targeting peptides or amino acid inserts described in WO2015038958, may be inserted into any parent AAV serotype, such as, but not limited to, AAV9 (SEQ ID NO: 135 for the DNA sequence and SEQ ID NO: 136 for the amino acid sequence). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 1260), KFPVALT (SEQ ID NO: 3 of WO2015038958; herein SEQ ID NO: 1261), LAVPFK (SEQ ID NO: 31 of WO2015038958; herein SEQ ID NO: 1262), AVPFK (SEQ ID NO: 32 of WO2015038958; herein SEQ ID NO: 1263), VPFK (SEQ ID NO: 33 of WO2015038958; herein SEQ ID NO: 1264), TLAVPF (SEQ ID NO: 34 of WO2015038958; herein SEQ ID NO: 1265), TLAVP (SEQ ID NO: 35 of WO2015038958; herein SEQ ID NO: 1266), TLAV (SEQ ID NO: 36 of WO2015038958; herein SEQ ID NO: 1267), SVSKPFL (SEQ ID NO: 28 of WO2015038958; herein SEQ ID NO: 1268), FTLTTPK (SEQ ID NO: 29 of WO2015038958; herein SEQ ID NO: 1269), MNATKNV (SEQ ID NO: 30 of WO2015038958; herein SEQ ID NO: 1270), QSSQTPR (SEQ ID NO: 54 of WO2015038958; herein SEQ ID NO: 1271), ILGTGTS (SEQ ID NO: 55 of WO2015038958; herein SEQ ID NO: 1272), TRTNPEA (SEQ ID NO: 56 of WO2015038958; herein SEQ ID NO: 1273), NGGTSSS (SEQ ID NO: 58 of WO2015038958; herein SEQ ID NO: 1274), or YTLSQGW (SEQ ID NO: 60 of WO2015038958; herein SEQ ID NO: 1275). Non-limiting examples of nucleotide sequences that may encode the amino acid inserts include the following,

```
AAGTTTCCTGTGGCGTTGACT (for SEQ ID NO: 3 of
WO2015038958; herein SEQ ID NO: 1276), ACTTTGGCGGTGCCTTTTAAG (SEQ ID NO: 24 and 49 of
WO2015038958; herein SEQ ID NO: 1277), AGTGTGAGTAAGCCTTTTTTG (SEQ ID NO: 25 of
WO2015038958; herein SEQ ID NO: 1278), TTTACGTTGACGACGCCTAAG (SEQ ID NO: 26 of
WO2015038958; herein SEQ ID NO: 1279), ATGAATGCTACGAAGAATGTG
(SEQ ID NO: 27 of WO2015038958; herein
SEQ ID NO: 1280), CAGTCGTCGCAGACGCCTAGG (SEQ ID NO: 48 of
WO2015038958; herein SEQ ID NO: 1281), ATTCTGGGGACTGGTACTTCG (SEQ ID NO: 50 and 52 of
WO2015038958; herein SEQ ID NO: 1282), ACGCGGACTAATCCTGAGGCT (SEQ ID NO: 51 of
WO2015038958; herein SEQ ID NO: 1283), AATGGGGGACTAGTAGTTCT (SEQ ID NO: 53 of
WO2015038958; herein SEQ ID NO: 1284), or TATACTTTGTCGCAGGGTTGG (SEQ ID NO: 59 of
WO2015038958; herein SEQ ID NO: 1285).
```

In one embodiment, the AAV serotype may be, or may have a sequence as described in International Patent Publication WO2017100671, the contents of which are herein incorporated by reference in their entirety, such as, but not limited to, AAV9 (SEQ ID NO: 45 of WO2017100671, herein SEQ ID NO: 9), PHP.N (SEQ ID NO: 46 of WO2017100671, herein SEQ ID NO: 2), PHP.S (SEQ ID NO: 47 of WO2017100671, herein SEQ ID NO: 8), or variants thereof. Further, any of the targeting peptides or amino acid inserts described in WO2017100671 may be inserted into any parent AAV serotype, such as, but not limited to, AAV9 (SEQ ID NO: 9 or SEQ ID NO: 131). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, AQTLAVPFKAQ (SEQ ID NO: 1 of WO2017100671; herein SEQ ID NO: 1286), AQSVSKPFLAQ (SEQ ID NO: 2 of WO2017100671; herein SEQ ID NO: 1287), AQFTLTTPKAQ (SEQ ID NO: 3 in the sequence listing of WO2017100671; herein SEQ ID NO: 1288), DGTLAVPFKAQ (SEQ ID NO: 4 in the sequence listing of WO2017100671; herein SEQ ID NO: 1289), ESTLAVPFKAQ (SEQ ID NO: 5 of WO2017100671; herein SEQ ID NO: 1290), GGTLAVPFKAQ (SEQ ID NO: 6 of WO2017100671; herein SEQ ID NO: 1291), AQTLATPFKAQ (SEQ ID NO: 7 and 33 of WO2017100671; herein SEQ ID NO: 1292), ATTLATPFKAQ (SEQ ID NO: 8 of WO2017100671; herein SEQ ID NO: 1293), DGTLATPFKAQ (SEQ ID NO: 9 of WO2017100671; herein SEQ ID NO: 1294), GGTLATPFKAQ (SEQ ID NO: 10 of WO2017100671; herein SEQ ID NO: 1295), SGSLAVPFKAQ (SEQ ID NO: 11 of WO2017100671; herein SEQ ID NO: 1296), AQTLAQPFKAQ (SEQ ID NO: 12 of WO2017100671; herein SEQ ID NO: 1297), AQTLQQPFKAQ (SEQ ID NO: 13 of WO2017100671; herein SEQ ID NO: 1298), AQTLSNPFKAQ (SEQ ID NO: 14 of WO2017100671; herein SEQ ID NO: 1299), AQTLAVPFSNP (SEQ ID NO: 15 of WO2017100671; herein SEQ ID NO: 1300), QGTLAVPFKAQ (SEQ ID NO: 16 of WO2017100671; herein SEQ ID NO: 1301), NQTLAVPFKAQ (SEQ ID NO: 17 of WO2017100671; herein SEQ ID NO: 1302), EGSLAVPFKAQ (SEQ ID NO: 18 of WO2017100671; herein SEQ ID NO: 1303), SGNLAVPFKAQ (SEQ ID NO: 19 of WO2017100671; herein SEQ ID NO: 1304), EGTLAVPFKAQ (SEQ ID NO: 20 of WO2017100671; herein SEQ ID NO: 1305), DSTLAVPFKAQ (SEQ ID NO: 21 in Table 1 of WO2017100671; herein SEQ ID NO: 1306), AVTLAVPFKAQ (SEQ ID NO: 22 of WO2017100671; herein SEQ ID NO: 1307), AQTLSTPFKAQ (SEQ ID NO: 23 of WO2017100671; herein SEQ ID NO: 1308), AQTLPQPFKAQ (SEQ ID NO: 24 and 32 of WO2017100671; herein SEQ ID NO: 1309), AQTLSQPFKAQ (SEQ ID NO: 25 of WO2017100671; herein SEQ ID NO: 1310), AQTLQLPFKAQ (SEQ ID NO: 26 of WO2017100671; herein SEQ ID NO: 1311), AQTLTMPFKAQ (SEQ ID NO: 27, and 34 of WO2017100671 and SEQ ID NO: 35 in the sequence listing of WO2017100671; herein SEQ ID NO: 1312), AQTLTTPFKAQ (SEQ ID NO: 28 of WO2017100671; herein SEQ ID NO: 1313), AQYTLSQGWAQ (SEQ ID NO: 29 of WO2017100671; herein SEQ ID NO: 1314), AQMNATKNVAQ (SEQ ID NO: 30 of WO2017100671; herein SEQ ID NO: 1315), AQVSGGHHSAQ (SEQ ID NO: 31 of WO2017100671; herein SEQ ID NO: 1316), AQTLTAPFKAQ (SEQ ID NO: 35 in Table 1 of WO2017100671; herein SEQ ID NO: 1317), AQTLSKPFKAQ (SEQ ID NO: 36 of WO2017100671; herein SEQ ID NO: 1318), QAVRTSL (SEQ ID NO: 37 of WO2017100671; herein SEQ ID NO: 1319), YTLSQGW (SEQ ID NO: 38 of WO2017100671; herein SEQ ID NO: 1275), LAKERLS (SEQ ID NO: 39 of WO2017100671; herein SEQ ID NO: 1320), TLAVPFK (SEQ ID NO: 40 in the sequence listing of WO2017100671; herein SEQ ID NO: 1260), SVSKPFL (SEQ ID NO: 41 of WO2017100671; herein SEQ ID NO: 1268), FTLTTPK (SEQ ID NO: 42 of WO2017100671;

herein SEQ ID NO: 1269), MNSTKNV (SEQ ID NO: 43 of WO2017100671; herein SEQ ID NO: 1321), VSGGHHS (SEQ ID NO: 44 of WO2017100671; herein SEQ ID NO: 1322), SAQTLAVPFKAQAQ (SEQ ID NO: 48 of WO2017100671; herein SEQ ID NO: 1323), SXXXLAVPFKAQAQ (SEQ ID NO: 49 of WO2017100671 wherein X may be any amino acid; herein SEQ ID NO: 1324), SAQXXXVPFKAQAQ (SEQ ID NO: 50 of WO2017100671 wherein X may be any amino acid; herein SEQ ID NO: 1325), SAQTLXXXFKAQAQ (SEQ ID NO: 51 of WO2017100671 wherein X may be any amino acid; herein SEQ ID NO: 1326), SAQTLAVXXXAQAQ (SEQ ID NO: 52 of WO2017100671 wherein X may be any amino acid; herein SEQ ID NO: 1327), SAQTLAVPFXXXAQ (SEQ ID NO: 53 of WO2017100671 wherein X may be any amino acid; herein SEQ ID NO: 1328), TNHQSAQ (SEQ ID NO: 65 of WO2017100671; herein SEQ ID NO: 1329), AQAQTGW (SEQ ID NO: 66 of WO2017100671; herein SEQ ID NO: 1330), DGTLATPFK (SEQ ID NO: 67 of WO2017100671; herein SEQ ID NO: 1331), DGTLATPFKXX (SEQ ID NO: 68 of WO2017100671 wherein X may be any amino acid; herein SEQ ID NO: 1332), LAVPFKAQ (SEQ ID NO: 80 of WO2017100671; herein SEQ ID NO: 1333), VPFKAQ (SEQ ID NO: 81 of WO2017100671; herein SEQ ID NO: 1334), FKAQ (SEQ ID NO: 82 of WO2017100671; herein SEQ ID NO: 1335), AQTLAV (SEQ ID NO: 83 of WO2017100671; herein SEQ ID NO: 1336), AQTLAVPF (SEQ ID NO: 84 of WO2017100671; herein SEQ ID NO: 1337), QAVR (SEQ ID NO: 85 of WO2017100671; herein SEQ ID NO: 1338), AVRT (SEQ ID NO: 86 of WO2017100671; herein SEQ ID NO: 1339), VRTS (SEQ ID NO: 87 of WO2017100671; herein SEQ ID NO: 1340), RTSL (SEQ ID NO: 88 of WO2017100671; herein SEQ ID NO: 1341), QAVRT (SEQ ID NO: 89 of WO2017100671; herein SEQ ID NO: 1342), AVRTS (SEQ ID NO: 90 of WO2017100671; herein SEQ ID NO: 1343), VRTSL (SEQ ID NO: 91 of WO2017100671; herein SEQ ID NO: 1344), QAVRTS (SEQ ID NO: 92 of WO2017100671; herein SEQ ID NO: 1345), or AVRTSL (SEQ ID NO: 93 of WO2017100671; herein SEQ ID NO: 1346).

Non-limiting examples of nucleotide sequences that may encode the amino acid inserts include the following, GATGGGACTTTGGCGGTGCCTTTAAGGCACAG (SEQ ID NO: 54 of WO2017100671; herein SEQ ID NO: 1347), GATGGGACGTTGGCGGTGCCTTTTAAGGCACAG (SEQ ID NO: 55 of WO2017100671; herein SEQ ID NO: 1348), CAGGCGGTTAGGACGTCTTTG (SEQ ID NO: 56 of WO2017100671; herein SEQ ID NO: 1349), CAGGTCTTCACGGACTCAGACTATCAG (SEQ ID NO: 57 and 78 of WO2017100671; herein SEQ ID NO: 1350), CAAGTAAAACCTCTACAAATGTGGTAAAATCG (SEQ ID NO: 58 of WO2017100671; herein SEQ ID NO: 1351), ACTCATCGACCAATACTTGTACTATCTCTCTAGAAC (SEQ ID NO: 59 of WO2017100671; herein SEQ ID NO: 1352), GGAAGTATTCCTTGGTTTTGAACCCA (SEQ ID NO: 60 of WO2017100671; herein SEQ ID NO: 1353), GGTCGCGGTTCTTGTTTGTGGAT (SEQ ID NO: 61 of WO2017100671; herein SEQ ID NO: 1354), CGACCTTGAAGCGCATGAACTCCT (SEQ ID NO: 62 of WO2017100671; herein SEQ ID NO: 1355), GTATTCCTTGGTTTTGAACCCAACCGGTCTGCGCCTGTGCMNNMNNMNNMNNMNNMNNMNNTTGGGCACTCTGGTGGMGTC (SEQ ID NO: 63 of WO2017100671 wherein N may be A, C, T, or G; herein SEQ ID NO: 1356), GTATTCCTTGGTTTTGAACCCAACCGGTCTGCGCMNNMNNMNNAAAAGGCACCG CCAAAGTTTG (SEQ ID NO: 69 of WO2017100671 wherein N may be A, C, T, or G; herein SEQ ID NO: 1357), GTATTCCTTGGTTTTGAACCCAACCGGTCTGCGCCTGTGCMNNMNNMNNCACCG CCAAAGTTTGGGCACT (SEQ ID NO: 70 of WO2017100671 wherein N may be A, C, T, or G; herein SEQ ID NO: 1358), GTATTCCTTGGTTTTGAACCCAACCGGTCTGCGCCTGTGCCTTAAAMNNMNNMN NCAAAGTTTGGGCACTCTGGTGG (SEQ ID NO: 71 of WO2017100671 wherein N may be A, C, T, or G; herein SEQ ID NO: 1359), GTATTCCTTGGTTTTGAACCCAACCGGTCTGCGCCTGTGCCTTAAAAGGCACMNN MNNMNNTTGGGCACTCTGGTGGTTTGTG (SEQ ID NO: 72 of WO2017100671 wherein N may be A, C, T, or G; herein SEQ ID NO: 1360), ACTTTGGCGGTGCCTTTTAAG (SEQ ID NO: 74 of WO2017100671; herein SEQ ID NO: 1277), AGTGTGAGTAAGCCTTTTTG (SEQ ID NO: 75 of WO2017100671; herein SEQ ID NO: 1278), TTTACGTTGACGACGCCTAAG (SEQ ID NO: 76 of WO2017100671; herein SEQ ID NO: 1279), TATACTTTGTCGCAGGGTTGG (SEQ ID NO: 77 of WO2017100671; herein SEQ ID NO: 1285), or CTTGCGAAGGAGCGGCTTTCG (SEQ ID NO: 79 of WO2017100671; herein SEQ ID NO: 1361).

In one embodiment, the AAV serotype may be, or may have a sequence as described in U.S. Pat. No. 9,624,274, the contents of which are herein incorporated by reference in their entirety, such as, but not limited to, AAV1 (SEQ ID NO: 181 of U.S. Pat. No. 9,624,274), AAV6 (SEQ ID NO: 182 of U.S. Pat. No. 9,624,274), AAV2 (SEQ ID NO: 183 of U.S. Pat. No. 9,624,274), AAV3b (SEQ ID NO: 184 of U.S. Pat. No. 9,624,274), AAV7 (SEQ ID NO: 185 of U.S. Pat. No. 9,624,274), AAV8 (SEQ ID NO: 186 of U.S. Pat. No. 9,624,274), AAV10 (SEQ ID NO: 187 of U.S. Pat. No. 9,624,274), AAV4 (SEQ ID NO: 188 of U.S. Pat. No. 9,624,274), AAV11 (SEQ ID NO: 189 of U.S. Pat. No. 9,624,274), bAAV (SEQ ID NO: 190 of U.S. Pat. No. 9,624,274), AAV5 (SEQ ID NO: 191 of U.S. Pat. No. 9,624,274), GPV (SEQ ID NO: 192 of U.S. Pat. No. 9,624,274; herein SEQ ID NO: 992), B19 (SEQ ID NO: 193 of U.S. Pat. No. 9,624,274; herein SEQ ID NO: 993), MVM (SEQ ID NO: 194 of U.S. Pat. No. 9,624,274; herein SEQ ID NO: 994), FPV (SEQ ID NO: 195 of U.S. Pat. No. 9,624,274; herein SEQ ID NO: 995), CPV (SEQ ID NO: 196 of U.S. Pat. No. 9,624,274; herein SEQ ID NO: 996) or variants thereof. Further, any of the structural protein inserts described in U.S. Pat. No. 9,624,274, may be inserted into, but not limited to, I-453 and I-587 of any parent AAV serotype, such as, but not limited to, AAV2 (SEQ ID NO: 183 of U.S. Pat. No. 9,624,274). The amino acid insert may be, but is not limited to, any of the following amino acid sequences, VNLTWSRASG (SEQ ID NO: 50 of U.S. Pat. No. 9,624,274; herein SEQ ID NO: 1362), EFCINHRGYWVCGD (SEQ ID NO:55 of U.S. Pat. No. 9,624,274; herein SEQ ID NO: 1363), EDGQVMDVDLS (SEQ ID NO: 85 of U.S. Pat. No. 9,624,274; herein SEQ ID NO: 1364), EKQRNGTLT (SEQ ID NO: 86 of U.S. Pat. No. 9,624,274; herein SEQ ID NO: 1365), TYQCRVTHPHLPRALMR (SEQ ID NO: 87 of U.S. Pat. No. 9,624,274; herein SEQ ID NO: 1366), RHSTTQPRKTKGSG (SEQ ID NO: 88 of U.S. Pat. No. 9,624,274; herein SEQ ID NO: 1367), DSNPRGVSAYLSR (SEQ ID NO: 89 of U.S. Pat. No. 9,624,274; herein SEQ ID NO: 1368), TITCLWDLAPSK (SEQ ID NO: 90 of U.S. Pat. No. 9,624,274; herein SEQ ID NO: 1369), KTKGSGFFVF (SEQ ID NO: 91 of U.S. Pat. No. 9,624,274; herein SEQ ID NO: 1370), THPHLPRALMRS (SEQ ID NO: 92 of U.S. Pat. No. 9,624,274; herein SEQ ID NO: 1371), GETYQCRVTHPHLPRALMRSTTK (SEQ ID NO: 93 of U.S. Pat. No. 9,624,274; herein SEQ ID NO: 1372), LPRALMRS (SEQ ID NO: 94 of U.S. Pat. No. 9,624,274; herein SEQ ID NO: 1373), INHRGYWV (SEQ ID NO: 95 of U.S. Pat. No. 9,624,274; herein SEQ ID NO: 1374), CDAGSVRTNAPD (SEQ ID NO: 60 of U.S. Pat. No. 9,624,274; herein SEQ ID NO: 1375), AKAVSNLTESRSESLQS (SEQ ID NO: 96 of U.S. Pat. No. 9,624,274; herein SEQ ID NO: 1376), SLTGDEFKKVLET (SEQ ID NO: 97 of U.S. Pat. No. 9,624,274; herein SEQ ID NO: 1377), REAVAYRFEED (SEQ ID NO: 98 of U.S. Pat. No. 9,624,274; herein SEQ ID NO: 1378), INPEIITLDG (SEQ ID NO: 99 of U.S. Pat. No. 9,624,274; herein SEQ ID NO: 1379), DISVTGAPVITATYL (SEQ ID NO: 100 of U.S. Pat. No. 9,624,274; herein SEQ ID NO: 1380), DISVTGAPVITA (SEQ ID NO: 101 of U.S. Pat. No. 9,624,274; herein SEQ ID NO: 1381), PKTVSNLTESSSESVQS (SEQ ID NO: 102 of U.S. Pat. No. 9,624,274; herein SEQ ID NO: 1382), SLMGDEFKAVLET (SEQ ID NO: 103 of U.S. Pat. No. 9,624,274; herein SEQ ID NO: 1383), QHSVAYTFEED (SEQ ID NO: 104 of U.S. Pat. No. 9,624,274; herein SEQ ID NO: 1384), INPEIITRDG (SEQ ID NO: 105 of U.S. Pat. No. 9,624,274; herein SEQ ID NO: 1385), DISLTGDPVITASYL (SEQ ID NO: 106 of U.S. Pat. No. 9,624,274; herein SEQ ID NO: 1386), DISLTGDPVITA (SEQ ID NO: 107 of U.S. Pat. No. 9,624,274; herein SEQ ID NO: 1387), DQSIDFEIDSA (SEQ ID NO: 108 of U.S. Pat. No. 9,624,274; herein SEQ ID NO: 1388), KNVSEDLPLPTFSPTLLGDS (SEQ ID NO: 109 of U.S. Pat. No. 9,624,274; herein SEQ ID NO: 1389), KNVSEDLPLPT (SEQ ID NO: 110 of U.S. Pat. No. 9,624,274; herein SEQ ID NO: 1390), CDSGRVRTDAPD (SEQ ID NO: 111 of U.S. Pat. No. 9,624,274; herein SEQ ID NO: 1391), FPEHLLVDFLQSLS (SEQ ID NO: 112 of U.S. Pat. No. 9,624,274; herein SEQ ID NO: 1392), DAEFRHDSG (SEQ ID NO: 65 of U.S. Pat. No. 9,624,274; herein SEQ ID NO: 1393), HYAAAQWDFGNTMCQL (SEQ ID NO: 113 of U.S. Pat. No. 9,624,274; herein SEQ ID NO: 1394), YAAQWDFGNTMCQ (SEQ ID NO: 114 of U.S. Pat. No. 9,624,274; herein SEQ ID NO: 1395), RSQKEGLHYT (SEQ ID NO: 115 of U.S. Pat. No. 9,624,274; herein SEQ ID NO: 1396), SSRTPSDKPVAHWANPQAE (SEQ ID NO: 116 of U.S. Pat. No. 9,624,274; herein SEQ ID NO: 1397), SRTPSDKPVAHWANP (SEQ ID NO: 117 of U.S. Pat. No. 9,624,274; herein SEQ ID NO: 1398), SSRTPSDKP (SEQ ID NO: 118 of U.S. Pat. No. 9,624,274; herein SEQ ID NO: 1399), NADGNVDYHMNSVP (SEQ ID NO: 119 of U.S. Pat. No. 9,624,274; herein SEQ ID NO: 1400), DGNVDYHMNSV (SEQ ID NO: 120 of U.S. Pat. No. 9,624,274; herein SEQ ID NO: 1401), RSFKEFLQSSLRALRQ (SEQ ID NO: 121 of U.S. Pat. No. 9,624,274; herein SEQ ID NO: 1402); FKEFLQSSLRA (SEQ ID NO: 122 of U.S. Pat. No. 9,624,274; herein SEQ ID NO: 1403), or QMWAPQWGPD (SEQ ID NO: 123 of U.S. Pat. No. 9,624,274; herein SEQ ID NO: 1404).

In one embodiment, the AAV serotype may be, or may have a sequence as described in U.S. Pat. No. 9,475,845, the contents of which are herein incorporated by reference in their entirety, such as, but not limited to, AAV capsid proteins comprising modification of one or more amino acids at amino acid positions 585 to 590 of the native AAV2 capsid protein. Further the modification may result in, but not limited to, the amino acid sequence RGNRQA (SEQ ID NO: 3 of U.S. Pat. No. 9,475,845; herein SEQ ID NO: 1405), SSSTDP (SEQ ID NO: 4 of U.S. Pat. No. 9,475,845; herein SEQ ID NO: 1406), SSNTAP (SEQ ID NO: 5 of U.S. Pat. No. 9,475,845; herein SEQ ID NO: 1407), SNSNLP (SEQ ID NO: 6 of U.S. Pat. No. 9,475,845; herein SEQ ID NO: 1408), SSTTAP (SEQ ID NO: 7 of U.S. Pat. No. 9,475,845; herein SEQ ID NO: 1409), AANTAA (SEQ ID NO: 8 of U.S. Pat. No. 9,475,845; herein SEQ ID NO: 1410), QQNTAP (SEQ ID NO: 9 of U.S. Pat. No. 9,475,845; herein SEQ ID NO: 1411), SAQAQA (SEQ ID NO: 10 of U.S. Pat. No. 9,475,845; herein SEQ ID NO: 1412), QANTGP (SEQ ID NO: 11 of U.S. Pat. No. 9,475,845; herein SEQ ID NO: 1413), NATTAP (SEQ ID NO: 12 of U.S. Pat. No. 9,475,845; herein SEQ ID NO: 1414), SSTAGP (SEQ ID NO: 13 and 20 of U.S. Pat. No. 9,475,845; herein SEQ ID NO: 1415), QQNTAA (SEQ ID NO: 14 of U.S. Pat. No. 9,475,845; herein SEQ ID NO: 1416), PSTAGP (SEQ ID NO: 15 of U.S. Pat. No. 9,475,845; herein SEQ ID NO: 1417), NQNTAP (SEQ ID NO: 16 of U.S. Pat. No. 9,475,845; herein SEQ ID NO: 1418), QAANAP (SEQ ID NO: 17 of U.S. Pat. No. 9,475,845; herein SEQ ID NO: 1419), SIVGLP (SEQ ID NO: 18 of U.S. Pat. No. 9,475,845; herein SEQ ID NO: 1420), AASTAA (SEQ ID NO: 19, and 27 of U.S. Pat. No. 9,475,845; herein SEQ ID NO: 1421), SQNTTA (SEQ ID NO: 21 of U.S. Pat. No. 9,475,845; herein SEQ ID NO: 1422), QQDTAP (SEQ ID NO: 22 of U.S. Pat. No. 9,475,845; herein SEQ ID NO: 1423), QTNTGP (SEQ ID NO: 23 of U.S. Pat. No. 9,475,845; herein SEQ ID NO: 1424), QTNGAP (SEQ ID NO: 24 of U.S. Pat. No. 9,475,845; herein SEQ ID NO: 1425), QQNAAP (SEQ ID NO: 25 of U.S. Pat. No. 9,475,845; herein SEQ ID NO: 1426), or AANTQA (SEQ ID NO: 26 of U.S. Pat. No. 9,475,845; herein SEQ ID NO: 1427). In one embodiment, the amino acid modification is a substitution at amino acid positions 262 through 265 in the native AAV2 capsid protein or the corresponding position in the capsid protein of another AAV with a targeting sequence. The targeting sequence may be, but is not limited to, any of the amino acid sequences, NGRAHA (SEQ ID NO: 38 of U.S. Pat. No. 9,475,845; herein SEQ ID NO: 1428), QPEHSST (SEQ ID NO: 39 and 50 of U.S. Pat. No. 9,475,845; herein SEQ ID NO: 1429), VNTANST (SEQ ID NO: 40 of U.S. Pat. No. 9,475,845; herein SEQ ID NO: 1430), HGPMQKS (SEQ ID NO: 41 of U.S. Pat. No. 9,475,845; herein SEQ ID NO: 1431), PHKPPLA (SEQ ID NO: 42 of U.S. Pat. No. 9,475,845; herein SEQ ID NO: 1432), IKNNEMW (SEQ ID NO: 43 of U.S. Pat. No. 9,475,845; herein SEQ ID NO: 1433), RNLDTPM (SEQ ID NO: 44 of U.S. Pat. No. 9,475,845; herein SEQ ID NO: 1434), VDSHRQS (SEQ ID NO: 45 of U.S. Pat. No. 9,475,845; herein SEQ ID NO: 1435), YDSKTKT (SEQ ID NO: 46 of U.S. Pat. No. 9,475,845; herein SEQ ID NO: 1436), SQLPHQK (SEQ ID NO: 47 of U.S. Pat. No. 9,475,845; herein SEQ ID NO: 1437), STMQQNT (SEQ ID NO: 48 of U.S. Pat. No. 9,475,845; herein SEQ ID NO: 1438), TERYMTQ (SEQ ID NO: 49 of U.S. Pat. No. 9,475,845; herein SEQ ID NO: 1439), DASLSTS (SEQ ID NO: 51 of U.S. Pat. No. 9,475,845; herein SEQ ID NO: 1440), DLPNKKT (SEQ ID NO: 52 of U.S. Pat. No. 9,475,845; herein SEQ ID NO: 1441), DLTAARL (SEQ ID NO: 53 of U.S. Pat. No. 9,475,845; herein SEQ ID NO: 1442), EPHQFNY (SEQ ID NO: 54 of U.S. Pat. No. 9,475,845; herein SEQ ID NO: 1443), EPQSNHT (SEQ ID NO: 55 of U.S. Pat. No. 9,475,845; herein SEQ ID NO: 1444), MSSWPSQ (SEQ ID NO: 56 of U.S. Pat. No. 9,475,845; herein SEQ ID NO: 1445), NPKHNAT (SEQ ID NO: 57 of U.S. Pat. No. 9,475,845; herein SEQ ID NO: 1446), PDGMRTT (SEQ ID NO: 58 of U.S. Pat. No. 9,475,845; herein SEQ ID NO: 1447), PNNNKTT (SEQ ID NO: 59 of U.S. Pat. No. 9,475,845; herein SEQ ID NO: 1448), QSTTHDS (SEQ ID NO: 60 of U.S. Pat. No. 9,475,845; herein SEQ ID NO: 1449), TGSKQKQ (SEQ ID NO: 61 of U.S. Pat. No. 9,475,845; herein SEQ ID NO: 1450), SLKHQAL (SEQ ID NO: 62 of U.S. Pat. No. 9,475,845; herein SEQ ID NO: 1451), SPIDGEQ (SEQ ID NO: 63 of U.S. Pat. No. 9,475,845; herein SEQ ID NO: 1452), WIFPWIQL (SEQ ID NO: 64 and 112 of U.S. Pat. No. 9,475,845; herein SEQ ID NO: 1453), CDCRGDCFC (SEQ ID NO: 65 of U.S. Pat. No. 9,475,845; herein SEQ ID NO: 1454), CNGRC (SEQ ID NO: 66 of U.S. Pat. No. 9,475,845; herein SEQ ID NO: 1455), CPRECES (SEQ ID NO: 67 of U.S. Pat. No. 9,475,845; herein SEQ ID NO: 1456), CTTHWGFTLC (SEQ ID NO: 68 and 123 of U.S. Pat. No. 9,475,845; herein SEQ ID NO: 1457), CGRRAGGSC (SEQ ID NO: 69 of U.S. Pat. No. 9,475,845; herein SEQ ID NO: 1458), CKGGRAKDC (SEQ ID NO: 70 of U.S. Pat. No. 9,475,845; herein SEQ ID NO: 1459), CVPELGHEC (SEQ ID NO: 71 and 115 of U.S. Pat. No. 9,475,845; herein SEQ ID NO: 1460), CRRETAWAK (SEQ ID NO: 72 of U.S. Pat. No. 9,475,845; herein SEQ ID NO: 1461), VSWFSHRYSPFAVS (SEQ ID NO: 73 of U.S. Pat. No. 9,475,845; herein SEQ ID NO: 1462), GYRDGYAGPILYN (SEQ ID NO: 74 of U.S. Pat. No. 9,475,845; herein SEQ ID NO: 1463), XXXYXXX (SEQ ID NO: 75 of U.S. Pat. No. 9,475,845; herein SEQ ID NO: 1464), YXNW (SEQ ID NO: 76 of U.S. Pat. No. 9,475,845; herein SEQ ID NO: 1465), RPLPPLP (SEQ ID NO: 77 of U.S. Pat. No. 9,475,845; herein SEQ ID NO: 1466), APPLPPR (SEQ ID NO: 78 of U.S. Pat. No. 9,475,845; herein SEQ ID NO: 1467), DVFYPYPYASGS (SEQ ID NO: 79 of U.S. Pat. No. 9,475,845; herein SEQ ID NO: 1468), MYWYPY (SEQ ID NO: 80 of U.S. Pat. No. 9,475,845; herein SEQ ID NO: 1469), DITWDQLWDLMK (SEQ ID NO: 81 of U.S. Pat. No. 9,475,845; herein SEQ ID NO: 1470), CWDDXWLC (SEQ ID NO: 82 of U.S. Pat. No. 9,475,845; herein SEQ ID NO: 1471), EWCEYLGGYLRCYA (SEQ ID NO: 83 of U.S. Pat. No. 9,475,845; herein SEQ ID NO: 1472), YXCXXGPXTWXCXP (SEQ ID NO: 84 of U.S. Pat. No. 9,475,845; herein SEQ ID NO: 1473), IEGPTLRQWLAARA (SEQ ID NO: 85 of U.S. Pat. No. 9,475,845; herein SEQ ID NO: 1474), LWXXX (SEQ ID NO: 86 of U.S. Pat. No. 9,475,845; herein SEQ ID NO: 1475), XFXXYLW (SEQ ID NO: 87 of U.S. Pat. No. 9,475,845; herein SEQ ID NO: 1476), SSIISHFRWGLCD (SEQ ID NO: 88 of U.S. Pat. No. 9,475,845; herein SEQ ID NO: 1477), MSRPACPPNDKYE (SEQ ID NO: 89 of U.S. Pat. No. 9,475,845; herein SEQ ID NO: 1478), CLRSGRGC (SEQ ID NO: 90 of U.S. Pat. No. 9,475,845; herein SEQ ID NO: 1479), CHWMFSPWC (SEQ ID NO: 91 of U.S. Pat. No. 9,475,845; herein SEQ ID NO: 1480), WXXF (SEQ ID NO: 92 of U.S. Pat. No. 9,475,845; herein SEQ ID NO: 1481), CSSRLDAC (SEQ ID NO: 93 of U.S. Pat. No. 9,475,845; herein SEQ ID NO: 1482), CLPVASC (SEQ ID NO: 94 of U.S. Pat. No. 9,475,845; herein SEQ ID NO: 1483), CGFECVRQCPERC (SEQ ID NO: 95 of U.S. Pat. No. 9,475,845; herein SEQ ID NO: 1484), CVALCREACGEGC (SEQ ID NO: 96 of U.S. Pat. No. 9,475,845; herein SEQ ID NO: 1485), SWCEPGWCR (SEQ ID NO: 97 of U.S. Pat. No. 9,475,845; herein SEQ ID NO: 1486), YSGKWGW (SEQ ID NO: 98 of U.S. Pat. No. 9,475,845; herein SEQ ID NO: 1487), GLSGGRS (SEQ ID NO: 99 of U.S. Pat. No. 9,475,845; herein SEQ ID NO: 1488), LMLPRAD (SEQ ID NO: 100 of U.S. Pat. No. 9,475,845; herein SEQ ID NO: 1489), CSCFRDVCC (SEQ ID NO: 101 of U.S. Pat. No. 9,475,845; herein SEQ ID NO: 1490), CRDVVSVIC (SEQ ID NO: 102 of U.S. Pat. No. 9,475,845; herein SEQ ID NO: 1491), MARSGL (SEQ ID NO: 103 of U.S. Pat. No. 9,475,845; herein SEQ ID NO: 1492), MARAKE (SEQ ID NO: 104 of U.S. Pat. No. 9,475,845; herein SEQ ID NO: 1493), MSRTMS (SEQ ID NO: 105 of U.S. Pat. No. 9,475,845; herein SEQ ID NO: 1494), KCCYSL (SEQ ID NO: 106 of U.S. Pat. No. 9,475,845; herein SEQ ID NO: 1495), MYWGDSHWLQYWYE (SEQ ID NO: 107 of U.S. Pat. No. 9,475,845; herein SEQ ID NO: 1496), MQLPLAT (SEQ ID NO: 108 of U.S. Pat. No. 9,475,845; herein SEQ ID NO: 1497), EWLS (SEQ ID NO: 109 of U.S. Pat. No. 9,475,845; herein SEQ ID NO: 1498), SNEW (SEQ ID NO: 110 of U.S. Pat. No. 9,475,845; herein SEQ ID NO: 1499), TNYL (SEQ ID NO: 111 of U.S. Pat. No. 9,475,845; herein SEQ ID NO: 1500), WDLAWMFRLPVG (SEQ ID NO: 113 of U.S. Pat. No. 9,475,845; herein SEQ ID NO: 1501), CTVALPGGYVRVC (SEQ ID NO: 114 of U.S. Pat. No. 9,475,845; herein SEQ ID NO: 1502), CVAYCIEHHCWTC (SEQ ID NO: 116 of U.S. Pat. No. 9,475,845; herein SEQ ID NO: 1503), CVFAHNYDYLVC (SEQ ID NO: 117 of U.S. Pat. No. 9,475,845; herein SEQ ID NO: 1504), CVFTSNYAFC (SEQ ID NO: 118 of U.S. Pat. No. 9,475,845; herein SEQ ID NO: 1505), VHSPNKK (SEQ ID NO: 119 of U.S. Pat. No. 9,475,845; herein SEQ ID NO: 1506), CRGDGWC (SEQ ID NO: 120 of U.S. Pat. No. 9,475,845; herein SEQ ID NO: 1507), XRGCDX (SEQ ID NO: 121 of U.S. Pat. No. 9,475,845; herein SEQ ID NO: 1508), PXXX (SEQ ID NO: 122 of U.S. Pat. No. 9,475,845; herein SEQ ID NO: 1509), SGKGPRQITAL (SEQ ID NO: 124 of U.S. Pat. No. 9,475,845; herein SEQ ID NO: 1510), AAAAAAAAAXXXXX (SEQ ID NO: 125 of U.S. Pat. No. 9,475,845; herein SEQ ID NO: 1511), VYMSPF (SEQ ID NO: 126 of U.S. Pat. No. 9,475,845; herein SEQ ID NO: 1512), ATWLPPR (SEQ ID NO: 127 of U.S. Pat. No. 9,475,845; herein SEQ ID NO: 1513), HTMYYHHYQHHL (SEQ ID NO: 128 of U.S. Pat. No. 9,475,845; herein SEQ ID NO: 1514), SEVGCRAGPLQWLCEKYFG (SEQ ID NO: 129 of U.S. Pat. No. 9,475,845; herein SEQ ID NO: 1515), CGLLPVGRPDRNVWRWLC (SEQ ID NO: 130 of U.S. Pat. No. 9,475,845; herein SEQ ID NO: 1516), CKGQCDRFKGLPWEC (SEQ ID NO: 131 of U.S. Pat. No. 9,475,845; herein SEQ ID NO: 1517), SGRSA (SEQ ID NO: 132 of U.S. Pat. No. 9,475,845; herein SEQ ID NO: 1518), WGFP (SEQ ID NO: 133 of U.S. Pat. No. 9,475,845; herein SEQ ID NO: 1519), AEPMPHSLNFSQYLWYT (SEQ ID NO: 134 of U.S. Pat. No. 9,475,845; herein SEQ ID NO: 1520), WAYXSP (SEQ ID NO: 135 of U.S. Pat. No. 9,475,845; herein SEQ ID NO: 1521), IELLQAR (SEQ ID NO: 136 of U.S. Pat. No. 9,475,845; herein SEQ ID NO: 1522), AYTKCSRQWRTCMTTH (SEQ ID NO: 137 of U.S. Pat. No. 9,475,845; herein SEQ ID NO: 1523), PQNSKIPGPTFLDPH (SEQ ID NO: 138 of U.S. Pat. No. 9,475,845; herein SEQ ID NO: 1524), SMEPALPDWWWKMFK (SEQ ID NO: 139 of U.S. Pat. No. 9,475,845; herein SEQ ID NO: 1525), ANTPCGPYTHDCPVKR (SEQ ID NO: 140 of U.S. Pat. No. 9,475,845; herein SEQ ID NO: 1526), TACHQHVRMVRP (SEQ ID NO: 141 of U.S. Pat. No. 9,475,845; herein SEQ ID NO: 1527), VPWMEPAYQRFL (SEQ ID NO: 142 of U.S. Pat. No. 9,475,845; herein SEQ ID NO: 1528), DPRATPGS (SEQ ID NO: 143 of U.S. Pat. No. 9,475,845; herein SEQ ID NO: 1529), FRPNRAQDYNTN (SEQ ID NO: 144 of U.S. Pat. No. 9,475,845; herein SEQ ID NO: 1530), CTKNSYLMC (SEQ ID NO: 145 of U.S. Pat. No. 9,475,845; herein SEQ ID NO: 1531), CXXTXXXGXGC (SEQ ID NO: 146 of U.S. Pat. No. 9,475,845; herein SEQ ID NO: 1532), CPIEDRPMC (SEQ ID NO: 147 of U.S. Pat. No. 9,475,845; herein SEQ ID NO: 1533), HEWSYLAPYPWF (SEQ ID NO: 148 of U.S. Pat. No. 9,475,845; herein SEQ ID NO: 1534), MCPKHPLGC (SEQ ID NO: 149 of U.S. Pat. No. 9,475,845; herein SEQ ID NO: 1535), RMWPSSTVNL-SAGRR (SEQ ID NO: 150 of U.S. Pat. No. 9,475,845; herein SEQ ID NO: 1536), SAKTAVSQRVWLPSHRGGEP (SEQ ID NO: 151 of U.S. Pat. No. 9,475,845; herein SEQ ID NO: 1537), KSREHVNNSACPSKRITAAL (SEQ ID NO: 152 of U.S. Pat. No. 9,475,845; herein SEQ ID NO: 1538), EGFR (SEQ ID NO: 153 of U.S. Pat. No. 9,475,845; herein SEQ ID NO: 1539), AGLGVR (SEQ ID NO: 154 of U.S. Pat. No. 9,475,845; herein SEQ ID NO: 1540), GTRQGHTMRLGVSDG (SEQ ID NO: 155 of U.S. Pat. No. 9,475,845; herein SEQ ID NO: 1541), IAGLATPGWSHWLAL (SEQ ID NO: 156 of U.S. Pat. No. 9,475,845; herein SEQ ID NO: 1542), SMSIARL (SEQ ID NO: 157 of U.S. Pat. No. 9,475,845; herein SEQ ID NO: 1543), HTFEPGV (SEQ ID NO: 158 of U.S. Pat. No. 9,475,845; herein SEQ ID NO: 1544), NTSLKRISNK-RIRRK (SEQ ID NO: 159 of U.S. Pat. No. 9,475,845; herein SEQ ID NO: 1545), LRIKRKRRKRKKTRK (SEQ ID NO: 160 of U.S. Pat. No. 9,475,845; herein SEQ ID NO: 1546), GGG, GFS, LWS, EGG, LLV, LSP, LBS, AGG, GRR, GGH and GTV.

In one embodiment, the AAV serotype may be, or may have a sequence as described in United States Publication No. US 20160369298, the contents of which are herein incorporated by reference in their entirety, such as, but not limited to, site-specific mutated capsid protein of AAV2 (SEQ ID NO: 97 of US 20160369298; herein SEQ ID NO: 1547) or variants thereof, wherein the specific site is at least one site selected from sites R447, G453, S578, N587, N587+1, S662 of VP1 or fragment thereof.

Further, any of the mutated sequences described in U.S. Patent Application Publication No. US20160369298, may be or may have, but not limited to, any of the following sequences SDSGASN (SEQ ID NO: 1 and SEQ ID NO: 231 of US20160369298; herein SEQ ID NO: 1548), SPSGASN (SEQ ID NO: 2 of US20160369298; herein SEQ ID NO: 1549), SHSGASN (SEQ ID NO: 3 of US20160369298; herein SEQ ID NO: 1550), SRSGASN (SEQ ID NO: 4 of US20160369298; herein SEQ ID NO: 1551), SKSGASN (SEQ ID NO: 5 of US20160369298; herein SEQ ID NO: 1552), SNSGASN (SEQ ID NO: 6 of US20160369298; herein SEQ ID NO: 1553), SGSGASN (SEQ ID NO: 7 of US20160369298; herein SEQ ID NO: 1554), SASGASN (SEQ ID NO: 8, 175, and 221 of US20160369298; herein SEQ ID NO: 1555), SESGTSN (SEQ ID NO: 9 of US20160369298; herein SEQ ID NO: 1556), STTGGSN (SEQ ID NO: 10 of US20160369298; herein SEQ ID NO: 1557), SSAGSTN (SEQ ID NO: 11 of US20160369298; herein SEQ ID NO: 1558), NNDSQA (SEQ ID NO: 12 of US20160369298; herein SEQ ID NO: 1559), NNRNQA (SEQ ID NO: 13 of US20160369298; herein SEQ ID NO: 1560), NNNKQA (SEQ ID NO: 14 of US20160369298; herein SEQ ID NO: 1561), NAKRQA (SEQ ID NO: 15 of US20160369298; herein SEQ ID NO: 1562), NDEHQA (SEQ ID NO: 16 of US20160369298; herein SEQ ID NO: 1563), NTSQKA (SEQ ID NO: 17 of US20160369298; herein SEQ ID NO: 1564), YYLSRTNTPSGTDTQSRLVFSQAGA (SEQ ID NO: 18 of US20160369298; herein SEQ ID NO: 1565), YYLSRTNTDSGTETQSGLDFSQAGA (SEQ ID NO: 19 of US20160369298; herein SEQ ID NO: 1566), YYLSRTNTESGTPTQSALEFSQAGA (SEQ ID NO: 20 of US20160369298; herein SEQ ID NO: 1567), YYLSRTNTHSGTHTQSPLHFSQAGA (SEQ ID NO: 21 of US20160369298; herein SEQ ID NO: 1568), YYLSRTNTSSGTITISHLIFSQAGA (SEQ ID NO: 22 of US20160369298; herein SEQ ID NO: 1569), YYLSRTN-TRSGIMTKSSLMFSQAGA (SEQ ID NO: 23 of US20160369298; herein SEQ ID NO: 1570), YYLSRTNTKSGRKTLSNLSFSQAGA (SEQ ID NO: 24 of US20160369298; herein SEQ ID NO: 1571), YYLSRTNDGSGPVTPSKLRFSQRGA (SEQ ID NO: 25 of US20160369298; herein SEQ ID NO: 1572), YYLSRT-NAASGHATHSDLKFSQPGA (SEQ ID NO: 26 of US20160369298; herein SEQ ID NO: 1573), YYLSRTNGQAGSLTMSELGFSQVGA (SEQ ID NO: 27 of US20160369298; herein SEQ ID NO: 1574), YYLSRTN-STGGNQTTSQLLFSQLSA (SEQ ID NO: 28 of US20160369298; herein SEQ ID NO: 1575), YFLSRTNNNTGLNTNSTLNFSQGRA (SEQ ID NO: 29 of US20160369298; herein SEQ ID NO: 1576), SKTGADNNNSEYSWTG (SEQ ID NO: 30 of US20160369298; herein SEQ ID NO: 1577), SKTDADNNNSEYSWTG (SEQ ID NO: 31 of US20160369298; herein SEQ ID NO: 1578), SKTEADNNNSEYSWTG (SEQ ID NO: 32 of US20160369298; herein SEQ ID NO: 1579), SKTPADNNNSEYSWTG (SEQ ID NO: 33 of US20160369298; herein SEQ ID NO: 1580), SKTHADNNNSEYSWTG (SEQ ID NO: 34 of US20160369298; herein SEQ ID NO: 1581), SKTQADNNNSEYSWTG (SEQ ID NO: 35 of US20160369298; herein SEQ ID NO: 1582), SKTIADNNNSEYSWTG (SEQ ID NO: 36 of US20160369298; herein SEQ ID NO: 1583), SKT-MADNNNSEYSWTG (SEQ ID NO: 37 of US20160369298; herein SEQ ID NO: 1584), SKTRADNNNSEYSWTG (SEQ ID NO: 38 of US20160369298; herein SEQ ID NO: 1585), SKT-NADNNNSEYSWTG (SEQ ID NO: 39 of US20160369298; herein SEQ ID NO: 1586), SKTVGRNNNSEYSWTG (SEQ ID NO: 40 of US20160369298; herein SEQ ID NO: 1587), SKTADRNNNSEYSWTG (SEQ ID NO: 41 of US20160369298; herein SEQ ID NO: 1588), SKKLSQNNNSKYSWQG (SEQ ID NO: 42 of US20160369298; herein SEQ ID NO: 1589), SKPTGNNNSDYSWPG (SEQ ID NO: 43 of US20160369298; herein SEQ ID NO: 1590), STQK-NENNNSNYSWPG (SEQ ID NO: 44 of US20160369298; herein SEQ ID NO: 1591), HKDDEGKF (SEQ ID NO: 45 of US20160369298; herein SEQ ID NO: 1592), HKDDNRKF (SEQ ID NO: 46 of US20160369298; herein SEQ ID NO: 1593), HKDDTNKF (SEQ ID NO: 47 of US20160369298; herein SEQ ID NO: 1594), HEDSDKNF (SEQ ID NO: 48 of US20160369298; herein SEQ ID NO: 1595), HRDGADSF (SEQ ID NO: 49 of US20160369298; herein SEQ ID NO: 1596), HGDNKSRF (SEQ ID NO: 50 of US20160369298; herein SEQ ID NO: 1597), KQGSEKTNVDFEEV (SEQ ID NO: 51 of US20160369298; herein SEQ ID NO: 1598), KQGSEKTNVDSEEV (SEQ ID NO: 52 of US20160369298; herein SEQ ID NO: 1599), KQGSEKTNVDVEEV (SEQ ID NO: 53 of US20160369298; herein SEQ ID NO: 1600), KQGSDKTNVDDAGV (SEQ ID NO: 54 of US20160369298; herein SEQ ID NO: 1601), KQGSSKTNVDPREV (SEQ ID NO: 55 of US20160369298; herein SEQ ID NO: 1602), KQGSRKTNVDHKQV (SEQ ID NO: 56 of US20160369298; herein SEQ ID NO: 1603), KQGSKGG-NVDTNRV (SEQ ID NO: 57 of US20160369298; herein SEQ ID NO: 1604), KQGSGEANVDNGDV (SEQ ID NO:

58 of US20160369298; herein SEQ ID NO: 1605), KQDAAADNIDYDHV (SEQ ID NO: 59 of US20160369298; herein SEQ ID NO: 1606), KQSGTRSNAAASSV (SEQ ID NO: 60 of US20160369298; herein SEQ ID NO: 1607), KENTNTNDTELTNV (SEQ ID NO: 61 of US20160369298; herein SEQ ID NO: 1608), QRGNNVAATADVNT (SEQ ID NO: 62 of US20160369298; herein SEQ ID NO: 1609), QRGNNEAATADVNT (SEQ ID NO: 63 of US20160369298; herein SEQ ID NO: 1610), QRGNNPAATADVNT (SEQ ID NO: 64 of US20160369298; herein SEQ ID NO: 1611), QRGNNHAATADVNT (SEQ ID NO: 65 of US20160369298; herein SEQ ID NO: 1612), QEENNIAATPGVNT (SEQ ID NO: 66 of US20160369298; herein SEQ ID NO: 1613), QPPNNMAATHEVNT (SEQ ID NO: 67 of US20160369298; herein SEQ ID NO: 1614), QHHNNSAATTIVNT (SEQ ID NO: 68 of US20160369298; herein SEQ ID NO: 1615), QTTNNRAAFNMVET (SEQ ID NO: 69 of US20160369298; herein SEQ ID NO: 1616), QKKNNNAASKKVAT (SEQ ID NO: 70 of US20160369298; herein SEQ ID NO: 1617), QGGNNKAADDAVKT (SEQ ID NO: 71 of US20160369298; herein SEQ ID NO: 1618), QAAKGGAADDAVKT (SEQ ID NO: 72 of US20160369298; herein SEQ ID NO: 1619), QDDRAAAANESVDT (SEQ ID NO: 73 of US20160369298; herein SEQ ID NO: 1620), QQQHDDAAYQRVHT (SEQ ID NO: 74 of US20160369298; herein SEQ ID NO: 1621), QSSSSLAAVSTVQT (SEQ ID NO: 75 of US20160369298; herein SEQ ID NO: 1622), QNNQTTAAIRNVTT (SEQ ID NO: 76 of US20160369298; herein SEQ ID NO: 1623), NYNKKSDNVDFT (SEQ ID NO: 77 of US20160369298; herein SEQ ID NO: 1624), NYNKKSENVDFT (SEQ ID NO: 78 of US20160369298; herein SEQ ID NO: 1625), NYNKKSLNVDFT (SEQ ID NO: 79 of US20160369298; herein SEQ ID NO: 1626), NYNKKSPNVDFT (SEQ ID NO: 80 of US20160369298; herein SEQ ID NO: 1627), NYSKKSHCVDFT (SEQ ID NO: 81 of US20160369298; herein SEQ ID NO: 1628), NYRKTIYVDFT (SEQ ID NO: 82 of US20160369298; herein SEQ ID NO: 1629), NYKEKKDVHFT (SEQ ID NO: 83 of US20160369298; herein SEQ ID NO: 1630), NYGHRAIVQFT (SEQ ID NO: 84 of US20160369298; herein SEQ ID NO: 1631), NYANHQFVVCT (SEQ ID NO: 85 of US20160369298; herein SEQ ID NO: 1632), NYDDDPTGVLLT (SEQ ID NO: 86 of US20160369298; herein SEQ ID NO: 1633), NYDDPTGVLLT (SEQ ID NO: 87 of US20160369298; herein SEQ ID NO: 1634), NFEQQNSVEWT (SEQ ID NO: 88 of US20160369298; herein SEQ ID NO: 1635), SQSGASN (SEQ ID NO: 89 and SEQ ID NO: 241 of US20160369298; herein SEQ ID NO: 1636), NNGSQA (SEQ ID NO: 90 of US20160369298; herein SEQ ID NO: 1637), YYLSRTNTPSGTITWSRLQFSQAGA (SEQ ID NO: 91 of US20160369298; herein SEQ ID NO: 1638), SKTSADNNNSEYSWTG (SEQ ID NO: 92 of US20160369298; herein SEQ ID NO: 1639), HKDDEEKF (SEQ ID NO: 93, 209, 214, 219, 224, 234, 239, and 244 of US20160369298; herein SEQ ID NO: 1640), KQGSEKTNVDIEEV (SEQ ID NO: 94 of US20160369298; herein SEQ ID NO: 1641), QRGNNQAATADVNT (SEQ ID NO: 95 of US20160369298; herein SEQ ID NO: 1642), NYNKKSVNVDFT (SEQ ID NO: 96 of US20160369298; herein SEQ ID NO: 1643), SQSGASNYNTPSGTTTTQSRLQFSTSADNNNSEYSWTGATKYH (SEQ ID NO: 106 of US20160369298; herein SEQ ID NO: 1644), SASGASNFNSEGGSLTQSSLGFSTDGENNNSDFSWTGATKYH (SEQ ID NO: 107 of US20160369298; herein SEQ ID NO: 1645), SQSGASNYNTPSGTTTTQSRLQFSTDGENNNSDFSWTGATKYH (SEQ ID NO: 108 of US20160369298; herein SEQ ID NO: 1646), SASGASNYNTPSGTITQSRLQFSTSADNNNSEFSWPGATTYH (SEQ ID NO: 109 of US20160369298; herein SEQ ID NO: 1647), SQSGASNFNSEGGSLTQSSLGFSTDGENNNSDFSWTGATKYH (SEQ ID NO: 110 of US20160369298; herein SEQ ID NO: 1648), SASGASNYNTPSGSLTQSSLGFSTDGENNNSDFSWTGATKYH (SEQ ID NO: 111 of US20160369298; herein SEQ ID NO: 1649), SQSGASNYNTPSGTITQSRLQFSTSADNNNSDFSWTGATKYH (SEQ ID NO: 112 of US20160369298; herein SEQ ID NO: 1650), SGAGASNFNSEGGSLTQSSLGFSTDGENNNSDFSWTGATKYH (SEQ ID NO: 113 of US20160369298; herein SEQ ID NO: 1651), SGAGASN (SEQ ID NO: 176 of US20160369298; herein SEQ ID NO: 1652), NSEGGSLTQSSLGFS (SEQ ID NO: 177, 185, 193 and 202 of US20160369298; herein SEQ ID NO: 1653), TDGENNNSDFS (SEQ ID NO: 178 of US20160369298; herein SEQ ID NO: 1654), SEFSWPGATT (SEQ ID NO: 179 of US20160369298; herein SEQ ID NO: 1655), TSADNNNSDFSWT (SEQ ID NO: 180 of US20160369298; herein SEQ ID NO: 1656), SQSGASNY (SEQ ID NO: 181, 187, and 198 of US20160369298; herein SEQ ID NO: 1657), NTPSGTTQSRLQFS (SEQ ID NO: 182, 188, 191, and 199 of US20160369298; herein SEQ ID NO: 1658), TSADNNNSEYSWTGATKYH (SEQ ID NO: 183 of US20160369298; herein SEQ ID NO: 1659), SASGASNF (SEQ ID NO: 184 of US20160369298; herein SEQ ID NO: 1660), TDGENNNSDFSWTGATKYH (SEQ ID NO: 186, 189, 194, 197, and 203 of US20160369298; herein SEQ ID NO: 1661), SASGASNY (SEQ ID NO: 190 and SEQ ID NO: 195 of US20160369298; herein SEQ ID NO: 1662), TSADNNNSEFSWPGATTYH (SEQ ID NO: 192 of US20160369298; herein SEQ ID NO: 1663), NTPSGSLTQSSLGFS (SEQ ID NO: 196 of US20160369298; herein SEQ ID NO: 1664), TSADNNNSDFSWTGATKYH (SEQ ID NO: 200 of US20160369298; herein SEQ ID NO: 1665), SGAGASNF (SEQ ID NO: 201 of US20160369298; herein SEQ ID NO: 1666), CTCCAGVVSVVSMRSRVCVNSGCAGCTDHCVVSRNSGTCVMSACACAA (SEQ ID NO: 204 of US20160369298; herein SEQ ID NO: 1667), CTCCAGAGAGGCAACAGACAAGCAGCTACCGCAGATGTCAACACACAA (SEQ ID NO: 205 of US20160369298; herein SEQ ID NO: 1668), SAAGASN (SEQ ID NO: 206 of US20160369298; herein SEQ ID NO: 1669), YFLSRTNTESGSTTQSTLRFSQAG (SEQ ID NO: 207 of US20160369298; herein SEQ ID NO: 1670), SKTSADNNNSDFS (SEQ ID NO: 208, 228, and 253 of US20160369298; herein SEQ ID NO: 1671), KQGSEKTDVDIDKV (SEQ ID NO: 210 of US20160369298; herein SEQ ID NO: 1672), STAGASN (SEQ ID NO: 211 of US20160369298; herein SEQ ID NO: 1673), YFLSRTNTTSGIETQSTLRFSQAG (SEQ ID NO: 212 and SEQ ID NO: 247 of US20160369298; herein SEQ ID NO: 1674), SKTDGENNNSDFS (SEQ ID NO: 213 and SEQ ID NO: 248 of US20160369298; herein SEQ ID NO: 1675), KQGAAADDVEIDGV (SEQ ID NO: 215 and SEQ ID NO: 250 of US20160369298; herein SEQ ID NO: 1676), SEAGASN (SEQ ID NO: 216 of US20160369298; herein SEQ ID NO: 1677), YYLSRTNTPSGTITQSRLQFSQAG (SEQ ID NO: 217, 232 and 242 of US20160369298; herein SEQ ID NO: 1678), SKTSADNNNSEYS (SEQ ID NO: 218, 233, 238, and 243 of US20160369298; herein SEQ ID NO: 1679), KQGSEKTNVDIEKV (SEQ ID NO: 220, 225 and 245 of US20160369298; herein SEQ ID NO: 1680), YFLSRTNDASGSDTKSTLLFSQAG (SEQ ID NO: 222 of US20160369298; herein SEQ ID NO: 1681), STTPSENNN-SEYS (SEQ ID NO: 223 of US20160369298; herein SEQ ID NO: 1682), SAAGATN (SEQ ID NO: 226 and SEQ ID NO: 251 of US20160369298; herein SEQ ID NO: 1683), YFLSRTNGEAGSATLSELRFSQAG (SEQ ID NO: 227 of US20160369298; herein SEQ ID NO: 1684), HGDDADRF (SEQ ID NO: 229 and SEQ ID NO: 254 of US20160369298; herein SEQ ID NO: 1685), KQGAEKSDVEVDRV (SEQ ID NO: 230 and SEQ ID NO: 255 of US20160369298; herein SEQ ID NO: 1686), KQDSGGDNIDIDQV (SEQ ID NO: 235 of US20160369298; herein SEQ ID NO: 1687), SDAGASN (SEQ ID NO: 236 of US20160369298; herein SEQ ID NO: 1688), YFLSRTNTEGGHDTQSTLRFSQAG (SEQ ID NO: 237 of US20160369298; herein SEQ ID NO: 1689), KEDGGGSDVAIDEV (SEQ ID NO: 240 of US20160369298; herein SEQ ID NO: 1690), SNAGASN (SEQ ID NO: 246 of US20160369298; herein SEQ ID NO: 1691), and YFLSRTNGEAGSATLSELRFSQPG (SEQ ID NO: 252 of US20160369298; herein SEQ ID NO: 1692). Non-limiting examples of nucleotide sequences that may encode the amino acid mutated sites include the following, AGCVVMDCAGGARSCASCAAC (SEQ ID NO: 97 of US20160369298; herein SEQ ID NO: 1693), AACRACRRSMRSMAGGCA (SEQ ID NO: 98 of US20160369298; herein SEQ ID NO: 1694), CACRRGGACRRCRMSRRSARSTIT (SEQ ID NO: 99 of US20160369298; herein SEQ ID NO: 1695), TATTTTCTT-GAGCAGAACAAACRVCVVSRSCGGAMNCVH-SACGMHSTCAVVSCTTV DSTTTTCTCAGSBCRGSGCG (SEQ ID NO: 100 of US20160369298; herein SEQ ID NO: 1696), TCAAMAM-MAVNSRVCSR-SAACAACAACAGTRASTTCTCGTGGMMAGGA (SEQ ID NO: 101 of US20160369298; herein SEQ ID NO: 1697), AAGSAARRCRSCRVSRVARVCRA-TRYCGMSNHCRVMVRSGTC (SEQ ID NO: 102 of US20160369298; herein SEQ ID NO: 1698), CAGVVSVVSMRSRVCVNSGCAGCTDHCVVSRN-SGTCVMSACA (SEQ ID NO: 103 of US20160369298; herein SEQ ID NO: 1699), AACTWCRVSVASMVSVHSDDTGTGSWSTKSACT (SEQ ID NO: 104 of US20160369298; herein SEQ ID NO: 1700), TTGTTGAACATCACCACGTGACGCACGTTC (SEQ ID NO: 256 of US20160369298; herein SEQ ID NO: 1701), TCCCCGTGGTTCTACTACATAATGTGGCCG (SEQ ID NO: 257 of US20160369298; herein SEQ ID NO: 1702), TTCCACACTCCGTTTTGGATAATGTTGAAC (SEQ ID NO: 258 of US20160369298; herein SEQ ID NO: 1703), AGGGACATCCCCAGCTCCATGCTGTGGTCG (SEQ ID NO: 259 of US20160369298; herein SEQ ID NO: 1704), AGGGACAACCCCTCCGACTCGCCCTAATCC (SEQ ID NO: 260 of US20160369298; herein SEQ ID NO: 1705), TCCTAGTAGAAGACACCCTCTCACTGCCCG (SEQ ID NO: 261 of US20160369298; herein SEQ ID NO: 1706), AGTACCATGTACACCCACTCTCCCAGTGCC (SEQ ID NO: 262 of US20160369298; herein SEQ ID NO: 1707), ATATGGACGTTCATGCTGATCACCATACCG (SEQ ID NO: 263 of US20160369298; herein SEQ ID NO: 1708), AGCAGGAGCTCCTTGGCCTCAGCGTGCGAG (SEQ ID NO: 264 of US20160369298; herein SEQ ID NO: 1709), ACAAGCAGCTTCACTATGACAACCACTGAC (SEQ ID NO: 265 of US20160369298; herein SEQ ID NO: 1710), CAGCCTAGGAACTGGCTTCCTGGACCCTGT-TACCGCCAGCAGAGAGTCTCAAMA MMAVN-SRVCSRSAACAACAACAGTRASTTCTCCTGGM-MAGGAGCTACCAAGTAC CACCTCAATGGCAGAGACTCTCTGGT-GAATCCCGGACCAGCTATGGCAAGCCAC RRGGACRRCRMSRRSARSTIT-TTTCCTCAGAGCGGGGTTCTCATCTITGGGAAGSA ARRCRSCRVSRVARVCRA-TRYCGMSNHCRVMVRSGTCATGATTACA-GACGAAGA GGAGATCTGGAC (SEQ ID NO: 266 of US20160369298; herein SEQ ID NO: 1711), TGGGACAATGGCGGTCGTCTCTCAGAGTTKTKKT (SEQ ID NO: 267 of US20160369298; herein SEQ ID NO: 1712), AGAGGACCKKTCCTCGATGGTTCATGGTG-GAGTTA (SEQ ID NO: 268 of US20160369298; herein SEQ ID NO: 1713), CCACTTAGGGCCTGGTCGA-TACCGTTCGGTG (SEQ ID NO: 269 of US20160369298; herein SEQ ID NO: 1714), and TCTCGCCC-CAAGAGTAGAAACCCTTCSTTYYG (SEQ ID NO: 270 of US20160369298; herein SEQ ID NO: 1715).

In some embodiments, the AAV serotype may comprise an ocular cell targeting peptide as described in International Patent Publication WO2016134375, the contents of which are herein incorporated by reference in their entirety, such as, but not limited to SEQ ID NO: 9, and SEQ ID NO:10 of WO2016134375. Further, any of the ocular cell targeting peptides or amino acids described in WO2016134375, may be inserted into any parent AAV serotype, such as, but not limited to, AAV2 (SEQ ID NO:8 of WO2016134375; herein SEQ ID NO: 1716), or AAV9 (SEQ ID NO: 11 of WO2016134375; herein SEQ ID NO: 1717). In some embodiments, modifications, such as insertions are made in AAV2 proteins at P34-A35, T138-A139, A139-P140, G453-T454, N587-R588, and/or R588-Q589. In certain embodiments, insertions are made at D384, G385, I560, T561, N562, E563, E564, E565, N704, and/or Y705 of AAV9. The ocular cell targeting peptide may be, but is not limited to, any of the following amino acid sequences, GSTPPPM (SEQ ID NO: 1 of WO2016134375; herein SEQ ID NO: 1718), or GETRAPL (SEQ ID NO: 4 of WO2016134375; herein SEQ ID NO: 1719).

In some embodiments, the AAV serotype may be modified as described in the U.S. Patent Application Publication No. US20170145405 the contents of which are herein incorporated by reference in their entirety. AAV serotypes may include, modified AAV2 (e.g., modifications at Y444F, Y500F, Y730F and/or S662V), modified AAV3 (e.g., modifications at Y705F, Y731F and/or T492V), and modified AAV6 (e.g., modifications at S663V and/or T492V).

In some embodiments, the AAV serotype may be modified as described in the International Publication No. WO2017083722; the contents of which are herein incorporated by reference in their entirety. AAV serotypes may include, AAV1 (Y705+731F+T492V), AAV2 (Y444+500+730F+T491V), AAV3 (Y705+731F), AAV5, AAV 5(Y436+693+719F), AAV6 (VP3 variant Y705F/Y731F/T492V), AAV8 (Y733F), AAV9, AAV9 (VP3 variant Y731F), and AAV10 (Y733F).

In some embodiments, the AAV serotype may comprise, as described in International Patent Publication WO2017015102; the contents of which are herein incorporated by reference in their entirety, an engineered epitope comprising the amino acids SPAKFA (SEQ ID NO: 24 of WO2017015102; herein SEQ ID NO: 1720) or NKDKLN (SEQ ID NO:2 of WO2017015102; herein SEQ ID NO: 1721). The epitope may be inserted in the region of amino acids 665 to 670 based on the numbering of the VP1 capsid of AAV8 (SEQ ID NO: 3 of WO2017015102) and/or residues 664 to 668 of AAV3B (SEQ ID NO: 3).

In one embodiment, the AAV serotype may be, or may have a sequence as described in International Patent Publication WO2017058892 (the contents of which are herein incorporated by reference in their entirety), such as, but not limited to, AAV variants with capsid proteins that may comprise a substitution at one or more (e.g., 2, 3, 4, 5, 6, or 7) of amino acid residues 262-268, 370-379, 451-459, 472-473, 493-500, 528-534, 547-552, 588-597, 709-710, 716-722 of AAV1, in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. The amino acid substitution may be, but is not limited to, any of the amino acid sequences described in WO2017058892. In one embodiment, the AAV may comprise an amino acid substitution at residues 256L, 258K, 259Q, 261S, 263A, 264S, 265T, 266G, 272H, 385S, 386Q, S472R, V473D, N500E 547S, 709A, 710N, 716D, 717N, 718N, 720L, A456T, Q457T, N458Q, K459S, T492S, K493A, S586R, S587G, S588N, T589R and/or 722T of AAV1 (SEQ ID NO: 1 of WO2017058892) in any combination, 244N, 246Q, 248R, 249E, 250I, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of AAV5 (SEQ ID NO:5 of WO2017058892) in any combination, 248R, 316V, 317Q, 318D, 319S, 443N, 530N, 531S, 532Q 533P, 534A, 535N, 540A, 541 T, 542Y, 543L, 545G, 546N, 697Q, 704D, 706T, 708E, 709Y and/or 710R of AAV5 (SEQ ID NO: 5 of WO2017058892) in any combination, 264S, 266G, 269N, 272H, 457Q, 588S and/or 589I of AAV6 (SEQ ID NO:6 WO2017058892) in any combination, 457T, 459N, 496G, 499N, 500N, 589Q, 590N and/or 592A of AAV8 (SEQ ID NO: 8 WO2017058892) in any combination, 451I, 452N, 453G, 454S, 455G, 456Q, 457N and/or 458Q of AAV9 (SEQ ID NO: 9 WO2017058892) in any combination.

In some embodiments, the AAV may include a sequence of amino acids at positions 155, 156 and 157 of VP1 or at positions 17, 18, 19 and 20 of VP2, as described in International Publication No. WO 2017066764, the contents of which are herein incorporated by reference in their entirety. The sequences of amino acid may be, but not limited to, N-S-S, S-X-S, S-S-Y, N-X-S, N-S-Y, S-X-Y and N-X-Y, where N, X and Y are, but not limited to, independently non-serine, or non-threonine amino acids, wherein the AAV may be, but not limited to AAV1, AAV2, AAV3, AAV4, AAV5, AAV6, AAV7, AAV8, AAV9, AAV10, AAV11 and AAV12. In some embodiments, the AAV may include a deletion of at least one amino acid at positions 156, 157 or 158 of VP1 or at positions 19, 20 or 21 of VP2, wherein the AAV may be, but not limited to AAV1, AAV2, AAV3, AAV4, AAV5, AAV6, AAV7, AAV8, AAV9, AAV10, AAV11 and AAV12.

In one embodiment, the AAV may be a serotype generated by Cre-recombination-based AAV targeted evolution (CREATE) as described by Deverman et al., (Nature Biotechnology 34(2):204-209 (2016)), the contents of which are herein incorporated by reference in their entirety. In one embodiment, AAV serotypes generated in this manner have improved CNS transduction and/or neuronal and astrocytic tropism, as compared to other AAV serotypes. As non-limiting examples, the AAV serotype may include a peptide such as, but not limited to, PHP.B, PHP.B2, PHP.B3, PHP.A, PHP.S, G2A12, G2A15, G2A3, G2B4, and G2B5. In one embodiment, these AAV serotypes may be AAV9 (SEQ ID NO: 9 or 136) derivatives with a 7-amino acid insert between amino acids 588-589. Non-limiting examples of these 7-amino acid inserts include TLAVPFK (PHP.B; SEQ ID NO: 1260), SVSKPFL (PHP.B2; SEQ ID NO: 1268), FTLTTPK (PHP.B3; SEQ ID NO: 1269), YTLSQGW (PHP.A; SEQ ID NO: 1275), QAVRTSL (PHP.S; SEQ ID NO: 1319), LAKERLS (G2A3; SEQ ID NO: 1320), MNSTKNV (G2B4; SEQ ID NO: 1321), and/or VSGGHHS (G2B5; SEQ ID NO: 1322).

In one embodiment, the AAV serotype may be as described in Jackson et al (Frontiers in Molecular Neuroscience 9:154 (2016)), the contents of which are herein incorporated by reference in their entirety.

In the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

In some embodiments, the AAV serotype is PHP.B or AAV9. In some embodiments, the AAV serotype is paired with a synapsin promoter to enhance neuronal transduction, as compared to when more ubiquitous promoters are used (i.e., CBA or CMV).

In one embodiment, the AAV serotype is a serotype comprising the AAVPHP.N (PHP.N) peptide, or a variant thereof.

In one embodiment the AAV serotypes is a serotype comprising the AAVPHP.B (PHP.B) peptide, or a variant thereof.

In one embodiment, the AAV serotype is a serotype comprising the AAVPHP.A (PHP.A) peptide, or a variant thereof.

In one embodiment, the AAV serotype is a serotype comprising the PHP.S peptide, or a variant thereof.

In one embodiment, the AAV serotype is a serotype comprising the PHP.B2 peptide, or a variant thereof.

In one embodiment, the AAV serotype is a serotype comprising the PHP.B3 peptide, or a variant thereof.

In one embodiment, the AAV serotype is a serotype comprising the G2B4 peptide, or a variant thereof.

In one embodiment, the AAV serotype is a serotype comprising the G2B5 peptide, or a variant thereof.

In one embodiment, the AAV serotype is VOY101, or a variant thereof. In one preferred embodiment, the VOY101 comprises an amino acid sequence of SEQ ID NO. 1. In another embodiment, the capsid sequence comprises a nucleic acid sequence of SEQ ID NO. 1809.

In one embodiment, the AAV serotype is VOY201, or a variant thereof. In one preferred embodiment, the VOY201 comprises a nucleic acid sequence of SEQ ID NO. 1810.

In one embodiment the AAV capsid is one that allows for blood brain barrier penetration following intravenous administration. Non-limiting examples of such AAV capsids include VOY101, VOY201 or AAV capsids comprising a peptide insert such as, but not limited to, AAVPHP.N (PHP.N), AAVPHP.B (PHP.B), PHP.S, G2A3, G2B4, G2B5, G2A12, G2A15, PHP.B2, PHP.B3, and AAVPHP.A (PHP.A). In one embodiment, the blood brain barrier penetrating capsid is VOY101. In one embodiment, the blood brain barrier penetrating capsid is VOY201. In one embodiment, the blood brain barrier penetrating capsid comprises the PHP.A peptide insert. In one embodiment, the blood brain barrier penetrating capsid comprises the PHP.B peptide insert. In one embodiment, the blood brain barrier penetrating capsid comprises the PHP.B2 peptide insert. In one embodiment, the blood brain barrier penetrating capsid comprises the PHP.B3 peptide insert. In one embodiment, the blood brain barrier penetrating capsid comprises the G2A3 peptide insert. In one embodiment, the blood brain barrier penetrating capsid comprises the G2B4 peptide insert. In one embodiment, the blood brain barrier penetrating capsid comprises the G2B5 peptide insert. In one embodiment, the blood brain barrier penetrating capsid comprises the PHP.N peptide insert. In one embodiment, the blood brain barrier penetrating capsid comprises the PHP.S peptide insert.

Viral Genome Component: Inverted Terminal Repeats (ITRs)

The AAV particles of the present invention comprise a viral genome with at least one ITR region and a payload region. In one embodiment, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the invention may be comprised of naturally occurring polynucleotide sequences or recombinantly derived polynucleotide sequences.

The ITRs may be derived from the same serotype as the capsid, selected from any of the serotypes listed in Table 1, or a derivative thereof. The ITR may be of a different serotype than the capsid. In one embodiment, the AAV particle has more than one ITR. In a non-limiting example, the AAV particle has a viral genome comprising two ITRs. In one embodiment, the ITRs are of the same serotype as one another. In another embodiment, the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment, the ITRs are 140-142 nucleotides in length. Non-limiting examples of ITR length are 102, 105, 130, 140, 141, 142, 145 nucleotides in length, and those having at least 90% identity thereto, or at least 95% identity thereto, or at least 98% identity thereto, or at least 99% identity thereto.

Viral Genome Component: Promoters

In one embodiment, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in their entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the invention in a target cell may require a specific promoter, including but not limited to, a promoter that is species specific, inducible, tissue-specific, or cell cycle-specific (Parr et al., Nat. Med. 3:1145-9 (1997); the contents of which are herein incorporated by reference in their entirety).

In one embodiment, the promoter is deemed to be efficient when it drives expression of the polypeptide(s) encoded in the payload region of the viral genome of the AAV particle.

In one embodiment, the promoter is a promoter deemed to be efficient when it drives expression in the cell being targeted.

In one embodiment, the promoter is a promoter having a tropism for the cell being targeted.

In one embodiment, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues.

In one embodiment, the promoter drives expression of the polypeptides of the invention for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated or mutated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons or subtypes of neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Application Publication No. US 20110212529, the contents of which are herein incorporated by reference in their entirety).

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In one embodiment, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In one embodiment, the promoter is a combination of a 382 nucleotide CMV-enhancer sequence and a 260 nucleotide CBA-promoter sequence.

In one embodiment, the viral genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EF1α, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015, 2(2): ENEURO.0001-15; the contents of which are herein incorporated by reference in their entirety) evaluated the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009, 16(7): 927-932; the contents of which are herein incorporated by reference in their entirety) evaluated an HβH construct with a hGUSB promoter, a HSV-1LAT promoter and an NSE promoter and found that the HβH construct showed weaker expression than NSE in mouse brain. Passini and Wolfe (J. Virol. 2001, 12382-12392, the contents of which are herein incorporated by reference in their entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920 nucleotide promoter which are both absent in the liver but NFH is abundant in the sensory proprioceptive neurons, brain and spinal cord and NFH is present in the heart. SCN8A is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements in the promoter region of the sodium channel gene SCN8A*, Mamm Genome (2007) 18:723-731; and Raymond et al. *Expression of Alternatively Spliced Sodium Channel α-subunit genes*, Journal of Biological Chemistry (2004) 279(44) 46234-46241; the contents of each of which are herein incorporated by reference in their entireties).

Any of the promoters taught by the aforementioned Yu, Soderblom, Gill, Husain, Passini, Xu, Drews or Raymond may be used in the present inventions.

In one embodiment, the promoter is not cell specific.

In one embodiment, the promoter is a ubiquitin c (UBC) promoter. The UBC promoter may have a size of 300-350 nucleotides. As a non-limiting example, the UBC promoter is 332 nucleotides in length.

In one embodiment, the promoter is a β-glucuronidase (GUSB) promoter. The GUSB promoter may have a size of 350-400 nucleotides. As a non-limiting example, the GUSB promoter is 378 nucleotides in length.

In one embodiment, the promoter is a neurofilament light (NFL) promoter. The NFL promoter may have a size of 600-700 nucleotides. As a non-limiting example, the NFL promoter is 650 nucleotides in length.

In one embodiment, the promoter is a neurofilament heavy (NFH) promoter. The NFH promoter may have a size of 900-950 nucleotides. As a non-limiting example, the NFH promoter is 920 nucleotides in length.

In one embodiment, the promoter is a SCN8A promoter. The SCN8A promoter may have a size of 450-500 nucleotides. As a non-limiting example, the SCN8A promoter is 470 nucleotides in length.

In one embodiment, the promoter is a frataxin (FXN) promoter.

In one embodiment, the promoter is a phosphoglycerate kinase 1 (PGK) promoter.

In one embodiment, the promoter is a chicken β-actin (CBA) promoter.

In one embodiment, the promoter is a cytomegalovirus (CMV) promoter.

In one embodiment, the promoter is a H1 promoter.

In one embodiment, the promoter is an engineered promoter.

In one embodiment, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12.

In one embodiment, the promoter is a RNA pol III promoter. As a non-limiting example, the RNA pol III promoter is U6. As a non-limiting example, the RNA pol III promoter is H1.

In one embodiment, the promoter is a cardiomyocyte-specific promoter. Non-limiting examples of cardiomyocyte-specific promoters include αMHC, cTnT, and CMV-MLC2k.

In one embodiment, the viral genome comprises two promoters. As a non-limiting example, the promoters are an EF1α promoter and a CMV promoter.

In one embodiment, the viral genome comprises an enhancer element, a promoter and/or a 5' UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5' UTR/intron may be, but is not limited to, SV40, and CBA-MVM. As a non-limiting example, the enhancer, promoter and/or intron used in combination may be: (1) CMV enhancer, CMV promoter, SV40 5' UTR intron; (2) CMV enhancer, CBA promoter, SV 40 5' UTR intron; (3) CMV enhancer, CBA promoter, CBA-MVM 5' UTR intron; (4) UBC promoter; (5) GUSB promoter; (6) NSE promoter; (7) Synapsin promoter; (8) MeCP2 promoter and (9) GFAP promoter.

In one embodiment, the viral genome comprises an engineered promoter.

In another embodiment, the viral genome comprises a promoter from a naturally expressed protein.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the invention to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5' UTR in the viral genome includes a Kozak sequence.

In one embodiment, the 5' UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A) (U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

In one embodiment, the viral genome may include at least one miRNA seed, binding site or full sequence. microRNAs (or miRNA or miR) are 19-25 nucleotide noncoding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In one embodiment, the viral genome may be engineered to include, alter or remove at least one miRNA binding site, full sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTR which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

In one embodiment, the viral genome of the AAV particles of the present invention comprise at least one polyadenylation sequence. The viral genome of the AAV particle may comprise a polyadenylation sequence between the 3' end of the payload coding sequence and the 5' end of the 3' ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

Viral Genome Component: Introns

In one embodiment, the viral genome of the AAV particles of the present invention comprises at least one element to enhance the transgene target specificity and expression (See e.g., Powell et al. *Viral Expression Cassette Elements to Enhance Transgene Target Specificity and Expression in Gene Therapy*, Discov. Med, 2015, 19(102): 49-57; the contents of which are herein incorporated by reference in their entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nucleotides. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500 nucleotides.

Viral Genome Component: Stuffer Sequences

In one embodiment, the viral genome of the AAV particles of the present invention comprises at least one element to improve packaging efficiency and expression, such as a stuffer or filler sequence. Non-limiting examples of stuffer sequences include albumin and/or alpha-1 antitrypsin. Any known viral, mammalian, or plant sequence may be manipulated for use as a stuffer sequence.

In one embodiment, the stuffer or filler sequence may be from about 100-3500 nucleotides in length. The stuffer sequence may have a length of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 nucleotides.

Viral Genome Component: miRNA

In one embodiment, the viral genome comprises at least one sequence encoding a miRNA to reduce the expression of the transgene is a specific tissue. miRNAs and their targeted tissues are well known in the art. As a non-limiting example, a miR-122 miRNA may be encoded in the viral genome to reduce the expression of the viral genome in the liver.

AAV Production

The present invention provides methods for the generation of parvoviral particles, e.g. AAV particles, by viral genome replication in a viral replication cell.

In accordance with the invention, the viral genome comprising a payload region will be incorporated into the AAV particle produced in the viral replication cell. Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, N J (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.*, 219:37-44 (1996); Zhao et al., *Vir.* 272:382-93 (2000); the contents of each of which are herein incorporated by reference in their entirety. In one embodiment, the AAV particles are made using the methods described in International Patent Publication WO2015191508, the contents of which are herein incorporated by reference in their entirety.

Viral replication cells commonly used for production of recombinant AAV viral particles include but are not limited to HEK293 cells, COS cells, HeLa cells, KB cells, and other mammalian cell lines as described in U.S. Pat. Nos. 6,156, 303, 5,387,484, 5,741,683, 5,691,176, and 5,688,676; U.S. Patent Application Publication No. 2002/0081721, and International Patent Publication Nos. WO 2000047757, WO 2000024916, and WO 1996017947, the contents of each of which are herein incorporated by reference in their entirety.

In some embodiments, the present invention provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, and 5) harvesting and purifying the AAV particle comprising a viral genome.

In some embodiments, the present invention provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

In some embodiments, the viral genome of the AAV particle of the invention optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes are described in International Publication Nos. WO 1996023810 and WO 1996030540; Heim et al., Current Biology 2:178-182 (1996); Heim et al., Proc. Natl. Acad. Sci. USA (1995); or Heim et al., Science 373:663-664 (1995); the contents of each of which are incorporated herein by reference in their entirety.

Genome Size

In one embodiment, the AAV particle which comprises a payload described herein may be single stranded or double stranded viral genome. The size of the viral genome may be small, medium, large or the maximum size. Additionally, the viral genome may comprise a promoter and a polyA tail.

In one embodiment, the viral genome which comprises a payload described herein may be a small single stranded viral genome. A small single stranded viral genome may be 2.1 to 3.5 kb in size such as about 2.1, 2.2, 2.3, 2.4, 2.5, 2.6, 2.7, 2.8, 2.9, 3.0, 3.1, 3.2, 3.3, 3.4, and 3.5 kb in size. As a non-limiting example, the small single stranded viral genome may be 3.2 kb in size. As another non-limiting example, the small single stranded viral genome may be 2.2 kb in size. Additionally, the viral genome may comprise a promoter and a polyA tail.

In one embodiment, the viral genome which comprises a payload described herein may be a small double stranded viral genome. A small double stranded viral genome may be 1.3 to 1.7 kb in size such as about 1.3, 1.4, 1.5, 1.6, and 1.7 kb in size. As a non-limiting example, the small double stranded viral genome may be 1.6 kb in size. Additionally, the viral genome may comprise a promoter and a polyA tail.

In one embodiment, the viral genome which comprises a payload described herein e.g., polynucleotide, siRNA or dsRNA, or miRNA may be a medium single stranded viral genome. A medium single stranded viral genome may be 3.6 to 4.3 kb in size such as about 3.6, 3.7, 3.8, 3.9, 4.0, 4.1, 4.2 and 4.3 kb in size. As a non-limiting example, the medium single stranded viral genome may be 4.0 kb in size. Additionally, the viral genome may comprise a promoter and a polyA tail.

In one embodiment, the viral genome which comprises a payload described herein may be a medium double stranded viral genome. A medium double stranded viral genome may be 1.8 to 2.1 kb in size such as about 1.8, 1.9, 2.0, and 2.1 kb in size. As a non-limiting example, the medium double stranded viral genome may be 2.0 kb in size. Additionally, the viral genome may comprise a promoter and a polyA tail.

In one embodiment, the viral genome which comprises a payload described herein may be a large single stranded viral genome. A large single stranded viral genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded viral genome may be 4.7 kb in size. As another non-limiting example, the large single stranded viral genome may be 4.8 kb in size. As yet another non-limiting example, the large single stranded viral genome may be 6.0 kb in size. Additionally, the viral genome may comprise a promoter and a polyA tail.

In one embodiment, the viral genome which comprises a payload described herein may be a large double stranded viral genome. A large double stranded viral genome may be 2.2 to 3.0 kb in size such as about 2.2, 2.3, 2.4, 2.5, 2.6, 2.7, 2.8, 2.9 and 3.0 kb in size. As a non-limiting example, the large double stranded viral genome may be 2.4 kb in size. Additionally, the viral genome may comprise a promoter and a polyA tail.

Payloads of the Invention

The AAV particles of the present disclosure comprise at least one payload region. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid. Payloads of the present invention typically encode polypeptides or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In one embodiment, the AAV particle comprises a viral genome with a payload region comprising nucleic acid sequences encoding more than one polypeptide of interest. In such an embodiment, a viral genome encoding more than one polypeptide may be replicated and packaged into a viral particle. A target cell transduced with a viral particle comprising more than one polypeptide may express each of the polypeptides in a single cell.

In one embodiment, the AAV payload region may comprise the components as shown in FIG. 1. The payload region 110 is located within the viral genome 100. At the 5' and/or the 3' end of the payload region 110 there may be at least one inverted terminal repeat (ITR) 120. In one embodiment, within the payload region, there is a promoter region 130, an intron region 140 and a coding region 150.

Where the AAV particle payload region encodes a polypeptide, the polypeptide may be a peptide or protein. As a non-limiting example, the payload region may encode at least one allele of apolipoprotein E (APOE) such as, but not limited to ApoE2, ApoE3 and/or ApoE4. As a second non-limiting example, the payload region may encode a human or a primate frataxin protein, or fragment or variant thereof. As another non-limiting example, the payload region may encode an antibody, or a fragment thereof. As another non-limiting example, the payload region may encode human AADC, or fragment or variant thereof. As another non-limiting example, the payload region may encode human ATP2A2, or fragment or variant thereof. As further another example, the payload region may encode human S100A1, or fragment or variant thereof. The AAV viral genomes encoding polypeptides described herein may be useful in the fields of human disease, viruses, infections veterinary applications and a variety of in vivo and in vitro settings.

In some embodiments, the AAV particles are useful in the field of medicine for the treatment, prophylaxis, palliation or amelioration of neurological diseases and/or disorders.

In some embodiments, the AAV particles are useful in the field of medicine for the treatment, prophylaxis, palliation or amelioration of tauopathy.

In some embodiments, the AAV particles are useful in the field of medicine for the treatment, prophylaxis, palliation or amelioration of Alzheimer's Disease.

In some embodiments, the AAV particles are useful in the field of medicine for the treatment, prophylaxis, palliation or amelioration of Friedreich's ataxia, or any disease stemming from a loss or partial loss of frataxin protein.

In some embodiments, the AAV particles are useful in the field of medicine for the treatment, prophylaxis, palliation or amelioration of Parkinson's Disease.

In some embodiments, the AAV particles are useful in the field of medicine for the treatment, prophylaxis, palliation or amelioration of Amyotrophic lateral sclerosis.

In some embodiments, the AAV particles are useful in the field of medicine for the treatment, prophylaxis, palliation or amelioration of Huntington's Disease.

In some embodiments, the AAV particles are useful in the field of medicine for treatment, prophylaxis, palliation or amelioration of cardiovascular diseases.

The Nature of the Polypeptides and Variants

Amino acid sequences encoded by payload regions of the viral genomes of the invention may be translated as a whole polypeptide, a plurality of polypeptides or fragments of polypeptides, which independently may be encoded by one or more nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multimolecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably at least about 90% homologous to a native sequence. "Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

Sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol Biol, 266 (4): 814-830; 1997).

As used herein when referring to proteins the term "half-loop" refers to a portion of an identified loop having at least half the number of amino acid residues as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions).

As used herein when referring to proteins the term "half-domain" means portion of an identified domain having at least half the number of amino acid residues as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0 5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involves deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Payloads: Nucleic Acids Encoding a Protein of Interest

In one embodiment, the payload region of the AAV particle comprises one or more nucleic acid sequences encoding a protein of interest.

Apolipoprotein E (APOE)

In one embodiment, the payload region of the AAV particle comprises one or more nucleic acid sequences encoding an allele of the apolipoprotein E (APOE) gene (e.g., ApoE2, ApoE3, and/or ApoE4).

In one embodiment, the payload region of the AAV particle comprises a nucleic acid sequence encoding an amino acid signal peptide with the sequence (SEQ ID NO: 1722)
MKVLWAALLVTFLAGCQA.

In one embodiment, the payload region of the AAV particle comprises a nucleic acid sequence encoding an amino acid signal peptide with the sequence (SEQ ID NO: 1723)
MSSGASRKSWDPGNPWPPDWPITGRKMKVLWAALLVTFLAGCQA.

In one embodiment, the payload region of the AAV particle comprises a nucleic acid sequence encoding an amino acid sequence, or fragment thereof, or variant thereof, described in Table 2.

In one embodiment, the payload region of the AAV particle comprises a nucleic acid sequence, or fragment thereof, or variant thereof, described in Table 2.

TABLE 2

| Apolipoprotein E Sequences | | |
|---|---|---|
| Identification | Reference | SEQ ID NO |
| APOE SEQ-001 | ENSP00000252486; NP_000032.1; NP_001289618.1; NP_001289619.1; NP_001289620.1 | 1724 |
| APOE SEQ-002 | ENSP00000252486; NP_000032.1; NP_001289618.1; NP_001289619.1; NP_001289620.1; Mature peptide | 1725 |
| APOE SEQ-003 | ENSP00000413135 | 1726 |
| APOE SEQ-004 | ENSP00000413135; Mature peptide | 1727 |
| APOE SEQ-005 | ENSP00000413653 | 1728 |
| APOE SEQ-006 | ENSP00000413653; Mature peptide | 1729 |
| APOE SEQ-007 | ENSP00000410423 | 1730 |
| APOE SEQ-008 | ENSP00000410423; Mature peptide | 1731 |
| APOE SEQ-009 | NP_001289617.1 | 1732 |
| APOE SEQ-010 | NP_001289617.1; Mature peptide | 1733 |
| APOE SEQ-011 | ENST00000252486.8 | 1734 |
| APOE SEQ-012 | CCDS12647.1 for ENST00000252486.8 | 1735 |
| APOE SEQ-013 | ENST00000446996.5 | 1736 |
| APOE SEQ-014 | ENST00000485628.2 | 1737 |
| APOE SEQ-015 | ENST00000434152.5 | 1738 |
| APOE SEQ-016 | ENST00000425718.1 | 1739 |
| APOE SEQ-017 | NM_000041.3 | 1740 |
| APOE SEQ-018 | NM_001302689.1 | 1741 |
| APOE SEQ-019 | NM_001302690.1 | 1742 |
| APOE SEQ-020 | NM_001302691.1 | 1743 |
| APOE SEQ-021 | NM_001302688.1 | 1744 |

In one embodiment, the payload region of the AAV particle comprises one or more nucleic acid sequences encoding one or more variants of SEQ ID NO: 1724. The variant may include, but is not limited to, one or more of the variants: E21K (the amino acid E (Glu) at position 21 in SEQ ID NO: 1724 is changed to K (Lys)), E31K (the amino acid E (Glu) at position 31 in SEQ ID NO: 1724 is changed to K (Lys)), R43C (the amino acid R (Arg) at position 43 in SEQ ID NO: 1724 is changed to C (Cys)), L46P (the amino acid L (Leu) at position 46 in SEQ ID NO: 1724 is changed to P (Pro)), T60A (the amino acid T (Thr) at position 60 in SEQ ID NO: 1724 is changed to A (Ala)), Q64H (the amino acid Q (Gln) at position 64 in SEQ ID NO: 1724 is changed to H (His)), Q99K (the amino acid Q (Gln) at position 99 in SEQ ID NO: 1724 is changed to K (Lys)), P102R (the amino acid P (Pro) at position 102 in SEQ ID NO: 1724 is changed to R (Arg)), A117T (the amino acid A (Ala) at position 117 in SEQ ID NO: 1724 is changed to T (Thr)), A124V (the amino acid A (Ala) at position 124 in SEQ ID NO: 1724 is changed to V (Val)), C130R (the amino acid C (Cys) at position 130 in SEQ ID NO: 1724 is changed to R (Arg)), G145D (the amino acid G (Gly) at position 145 in SEQ ID NO: 1724 is changed to D (Asp)), G145GEVQAMLG (the amino acid G (Gly) at position 145 in SEQ ID NO: 1724 is changed to be GEVQAMLG (Gly-Glu-Val-Gln-Ala-Met-Leu-Gly)), R152Q (the amino acid R (Arg) at position 152 in SEQ ID NO: 1724 is changed to Q (Gln)), R154C (the amino acid R (Arg) at position 154 in SEQ ID NO: 1724 is changed to C (Cys)), R154S (the amino acid R (Arg) at position 154 in SEQ ID NO: 1724 is changed to S (Ser)), R160C (the amino acid R (Arg) at position 160 in SEQ ID NO: 1724 is changed to C (Cys)), R163H (the amino acid R (Arg) at position 163 in SEQ ID NO: 1724 is changed to H (His)), R163P (the amino acid R (Arg) at position 163 in SEQ ID NO: 1724 is changed to P (Pro)), K164E (the amino acid K (Lys) at position 164 in SEQ ID NO: 1724 is changed to E (Glu)), K164Q (the amino acid K (Lys) at position 164 in SEQ ID NO: 1724 is changed to Q (Gln)), A170P (the amino acid A (Ala) at position 170 in SEQ ID NO: 1724 is changed to P (Pro)), R176C (the amino acid R (Arg) at position 176 in SEQ ID NO: 1724 is changed to C (Cys)), R242Q (the amino acid R (Arg) at position 242 in SEQ ID NO: 1724 is changed to Q (Gln)), R246C (the amino acid R (Arg) at position 246 in SEQ ID NO: 1724 is changed to C (Cys)), V254E (the amino acid V (Val) at position 254 in SEQ ID NO: 1724 is changed to E (Glu)), EE262-263KK (the amino acids EE (Glu-Glu) at positions 262-263 in SEQ ID NO: 1724 are changed to KK (Lys-Lys)), R269G (the amino acid R (Arg) at position 269 in SEQ ID NO: 1724 is changed to G (Gly)), L270E (the amino acid L (Leu) at position 270 in SEQ ID NO: 1724 is changed to E (Glu)), R292H (the amino acid R (Arg) at position 292 in SEQ ID NO: 1724 is changed to H (His)), S314R (the amino acid S (Ser) at position 314 in SEQ ID NO: 1724 is changed to R (Arg)), the removal of amino acid 167, or a combination thereof. As a non-limiting example, the payload region of the AAV particle comprises one or more nucleic acid sequences encoding an amino acid sequence where the amino acid C (Cys) at position 130 in SEQ ID NO: 1724 is changed to R (Arg). As a non-limiting example, the payload region of the AAV particle comprises one or more nucleic acid sequences encoding an amino acid sequence where the amino acid R (Arg) at position 176 in SEQ ID NO: 1724 is changed to C (Cys). As a non-limiting example, the payload region of the AAV particle comprises one or more nucleic acid sequences encoding an amino acid sequence where the amino acid C (Cys) at position 130 in SEQ ID NO: 1724 is changed to R and the amino acid R (Arg) at position 176 in SEQ ID NO: 1724 is changed to C (Cys).

In some embodiments, the payload region of the AAV particle comprises one or more nucleic acid sequences encoding an ApoE molecule comprising a signal peptide sequence as given in SEQ ID NO: 1722 or 1723. As a non-limiting example, the signal peptide may be cleaved during cellular processing to yield a mature peptide as given in SEQ ID NOs: 1725, 1727, 1729, 1731, and 1733. Alternatively, the payload region of the AAV particle comprises one or more nucleic acid sequences encoding an ApoE molecule that lacks a signal peptide sequences, as given in SEQ ID NOs: 1725, 1727, 1729, 1731, and 1733.

In one embodiment, the payload region of the AAV particle comprises one or more nucleic acid sequences encoding one or more variants of SEQ ID NO: 1725. The variant may include, but is not limited to, one or more of the variants: C112R (the amino acid C (Cys) at position 112 in SEQ ID NO: 1725 is changed to R (Arg)), or R158C (the amino acid R (Arg) at position 158 in SEQ ID NO: 1725 is changed to C (Cys).

In one embodiment, the payload region of the AAV particle comprises one or more nucleic acid sequences that encode ApoE2 (cys112, cys158).

In one embodiment, the payload region of the AAV particle comprises one or more nucleic acid sequences that encode ApoE3 (cys112, arg158).

In one embodiment, the payload region of the AAV particle comprises one or more nucleic acid sequences that encode ApoE4 (arg112, arg158).

Frataxin (FXN)

In one embodiment, the payload region of the AAV particle comprises one or more nucleic acid sequences encoding frataxin (FXN).

In one embodiment, the payload region of the AAV particle comprises a nucleic acid sequence encoding an amino acid sequence, or fragment thereof, or variant thereof, described in Table 3.

In one embodiment, the payload region of the AAV particle comprises a nucleic acid sequence, or fragment thereof, or variant thereof, described in Table 3.

TABLE 3

| Frataxin Sequences | | |
|---|---|---|
| Identification | Reference | SEQ ID NO |
| FXN SEQ-001 | NP_000135.2 | 1745 |
| FXN SEQ-002 | NP_852090.1 | 1746 |
| FXN SEQ-003 | NP_001155178.1 | 1747 |
| FXN SEQ-004 | NM_000144.4 | 1748 |
| FXN SEQ-005 | NM_181425.2 | 1749 |
| FXN SEQ-006 | NM_001161706.1 | 1750 |

Aromatic L-Amino Acid Decarboxylase (AADC)

In one embodiment, the payload region of the AAV particle comprises one or more nucleic acid sequences encoding Aromatic L-Amino Acid Decarboxylase (AADC).

In one embodiment, the payload region of the AAV particle comprises a nucleic acid sequence encoding an amino acid sequence, or fragment thereof, or variant thereof, described in Table 4.

In one embodiment, the payload region of the AAV particle comprises a nucleic acid sequence, or fragment thereof, or variant thereof, described in Table 4.

TABLE 4

| Aromatic L-Amino Acid Decarboxylase Sequences | | |
|---|---|---|
| Identification | Reference | SEQ ID NO |
| AADC SEQ-001 | NP_000781.1 | 1751 |
| AADC SEQ-002 | NM_000790.3 | 1752 |

ATPase Sarcoplasmic/Endoplasmic Reticulum Ca2+ Transporting 2 (ATP2A2)

In one embodiment, the payload region of the AAV particle comprises one or more nucleic acid sequences encoding ATPase Sarcoplasmic/Endoplasmic Reticulum Ca2+ Transporting 2 (ATP2A2).

In one embodiment, the payload region of the AAV particle comprises a nucleic acid sequence encoding an amino acid sequence, or fragment thereof, or variant thereof, described in Table 5.

In one embodiment, the payload region of the AAV particle comprises a nucleic acid sequence, or fragment thereof, or variant thereof, described in Table 5.

TABLE 5

| ATPase Sarcoplasmic/Endoplasmic Reticulum Ca2+ Transporting 2 | | |
|---|---|---|
| Identification | Reference | SEQ ID NO |
| ATP2A2 SEQ-001 | NP_001672.1 | 1803 |
| ATP2A2 SEQ-002 | NP_733765.1 | 1804 |
| ATP2A2 SEQ-003 | NM_001681.3 | 1805 |
| ATP2A2 SEQ-004 | NM_170665.3 | 1806 |

S100 Calcium Binding Protein A) (S100A1)

In one embodiment, the payload region of the AAV particle comprises one or more nucleic acid sequences encoding S100 Calcium Binding Protein A1 (S100A1).

In one embodiment, the payload region of the AAV particle comprises a nucleic acid sequence encoding an amino acid sequence, or fragment thereof, or variant thereof, described in Table 6.

In one embodiment, the payload region of the AAV particle comprises a nucleic acid sequence, or fragment thereof, or variant thereof, described in Table 6.

TABLE 6

| S100 Calcium Binding Protein A1 | | |
|---|---|---|
| Identification | Reference | SEQ ID NO |
| S100A1 SEQ-001 | NP_006262.1 | 1807 |
| S100A1 SEQ-002 | NM_006271.1 | 1808 |

Anti Tau Paired Helical Filaments (Tau-PHFs) Antibodies

In one embodiment, the payload region of the AAV particle comprises one or more nucleic acid sequences encoding the heavy chain and/or light chain of an antibody specific to Paired Helical Filaments (PHF) formed by abnormally folded Tau proteins (Tau-PHFs). The payload region may also comprise one or more nucleic acid sequences encoding a linker region between the nucleic acid sequences encoding the heavy and light chain. As a non-limiting example, the linker region comprises a furin cleavage recognition sequence (nucleic acid sequence shown as SEQ ID NO: 1811) and/or a 2A cis-acting hydrolase element (nucleic acid sequence shown as SEQ ID NO: 1812). As a non-limiting example, the nucleic acid sequence of the linker region is SEQ ID NO: 1813. As a non-limiting example, the antibody that specifically binds to Tau paired helical filaments is PHF-1. The PHF-1 antibody may comprise heavy chains and light chains as taught in this disclosure.

In one embodiment, the payload region of the AAV particle comprises a nucleic acid sequence encoding an amino acid sequence, or fragment thereof, or variant thereof, described in Table 7.

In one embodiment, the payload region of the AAV particle comprises a nucleic acid sequence, or fragment thereof, or variant thereof, described in Table 7.

TABLE 7

Anti Tau Paired Helical Filament Antibodies

| Identification | Reference | SEQ ID NO |
|---|---|---|
| PHF-1 SEQ-001 | Heavy Chain | 1814 |
| PHF-1 SEQ-002 | Light Chain | 1815 |

In one embodiment, the payload region of the AAV particle comprises a nucleic acid sequence SEQ ID NO: 1816 which comprises (5' to 3') the kozak (SEQ ID NO: 1817), heavy chain (SEQ ID NO: 1814), linker region (which includes the furin cleavage recognition sequence (SEQ ID NO: 1811) and the 2A cis-acting hydrolase element sequence (SEQ ID NO: 1812)), light chain sequence (SEQ ID NO: 1812) of PHF-1, and the stop codon TAG described in FIG. 5A of WO2015035190, the contents of which are herein incorporated by reference in their entirety.

In one embodiment, the payload region of the AAV particle comprises a nucleic acid sequence SEQ ID NO: 1818, which comprises (5' to 3') the kozak (SEQ ID NO: 1817), light chain (SEQ ID NO: 1815), linker region (which includes the furin cleavage recognition sequence (SEQ ID NO: 1811) and the 2A cis-acting hydrolase element sequence (SEQ ID NO: 1812)), heavy chain (SEQ ID NO: 1814) of PHF-1, and the stop codon TAG.

In one embodiment, the payload region of the AAV particle comprises a nucleic acid encoding the heavy chain and/or light chain of PHF-1 as taught in FIG. 5A of WO2015035190, the contents of which are herein incorporated by reference, wherein the heavy chain and/or light chain of PHF-1 in WO2015035190 has been altered (e.g., modified and/or mutated). The sequence may be mutated or modified to change the state or structure of a molecule. As a non-limiting example, the sequence may include an addition of an amino acid, an amino acid substitution, and/or a deletion of an amino acid.

In one embodiment, the payload region of the AAV particle comprises a nucleic acid encoding the light chain of PHF-1 where the light chain sequence has been altered to remove the second methionine at the beginning of the light chain amino acid sequence. As a non-limiting example, the payload region of the AAV particle comprises a nucleic acid encoding an amino acid sequence encoding a light chain of PHF-1 as shown in Table 8.

TABLE 8

Anti Tau Paired Helical Filament Antibodies

| Identification | Reference | SEQ ID NO |
|---|---|---|
| PHF-1 SEQ-003 | Light Chain | 1819 |

In one embodiment, the payload region of the AAV particle comprises a nucleic acid sequence SEQ ID NO: 1820, which comprises (5' to 3') the kozak (SEQ ID NO: 1817), heavy chain (SEQ ID NO: 1814), linker region (which includes the furin cleavage recognition sequence (SEQ ID NO: 1811) and the 2A cis-acting hydrolase element sequence (SEQ ID NO: 1812)), light chain sequence (SEQ ID NO: 1819) with one codon of "ATG" at the 5' end of the light chain sequence of PHF-1, and the stop codon TAG.

In one embodiment, the payload region of the AAV particle comprises a nucleic acid sequence SEQ ID NO: 1821, which comprises (5' to 3') the kozak (SEQ ID NO: 1817), light chain sequence with one codon of "ATG" at the 5' end of the light chain sequence (SEQ ID NO: 1819), linker region (which includes the furin cleavage recognition sequence (SEQ ID NO: 1811) and the 2A cis-acting hydrolase element sequence (SEQ ID NO: 1812)), heavy chain of PHF-1 (SEQ ID NO: 1814), and the stop codon TAG.

Payloads: Modulatory Polynucleotides as Payloads

The AAV particles of the present disclosure comprise at least one payload region comprising one or more modulatory polynucleotides, e.g., RNA or DNA molecules as therapeutic agents. Exemplary modulatory polynucleotides may be miRNAs, dsRNA and siRNA duplexes. RNA interference mediated gene silencing can specifically inhibit targeted gene expression. The present invention then provides small double stranded RNA (dsRNA) molecules (small interfering RNA, siRNA) targeting a gene of interest, pharmaceutical compositions comprising such siRNAs, as well as processes of their design. The present invention also provides methods of their use for inhibiting gene expression and protein production of gene of interest, for treating a neurological disease.

The present invention provides small interfering RNA (siRNA) duplexes (and modulatory polynucleotides encoding them) that target the mRNA of a gene of interest to interfere with the gene expression and/or protein production.

In one embodiment, the siRNA duplexes of the present invention may target the gene of interest along any segment of their respective nucleotide sequence.

In one embodiment, the siRNA duplexes of the present invention may target the gene of interest at the location of a single-nucleotide polymorphism (SNP) or variant within the nucleotide sequence.

In some embodiments, a nucleic acid sequence encoding such siRNA molecules, or a single strand of the siRNA molecules, is inserted into the viral genome of the AAV particle and introduced into cells, specifically cells in the central nervous system.

AAV particles have been investigated for siRNA delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector and (v) the non-integrative nature in a host chromosome thereby reducing potential for long-term expression. Moreover, infection with AAV particles has minimal influence on changing the pattern of cellular gene expression (Stilwell and Samulski et al., Biotechniques, 2003, 34, 148-150; the contents of which are incorporated herein by reference in their entirety).

The encoded siRNA duplex of the present invention contains an antisense strand and a sense strand hybridized together forming a duplex structure, wherein the antisense strand is complementary to the nucleic acid sequence of the targeted gene, and wherein the sense strand is homologous to the nucleic acid sequence of the targeted gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

According to the present invention, each strand of the siRNA duplex targeting a gene of interest is about 19 to 25, 19 to 24 or 19 to 21 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding the target gene, and the region of complementarity is 30 nucleotides or less, and at least 15 nucleotides in length. Generally, the dsRNA is 19 to 25, 19 to 24 or 19 to 21 nucleotides in length. In some embodiments, the dsRNA is from about 15 to about 25 nucleotides in length, and in other embodiments the dsRNA is from about 25 to about 30 nucleotides in length. In some embodiments, the dsRNA is about 15 nucleotides in length, 16 nucleotides in length, 17 nucleotides in length, 18 nucleotides in length, 19 nucleotides, 20 nucleotides, 21 nucleotides, 22 nucleotides, 23 nucleotides, 24 nucleotides in length, 25 nucleotides in length, 26 nucleotides in length, 27 nucleotides in length, 28 nucleotides in length, 29 nucleotides in length, or 30 nucleotides in length.

The dsRNA, whether directly administered or encoded in an expression vector upon contacting with a cell expressing the target protein, inhibits the expression of the protein by at least 10%, at least 20%, at least 25%, at least 30%, at least 35% or at least 40% or more, such as when assayed by a method as described herein.

According to the present invention, the siRNA duplexes or dsRNA molecules s are designed and tested for their ability in reducing expression of the target gene (e.g., mRNA levels of the target gene) in cultured cells. siRNA design tools are available in the art. Any commercial softwares may be used to design the siRNA duplexes against a gene of interest.

According to the present invention, AAV particles comprising a payload region having the nucleic acids of the siRNA duplexes, one strand of the siRNA duplex or the dsRNA targeting a gene of interest are produced, the AAV particle serotypes may be or may include a capsid and/or a peptide insert such as, but not limited to VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In one embodiment, the siRNA duplexes or encoded dsRNA molecules may be used to reduce the expression of target protein by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of target protein expression may be reduced 50-90%.

In one embodiment, the siRNA duplexes or encoded dsRNA molecules may be used to reduce the expression of target mRNA by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of target mRNA expression may be reduced 50-90%.

In one embodiment, the siRNA duplexes or encoded dsRNA molecules may be used to reduce the expression of target protein and/or mRNA in at least one region of the CNS. The expression of target protein and/or mRNA is reduced by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of target protein and mRNA in the neurons (e.g., cortical neurons) is reduced by 50-90%. As a non-limiting example, the expression of target protein and mRNA in the neurons (e.g., cortical neurons) is reduced by 40-50%.

In some embodiments, the AAV particle of the present invention comprising the nucleic acid sequence of at least one siRNA duplex targeting a gene of interest is administered to the subject in need for treating and/or ameliorating a disease, e.g., a neurological disorder or a cardiovascular disease. The AAV particle serotype may be or include a peptide such as but is not limited to VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5, PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv-1, AAV Clv1-10, AAV CLv1-2, AAV CLv-12, AAV CLv1-3, AAV Clv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, an AAVPHP.B particle (an AAV particle comprising a PHP.B peptide insert) comprising the nucleic acid sequence of at least one siRNA duplex targeting a gene of interest is administered to the subject in need for treating and/or ameliorating a neurological disease.

In some embodiments, an AAVPHP.A particle (an AAV particle comprising a PHP.A peptide insert) comprising the nucleic acid sequence of at least one siRNA duplex targeting a gene of interest is administered to the subject in need for treating and/or ameliorating a neurological disease.

In some embodiments, an AAVPHP.N particle (an AAV particle comprising a PHP.N peptide insert) comprising the nucleic acid sequence of at least one siRNA duplex targeting a gene of interest is administered to the subject in need for treating and/or ameliorating a neurological disease.

In some embodiments, an AAV particle comprising a PHP.S peptide insert, comprises the nucleic acid sequence of at least one siRNA duplex targeting a gene of interest, and the AAV particle may be administered to the subject in need for treating and/or ameliorating a neurological disease.

In some embodiments, an AAV particle that has a serotype of VOY101 comprising the nucleic acid sequence of at least one siRNA duplex targeting a gene of interest is administered to the subject in need for treating and/or ameliorating a neurological disease. In one embodiment, the VOY101 capsid comprises an amino acid sequence of SEQ ID NO. 1. In one embodiment, the VOY101 capsid comprises a nucleic acid sequence of SEQ ID NO. 1809.

In some embodiments, an AAV particle that has the serotype of VOY201 comprising the nucleic acid sequence of at least one siRNA duplex targeting a gene of interest is administered to the subject in need for treating and/or ameliorating a neurological disease. In one embodiment, the VOY201 capsid comprises a nucleic acid sequence of SEQ ID NO. 1810.

In some embodiments, an AAV particle that has a serotype of a variant of the AAV9 comprising the nucleic acid sequence of at least one siRNA duplex targeting a gene of interest is administered to the subject in need for treating and/or ameliorating a neurological disease.

In some embodiments, a first AAV particle comprising the nucleic acid sequence of at least one siRNA duplex (e.g., payload) targeting a gene of interest may be selected for administration to a subject, where the first AAV particle provides a higher level of viral genome to cells (e.g., astrocytes) as compared to a second AAV particle comprising the same payload. In one embodiment, the level of the first viral genome may provide 0.1, 0.2, 0.3, 0.4, 0.5, 0.6, 0.7, 0.8, 0.9, 1, 2, 3, 4, 5, 6, 7, 8, 9 or more than 9 times higher in cells (e.g., astrocytes) as compared to the level in cells of a subject of the second AAV particle. In one embodiment, the level of the first viral genome may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or more than 99% higher than the level of the second viral genome in cells (e.g., astrocytes). In one embodiment, the level of the first viral genome may be 1-10%, 5-10%, 10-15%, 10-20%, 15-20%, 20-30%, 25-30%, 25-35%, 30-35%, 30-40%, 35-40%, 35-45%, 40-45%, 40-50%, 45-50%, 45-55%, 50-55%, 50-60%, 55-60%, 55-65%, 60-65%, 60-70%, 65-70%, 65-75%, 70-75%, 70-80%, 75-80%, 75-85%, 80-85%, 80-90%, 85-90%, 85-95%, 90-95%, 90-99%, or 95-99% higher than the level of the second viral genome in cells (e.g., astrocytes).

In some embodiments, a first AAV particle comprising the nucleic acid sequence of at least one siRNA duplex targeting the gene of interest may be selected for administration to a subject, where the first particle provides a higher viral genome to the astrocytes as compared to the amount seen in the liver of the subject. The first particle may provide 1, 2, 3, 4, 5, 6, 7, 8, 9 or more than 9 times more viral genome to the astrocytes as compared to the amount in the liver.

In some embodiments, the siRNA molecules or the AAV particles comprising such siRNA molecules may be introduced directly into the central nervous system of the subject, for example, by infusion into the putamen.

In some embodiments, the siRNA molecules or the AAV particles comprising such siRNA molecules may be introduced directly into the central nervous system of the subject, for example, by infusion to the thalamus a subject.

In some embodiments, the siRNA molecules or the AAV particles comprising such siRNA molecules may be introduced directly into the central nervous system of the subject, for example, by infusion to the white matter a subject.

In some embodiments, the siRNA molecules or the AAV particles comprising such siRNA molecules may be introduced to the central nervous system of the subject, for example, by intravenous administration to a subject.

In some embodiments, the AAV particles comprising at least one siRNA duplex targeting a gene of interest may be used as a solo therapy or in combination therapy for treatment of a disease, for example, in combination with one or more neuroprotective agents for treatment of neuronal degeneration.

siRNA Molecules

The present invention relates to RNA interference (RNAi) induced inhibition of gene expression for treating neurological disorders. Provided herein are siRNA duplexes or encoded dsRNA that target a gene of interest (referred to herein collectively as "siRNA molecules"). Such siRNA duplexes or encoded dsRNA can reduce or silence target gene expression in cells, for example, astrocytes or microglia, cortical, hippocampal, entorhinal, thalamic, sensory or motor neurons, thereby, ameliorating symptoms of neurological disease.

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs containing RNA Induced Silencing Complex (RISC) targets mRNAs presenting a perfect sequence complementarity with nucleotides 2-7 in the 5' region of the miRNA which is called the seed region, and other base pairs with its 3' region. miRNA mediated down regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., *Nature*, 2001, 411, 494-498). Since this initial report, post-transcriptional gene silencing by siRNAs quickly emerged as a powerful tool for genetic analysis in mammalian cells and has the potential to produce novel therapeutics.

In vitro synthetized siRNA molecules may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that facilitates searching through the genome for RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complex are mRNAs presenting a perfect sequence complementarity. Then, siRNA mediated gene silencing occurs, cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases it requires higher concentration of the ss-siRNA to achieve the effective gene silencing potency of the corresponding duplex.

Any of the foregoing molecules may be encoded by an AAV particle or viral genome.

Target Genes

Non-limiting examples of the neurological diseases which may be treated with the modulatory polynucleotides of the invention include tauopathies, Alzheimer Disease, Huntington's Disease, and/or Amyotrophic Lateral Sclerosis. Target genes may be any of the genes associated with any neurological disease such as, but not limited to, those listed herein.

In one embodiment, the target gene is an allele of the apolipoprotein E (APOE) gene (e.g., ApoE2, ApoE3, and/or ApoE4). As a non-limiting example, the target gene is APOE and the target gene has one of the sequences taught in Table 2, a fragment or variant thereof.

In another embodiment, the target gene is superoxide dismutase (SOD1). As a non-limiting example, the target gene is SOD1 and the target gene has a sequence of SEQ ID NO: 1753 (NCBI reference number NM_000454.4), a fragment or variant thereof.

In another embodiment, the target gene is huntingtin (HTT). As a non-limiting example, the target gene is HTT having a nucleotide sequence of SEQ ID NO: 1754 (NCBI reference number NM_002111.7), a fragment or variant thereof. As a non-limiting example, the target gene is HTT and the target gene encodes an amino acid sequence of SEQ ID NO: 1755 (NCBI reference number NP_002102.4), a fragment or variant thereof.

In yet another embodiment, the target gene is microtubule-associated protein tau (MAPT). As a non-limiting example, the target gene is MAPT having a nucleotide sequence of any of the nucleic acid sequences shown in Table 9, a fragment or variant thereof. As a non-limiting example, the target gene is MAPT and the target gene encodes an amino acid sequence of any of the amino acid sequences shown in Table 9, a fragment or variant thereof.

TABLE 9

Microtubule-Associated Protein Tau Sequences

| Identification | Reference | SEQ ID NO |
|---|---|---|
| MAPT SEQ-001 | NP_058519.3 | 1756 |
| MAPT SEQ-002 | NP_005901.2 | 1757 |
| MAPT SEQ-003 | NP_058518.1 | 1758 |
| MAPT SEQ-004 | NP_058525.1 | 1759 |
| MAPT SEQ-005 | NP_001116539.1 | 1760 |
| MAPT SEQ-006 | NP_001116538.2 | 1761 |
| MAPT SEQ-007 | NP_001190180.1 | 1762 |
| MAPT SEQ-008 | NP_001190181.1 | 1763 |
| MAPT SEQ-009 | NM_016835.4 | 1764 |
| MAPT SEQ-010 | NM_005910.5 | 1765 |
| MAPT SEQ-011 | NM_016834.4 | 1766 |

TABLE 9-continued

Microtubule-Associated Protein Tau Sequences

| Identification | Reference | SEQ ID NO |
|---|---|---|
| MAPT SEQ-012 | NM_016841.4 | 1767 |
| MAPT SEQ-013 | NM_001123067.3 | 1768 |
| MAPT SEQ-014 | NM_001123066.3 | 1769 |
| MAPT SEQ-015 | NM_001203251.1 | 1770 |
| MAPT SEQ-016 | NM_001203252.1 | 1771 |

Design and Sequences of siRNA Duplexes

Some guidelines for designing siRNAs have been proposed in the art. These guidelines generally recommend generating a 19-nucleotide duplexed region, symmetric 2-3 nucleotide 3' overhangs, 5-phosphate and 3-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

According to the present invention, siRNA molecules (e.g., siRNA duplexes or encoded dsRNA) that target a gene of interest are designed. Such siRNA molecules can specifically suppress target gene expression and protein production. In some aspects, the siRNA molecules are designed and used to selectively "knock out" target gene variants in cells, i.e., transcripts that are identified in neurological disease. In some aspects, the siRNA molecules are designed and used to selectively "knock down" target gene variants in cells.

In one embodiment, an siRNA molecule of the present invention comprises a sense strand and a complementary antisense strand in which both strands are hybridized together to form a duplex structure. The antisense strand has sufficient complementarity to the target mRNA sequence to direct target-specific RNAi, i.e., the siRNA molecule has a sequence sufficient to trigger the destruction of the target mRNA by the RNAi machinery or process.

In some embodiments, the antisense strand and target mRNA sequences have 100% complementarity. The antisense strand may be complementary to any part of the target mRNA sequence.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

According to the present invention, the siRNA molecule has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one embodiment, the siRNA molecule has a length from about 19 to 25, 19 to 24 or 19 to 21 nucleotides.

In some embodiments, the siRNA molecules of the present invention can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention may comprise an antisense sequence and a sense sequence, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

DNA expression plasmids can be used to stably express the siRNA duplexes or dsRNA of the present invention in cells and achieve long-term inhibition of the target gene. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

In other embodiments, the siRNA molecules of the present invention can be encoded in AAV particles for delivery to a cell. In one embodiment, the siRNA may be inserted to an AAV viral genome, flanked by the ITRs.

According to the present invention, the AAV particles comprising the nucleic acids encoding the siRNA molecules targeting mRNA of a gene of interest may include AAV particle serotypes, and/or may include a peptide insertion such as, but are not limited to, VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5, PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11I/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, the siRNA duplexes or encoded dsRNA of the present invention suppress (or degrade) target mRNA. Accordingly, the siRNA duplexes or encoded dsRNA can be used to substantially inhibit target gene expression in a cell, for example a neuron or astrocyte. In some aspects, the inhibition of target gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, siRNA molecules targeting a gene of interest may be designed using any available design tools. According to the present invention, the siRNA molecules are designed and tested for their ability in reducing target gene mRNA levels in cultured cells.

In one embodiment, the siRNA molecules are designed and tested for their ability in reducing ApoE2 levels in cultured cells.

In one embodiment, the siRNA molecules are designed and tested for their ability in reducing ApoE3 levels in cultured cells.

In one embodiment, the siRNA molecules are designed and tested for their ability in reducing ApoE4 levels in cultured cells.

In one embodiment, the siRNA molecules are designed and tested for their ability in reducing SOD1 levels in cultured cells.

In one embodiment, the siRNA molecules are designed and tested for their ability in reducing HTT levels in cultured cells.

In one embodiment, the siRNA molecules are designed and tested for their ability in reducing Tau levels in cultured cells.

In one embodiment, the siRNA molecules comprise a miRNA seed match for the guide strand. In another embodiment, the siRNA molecules comprise a miRNA seed match for the passenger strand. In yet another embodiment, the siRNA duplexes or encoded dsRNA targeting a gene of interest do not comprise a seed match for the guide or passenger strand.

In one embodiment, the siRNA duplexes or encoded dsRNA targeting a gene of interest may have almost no significant full-length off targets for the guide strand. In another embodiment, the siRNA duplexes or encoded dsRNA targeting a gene of interest may have almost no significant full-length off targets for the passenger strand. The siRNA duplexes or encoded dsRNA targeting a gene of interest may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off targets for the passenger strand. In yet another embodiment, the siRNA duplexes or encoded dsRNA targeting a gene of interest may have almost no significant full-length off targets for the guide strand or the passenger strand. The siRNA duplexes or encoded dsRNA targeting a gene of interest may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off targets for the guide or passenger strand.

In one embodiment, the siRNA duplexes or encoded dsRNA targeting a gene of interest may have high activity in vitro. In another embodiment, the siRNA molecules may have low activity in vitro. In yet another embodiment, the siRNA duplexes or dsRNA targeting the gene of interest may have high guide strand activity and low passenger strand activity in vitro.

In one embodiment, the siRNA molecules have a high guide strand activity and low passenger strand activity in vitro. The target knock-down (KD) by the guide strand may be at least 60%, 65%, 70%, 75%, 80%, 85%, 90%, 95%, 99%, 99.5% or 100%. The target knock-down by the guide strand may be 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%.

In one embodiment, the $IC_{50}$ of the passenger strand for the nearest off target is greater than 100 multiplied by the $IC_{50}$ of the guide strand for the target. As a non-limiting example, if the $IC_{50}$ of the passenger strand for the nearest off target is greater than 100 multiplied by the $IC_{50}$ of the guide strand for the target then the siRNA molecules are said to have high guide strand activity and a low passenger strand activity in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo.

In one embodiment, the guide to passenger (G:P) (also referred to as the antisense to sense) strand ratio expressed is 1:10, 1:9, 1:8, 1:7, 1:6, 1:5, 1:4, 1:3, 1:2, 1:1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The guide to passenger ratio refers to the ratio of the guide strands to the passenger strands after the excision of the guide strand. For example, an 80:20 guide to passenger ratio would have 8 guide strands to every 2 passenger strands clipped out of the precursor. As a non-limiting example, the guide-to-passenger strand ratio is 80:20 in vitro. As a non-limiting example, the guide-to-passenger strand ratio is 80:20 in vivo. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In one embodiment, the passenger to guide (P:G) (also referred to as the sense to antisense) strand ratio expressed is 1:10, 1:9, 1:8, 1:7, 1:6, 1:5, 1:4, 1:3, 1:2, 1:1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the excision of the guide strand. For example, an 80:20 passenger to guide ratio would have 8 passenger strands to every 2 guide strands clipped out of the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In one embodiment, the integrity of the viral genome encoding the dsRNA is at least 60%, 65%, 70%, 75%, 80%, 85%, 90%, 95%, 99% or more than 99% of the full length of the construct. As a non-limiting example, the integrity of the viral genome is 80% of the full length of the construct.

In one embodiment, the passenger and/or guide strand is designed based on the method and rules outlined in European Patent Publication No. EP1752536, the contents of which are herein incorporated by reference in their entirety. As a non-limiting example, the 3'-terminal base of the sequence is adenine, thymine or uracil. As a non-limiting example, the 5'-terminal base of the sequence is guanine or cytosine. As a non-limiting example, the 3'-terminal sequence comprises seven bases rich in one or more bases of adenine, thymine and uracil. As a non-limiting example, the base number is at such a level as causing RNA interference without expressing cytotoxicity.

Molecular Scaffold

In one embodiment, the siRNA molecules may be encoded in a modulatory polynucleotide which also comprises a molecular scaffold. As used herein a "molecular scaffold" is a framework or starting molecule that forms the sequence or structural basis against which to design or make a subsequent molecule.

In one embodiment, the modulatory polynucleotide which comprises the payload (e.g., siRNA, miRNA or other RNAi agent described herein) includes a molecular scaffold which comprises at least one 5' flanking sequence which may be of any length and may be derived in whole or in part from wild type microRNA sequence or be completely artificial. A 3' flanking sequence may mirror the 5' flanking sequence in size and origin. Either flanking sequence may be absent. In one embodiment, both the 5' and 3' flanking sequences are absent. The 3' flanking sequence may optionally contain one or more CNNC motifs, where "N" represents any nucleotide.

In some embodiments the 5' and 3' flanking sequences are the same length.

In some embodiments the 5' flanking sequence is from 1-10 nucleotides in length, from 5-15 nucleotides in length, from 10-30 nucleotides in length, from 20-50 nucleotides in length, greater than 40 nucleotides in length, greater than 50 nucleotides in length, greater than 100 nucleotides in length or greater than 200 nucleotides in length.

In some embodiments, the 5' flanking sequence may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides in length.

In some embodiments the 3' flanking sequence is from 1-10 nucleotides in length, from 5-15 nucleotides in length, from 10-30 nucleotides in length, from 20-50 nucleotides in length, greater than 40 nucleotides in length, greater than 50 nucleotides in length, greater than 100 nucleotides in length or greater than 200 nucleotides in length.

In some embodiments, the 3' flanking sequence may be 1, 2, 3, 4, 5, 6, 7, 8, 9, 10, 11, 12, 13,14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides in length.

In some embodiments the 5' and 3' flanking sequences are the same sequence. In some embodiments they differ by 2%, 3%, 4%, 5%, 10%, 20% or more than 30% when aligned to each other.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

Forming the stem of a stem loop structure is a minimum of at least one payload sequence. In some embodiments, the payload sequence comprises at least one nucleic acid sequence which is in part complementary or will hybridize to the target sequence. In some embodiments, the payload is an siRNA molecule or fragment of an siRNA molecule.

In some embodiments, the 5' arm of the stem loop comprises a sense sequence.

In some embodiments, the 3' arm of the stem loop comprises an antisense sequence. The antisense sequence, in some instances, comprises a "G" nucleotide at the 5' most end.

In other embodiments, the sense sequence may reside on the 3' arm while the antisense sequence resides on the 5' arm of the stem of the stem loop structure.

The sense and antisense sequences may be completely complementary across a substantial portion of their length. In other embodiments, the sense sequence and antisense sequence may be at least 70, 80, 90, 95 or 99% complementary across independently at least 50, 60, 70, 80, 85, 90, 95, or 99% of the length of the strands.

Neither the identity of the sense sequence nor the homology of the antisense sequence need be 100% complementary to the target.

Separating the sense and antisense sequence of the stem loop structure is a loop (also known as a loop motif). The loop may be of any length, between 4-30 nucleotides, between 4-20 nucleotides, between 4-15 nucleotides, between 5-15 nucleotides, between 6-12 nucleotides, 6 nucleotides, 7, nucleotides, 8 nucleotides, 9 nucleotides, 10 nucleotides, 11 nucleotides, and/or 12 nucleotides.

In some embodiments, the loop comprises at least one UGUG motif. In some embodiments, the UGUG motif is located at the 5' terminus of the loop.

Spacer regions may be present in the modulatory polynucleotide to separate one or more modules from one another. There may be one or more such spacer regions present.

In one embodiment, a spacer region of between 8-20, i.e., 8, 9, 10, 11, 12, 13, 14, 15, 16, 17, 18, 19, or 20 nucleotides may be present between the sense sequence and a flanking sequence.

In one embodiment, the spacer is 13 nucleotides and is located between the 5' terminus of the sense sequence and a flanking sequence. In one embodiment, a spacer is of sufficient length to form approximately one helical turn of the sequence.

In one embodiment, a spacer region of between 8-20, i.e., 8, 9, 10, 11, 12, 13, 14, 15, 16, 17, 18, 19, or 20 nucleotides may be present between the antisense sequence and a flanking sequence.

In one embodiment, the spacer sequence is between 10-13, i.e., 10, 11, 12 or 13 nucleotides and is located between the 3' terminus of the antisense sequence and a flanking sequence. In one embodiment, a spacer is of sufficient length to form approximately one helical turn of the sequence.

In one embodiment, the modulatory polynucleotide comprises in the 5' to 3' direction, a 5' flanking sequence, a 5' arm, a loop motif, a 3' arm and a 3' flanking sequence. As a non-limiting example, the 5' arm may comprise a sense sequence and the 3' arm comprises the antisense sequence. In another non-limiting example, the 5' arm comprises the antisense sequence and the 3' arm comprises the sense sequence.

In one embodiment, the 5' arm, payload (e.g., sense and/or antisense sequence), loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the molecular scaffold of the modulatory polynucleotides is aligned in order to have the rate of excision of the guide strand be greater than the rate of excision of the passenger strand. The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In one embodiment, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In one embodiment, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In one embodiment, the efficiency of the excision of the guide strand is greater than the excision of the passenger strand from the molecular scaffold. The excision of the guide strand may be 2, 3, 4, 5, 6, 7, 8, 9, 10 or more than 10 times more efficient than the excision of the passenger strand from the molecular scaffold.

In one embodiment, the molecular scaffold comprises a dual-function targeting modulatory polynucleotide. As used herein, a "dual-function targeting" modulatory polynucleotide is a polynucleotide where both the guide and passenger strands knock down the same target or the guide and passenger strands knock down different targets.

In one embodiment, the molecular scaffold of the modulatory polynucleotides described herein comprise a 5' flanking region, a loop region and a 3' flanking region. Non-limiting examples of the sequences for the 5' flanking region, loop region and the 3' flanking region which may be used in the molecular scaffolds described herein are shown in Tables 10-12.

TABLE 10

5' Flanking Regions for Molecular Scaffold

| 5' Flanking Region Name | 5' Flanking Region Sequence | 5' Flanking Region SEQ ID NO |
|---|---|---|
| 5F1 | UUUAUGCCUCAUCCUCUGAGUGCUGAAGGCUUGCUGUAGGCUGUAUGCUG | 1772 |
| 5F2 | GUGCUGGGCGGGGGGCGGCGGGCCCUCCCGCAGAACACCAUGCGCUCUUCGGAA | 1773 |
| 5F3 | GAAGCAAAGAAGGGGCAGAGGGAGCCCGUGAGCUGAGUGGGCCAGGGACUGGGAGAAGGAGUGAGGAGGCAGGGCCGGCAUGCCUCUGCUGCUGGCCAGA | 1774 |
| 5F4 | GUGCUGGGCGGGGGGCGGCGGGCCCUCCCGCAGAACACCAUGCGCUCUUCGGGA | 1775 |
| 5F5 | GUGCUGGGCGGGGGGCGGCGGGCCCUCCCGCAGAACACCAUGCGCUCCACGGAA | 1776 |
| 5F6 | GGGCCCUCCCGCAGAACACCAUGCGCUCCACGGAA | 1777 |
| 5F7 | CUCCCGCAGAACACCAUGCGCUCCACGGAA | 1778 |
| 5F8 | GUGCUGGGCGGGGGGCGGCGGGCCCUCCCGCAGAACACCAUGCGCUCCACGGAAG | 1779 |
| 5F9 | GUGCUGGGCGGGGGGCGGCGGGCCCUCCCGCAGAACACCAUGCGCUCCUCGGAA | 1780 |

TABLE 11

Loop Motif

| Loop Motif Region Name | Loop Motif Region Sequence | Loop Motif Region SEQ ID NO |
|---|---|---|
| L1 | UGUGACCUGG | 1781 |
| L2 | UGUGAUUUGG | 1782 |
| L3 | UAUAAUUUGG | 1783 |
| L4 | CCUGACCCAGU | 1784 |
| L5 | GUCUGCACCUGUCACUAG | 1785 |
| L6 | GUGACCCAAG | 1786 |
| L7 | GUGGCCACUGAGAAG | 1787 |
| L8 | GUGACCCAAU | 1788 |
| L9 | GUGACCCAAC | 1789 |

TABLE 12

3' Flanking Regions for Molecular Scaffold

| 3' Flanking Region Name | 3' Flanking Region Sequence | 3' Flanking Region SEQ ID NO |
|---|---|---|
| 3F1 | AGUGUAUGAUGCCUGUUACUAGCAUUCACAUGGAACAAAUUGCUGCCGUG | 1791 |
| 3F2 | CUGAGGAGCGCCUUGACAGCAGCCAUGGGAGGGCCGCCCCCUACCUCAGUGA | 1792 |
| 3F3 | CUGUGGAGCGCCUUGACAGCAGCCAUGGGAGGGCCGCCCCCUACCUCAGUGA | 1793 |
| 3F4 | UGGCCGUGUAGUGCUACCCAGCGCUGGCUGCCUCCUCAGCAUUGCAAUUCCUCUCCCAUCUGGGCACCAGUCAGCUACCCUGGUGGGAAUCUGGGUAGCC | 1794 |
| 3F5 | GGCCGUGUAGUGCUACCCAGCGCUGGCUGCCUCCUCAGCAUUGCAAUUCCUCUCCCAUCUGGGCACCAGUCAGCUACCCUGGUGGGAAUCUGGGUAGCC | 1795 |
| 3F6 | UCCUGAGGAGCGCCUUGACAGCAGCCAUGGGAGGGCCGCCCCCUACCUCAGUGA | 1796 |
| 3F7 | CUGAGGAGCGCCUUGACAGCAGCCAUGGGAGGGCC | 1797 |
| 3F8 | CUGCGGAGCGCCUUGACAGCAGCCAUGGGAGGGCCGCCCCCUACCUCAGUGA | 1798 |

Any of the regions described in Tables 8-10 may be used in the molecular scaffolds described herein.

In one embodiment, the molecular scaffold may comprise one 5' flanking region listed in Table 10. As a non-limiting example, the molecular scaffold may comprise the 5' flanking region 5F1, 5F2, 5F3, 5F4, 5F5, 5F6, 5F7, 5F8 or 5F9.

In one embodiment, the molecular scaffold may comprise one loop motif region listed in Table 11. As a non-limiting example, the molecular scaffold may comprise the loop motif region L1, L2, L3, L4, L5, L6, L7, L8, L9, or L10.

In one embodiment, the molecular scaffold may comprise one 3' flanking region listed in Table 12. As a non-limiting example, the molecular scaffold may comprise the 3' flanking region 3F1, 3F2, 3F3, 3F4, 3F5, 3F6, 3F7 or 3F8.

In one embodiment, the molecular scaffold may comprise at least one 5' flanking region and at least one loop motif region as described in Tables 10 and 11. As a non-limiting example, the molecular scaffold may comprise 5F1 and L1, 5F1 and L2, 5F1 and L3, 5F1 and L4, 5F1 and L5, 5F1 and L6, 5F1 and L7, 5F1 and L8, 5F1 and L9, 5F1 and L10, 5F2 and L1, 5F2 and L2, 5F2 and L3, 5F2 and L4, 5F2 and L5, 5F2 and L6, 5F2 and L7, 5F2 and L8, 5F2 and L9, 5F2 and L10, 5F3 and L1, 5F3 and L2, 5F3 and L3, 5F3 and L4, 5F3 and L5, 5F3 and L6, 5F3 and L7, 5F3 and L8, 5F3 and L9, 5F3 and L10, 5F4 and L1, 5F4 and L2, 5F4 and L3, 5F4 and L4, 5F4 and L5, 5F4 and L6, 5F4 and L7, 5F4 and L8, 5F4 and L9, 5F4 and L10, 5F5 and L1, 5F5 and L2, 5F5 and L3, 5F5 and L4, 5F5 and L5, 5F5 and L6, 5F5 and L7, 5F5 and L8, 5F5 and L9, 5F5 and L10, 5F6 and L1, 5F6 and L2, 5F6 and L3, 5F6 and L4, 5F6 and L5, 5F6 and L6, 5F6 and L7, 5F6 and L8, 5F6 and L9, 5F6 and L10, 5F7 and L1, 5F7 and L2, 5F7 and L3, 5F7 and L4, 5F7 and L5, 5F7 and L6, 5F7 and L7, 5F7 and L8, 5F7 and L9, 5F7 and L10, 5F8 and L1, 5F8 and L2, 5F8 and L3, 5F8 and L4, 5F8 and L5, 5F8 and L6, 5F8 and L7, 5F8 and L8, 5F8 and L9, 5F8 and L10, 5F9 and L1, 5F9 and L2, 5F9 and L3, 5F9 and L4, 5F9 and L5, 5F9 and L6, 5F9 and L7, 5F9 and L8, 5F9 and L9, or 5F9 and L10.

In one embodiment, the molecular scaffold may comprise at least one 3' flanking region and at least one loop motif region as described in Tables 11 and 12. As a non-limiting example, the molecular scaffold may comprise 3F1 and L1, 3F1 and L2, 3F1 and L3, 3F1 and L4, 3F1 and L5, 3F1 and L6, 3F1 and L7, 3F1 and L8, 3F1 and L9, 3F1 and L10, 3F2 and L1, 3F2 and L2, 3F2 and L3, 3F2 and L4, 3F2 and L5, 3F2 and L6, 3F2 and L7, 3F2 and L8, 3F2 and L9, 3F2 and L10, 3F3 and L1, 3F3 and L2, 3F3 and L3, 3F3 and L4, 3F3 and L5, 3F3 and L6, 3F3 and L7, 3F3 and L8, 3F3 and L9, 3F3 and L10, 3F4 and L1, 3F4 and L2, 3F4 and L3, 3F4 and L4, 3F4 and L5, 3F4 and L6, 3F4 and L7, 3F4 and L8, 3F4 and L9, 3F4 and L10, 3F5 and L1, 3F5 and L2, 3F5 and L3, 3F5 and L4, 3F5 and L5, 3F5 and L6, 3F5 and L7, 3F5 and L8, 3F5 and L9, 3F5 and L10, 3F6 and L1, 3F6 and L2, 3F6 and L3, 3F6 and L4, 3F6 and L5, 3F6 and L6, 3F6 and L7, 3F6 and L8, 3F6 and L9, 3F6 and L10, 3F7 and L1, 3F7 and L2, 3F7 and L3, 3F7 and L4, 3F7 and L5, 3F7 and L6, 3F7 and L7, 3F7 and L8, 3F7 and L9, 3F7 and L10, 3F8 and L1, 3F8 and L2, 3F8 and L3, 3F8 and L4, 3F8 and L5, 3F8 and L6, 3F8 and L7, 3F8 and L8, 3F8 and L9, or 3F8 and L10.

In one embodiment, the molecular scaffold may comprise at least one 5' flanking region and at least 3' flanking region as described in Tables 10 and 12. As a non-limiting example, the molecular scaffold may comprise 5F1 and 3F1, 5F1 and 3F2, 5F1 and 3F3, 5F1 and 3F4, 5F1 and 3F5, 5F1 and 3F6, 5F1 and 3F7, 5F1 and 3F8, 5F2 and 3F1, 5F2 and 3F2, 5F2 and 3F3, 5F2 and 3F4, 5F2 and 3F5, 5F2 and 3F6, 5F2 and 3F7, 5F2 and 3F8, 5F3 and 3F1, 5F3 and 3F2, 5F3 and 3F3, 5F3 and 3F4, 5F3 and 3F5, 5F3 and 3F6, 5F3 and 3F7, 5F3 and 3F8, 5F4 and 3F1, 5F4 and 3F2, 5F4 and 3F3, 5F4 and 3F4, 5F4 and 3F5, 5F4 and 3F6, 5F4 and 3F7, 5F4 and 3F8, 5F5 and 3F1, 5F5 and 3F2, 5F5 and 3F3, 5F5 and 3F4, 5F5 and 3F5, 5F5 and 3F6, 5F5 and 3F7, 5F5 and 3F8, 5F6 and 3F1, 5F6 and 3F2, 5F6 and 3F3, 5F6 and 3F4, 5F6 and 3F5, 5F6 and 3F6, 5F6 and 3F7, 5F6 and 3F8, 5F7 and 3F1, 5F7 and 3F2, 5F7 and 3F3, 5F7 and 3F4, 5F7 and 3F5, 5F7 and 3F6, 5F7 and 3F7, 5F7 and 3F8, 5F8 and 3F1, 5F8 and 3F2, 5F8 and 3F3, 5F8 and 3F4, 5F8 and 3F5, 5F8 and 3F6, 5F8 and 3F7, 5F8 and 3F8, 5F9 and 3F1, 5F9 and 3F2, 5F9 and 3F3, 5F9 and 3F4, 5F9 and 3F5, 5F9 and 3F6, 5F9 and 3F7, or 5F9 and 3F8.

In one embodiment, the molecular scaffold may comprise at least one 5' flanking region, at least one loop motif region and at least one 3' flanking region as described in Tables 10-12. As a non-limiting example, the molecular scaffold may comprise 5F1, L1 and 3F1; 5F1, L1 and 3F2; 5F1, L1 and 3F3; 5F1, L1 and 3F4; 5F1, L1 and 3F5; 5F1, L1 and 3F6; 5F1, L1 and 3F7; 5F1, L1 and 3F8; 5F2, L1 and 3F1; 5F2, L1 and 3F2; 5F2, L1 and 3F3; 5F2, L1 and 3F4; 5F2, L1 and 3F5; 5F2, L1 and 3F6; 5F2, L1 and 3F7; 5F2, L1 and 3F8; 5F3, L1 and 3F1; 5F3, L1 and 3F2; 5F3, L1 and 3F3; 5F3, L1 and 3F4; 5F3, L1 and 3F5; 5F3, L1 and 3F6; 5F3, L1 and 3F7; 5F3, L1 and 3F8; 5F4, L1 and 3F1; 5F4, L1 and 3F2; 5F4, L1 and 3F3; 5F4, L1 and 3F4; 5F4, L1 and 3F5; 5F4, L1 and 3F6; 5F4, L1 and 3F7; 5F4, L1 and 3F8; 5F5, L1 and 3F1; 5F5, L1 and 3F2; 5F5, L1 and 3F3; 5F5, L1 and 3F4; 5F5, L1 and 3F5; 5F5, L1 and 3F6; 5F5, L1 and 3F7; 5F5, L1 and 3F8; 5F6, L1 and 3F1; 5F6, L1 and 3F2; 5F6, L1 and 3F3; 5F6, L1 and 3F4; 5F6, L1 and 3F5; 5F6, L1 and 3F6; 5F6, L1 and 3F7; 5F6, L1 and 3F8; 5F7, L1 and 3F1; 5F7, L1 and 3F2; 5F7, L1 and 3F3; 5F7, L1 and 3F4; 5F7, L1 and 3F5; 5F7, L1 and 3F6; 5F7, L1 and 3F7; 5F7, L1 and 3F8; 5F8, L1 and 3F1; 5F8, L1 and 3F2; 5F8, L1 and 3F3; 5F8, L1 and 3F4; 5F8, L1 and 3F5; 5F8, L1 and 3F6; 5F8, L1 and 3F7; 5F8, L1 and 3F8; 5F9, L1 and 3F1; 5F9, L1 and 3F2; 5F9, L1 and 3F3; 5F9, L1 and 3F4; 5F9, L1 and 3F5; 5F9, L1 and 3F6; 5F9, L1 and 3F7; 5F9, L1 and 3F8; 5F1, L2 and 3F1; 5F1, L2 and 3F2; 5F1, L2 and 3F3; 5F1, L2 and 3F4; 5F1, L2 and 3F5; 5F1, L2 and 3F6; 5F1, L2 and 3F7; 5F1, L2 and 3F8; 5F2, L2 and 3F1; 5F2, L2 and 3F2; 5F2, L2 and 3F3; 5F2, L2 and 3F4; 5F2, L2 and 3F5; 5F2, L2 and 3F6; 5F2, L2 and 3F7; 5F2, L2 and 3F8; 5F3, L2 and 3F1; 5F3, L2 and 3F2; 5F3, L2 and 3F3; 5F3, L2 and 3F4; 5F3, L2 and 3F5; 5F3, L2 and 3F6; 5F3, L2 and 3F7; 5F3, L2 and 3F8; 5F4, L2 and 3F1; 5F4, L2 and 3F2; 5F4, L2 and 3F3; 5F4, L2 and 3F4; 5F4, L2 and 3F5; 5F4, L2 and 3F6; 5F4, L2 and 3F7; 5F4, L2 and 3F8; 5F5, L2 and 3F1; 5F5, L2 and 3F2; 5F5, L2 and 3F3; 5F5, L2 and 3F4; 5F5, L2 and 3F5; 5F5, L2 and 3F6; 5F5, L2 and 3F7; 5F5, L2 and 3F8; 5F6, L2 and 3F1; 5F6, L2 and 3F2; 5F6, L2 and 3F3; 5F6, L2 and 3F4; 5F6, L2 and 3F5; 5F6, L2 and 3F6; 5F6, L2 and 3F7; 5F6, L2 and 3F8; 5F7, L2 and 3F1; 5F7, L2 and 3F2; 5F7, L2 and 3F3; 5F7, L2 and 3F4; 5F7, L2 and 3F5; 5F7, L2 and 3F6; 5F7, L2 and 3F7; 5F7, L2 and 3F8; 5F8, L2 and 3F1; 5F8, L2 and 3F2; 5F8, L2 and 3F3; 5F8, L2 and 3F4; 5F8, L2 and 3F5; 5F8, L2 and 3F6; 5F8, L2 and 3F7; 5F8, L2 and 3F8; 5F9, L2 and 3F1; 5F9, L2 and 3F2; 5F9, L2 and 3F3; 5F9, L2 and 3F4; 5F9, L2 and 3F5; 5F9, L2 and 3F6; 5F9, L2 and 3F7; 5F9, L2 and 3F8; 5F1, L3 and 3F1; 5F1, L3 and 3F2; 5F1, L3 and 3F3; 5F1, L3 and 3F4; 5F1, L3 and 3F5; 5F1, L3 and 3F6; 5F1, L3 and 3F7; 5F1, L3 and 3F8; 5F2, L3 and 3F1; 5F2, L3 and 3F2; 5F2, L3 and 3F3; 5F2, L3 and 3F4; 5F2, L3 and 3F5; 5F2, L3 and 3F6; 5F2, L3 and 3F7; 5F2, L3 and 3F8; 5F3, L3 and 3F1; 5F3, L3 and 3F2; 5F3, L3 and 3F3; 5F3, L3 and 3F4; 5F3, L3 and 3F5; 5F3, L3 and 3F6; 5F3, L3 and 3F7; 5F3, L3 and 3F8; 5F4, L3 and 3F1; 5F4, L3 and 3F2; 5F4, L3 and 3F3; 5F4, L3 and 3F4; 5F4, L3 and 3F5; 5F4, L3 and 3F6; 5F4, L3 and 3F7; 5F4, L3 and 3F8; 5F5, L3 and 3F1; 5F5, L3 and 3F2; 5F5, L3 and 3F3; 5F5, L3 and 3F4; 5F5, L3 and 3F5; 5F5, L3 and 3F6; 5F5, L3 and 3F7; 5F5, L3 and 3F8; 5F6, L3 and 3F1; 5F6, L3 and 3F2; 5F6, L3 and 3F3; 5F6, L3 and 3F4; 5F6, L3 and 3F5; 5F6, L3 and 3F6; 5F6, L3 and 3F7; 5F6, L3 and 3F8; 5F7, L3 and 3F1; 5F7, L3 and 3F2; 5F7, L3 and 3F3; 5F7, L3 and 3F4; 5F7, L3 and 3F5; 5F7, L3 and 3F6; 5F7, L3 and 3F7; 5F7, L3 and 3F8; 5F8, L3 and 3F1; 5F8, L3 and 3F2; 5F8, L3 and 3F3; 5F8, L3 and 3F4; 5F8, L3 and 3F5; 5F8, L3 and 3F6; 5F8, L3 and 3F7; 5F8, L3 and 3F8; 5F9, L3 and 3F1; 5F9, L3 and 3F2; 5F9, L3 and 3F3; 5F9, L3 and 3F4; 5F9, L3 and 3F5; 5F9, L3 and 3F6; 5F9, L3 and 3F7; 5F9, L3 and 3F8; 5F1, L4 and 3F1; 5F1, L4 and 3F2; 5F1, L4 and 3F3; 5F1, L4 and 3F4; 5F1, L4 and 3F5; 5F1, L4 and 3F6; 5F1, L4 and 3F7; 5F1, L4 and 3F8; 5F2, L4 and 3F1; 5F2, L4 and 3F2; 5F2, L4 and 3F3; 5F2, L4 and 3F4; 5F2, L4 and 3F5; 5F2, L4 and 3F6; 5F2, L4 and 3F7; 5F2, L4 and 3F8; 5F3, L4 and 3F1; 5F3, L4 and 3F2; 5F3, L4 and 3F3; 5F3, L4 and 3F4; 5F3, L4 and 3F5; 5F3, L4 and 3F6; 5F3, L4 and 3F7; 5F3, L4 and 3F8; 5F4, L4 and 3F1; 5F4, L4 and 3F2; 5F4, L4 and 3F3; 5F4, L4 and 3F4; 5F4, L4 and 3F5; 5F4, L4 and 3F6; 5F4, L4 and 3F7; 5F4, L4 and 3F8; 5F5, L4 and 3F1; 5F5, L4 and 3F2; 5F5, L4 and 3F3; 5F5, L4 and 3F4; 5F5, L4 and 3F5; 5F5, L4 and 3F6; 5F5, L4 and 3F7; 5F5, L4 and 3F8; 5F6, L4 and 3F1; 5F6, L4 and 3F2; 5F6, L4 and 3F3; 5F6, L4 and 3F4; 5F6, L4 and 3F5; 5F6, L4 and 3F6; 5F6, L4 and 3F7; 5F6, L4 and 3F8; 5F7, L4 and 3F1; 5F7, L4 and 3F2; 5F7, L4 and 3F3; 5F7, L4 and 3F4; 5F7, L4 and 3F5; 5F7, L4 and 3F6; 5F7, L4 and 3F7; 5F7, L4 and 3F8; 5F8, L4 and 3F1; 5F8, L4 and 3F2; 5F8, L4 and 3F3; 5F8, L4 and 3F4; 5F8, L4 and 3F5; 5F8, L4 and 3F6; 5F8, L4 and 3F7; 5F8, L4 and 3F8; 5F9, L4 and 3F1; 5F9, L4 and 3F2; 5F9, L4 and 3F3; 5F9, L4 and 3F4; 5F9, L4 and 3F5; 5F9, L4 and 3F6; 5F9, L4 and 3F7; 5F9, L4 and 3F8; 5F1, L5 and 3F1; 5F1, L5 and 3F2; 5F1, L5 and 3F3; 5F1, L5 and 3F4; 5F1, L5 and 3F5; 5F1, L5 and 3F6; 5F1, L5 and 3F7; 5F1, L5 and 3F8; 5F2, L5 and 3F1; 5F2, L5 and 3F2; 5F2, L5 and 3F3; 5F2, L5 and 3F4; 5F2, L5 and 3F5; 5F2, L5 and 3F6; 5F2, L5 and 3F7; 5F2, L5 and 3F8; 5F3, L5 and 3F1; 5F3, L5 and 3F2; 5F3, L5 and 3F3; 5F3, L5 and 3F4; 5F3, L5 and 3F5; 5F3, L5 and 3F6; 5F3, L5 and 3F7; 5F3, L5 and 3F8; 5F4, L5 and 3F1; 5F4, L5 and 3F2; 5F4, L5 and 3F3; 5F4, L5 and 3F4; 5F4, L5 and 3F5; 5F4, L5 and 3F6; 5F4, L5 and 3F7; 5F4, L5 and 3F8; 5F5, L5 and 3F1; 5F5, L5 and 3F2; 5F5, L5 and 3F3; 5F5, L5 and 3F4; 5F5, L5 and 3F5; 5F5, L5 and 3F6; 5F5, L5 and 3F7; 5F5, L5 and 3F8; 5F6, L5 and 3F1; 5F6, L5 and 3F2; 5F6, L5 and 3F3; 5F6, L5 and 3F4; 5F6, L5 and 3F5; 5F6, L5 and 3F6; 5F6, L5 and 3F7; 5F6, L5 and 3F8; 5F7, L5 and 3F1; 5F7, L5 and 3F2; 5F7, L5 and 3F3; 5F7, L5 and 3F4; 5F7, L5 and 3F5; 5F7, L5 and 3F6; 5F7, L5 and 3F7; 5F7, L5 and 3F8; 5F8, L5 and 3F1; 5F8, L5 and 3F2; 5F8, L5 and 3F3; 5F8, L5 and 3F4; 5F8, L5 and 3F5; 5F8, L5 and 3F6; 5F8, L5 and 3F7; 5F8, L5 and 3F8; 5F9, L5 and 3F1; 5F9, L5 and 3F2; 5F9, L5 and 3F3; 5F9, L5 and 3F4; 5F9, L5 and 3F5; 5F9, L5 and 3F6; 5F9, L5 and 3F7; or 5F9, L5 and 3F8.

In one embodiment, the molecular scaffold may comprise one or more linkers known in the art. The linkers may separate regions or one molecular scaffold from another. As a non-limiting example, the molecular scaffold may be polycistronic.

In one embodiment, the modulatory polynucleotide is designed using at least one of the following properties: loop variant, seed mismatch/bulge/wobble variant, stem mismatch, loop variant and basal stem mismatch variant, seed mismatch and basal stem mismatch variant, stem mismatch and basal stem mismatch variant, seed wobble and basal stem wobble variant, or a stem sequence variant.

Introduction into Cells siRNA molecules may be delivered to target cells for targeting the gene of interest inside the target cells. In some embodiments, the cells may include, but are not limited to, cells of mammalian origin, cells of human origins, embryonic stem cells, induced pluripotent stem cells, neural stem cells, neural progenitor cells, and differentiated neural cells.

In some embodiments, the siRNA molecules (e.g., siRNA duplexes) of may be introduced into target cells using viral vectors such as AAV particles. These AAV particles are engineered and optimized to facilitate the entry of siRNA molecule into cells that are not readily amendable to transfection, e.g., neurons. Also, some synthetic viral vectors possess an ability to integrate the shRNA into the cell genome, thereby leading to stable siRNA expression and long-term knockdown of a target gene. In this manner, viral vectors are engineered as vehicles for specific delivery while lacking the deleterious replication and/or integration features found in wild-type virus.

In some embodiments, the siRNA molecules are introduced into a cell by contacting the cell with a composition comprising a lipophilic carrier and an AAV particle comprising a nucleic acid sequence encoding the siRNA molecules. In other embodiments, the siRNA molecule is introduced into a cell by transfecting or infecting the cell with an AAV particle comprising nucleic acid sequences capable of producing the siRNA molecule when transcribed in the cell. In some embodiments, the siRNA molecule is introduced into a cell by injecting into the cell an AAV particle comprising a nucleic acid sequence capable of producing the siRNA molecule when transcribed in the cell.

In some embodiments, an AAV particle comprising a nucleic acid sequence encoding the siRNA molecules of the present invention may be transduced into cells.

In other embodiments, the AAV particles comprising the nucleic acid sequence encoding the siRNA molecules may be delivered into cells by electroporation (e.g. U.S. Patent Application Publication No. 20050014264; the contents of which are herein incorporated by reference in their entirety).

Other methods for introducing AAV particles comprising the nucleic acid sequence for the siRNA molecules described herein may include photochemical internalization as described in U. S. Patent Application Publication No. 20120264807; the contents of which are herein incorporated by reference in their entirety.

In one embodiment, the AAV particles from any relevant species, such as, but not limited to, human, dog, mouse, rat or monkey may be introduced into cells.

In one embodiment, the AAV particles may be introduced into cells which are relevant to the disease to be treated. As a non-limiting example, the disease is a tauopathy and/or Alzheimer's Disease and the target cells are entorhinal cortex, hippocampal or cortical neurons.

In one embodiment, the AAV particles may be introduced into cells which have a high level of endogenous expression of the target sequence.

In another embodiment, the AAV particles may be introduced into cells which have a low level of endogenous expression of the target sequence.

In one embodiment, the cells may be those which have a high efficiency of AAV transduction.

In other embodiments, AAV particles comprising a nucleic acid sequence encoding the siRNA molecules of the present invention may be used to deliver siRNA molecules to the central nervous system (e.g., U.S. Pat. No. 6,180,613; the contents of which are herein incorporated by reference in their entirety).

In some aspects, the AAV particles comprising a nucleic acid sequence encoding the siRNA molecules of the present invention may further comprise a modified capsid including peptides from non-viral origin. In other aspects, the AAV particle may contain a CNS specific (e.g., tropism for CNS or CNS tissues) chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In one embodiment, the AAV particle comprising a nucleic acid sequence encoding the siRNA molecules of the present invention may encode siRNA molecules which are polycistronic molecules. The siRNA molecules may additionally comprise one or more linkers between regions of the siRNA molecules.

In one embodiment, an AAV particle may comprise at least one of the modulatory polynucleotides encoding at least one of the siRNA sequences or duplexes described herein.

In one embodiment, an expression vector or viral genome may comprise, from ITR to ITR recited 5' to 3', an ITR, a promoter, an intron, a modulatory polynucleotide, a polyA sequence and an ITR.

In one embodiment, the encoded siRNA molecule may be located downstream of a promoter in an expression vector such as, but not limited to, CMV, U6, H1, CBA or a CBA promoter with a SV40 intron. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the encoded siRNA molecule may be located upstream of the polyadenylation sequence in an expression vector. Further, the encoded siRNA molecule may be located downstream of a promoter such as, but not limited to, CMV, U6, CBA or a CBA promoter with a SV40 intron in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the encoded siRNA molecule may be located in a scAAV.

In one embodiment, the encoded siRNA molecule may be located in an ssAAV.

In one embodiment, the encoded siRNA molecule may be located near the 5' end of the flip ITR in an expression vector. In another embodiment, the encoded siRNA molecule may be located near the 3' end of the flip ITR in an expression vector. In yet another embodiment, the encoded siRNA molecule may be located near the 5' end of the flop ITR in an expression vector. In yet another embodiment, the encoded siRNA molecule may be located near the 3' end of the flop ITR in an expression vector. In one embodiment, the encoded siRNA molecule may be located between the 5' end of the flip ITR and the 3' end of the flop ITR in an expression vector. In one embodiment, the encoded siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

In one embodiment, AAV particle comprising the nucleic acid sequence for the siRNA molecules may be formulated for CNS delivery. Agents that cross the brain blood barrier may be used. Capsids engineered for efficient crossing of the blood brain barrier may be used. Non-limiting examples of such capsids or peptide inserts include VOY101, VOY201, AAVPHP.N, AAVPHP.A, AAVPHP.B, PHP.B2, PHP.B3, G2A3, G2B4, G2B5, PHP.S, and variants thereof. For example, some cell penetrating peptides that can target siRNA molecules to the brain blood barrier endothelium may be used to formulate the siRNA duplexes targeting the gene of interest.

In one embodiment, AAV particle comprising the nucleic acid sequence for the payloads of interest (e.g., Frataxin, APOE, Tau) of the present invention may be formulated for CNS delivery. Agents that cross the brain blood barrier may be used. Capsids engineered for efficient crossing of the blood brain barrier may be used. Non-limiting examples of such capsids or peptide inserts include VOY101, VOY201, AAVPHP.N, AAVPHP.A, AAVPHP.B, PHP.B2, PHP.B3, G2A3, G2B4, G2B5, PHP.S, and variants thereof. For example, some cell penetrating peptides that deliver the payload to the brain blood barrier endothelium may be used to formulate the payload of the gene of interest.

In one embodiment, the AAV particle comprising a nucleic acid sequence encoding the siRNA molecules of the present invention may be administered directly to the CNS. As a non-limiting example, the vector comprises a nucleic acid sequence encoding the siRNA molecules targeting ApoE2. As a non-limiting example, the vector comprises a nucleic acid sequence encoding the siRNA molecules targeting ApoE3. As a non-limiting example, the vector comprises a nucleic acid sequence encoding the siRNA molecules targeting ApoE4. As a non-limiting example, the vector comprises a nucleic acid sequence encoding the siRNA molecules targeting SOD1. As a non-limiting example, the vector comprises a nucleic acid sequence encoding the siRNA molecules targeting HITT. As a non-limiting example, the vector comprises a nucleic acid sequence encoding the siRNA molecules targeting Tau.

In specific embodiments, compositions of AAV particles comprising a nucleic acid sequence encoding the siRNA molecules of the present invention may be administered in a way which facilitates the vectors or siRNA molecule to enter the central nervous system and penetrate into CNS tissues and/or cells.

In one embodiment, the AAV particle may be administered to a subject (e.g., to the CNS of a subject via intrathecal administration) in a therapeutically effective amount for the siRNA duplexes or dsRNA to target the motor neurons and astrocytes in the spinal cord and/or brain stem. As a non-limiting example, the siRNA duplexes or dsRNA may reduce the expression of a target protein or mRNA. As another non-limiting example, the siRNA duplexes or dsRNA can suppress a target gene or protein and reduce target gene or protein mediated toxicity. The reduction of target protein and/or mRNA as well as target gene and/or protein mediated toxicity may be accomplished with almost no enhanced inflammation.

II. Formulation and Delivery

Pharmaceutical Compositions

According to the present invention the AAV particles may be prepared as pharmaceutical compositions. It will be understood that such compositions necessarily comprise one or more active ingredients and, most often, a pharmaceutically acceptable excipient.

Relative amounts of the active ingredient (e.g. AAV particle), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the AAV particle pharmaceutical compositions described herein may comprise at least one payload. As a non-limiting example, the pharmaceutical compositions may contain an AAV particle with 1, 2, 3, 4 or 5 payloads.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients or subjects.

Formulations

Formulations of the present invention can include, without limitation, saline, liposomes, such preparatory methods include the step of associating the active ingredient with an lipid nanoparticles, polymers, peptides, proteins, cells transfected with viral vectors (e.g., for transfer or transplantation into a subject) and combinations thereof.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general excipient and/or one or more other accessory ingredients. As used herein, the phrase "active ingredient" generally refers either to an AAV particle carrying a payload region encoding the polypeptides of the invention or to the end product encoded by a viral genome of an AAV particle as described herein.

Formulations of the AAV particles and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In one embodiment, the AAV particles of the invention may be formulated in PBS with 0.001% of pluronic acid (F-68) at a pH of about 7.0.

In some embodiments, the AAV formulations described herein may contain sufficient AAV particles for expression of at least one expressed functional payload. As a non-limiting example, the AAV particles may contain viral genomes encoding 1, 2, 3, 4 or 5 functional payloads.

In some embodiments, the formulations described herein may contain at least one AAV particle comprising the nucleic acid sequence encoding a protein of interest. The protein of interest may include but are not limited to an antibody, AADC, APOE2, Frataxin, ATP2A2, and/or S100A1.

In some embodiments, the formulations described herein may contain at least one AAV particle comprising the nucleic acid sequence encoding the siRNA molecules described herein. In one embodiment, the siRNA molecules may target gene of interest at one target site. In another embodiment, the formulation comprises a plurality of AAV particles, each AAV particle comprising a nucleic acid sequence encoding a siRNA molecule targeting the gene of interest at a different target site. The target gene may be targeted at 2, 3, 4, 5 or more than 5 sites. In one embodiment, the target gene may include but is not limited to SOD1, HTT, APOE, and MAPT.

According to the present invention AAV particles may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.*, 2009, 19, 137-140; the contents of which are incorporated herein by reference in their entirety).

In other embodiments, the AAV particles of the present invention may be formulated for delivery to other tissues and organs, e.g., cardiovascular tissues.

Excipients and Diluents

The AAV particles of the invention can be formulated using one or more excipients or diluents to (1) increase stability; (2) increase cell transfection or transduction; (3) permit the sustained or delayed release of the payload; (4) alter the biodistribution (e.g., target the viral particle to specific tissues or cell types); (5) increase the translation of encoded protein; (6) alter the release profile of encoded protein and/or (7) allow for regulatable expression of the payload of the invention.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, M D, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, AAV particle formulations may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present invention may be approved by the US Food and Drug Administration (FDA).

In one embodiment, the AAV particle pharmaceutical compositions comprise at least one inactive ingredient such as, but not limited to, 1,2,6-Hexanetriol; 1,2-Dimyristoyl-Sn-Glycero-3-(Phospho-S-(1-Glycerol)); 1,2-Dimyristoyl-Sn-Glycero-3-Phosphocholine; 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-O-Tolylbiguanide; 2-Ethyl-1,6-Hexanediol; Acetic Acid; Acetic Acid, Glacial; Acetic Anhydride; Acetone; Acetone Sodium Bisulfite; Acetylated Lanolin Alcohols; Acetylated Monoglycerides; Acetylcysteine; Acetyltryptophan, DL-; Acrylates Copolymer; Acrylic Acid-Isooctyl Acrylate Copolymer, Acrylic Adhesive 788; Activated Charcoal; Adcote 72A103; Adhesive Tape; Adipic Acid; Aerotex Resin 3730; Alanine; Albumin Aggregated; Albumin Colloidal; Albumin Human; Alcohol; Alcohol, Dehydrated; Alcohol, Denatured; Alcohol, Diluted; Alfadex; Alginic Acid; Alkyl Ammonium Sulfonic Acid Betaine; Alkyl Aryl Sodium Sulfonate; Allantoin; Allyl .Alpha.-Ionone; Almond Oil; Alpha-Terpineol; Alpha-Tocopherol; Alpha-Tocopherol Acetate, Dl-; Alpha-Tocopherol, Dl-; Aluminum Acetate; Aluminum Chlorhydroxy Allantoinate; Aluminum Hydroxide; Aluminum Hydroxide-Sucrose, Hydrated; Aluminum Hydroxide Gel; Aluminum Hydroxide Gel F 500; Aluminum Hydroxide Gel F 5000; Aluminum Monostearate; Aluminum Oxide; Aluminum Polyester; Aluminum Silicate; Aluminum Starch Octenylsuccinate; Aluminum Stearate; Aluminum Subacetate; Aluminum Sulfate Anhydrous; Amerchol C; Amerchol-Cab; Aminomethylpropanol; Ammonia; Ammonia Solution; Ammonia Solution, Strong; Ammonium Acetate; Ammonium Hydroxide; Ammonium Lauryl Sulfate; Ammonium Nonoxynol-4 Sulfate; Ammonium Salt Of C-12-C-15 Linear Primary Alcohol Ethoxylate; Ammonium Sulfate; Ammonyx; Amphoteric-2; Amphoteric-9; Anethole; Anhydrous Citric Acid; Anhydrous Dextrose; Anhydrous Lactose; Anhydrous Trisodium Citrate; Aniseed Oil; Anoxid Sbn; Antifoam; Antipyrine; Apaflurane; Apricot Kernel Oil Peg-6 Esters; Aquaphor; Arginine; Arlacel; Ascorbic Acid; Ascorbyl Palmitate; Aspartic Acid; Balsam Peru; Barium Sulfate; Beeswax; Beeswax, Synthetic; Beheneth-10; Bentonite; Benzalkonium Chloride; Benzenesulfonic Acid; Benzethonium Chloride; Benzododecinium Bromide; Benzoic Acid; Benzyl Alcohol; Benzyl Benzoate; Benzyl Chloride; Betadex; Bibapcitide; Bismuth Subgallate; Boric Acid; Brocrinat; Butane; Butyl Alcohol; Butyl Ester Of Vinyl Methyl Ether/Maleic Anhydride Copolymer (125000 Mw); Butyl Stearate; Butylated Hydroxyanisole; Butylated Hydroxytoluene; Butylene Glycol; Butylparaben; Butyric Acid; C20-40 Pareth-24; Caffeine; Calcium; Calcium Carbonate; Calcium Chloride; Calcium Gluceptate; Calcium Hydroxide; Calcium Lactate; Calcobutrol; Caldiamide Sodium; Caloxetate Trisodium; Calteridol Calcium; Canada Balsam; Caprylic/Capric Triglyceride; Caprylic/Capric/Stearic Triglyceride; Captan; Captisol; Caramel; Carbomer 1342; Carbomer 1382; Carbomer 934; Carbomer 934p; Carbomer 940; Carbomer 941; Carbomer 980; Carbomer 981; Carbomer Homopolymer Type B (Allyl Pentaerythritol Crosslinked); Carbomer Homopolymer Type C (Allyl Pentaerythritol Crosslinked); Carbon Dioxide; Carboxy Vinyl Copolymer; Carboxymethylcellulose; Carboxymethylcellulose Sodium; Carboxypolymethylene; Carrageenan; Carrageenan Salt; Castor Oil; Cedar Leaf Oil; Cellulose; Cellulose, Microcrystalline; Cerasynt-Se; Ceresin; Ceteareth-12; Ceteareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chlorobutanol; Chlorobutanol Hemihydrate; Chlorobutanol, Anhydrous; Chlorocresol; Chloroxylenol; Cholesterol; Choleth; Choleth-24; Citrate; Citric Acid; Citric Acid Monohydrate; Citric Acid, Hydrous; Cocamide Ether Sulfate; Cocamine Oxide; Coco Betaine; Coco Diethanolamide; Coco Monoethanolamide; Cocoa Butter; Coco-Glycerides; Coconut Oil; Coconut Oil, Hydrogenated; Coconut Oil/Palm Kernel Oil Glycerides, Hydrogenated; Cocoyl Caprylocaprate; Cola Nitida Seed Extract; Collagen; Coloring Suspension; Corn Oil; Cottonseed Oil; Cream Base; Creatine; Creatinine; Cresol; Croscarmellose Sodium; Crospovidone; Cupric Sulfate; Cupric Sulfate Anhydrous; Cyclomethicone; Cyclomethicone/Dimethicone Copolyol; Cysteine; Cysteine Hydrochloride; Cysteine Hydrochloride Anhydrous; Cysteine, D1-; D&C Red No. 28; D&C Red No. 33; D&C Red No. 36; D&C Red No. 39; D&C Yellow No. 10; Dalfampridine; Daubert 1-5 Pestr (Matte) 164z; Decyl Methyl Sulfoxide; Dehydag Wax Sx; Dehydroacetic Acid; Dehymuls E; Denatonium Benzoate; Deoxycholic Acid; Dextran; Dextran 40; Dextrin; Dextrose; Dextrose Monohydrate; Dextrose Solution; Diatrizoic Acid; Diazolidinyl Urea; Dichlorobenzyl Alcohol; Dichlorodifluoromethane; Dichlorotetrafluoroethane; Diethanolamine; Diethyl Pyrocarbonate; Diethyl Sebacate; Diethylene Glycol Monoethyl Ether, Diethylhexyl Phthalate; Dihydroxyaluminum Aminoacetate; Diisopropanolamine; Diisopropyl Adipate; Diisopropyl Dilinoleate; Dimethicone 350; Dimethicone Copolyol; Dimethicone Mdx4-4210; Dimethicone Medical Fluid 360; Dimethyl Isosorbide; Dimethyl Sulfoxide; Dimethylaminoethyl Methacrylate-Butyl Methacrylate-Methyl Methacrylate Copolymer; Dimethyldioctadecylammonium Bentonite; Dimethylsiloxane/Methylvinylsiloxane Copolymer, Dinoseb Ammonium Salt; Dipalmitoylphosphatidylglycerol, D1-; Dipropylene Glycol; Disodium Cocoamphodiacetate; Disodium Laureth Sulfosuccinate; Disodium Lauryl Sulfosuccinate; Disodium Sulfosalicylate; Disofenin; Divinylbenzene Styrene Copolymer, Dmdm Hydantoin; Docosanol; Docusate Sodium; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Edetate Calcium Disodium; Edetate Disodium; Edetate Disodium Anhydrous; Edetate Sodium; Edetic Acid; Egg Phospholipids; Entsufon; Entsufon Sodium; Epilactose; Epitetracycline Hydrochloride; Essence Bouquet 9200; Ethanolamine Hydrochloride; Ethyl Acetate; Ethyl Oleate; Ethylcelluloses; Ethylene Glycol; Ethylene Vinyl Acetate Copolymer, Ethylenediamine; Ethylenediamine Dihydrochloride; Ethylene-Propylene Copolymer; Ethylene-Vinyl Acetate Copolymer (28% Vinyl Acetate); Ethylene-Vinyl Acetate Copolymer (9% Vinylacetate); Ethylhexyl Hydroxystearate; Ethylparaben; Eucalyptol; Exametazime; Fat, Edible; Fat, Hard; Fatty Acid Esters; Fatty Acid Pentaerythriol Ester, Fatty Acids; Fatty Alcohol Citrate; Fatty Alcohols; Fd&C Blue No. 1; Fd&C Green No. 3; Fd&C Red No. 4; Fd&C Red No. 40; Fd&C Yellow No. 10 (Delisted); Fd&C Yellow No. 5; Fd&C Yellow No. 6; Ferric Chloride; Ferric Oxide; Flavor 89-186; Flavor 89-259; Flavor Df-119; Flavor Df-1530; Flavor Enhancer, Flavor FIG. 827118; Flavor Raspberry Pfc-8407; Flavor Rhodia Pharmaceutical No. Rf 451; Fluorochlorohydrocarbons; Formaldehyde; Formaldehyde Solution; Fractionated Coconut Oil; Fragrance 3949-5; Fragrance 520a; Fragrance 6.007; Fragrance 91-122; Fragrance 9128-Y; Fragrance 93498g; Fragrance Balsam Pine No. 5124; Fragrance Bouquet 10328; Fragrance Chemoderm 6401-B; Fragrance Chemoderm 6411; Fragrance Cream No. 73457; Fragrance Cs-28197; Fragrance Felton 066m; Fragrance Firmenich 47373; Fragrance Givaudan Ess 9090/ic; Fragrance H-6540; Fragrance Herbal 10396; Fragrance Nj-1085; Fragrance P O F1-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Gadolinium Oxide; Galactose; Gamma Cyclodextrin; Gelatin; Gelatin, Cross-linked; Gelfoam Sponge; Gellan Gum (Low Acyl); Gelva 737; Gentisic Acid; Gentisic Acid Ethanolamide; Gluceptate Sodium; Gluceptate Sodium Dihydrate; Gluconolactone; Glucuronic Acid; Glutamic Acid, D1-; Glutathione; Glycerin; Glycerol Ester Of Hydrogenated Rosin; Glyceryl Citrate; Glyceryl Isostearate; Glyceryl Laurate; Glyceryl Monostearate; Glyceryl Oleate; Glyceryl Oleate/Propylene Glycol; Glyceryl Palmitate; Glyceryl Ricinoleate; Glyceryl Stearate; Glyceryl Stearate-Laureth-23; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; Glycine; Glycine Hydrochloride; Glycol Distearate; Glycol Stearate; Guanidine Hydrochloride; Guar Gum; Hair Conditioner (18n195-1m); Heptane; Hetastarch; Hexylene Glycol; High Density Polyethylene; Histidine; Human Albumin Microspheres; Hyaluronate Sodium; Hydrocarbon; Hydrocarbon Gel, Plasticized; Hydrochloric Acid; Hydrochloric Acid, Diluted; Hydrocortisone; Hydrogel Polymer, Hydrogen Peroxide; Hydrogenated Castor Oil; Hydrogenated Palm Oil; Hydrogenated Palm/Palm Kernel Oil Peg-6 Esters; Hydrogenated Polybutene 635-690; Hydroxide Ion; Hydroxyethyl Cellulose; Hydroxyethylpiperazine Ethane Sulfonic Acid; Hydroxymethyl Cellulose; Hydroxyoctacosanyl Hydroxystearate; Hydroxypropyl Cellulose; Hydroxypropyl Methylcellulose 2906; Hydroxypropyl-Beta-cyclodextrin; Hypromellose 2208 (15000 Mpa·S); Hypromellose 2910 (15000 Mpa·S); Hypromelloses; Imidurea; Iodine; Iodoxamic Acid; Iofetamine Hydrochloride; Irish Moss Extract; Isobutane; Isoceteth-20; Isoleucine; Isooctyl Acrylate; Isopropyl Alcohol; Isopropyl Isostearate; Isopropyl Myristate; Isopropyl Myristate-Myristyl Alcohol; Isopropyl Palmitate; Isopropyl Stearate; Isostearic Acid; Isostearyl Alcohol; Isotonic Sodium Chloride Solution; Jelene; Kaolin; Kathon Cg; Kathon Cg II; Lactate; Lactic Acid; Lactic Acid, D1-; Lactic Acid, L-; Lactobionic Acid; Lactose; Lactose Monohydrate; Lactose, Hydrous; Laneth; Lanolin; Lanolin Alcohol-Mineral Oil; Lanolin Alcohols; Lanolin Anhydrous; Lanolin Cholesterols; Lanolin Nonionic Derivatives; Lanolin, Ethoxylated; Lanolin, Hydrogenated; Lauralkonium Chloride; Lauramine Oxide; Laurdimonium Hydrolyzed Animal Collagen; Laureth Sulfate; Laureth-2; Laureth-23; Laureth-4; Lauric Diethanolamide; Lauric Myristic Diethanolamide; Lauroyl Sarcosine; Lauryl Lactate; Lauryl Sulfate; *Lavandula Angustifolia* Flowering Top; Lecithin; Lecithin Unbleached; Lecithin, Egg; Lecithin, Hydrogenated; Lecithin, Hydrogenated Soy; Lecithin, Soybean; Lemon Oil; Leucine; Levulinic Acid; Lidofenin; Light Mineral Oil; Light Mineral Oil (85 Ssu); Limonene, (+/−)-; Lipocol Sc-15; Lysine; Lysine Acetate; Lysine Monohydrate; Magnesium Aluminum Silicate; Magnesium Aluminum Silicate Hydrate; Magnesium Chloride; Magnesium Nitrate; Magnesium Stearate; Maleic Acid; Mannitol; Maprofix; Mebrofenin; Medical Adhesive Modified S-15; Medical Antiform A-F Emulsion; Medronate Disodium; Medronic Acid; Meglumine; Menthol; Metacresol; Metaphosphoric Acid; Methanesulfonic Acid; Methionine; Methyl Alcohol; Methyl Gluceth-10; Methyl Gluceth-20; Methyl Gluceth-20 Sesquistearate; Methyl Glucose Sesquistearate; Methyl Laurate; Methyl Pyrrolidone; Methyl Salicylate; Methyl Stearate; Methylboronic Acid; Methylcellulose (4000 Mpa·S); Methylcelluloses; Methylchloroisothiazolinone; Methylene Blue; Methylisothiazolinone; Methylparaben; Microcrystalline Wax; Mineral Oil; Mono And Diglyceride; Monostearyl Citrate; Monothioglycerol; Multisterol Extract; Myristyl Alcohol; Myristyl Lactate; Myristyl-.Gamma.-Picolinium Chloride; N-(Carbamoyl-Methoxy Peg-40)-1,2-Distearoyl-Cephalin Sodium; N,N-Dimethylacetamide; Niacinamide; Nioxime; Nitric Acid; Nitrogen; Nonoxynol Iodine; Nonoxynol-15; Nonoxynol-9; Norflurane; Oatmeal; Octadecene-1/Maleic Acid Copolymer, Octanoic Acid; Octisalate; Octoxynol-1; Octoxynol-40; Octoxynol-9; Octyldodecanol; Octylphenol Polymethylene; Oleic Acid; Oleth-10/Oleth-5; Oleth-2; Oleth-20; Oleyl Alcohol; Oleyl Oleate; Olive Oil; Oxidronate Disodium; Oxyquinoline; Palm Kernel Oil; Palmitamine Oxide; Parabens; Paraffin; Paraffin, White Soft; Parfum Creme 45/3; Peanut Oil; Peanut Oil, Refined; Pectin; Peg 6-32 Stearate/Glycol Stearate; Peg Vegetable Oil; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Sorbitan Isostearate; Peg-22 Methyl Ether/Dodecyl Glycol Copolymer, Peg-25 Propylene Glycol Stearate; Peg-4 Dilaurate; Peg-4 Laurate; Peg-40 Castor Oil; Peg-40 Sorbitan Diisostearate; Peg-45/Dodecyl Glycol Copolymer; Peg-5 Oleate; Peg-50 Stearate; Peg-54 Hydrogenated Castor Oil; Peg-6 Isostearate; Peg-60 Castor Oil; Peg-60 Hydrogenated Castor Oil; Peg-7 Methyl Ether, Peg-75 Lanolin; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume Bouquet; Perfume E-1991; Perfume Gd 5604; Perfume Tana 90/42 Scba; Perfume W-1952-1; Petrolatum; Petrolatum, White; Petroleum Distillates; Phenol; Phenol, Liquefied; Phenonip; Phenoxyethanol; Phenylalanine; Phenylethyl Alcohol; Phenylmercuric Acetate; Phenylmercuric Nitrate; Phosphatidyl Glycerol, Egg; Phospholipid; Phospholipid, Egg; Phospholipon 90g; Phosphoric Acid; Pine Needle Oil (*Pinus Sylvestris*); Piperazine Hexahydrate; Plastibase-50w; Polacrilin; Polidronium Chloride; Poloxamer 124; Poloxamer 181; Poloxamer 182; Poloxamer 188; Poloxamer 237; Poloxamer 407; Poly(Bis(P-Carboxyphenoxy)Propane Anhydride):Sebacic Acid; Poly(Dimethylsiloxane/Methylvinylsiloxane/Methylhydrogensiloxane) Dimethylvinyl Or Dimethylhydroxy Or Trimethyl Endblocked; Poly(D1-Lactic-Co-Glycolic Acid), (50:50; Poly(D1-Lactic-Co-Glycolic Acid), Ethyl Ester Terminated, (50:50; Polyacrylic Acid (250000 Mw); Polybutene (1400 Mw); Polycarbophil; Polyester, Polyester Polyamine Copolymer, Polyester Rayon; Polyethylene Glycol 1000; Polyethylene Glycol 1450; Polyethylene Glycol 1500; Polyethylene Glycol 1540; Polyethylene Glycol 200; Polyethylene Glycol 300; Polyethylene Glycol 300-1600; Polyethylene Glycol 3350; Polyethylene Glycol 400; Polyethylene Glycol 4000; Polyethylene Glycol 540; Polyethylene Glycol 600; Polyethylene Glycol 6000; Polyethylene Glycol 8000; Polyethylene Glycol 900; Polyethylene High Density Containing Ferric Oxide Black (<1%); Polyethylene Low Density Containing Barium Sulfate (20-24%); Polyethylene T; Polyethylene Terephthalates; Polyglactin; Polyglyceryl-3 Oleate; Polyglyceryl-4 Oleate; Polyhydroxyethyl Methacrylate; Polyisobutylene; Polyisobutylene (1100000 Mw); Polyisobutylene (35000 Mw); Polyisobutylene 178-236; Polyisobutylene 241-294; Polyisobutylene 35-39; Polyisobutylene Low Molecular Weight; Polyisobutylene Medium Molecular Weight; Polyisobutylene/Polybutene Adhesive; Polylactide; Polyols; Polyoxyethylene-Polyoxypropylene 1800; Polyoxyethylene Alcohols; Polyoxyethylene Fatty Acid Esters; Polyoxyethylene Propylene; Polyoxyl 20 Cetostearyl Ether, Polyoxyl 35 Castor Oil; Polyoxyl 40 Hydrogenated Castor Oil; Polyoxyl 40 Stearate; Polyoxyl 400 Stearate; Polyoxyl 6 And Polyoxyl 32 Palmitostearate; Polyoxyl Distearate; Polyoxyl Glyceryl Stearate; Polyoxyl Lanolin; Polyoxyl Palmitate; Polyoxyl Stearate; Polypropylene; Polypropylene Glycol; Polyquaternium-10; Polyquaternium-7 (70/30 Acrylamide/Dadmac; Polysiloxane; Polysorbate 20; Polysorbate 40; Polysorbate 60; Polysorbate 65; Polysorbate 80; Polyurethane; Polyvinyl Acetate; Polyvinyl Alcohol; Polyvinyl Chloride; Polyvinyl Chloride-Polyvinyl Acetate Copolymer; Polyvinylpyridine; Poppy Seed Oil; Potash; Potassium Acetate; Potassium Alum; Potassium Bicarbonate; Potassium Bisulfite; Potassium Chloride; Potassium Citrate; Potassium Hydroxide; Potassium Metabisulfite; Potassium Phosphate, Dibasic; Potassium Phosphate, Monobasic; Potassium Soap; Potassium Sorbate; Povidone Acrylate Copolymer, Povidone Hydrogel; Povidone K17; Povidone K25; Povidone K29/32; Povidone K30; Povidone K90; Povidone K90f; PovidonelEicosene Copolymer, Povidones; Ppg-12/Smdi Copolymer, Ppg-15 Stearyl Ether; Ppg-20 Methyl Glucose Ether Distearate; Ppg-26 Oleate; Product Wat; Proline; Promulgen D; Promulgen G; Propane; Propellant A-46; Propyl Gallate; Propylene Carbonate; Propylene Glycol; Propylene Glycol Diacetate; Propylene Glycol Dicaprylate; Propylene Glycol Monolaurate; Propylene Glycol Monopalmitostearate; Propylene Glycol Palmitostearate; Propylene Glycol Ricinoleate; Propylene Glycol/Diazolidinyl Urea/Methylparaben/Propylparben; Propylparaben; Protamine Sulfate; Protein Hydrolysate; Pvm/Ma Copolymer; Quaternium-15; Quaternium-15 Cis-Form; Quaternium-52; Ra-2397; Ra-3011; Saccharin; Saccharin Sodium; Saccharin Sodium Anhydrous; Safflower Oil; Sd Alcohol 3a; Sd Alcohol 40; Sd Alcohol 40-2; Sd Alcohol 40b; Sepineo P 600; Serine; Sesame Oil; Shea Butter; Silastic Brand Medical Grade Tubing; Silastic Medical Adhesive,Silicone Type A; Silica, Dental; Silicon; Silicon Dioxide; Silicon Dioxide, Colloidal; Silicone; Silicone Adhesive 4102; Silicone Adhesive 4502; Silicone Adhesive Bio-Psa Q7-4201; Silicone Adhesive Bio-Psa Q7-4301; Silicone Emulsion; Silicone/Polyester Film Strip; Simethicone; Simethicone Emulsion; Sipon Ls 20np; Soda Ash; Sodium Acetate; Sodium Acetate Anhydrous; Sodium Alkyl Sulfate; Sodium Ascorbate; Sodium Benzoate; Sodium Bicarbonate; Sodium Bisulfate; Sodium Bisulfite; Sodium Borate; Sodium Borate Decahydrate; Sodium Carbonate; Sodium Carbonate Decahydrate; Sodium Carbonate Monohydrate; Sodium Cetostearyl Sulfate; Sodium Chlorate; Sodium Chloride; Sodium Chloride Injection; Sodium Chloride Injection, Bacteriostatic; Sodium Cholesteryl Sulfate; Sodium Citrate; Sodium Cocoyl Sarcosinate; Sodium Desoxycholate; Sodium Dithionite; Sodium Dodecylbenzenesulfonate; Sodium Formaldehyde Sulfoxylate; Sodium Gluconate; Sodium Hydroxide; Sodium Hypochlorite; Sodium Iodide; Sodium Lactate; Sodium Lactate, L-; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Nitrate; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Dodecahydrate; Sodium Phosphate, Dibasic, Heptahydrate; Sodium Phosphate, Monobasic; Sodium Phosphate, Monobasic, Anhydrous; Sodium Phosphate, Monobasic, Dihydrate; Sodium Phosphate, Monobasic, Monohydrate; Sodium Polyacrylate (2500000 Mw); Sodium Pyrophosphate; Sodium Pyrrolidone Carboxylate; Sodium Starch Glycolate; Sodium Succinate Hexahydrate; Sodium Sulfate; Sodium Sulfate Anhydrous; Sodium Sulfate Decahydrate; Sodium Sulfite; Sodium Sulfosuccinated Undecyclenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Xylenesulfonate; Somay 44; Sorbic Acid; Sorbitan;

Sorbitan Isostearate; Sorbitan Monolaurate; Sorbitan Monooleate; Sorbitan Monopalmitate; Sorbitan Monostearate; Sorbitan Sesquioleate; Sorbitan Trioleate; Sorbitan Tristearate; Sorbitol; Sorbitol Solution; Soybean Flour; Soybean Oil; Spearmint Oil; Spermaceti; Squalane; Stabilized Oxychloro Complex; Stannous 2-Ethylhexanoate; Stannous Chloride; Stannous Chloride Anhydrous; Stannous Fluoride; Stannous Tartrate; Starch; Starch 1500, Pregelatinized; Starch, Corn; Stearalkonium Chloride; Stearalkonium Hectorite/Propylene Carbonate; Stearamidoethyl Diethylamine; Steareth-10; Steareth-100; Steareth-2; Steareth-20; Steareth-21; Steareth-40; Stearic Acid; Stearic Diethanolamide; Stearoxytrimethylsilane; Steartrimonium Hydrolyzed Animal Collagen; Stearyl Alcohol; Sterile Water For Inhalation; Styrene/Isoprene/Styrene Block Copolymer, Succimer, Succinic Acid; Sucralose; Sucrose; Sucrose Distearate; Sucrose Polyesters; Sulfacetamide Sodium; Sulfobutylether .Beta.-Cyclodextrin; Sulfur Dioxide; Sulfuric Acid; Sulfurous Acid; Surfactol Qs; Tagatose, D-; Talc; Tall Oil; Tallow Glycerides; Tartaric Acid; Tartaric Acid, D1-; Tenox; Tenox-2; Tert-Butyl Alcohol; Tert-Butyl Hydroperoxide; Tert-Butylhydroquinone; Tetrakis(2-Methoxyisobutylisocyanide)Copper(I) Tetrafluoroborate; Tetrapropyl Orthosilicate; Tetrofosmin; Theophylline; Thimerosal; Threonine; Thymol; Tin; Titanium Dioxide; Tocopherol; Tocophersolan; Total parenteral nutrition, lipid emulsion; Triacetin; Tricaprylin; Trichloromonofluoromethane; Trideceth-10; Triethanolamine Lauryl Sulfate; Trifluoroacetic Acid; Triglycerides, Medium Chain; Trihydroxystearin; Trilaneth-4 Phosphate; Trilaureth-4 Phosphate; Trisodium Citrate Dihydrate; Trisodium Hedta; Triton 720; Triton X-200; Trolamine; Tromantadine; Tromethamine (TRIS); Tryptophan; Tyloxapol; Tyrosine; Undecylenic Acid; Union 76 Amsco-Res 6038; Urea; Valine; Vegetable Oil; Vegetable Oil Glyceride, Hydrogenated; Vegetable Oil, Hydrogenated; Versetamide; Viscarin; Viscose/Cotton; Vitamin E; Wax, Emulsifying; Wecobee Fs; White Ceresin Wax; White Wax; Xanthan Gum; Zinc; Zinc Acetate; Zinc Carbonate; Zinc Chloride; and Zinc Oxide.

Pharmaceutical composition formulations of AAV particles disclosed herein may include cations or anions. In one embodiment, the formulations include metal cations such as, but not limited to, $Zn^{2+}$, $Ca^{2+}$, $Cu^{2+}$, $Mn^{2+}$, $Mg+$ and combinations thereof. As a non-limiting example, formulations may include polymers and complexes with a metal cation (See e.g., U.S. Pat. Nos. 6,265,389 and 6,555,525, the contents of each of which are herein incorporated by reference in their entirety).

Formulations of the invention may also include one or more pharmaceutically acceptable salts. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C.G. Wermuth (eds.), Wiley-VCH, 2008, and Berge et al., Journal of Pharmaceutical Science, 66, 1-19 (1977); the contents of each of which are incorporated herein by reference in their entirety.

The term "pharmaceutically acceptable solvate," as used herein, means a compound of the invention wherein molecules of a suitable solvent are incorporated in the crystal lattice. A suitable solvent is physiologically tolerable at the dosage administered. Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

III. Administration and Dosing

Administration

In one embodiment, the AAV particle may be administered to a subject (e.g., to the CNS of a subject) in a therapeutically effective amount to reduce the symptoms of neurological disease of a subject (e.g., determined using a known evaluation method).

The AAV particles of the present invention may be administered by any delivery route which results in a therapeutically effective outcome. These include, but are not limited to, enteral (into the intestine), gastroenteral, epidural (into the dura mater), oral (by way of the mouth), transdermal, intracerebral (into the cerebrum), intracerebroventricular (into the cerebral ventricles), sub-pial (between pia and CNS parenchyma), intracarotid arterial (into the intracarotid artery), epicutaneous (application onto the skin), intradermal, (into the skin itself), subcutaneous (under the skin), nasal administration (through the nose), intravenous (into a vein), intravenous bolus, intravenous drip, intra-arterial (into an artery), systemic, intramuscular (into a muscle), intracardiac (into the heart), intraosseous infusion (into the bone marrow), intrathecal (into the spinal canal), intraparenchymal (into brain tissue), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), or in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

In some embodiments, the AAV particles and compositions comprising the AAV particles may be administered in a way which allows them to cross the blood-brain barrier, vascular barrier, or other epithelial barrier. The AAV particles of the present invention may be administered in any suitable form, either as a liquid solution or suspension, as a solid form suitable for liquid solution or suspension in a liquid solution. The AAV particles may be formulated with any appropriate and pharmaceutically acceptable excipient.

In one embodiment, the AAV particles of the present invention may be delivered to a subject via a single route administration.

In one embodiment, the AAV particles of the present invention may be delivered to a subject via a multi-site route of administration. AAV particles may be administered at 2, 3, 4, 5 or more than 5 sites.

In one embodiment, a subject may be administered the AAV particles of the present invention using a bolus infusion.

In one embodiment, a subject may be administered the AAV particles of the present invention using sustained delivery over a period of minutes, hours or days. The infusion rate may be changed depending on the subject, distribution, formulation or another delivery parameter.

In one embodiment, the AAV particles of the present invention may be delivered by intramuscular delivery route. (See, e.g., U.S. Pat. No. 6,506,379; the contents of which are incorporated herein by reference in their entirety). Non-limiting examples of intramuscular administration include an intravenous injection or a subcutaneous injection.

In one embodiment, the AAV particles of the present invention may be delivered by intraocular delivery route. A non-limiting example of intraocular administration include an intravitreal injection.

In some embodiments, the AAV particles that may be administered to a subject by peripheral injections. Non-limiting examples of peripheral injections include intraperitoneal, intramuscular, intravenous, conjunctival or joint injection. It was disclosed in the art that the peripheral administration of AAV particles can be transported to the central nervous system, for example, to the motor neurons (e.g., U. S. Patent Application Publication Nos. 20100240739; and 20100130594; the contents of each of which are incorporated herein by reference in their entirety).

In one embodiment, the AAV particles may be delivered by injection into the CSF pathway. Non-limiting examples of delivery to the CSF pathway include intrathecal and intracerebroventricular administration.

In one embodiment, the AAV particles may be delivered by systemic delivery. As a non-limiting example, the systemic delivery may be by intravascular administration.

In one embodiment, the AAV particles of the present invention may be administered to a subject by intracranial delivery (See, e.g., U.S. Pat. No. 8,119,611; the content of which are incorporated herein by reference in their entirety).

In some embodiments, the AAV particles of the present invention may be administered by injection. As a non-limiting example, the AAV particles of the present invention may be administered to a subject by injection.

In some embodiments, the AAV particles of the present invention may be administered by muscular injection. As a non-limiting example, the AAV particles of the present invention may be administered to a subject by muscular administration.

In some embodiments, the AAV particles of the present invention may be administered by intramuscular administration. As a non-limiting example, the AAV particles of the present invention may be administered to a subject by intramuscular administration.

In one embodiment, the AAV particles of the present invention are administered to a subject and transduce muscle of a subject. As a non-limiting example, the AAV particles are administered by intramuscular administration.

In some embodiments, the AAV particles of the present invention may be administered via intraparenchymal injection. As a non-limiting example, the AAV particles of the present invention may be administered to a subject by intraparenchymal administration.

In some embodiments, the AAV particles of the present invention may be administered by intravenous administration. As a non-limiting example, the AAV particles of the present invention may be administered to a subject by intravenous administration.

In one embodiment, the AAV particles of the present invention may be administered via intravenous delivery.

In one embodiment, the AAV particles of the present invention may be administrated via intracarotid artery delivery.

In one embodiment, the AAV particles of the present invention may be administered via a single dose intravenous delivery. As a non-limiting example, the single dose intravenous delivery may be a one-time treatment. In the context of neurological disease, the single dose intravenous delivery can produce durable relief for subjects with a neurological disease and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In one embodiment, the AAV particles of the present invention may be administered via intravenous delivery to the DRG nociceptive neurons.

In one embodiment, the AAV particles of the present invention may be administered via a single dose intravenous delivery to the DRG nociceptive neurons. As a non-limiting example, the single dose intravenous delivery may be a one-time treatment. In the context of neurological disease, the single dose intravenous delivery can produce durable relief for subjects with a neurological disease and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In some embodiments, the AAV particles of the present invention may be administered by intrathecal injection. As a non-limiting example, the AAV particles of the present invention may be administered by intrathecal injection.

In one embodiment, the AAV particle may be administered to the cisterna magna in a therapeutically effective amount to transduce spinal cord motor neurons and/or astrocytes. As a non-limiting example, the AAV particle may be administered intrathecally.

In one embodiment, the AAV particle may be administered using intrathecal infusion in a therapeutically effective amount to transduce spinal cord motor neurons and/or astrocytes.

In some embodiments, the AAV particles of the present invention may be administered via a single dose intrathecal injection. As a non-limiting example, the single dose intrathecal injection may be a one-time treatment. In the context of neurological disease, the single dose intrathecal injection can produce durable relief for subjects with a neurological disease and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In some embodiments, the AAV particles of the present invention may be administered via intrathecal injection to the DRG nociceptive neurons.

In some embodiments, the AAV particles of the present invention may be administered via a single dose intrathecal injection to the DRG nociceptive neurons. As a non-limiting example, the single dose intrathecal injection may be a one-time treatment. In the context of neurological disease, the single dose intrathecal injection can produce durable relief for subjects with a neurological disease and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In one embodiment, the AAV particle described herein is administered via intrathecal (IT) infusion at C1. The infusion may be for 1, 2, 3, 4, 6, 7, 8, 9, 10, 11, 12, 13, 14, 15 or more than 15 hours.

In some embodiments, the AAV particles of the present invention may be administered by intraparenchymal injection. As a non-limiting example, the AAV particles of the present invention may be administered to a subject by intraparenchymal injection.

In some embodiments, the AAV particles of the present invention may be administered by intraparenchymal injection and intrathecal injection. As a non-limiting example, the AAV particles of the present invention may be administered via intraparenchymal injection and intrathecal injection.

In some embodiments, the AAV particles of the present invention may be administered by subcutaneous injection. As a non-limiting example, the AAV particles of the present invention may be administered to a subject by subcutaneous injection.

In some embodiments, the AAV particles of the present invention may be administered topically. As a non-limiting example, the AAV particles of the present invention may be administered to a subject topically.

In one embodiment, the AAV particles may be delivered by direct injection into the brain. As a non-limiting example, the brain delivery may be by intrastriatal administration.

In one embodiment, the AAV particles of the present invention may be administered via intrastriatal injection.

In one embodiment, the AAV particles of the present invention may be administered via intrastriatal injection and another route of administration described herein.

In one embodiment, the AAV particles may be delivered by more than one route of administration. As non-limiting examples of combination administrations, AAV particles may be delivered by intrathecal and intracerebroventricular, or by intravenous and intraparenchymal administration.

In one embodiment, the AAV particle may be administered to the CNS in a therapeutically effective amount to improve function and/or survival for a subject with a neurological disease. As a non-limiting example, the vector may be administered intravenously.

The AAV particle may be administered in a "therapeutically effective" amount, i.e., an amount that is sufficient to alleviate and/or prevent at least one symptom associated with the disease, or provide improvement in the condition of the subject.

In one embodiment, the catheter may be located at more than one site in the spine for multi-site delivery. The AAV particle may be delivered in a continuous and/or bolus infusion. Each site of delivery may be a different dosing regimen or the same dosing regimen may be used for each site of delivery. As a non-limiting example, the sites of delivery may be in the cervical and the lumbar region. As another non-limiting example, the sites of delivery may be in the cervical region. As another non-limiting example, the sites of delivery may be in the lumbar region.

In one embodiment, a subject may be analyzed for spinal anatomy and pathology prior to delivery of the AAV particle described herein. As a non-limiting example, a subject with scoliosis may have a different dosing regimen and/or catheter location compared to a subject without scoliosis.

In one embodiment, the orientation of the spine of the subject during delivery of the AAV particle may be vertical to the ground.

In another embodiment, the orientation of the spine of the subject during delivery of the AAV particle may be horizontal to the ground.

In one embodiment, the spine of the subject may be at an angle as compared to the ground during the delivery of the AAV particle. The angle of the spine of the subject as compared to the ground may be at least 10, 20, 30, 40, 50, 60, 70, 80, 90, 100, 110, 120, 130, 140, 150 or 180 degrees.

In one embodiment, the delivery method and duration is chosen to provide broad transduction in the spinal cord. As a non-limiting example, intrathecal delivery is used to provide broad transduction along the rostral-caudal length of the spinal cord. As another non-limiting example, multi-site infusions provide a more uniform transduction along the rostral-caudal length of the spinal cord. As yet another non-limiting example, prolonged infusions provide a more uniform transduction along the rostral-caudal length of the spinal cord.

Parenteral and Injectable Administration

In some embodiments, pharmaceutical compositions, AAV particles of the present invention may be administered parenterally. Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of active ingredients, it is often desirable to slow the absorption of active ingredients from subcutaneous or intramuscular injections. This may be accomplished by the use of liquid suspensions of crystalline or amorphous material with poor water solubility. The rate of absorption of active ingredients depends upon the rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Depot Administration

As described herein, in some embodiments, pharmaceutical compositions, AAV particles of the present invention are formulated in depots for extended release. Generally, specific organs or tissues ("target tissues") are targeted for administration.

In some aspects of the invention, pharmaceutical compositions, AAV particles of the present invention are spatially retained within or proximal to target tissues. Provided are methods of providing pharmaceutical compositions, AAV particles, to target tissues of mammalian subjects by contacting target tissues (which comprise one or more target cells) with pharmaceutical compositions, AAV particles, under conditions such that they are substantially retained in target tissues, meaning that at least 10, 20, 30, 40, 50, 60, 70, 80, 85, 90, 95, 96, 97, 98, 99, 99.9, 99.99 or greater than 99.99% of the composition is retained in the target tissues. Advantageously, retention is determined by measuring the amount of pharmaceutical compositions, and AAV particles that enter one or more target cells. For example, at least 1%, 5%, 10%, 20%, 30%, 40%, 50%, 60%, 70%, 80%, 85%, 90%, 95%, 96%, 97%, 98%, 99%, 99.9%, 99.99% or greater than 99.99% of pharmaceutical compositions, AAV particles, administered to subjects are present intracellularly at a period of time following administration. For example, intramuscular injection to mammalian subjects may be performed using aqueous compositions comprising pharmaceutical compositions, AAV particles of the present invention and one or more transfection reagents, and retention is determined by measuring the amount of pharmaceutical compositions, AAV particles, present in target cells.

Certain aspects of the invention are directed to methods of providing pharmaceutical compositions, AAV particles of the present invention to target tissues of mammalian subjects, by contacting target tissues (comprising one or more target cells) with pharmaceutical compositions, AAV particles under conditions such that they are substantially retained in such target tissues. Pharmaceutical compositions, AAV particles comprise enough active ingredient such that the effect of interest is produced in at least one target cell. In some embodiments, pharmaceutical compositions, AAV particles generally comprise one or more cell penetration agents, although "naked" formulations (such as without cell penetration agents or other agents) are also contemplated, with or without pharmaceutically acceptable carriers.

Pulmonary Administration

In some embodiments, pharmaceutical compositions, AAV particles of the present invention may be prepared, packaged, and/or sold in formulations suitable for pulmonary administration. In some embodiments, such administration is via the buccal cavity. In some embodiments, formulations may comprise dry particles comprising active ingredients. In such embodiments, dry particles may have a diameter in the range from about 0.5 nm to about 7 nm or from about 1 nm to about 6 nm. In some embodiments, formulations may be in the form of dry powders for administration using devices comprising dry powder reservoirs to which streams of propellant may be directed to disperse such powder. In some embodiments, self-propelling solvent/powder dispensing containers may be used. In such embodiments, active ingredients may be dissolved and/or suspended in low-boiling propellant in sealed containers. Such powders may comprise particles wherein at least 98% of the particles by weight have diameters greater than 0.5 nm and at least 95% of the particles by number have diameters less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally, propellants may constitute 50% to 99.9% (w/w) of the composition, and active ingredient may constitute 0.1% to 20% (w/w) of the composition. Propellants may further comprise additional ingredients such as liquid non-ionic and/or solid anionic surfactant and/or solid diluent (which may have particle sizes of the same order as particles comprising active ingredients).

Pharmaceutical compositions formulated for pulmonary delivery may provide active ingredients in the form of droplets of solution and/or suspension. Such formulations may be prepared, packaged, and/or sold as aqueous and/or dilute alcoholic solutions and/or suspensions, optionally sterile, comprising active ingredients, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and Buccal Administration

In some embodiments, pharmaceutical compositions, AAV particles of the present invention may be administered nasally and/or intranasal. In some embodiments, formulations described herein useful for pulmonary delivery may also be useful for intranasal delivery. In some embodiments, formulations for intranasal administration comprise a coarse powder comprising the active ingredient and having an average particle size from about 0.2 μm to 500 μm. Such formulations are administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, comprise 0.1% to 20% (w/w) active ingredient, the balance comprising an orally dissolvable and/or degradable composition and, optionally, one or more of the additional ingredients described herein. Alternately, formulations suitable for buccal administration may comprise powders and/or an aerosolized and/or atomized solutions and/or suspensions comprising active ingredients. Such powdered, aerosolized, and/or aerosolized formulations, when dispersed, may comprise average particle and/or droplet sizes in the range of from about 0.1 nm to about 200 nm, and may further comprise one or more of any additional ingredients described herein.

Ophthalmic or Otic Administration

In some embodiments, pharmaceutical compositions, AAV particles of the present invention may be prepared, packaged, and/or sold in formulations suitable for ophthalmic and/or otic administration. Such formulations may, for example, be in the form of eye and/or ear drops including, for example, a 0.1/1.0% (w/w) solution and/or suspension of the active ingredient in aqueous and/or oily liquid excipients. Such drops may further comprise buffering agents, salts, and/or one or more other of any additional ingredients described herein. Other ophthalmically-administrable formulations which are useful include those which comprise active ingredients in microcrystalline form and/or in liposomal preparations. Subretinal inserts may also be used as forms of administration.

Delivery, Dose and Regimen

The present invention provides methods of administering AAV particles in accordance with the invention to a subject in need thereof. The pharmaceutical, diagnostic, or prophylactic AAV particles and compositions of the present invention may be administered to a subject using any amount and any route of administration effective for preventing, treating, managing, or diagnosing diseases, disorders and/or conditions. The exact amount required will vary from subject to subject, depending on the species, age, and general condition of the subject, the severity of the disease, the particular composition, its mode of administration, its mode of activity, and the like. The subject may be a human, a mammal, or an animal. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate diagnostic dose level for any particular individual will depend upon a variety of factors including the disorder being treated and the severity of the disorder, the activity of the specific payload employed; the specific composition employed; the age, body weight, general health, sex and diet of the patient; the time of administration, route of administration, and rate of excretion of the specific AAV particle employed; the duration of the treatment; drugs used in combination or coincidental with the specific AAV particle employed; and like factors well known in the medical arts.

In one embodiment, delivery of the AAV particles of the present invention results in minimal serious adverse events (SAEs) as a result of the delivery of the AAV particles.

In one embodiment, the AAV particle may be delivered in a multi-dose regimen. The multi-dose regimen may be 2, 3, 4, 5, 6, 7, 8, 9, 10 or more than 10 doses.

In one embodiment, the AAV particle may be delivered to a subject via a multi-site route of administration. A subject may be administered the AAV particle at 2, 3, 4, 5 or more than 5 sites.

In certain embodiments, AAV particle pharmaceutical compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect. It will be understood that the above dosing concentrations may be converted to vg or viral genomes per kg or into total viral genomes administered by one of skill in the art.

In certain embodiments, AAV particle pharmaceutical compositions in accordance with the present disclosure may be administered at about 10 to about 600 µl/site, 50 to about 500 µl/site, 100 to about 400 µl/site, 120 to about 300 µl/site, 140 to about 200 µl/site, about 160 µl/site. As non-limiting examples, AAV particles may be administered at 50 µl/site and/or 150 µl/site.

In one embodiment, delivery of the compositions in accordance with the present invention to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions comprising the AAV particles in accordance with the present invention to cells may comprise a total concentration per subject between about $1 \times 10^6$ VG (Viral Genome) and about $1 \times 10^{16}$ VG. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $5 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $3 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $6.1 \times 10^{12}$, $6.2 \times 10^{12}$, $6.3 \times 10^{12}$, $6.4 \times 10^{12}$, $6.5 \times 10^{12}$, $6.6 \times 10^{12}$, $6.7 \times 10^{12}$, $6.8 \times 10^{12}$, $6.9 \times 10^{12}$, $7 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{12}$, $8.8 \times 10^{12}$, $8.9 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/subject.

In one embodiment, delivery of compositions comprising the AAV particles in accordance with the present invention to cells may comprise a total concentration per subject between about $1 \times 10^6$ VG/kg and about $1 \times 10^{16}$ VG/kg. In some embodiments, delivery may comprise a composition concentration of about $1 \times 10^6$, $2 \times 10^6$, $3 \times 10^6$, $4 \times 10^6$, $5 \times 10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $3\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/kg. In one embodiment, the delivery comprises a composition concentration of $1\times10^{13}$ VG/kg. In one embodiment, the delivery comprises a composition concentration of $2.1\times10^{12}$ VG/kg. In one embodiment, the delivery comprises a composition concentration of $1\times10^{13}$ VG/kg. In one embodiment, the delivery comprises a composition concentration of $6.7\times10^{12}$ VG/kg. In one embodiment, the delivery comprises a composition concentration of $7\times10^{12}$ VG/kg. In one embodiment, the delivery comprises a composition concentration of $2\times10^{13}$ VG/kg. In one embodiment, the delivery comprises a composition concentration of $3\times10^{11}$ VG/kg. In one embodiment, the delivery comprises a composition concentration of $3\times10^{12}$ VG/kg. In one embodiment, the delivery comprises a composition concentration of $3\times10^{13}$ VG/kg. In one embodiment, the delivery comprises a composition concentration of $6.3\times10^{12}$ VG/kg.

In one embodiment, delivery of AAV particles to cells of the central nervous system (e.g., parenchyma) may comprise a total dose between about $1\times10^6$ VG and about $1\times10^{16}$ VG. In some embodiments, delivery may comprise a total dose of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.9\times10^{10}$, $2\times10^{10}$, $3\times10^{10}$, $3.73\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $2.5\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG. As a non-limiting example, the total dose is $1\times10^{13}$ VG. As another non-limiting example, the total dose is $2.1\times10^{12}$ VG. As another non-limiting example, the total dose is $6.3\times10^{12}$ VG.

In one embodiment, about $10^5$ to $10^6$ viral genome (unit) may be administered per dose.

In one embodiment, delivery of the compositions comprising the AAV particles in accordance with the present invention to cells may comprise a total concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}3$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL.

In one embodiment, delivery of AAV particles to cells of the central nervous system (e.g., parenchyma) may comprise a composition concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL. In one embodiment, the delivery comprises a composition concentration of $1\times10^{13}$ VG/mL. In one embodiment, the delivery comprises a composition concentration of $2.1\times10^{12}$ VG/mL. In one embodiment, the delivery comprises a composition concentration of $1\times10^{13}$ VG/mL. In one embodiment, the delivery comprises a composition concentration of $2\times10^{13}$ VG/mL. In one embodiment, the delivery comprises a composition concentration of $3\times10^{11}$ VG/mL. In one embodiment, the delivery comprises a composition concentration of $3\times10^{12}$ VG/mL. In one embodiment, the delivery comprises a composition concentration of $6.3\times10^{12}$ VG/mL. In one embodiment, the delivery comprises a composition concentration of $3\times10^{13}$ VG/mL.

In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

The desired dosage of the AAV particles of the present invention may be administered as a "pulse dose" or as a "continuous flow". As used herein, a "pulse dose" is a series of single unit doses of any therapeutic administered with a set frequency over a period of time. As used herein, a "continuous flow" is a dose of therapeutic administered continuously for a period of time in a single route/single point of contact, i.e., continuous administration event. A total daily dose, an amount given or prescribed in 24 hour period, may be administered by any of these methods, or as a combination of these methods, or by any other methods suitable for a pharmaceutical administration.

In one embodiment, delivery of the AAV particles of the present invention to a subject provides regulating activity of a target gene in a subject. The regulating activity may be an increase in the production of the target protein in a subject or the decrease of the production of target protein in a subject. The regulating activity can be for at least 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 20 months, 21 months, 22 months, 23 months, 2 years, 3 years, 4 years, 5 years, 6 years, 7 years, 8 years, 9 years, 10 years or more than 10 years.

In some embodiments, the AAV particle of the present invention may be administered to a subject using a single dose, one-time treatment. The dose of the one-time treatment may be administered by any methods known in the art and/or described herein. As used herein, a "one-time treatment" refers to a composition which is only administered one time. If needed, a booster dose may be administered to the subject to ensure the appropriate efficacy is reached. A booster may be administered 1 month, 2 months, 3 months, 4 months, 5 months, 6 months, 7 months, 8 months, 9 months, 10 months, 11 months, 12 months, 1 year, 13 months, 14 months, 15 months, 16 months, 17 months, 18 months, 19 months, 20 months, 21 months, 22 months, 23 months, 24 months, 2 years, 3 years, 4 years, 5 years, 6 years, 7 years, 8 years, 9 years, 10 years, or more than 10 years after the one-time treatment.

Delivery Methods

In one embodiment, the AAV particles or pharmaceutical compositions of the present invention may be administered or delivered using the methods for treatment of disease described in U.S. Pat. No. 8,999,948, or International Publication No. WO2014178863, the contents of each of which are herein incorporated by reference in their entirety.

In one embodiment, the AAV particles or pharmaceutical compositions of the present invention may be administered or delivered using the methods for delivering gene therapy in Alzheimer's Disease or other neurodegenerative conditions as described in U.S. Patent Application Publication No. 20150126590, the contents of which are herein incorporated by reference in their entirety.

In one embodiment, the AAV particles or pharmaceutical compositions of the present invention may be administered or delivered using the methods for delivery of a CNS gene therapy as described in U.S. Pat. Nos. 6,436,708, and 8,946,152, and International Publication No. WO2015168666, the contents of each of which are herein incorporated by reference in their entirety.

In one embodiment, the AAV particle or pharmaceutical compositions of the present invention may be administered or delivered using the methods for delivering proteins using AAV particles described in European Patent Application No. EP2678433, the contents of which are herein incorporated by reference in their entirety.

In one embodiment, the AAV particle or pharmaceutical compositions of the present invention may be administered or delivered using the methods for delivering DNA to the bloodstream described in U.S. Pat. No. 6,211,163, the contents of which are herein incorporated by reference in their entirety.

In one embodiment, the AAV particle or pharmaceutical compositions of the present invention may be administered or delivered using the methods for delivering a payload to the central nervous system described in U.S. Pat. No. 7,588,757, the contents of which are herein incorporated by reference in their entirety.

In one embodiment, the AAV particle or pharmaceutical compositions of the present invention may be administered or delivered using the methods for delivering a payload described in U.S. Pat. No. 8,283,151, the contents of which are herein incorporated by reference in their entirety.

In one embodiment, the AAV particle or pharmaceutical compositions of the present invention may be administered or delivered using the methods for delivering a payload using a glutamic acid decarboxylase (GAD) delivery vector described in International Patent Publication No. WO2001089583, the contents of which are herein incorporated by reference in their entirety.

In one embodiment, the AAV particle or pharmaceutical compositions of the present invention may be administered or delivered using the methods for delivering a payload to neural cells described in International Patent Publication No. WO2012057363, the contents of which are herein incorporated by reference in their entirety.

Delivery to Cells

The present disclosure provides a method of delivering to a cell or tissue or an organ any of the above-described AAV particles, comprising contacting the cell or tissue or organ with said AAV particle or contacting the cell or tissue or organ with a formulation comprising said AAV particle, or contacting the cell or tissue or organ with any of the described compositions, including pharmaceutical compositions comprising the AAV particles. The method of delivering the AAV particle to a cell or tissue or organ can be accomplished in vitro, ex vivo, or in vivo.

Delivery to Subjects

The present disclosure additionally provides a method of delivering to a subject, including a mammalian subject, any of the above-described AAV particles comprising administering to the subject said AAV particle, or administering to the subject a formulation comprising said AAV particle, or administering to the subject any of the described compositions, including pharmaceutical compositions.

In one embodiment, the mammalian subject is human. In some aspects, the human subject is a patient with a disease, for example, a neurological disease, or a cardiovascular disease.

Combinations

The AAV particles may be used in combination with one or more other therapeutic, prophylactic, research or diagnostic agents. By "in combination with," it is not intended to imply that the agents must be administered at the same time and/or formulated for delivery together, although these methods of delivery are within the scope of the present invention. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, research, or diagnostic compositions in combination with agents that may improve their bioavailability, reduce and/or modify their metabolism, inhibit their excretion, and/or modify their distribution within the body.

Measurement of Expression

Expression of payloads from viral genomes may be determined using various methods known in the art such as, but not limited to immunochemistry (e.g., IHC), in situ hybridization (ISH), enzyme-linked immunosorbent assay (ELISA), affinity ELISA, ELISPOT, flow cytometry, immunocytology, surface plasmon resonance analysis, kinetic exclusion assay, liquid chromatography-mass spectrometry (LCMS), high-performance liquid chromatography (HPLC), BCA assay, immunoelectrophoresis, Western blot, SDS-PAGE, protein immunoprecipitation, and/or PCR.

Bioavailability

The AAV particles, when formulated into a composition with a delivery agent as described herein, can exhibit an increase in bioavailability as compared to a composition lacking a delivery agent as described herein. As used herein, the term "bioavailability" refers to the systemic availability of a given amount of AAV particle or expressed payload administered to a mammal Bioavailability can be assessed by measuring the area under the curve (AUC) or the maximum serum or plasma concentration ($C_{max}$) of the composition following. AUC is a determination of the area under the curve plotting the serum or plasma concentration of a compound (e.g., AAV particles or expressed payloads) along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in its entirety.

The $C_{max}$ value is the maximum concentration of the AAV particle or expressed payload achieved in the serum or plasma of a mammal following administration of the AAV particle to the mammal. The $C_{max}$ value can be measured using methods known to those of ordinary skill in the art. The phrases "increasing bioavailability" or "improving the pharmacokinetics," as used herein mean that the systemic availability of a first AAV particle or expressed payload, measured as AUC, $C_{max}$, or $C_{min}$ in a mammal is greater, when co-administered with a delivery agent as described herein, than when such co-administration does not take place. In some embodiments, the bioavailability can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

As used herein "therapeutic window" refers to the range of plasma concentrations, or the range of levels of therapeutically active substance at the site of action, with a high probability of eliciting a therapeutic effect. In some embodiments, the therapeutic window of the AAV particle as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the AAV particles as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Biological Effect

In one embodiment, the biological effect of the AAV particles delivered to the animals may be categorized by analyzing the payload expression in the animals. The payload expression may be determined from analyzing a biological sample collected from a mammal administered the AAV particles of the present invention. For example, a protein expression of 50-200 pg/ml for the protein encoded by the AAV particles delivered to the mammal may be seen as a therapeutically effective amount of protein in the mammal.

IV. Methods and Uses of the Compositions of the Invention

Gene Expression

The AAV particles, compositions comprising the AAV particles of the present invention may be used for regulating expression of a gene of interest in a cell, tissue, organ or subject.

In accordance with the present invention, methods for increasing expression of a target protein in a cell, tissue, organ or subject are provided; the method comprising administering the cell, tissue, organ or subject an effective amount of the AAV particles comprising a functional payload that comprises a nucleic acid sequence encoding the target protein.

Accordingly, the target protein may be increased by at least about 10%, preferably by at least about 10%, 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the AAV particles, compositions and formulations of the present invention may be used to increase the expression of a target protein in a cell of the CNS, such as a neuron, astrocyte and/or oligodendrocyte. In some embodiments, the gene may encode a protein including but not limited to an antibody, AADC, APOE2, and Frataxin.

In some embodiments, AAV particles, compositions and formulations of the present invention may be used to decrease, inhibit and suppress the expression of a gene of interest in a cell, tissue, organ or subject. Accordingly, the AAV particles comprise at least one functional payload that comprises siRNA duplexes or dsRNA specific to the target gene of interest.

In some embodiments, the present invention provides methods for inhibiting/silencing target gene expression in a cell. Accordingly, the siRNA duplexes or encoded dsRNA can be used to substantially inhibit target gene expression in a cell, such as but not limited to, astrocytes or microglia, cortical, hippocampal, entorhinal, thalamic, motor or primary sensory neurons. In some aspects, the inhibition of target gene expression refers to an inhibition by at least about 20%, such as by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the gene to be inhibited may include but are not limited to SOD1, HTT, APOE, and/or MAPT.

Neurological Disease

Various neurological diseases may be treated with pharmaceutical compositions, AAV particles, especially blood brain barrier crossing AAV particles of the present invention. As a non-limiting example, the neurological disease may be Absence of the Septum Pellucidum, Acid Lipase Disease, Acid Maltase Deficiency, Acquired Epileptiform Aphasia, Acute Disseminated Encephalomyelitis, Attention Deficit-Hyperactivity Disorder (ADHD), Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS-Neurological Complications, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Cerebral Autosomal Dominant Arteriopathy with Sub-cortical Infarcts and Leukoencephalopathy (CADASIL), Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy (familial infantile), Encephalotrigeminal Angiomatosis, Epilepsy, Epileptic Hemiplegia, Erb's Palsy, Erb-Duchenne and Dejerine-Klumpke Palsies, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus-Neurological Sequelae, Lyme Disease-Neurological Complications, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mini Stroke, Mitochondrial Myopathy, Moebius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myoclonic Encephalopathy of Infants, Myoclonus, Myopathy, Myopathy-Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy-Hereditary, Neurosarcoidosis, Neurosyphilis, Neurotoxicity, Nevus Cavernosus, Niemann-Pick Disease, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain-Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Short-lasting, Unilateral, Neuralgiform (SUNCT) Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, X-Linked Spinal and Bulbar Muscular Atrophy.

The present disclosure additionally provides a method for treating or ameliorating neurological disorders in a mammalian subject, including a human subject, comprising administering to the subject a pharmaceutically effective amount of any of the AAV particles or pharmaceutical compositions of the invention. In one embodiment, the AAV particle is a blood brain barrier crossing particle. In some embodiments, neurological disorders treated according to the methods described herein include, but are not limited to, tauopathies, Alzheimer's disease (AD), Amyotrophic lateral sclerosis (ALS), Huntington's Disease (HD), Parkinson's Disease (PD), and/or Friedreich's Ataxia (FA). In some embodiments, at least one symptom of neurological disorders in the subject is ameliorated and/or treated.

The present disclosure provides a method for administering to a subject in need thereof, including a human subject, a therapeutically effective amount of the AAV particles of the invention to slow, stop or reverse disease progression. As a non-limiting example, disease progression may be measured by tests or diagnostic tool(s) known to those skilled in the art. As another non-limiting example, disease progression may be measured by change in the pathological features of the brain, CSF or other tissues of the subject.

Tauopathies

Tauopathies are a group of neurodegenerative diseases characterized by the dysfunction and/or aggregation of the microtubule associated protein tau. Tau is normally a very soluble protein known to associate with microtubules based on the extent of its phosphorylation. Tau is considered a critical component of intracellular trafficking processes, particularly in neuronal cells, given their unique structure. Hyperphosphorylation of tau depresses its binding to microtubules and microtubule assembly activity. Further, hyperphosphorylation of tau renders it prone to misfolding and aggregation. In tauopathies, the tau becomes hyperphosphorylated, misfolds and aggregates as NFT of paired helical filaments (PHF), twisted ribbons or straight filaments. These NFT are largely considered indicative of impending neuronal cell death and thought to contribute to widespread neuronal cell loss, leading to a variety of behavioral and cognitive deficits.

The first genetically defined tauopathy was described when mutations in the tau gene were shown to lead to an autosomal dominantly inherited tauopathy known as frontotemporal dementia and parkinsonism linked to chromosome 17 (FTDP-17). This was the first causal evidence that changes in tau could lead to neurodegenerative changes in the brain. These molecules are considered to be more amyloidogenic, meaning they are more likely to become hyperphosphorylated and more likely to aggregate into NFT (Hutton, M. et al., 1998, Nature 393(6686):702-5).

Other known tauopathies include, but are not limited to, Alzheimer's disease (AD), frontotemporal dementia (FTD), Frontotemporal lobar degeneration (FTLD), chronic traumatic encephalopathy (CTE), Progressive Supranuclear Palsy (PSP), Down's syndrome, Pick's disease, Corticobasal degeneration (CBD), Amyotrophic lateral sclerosis (ALS), Prion diseases, Creutzfeldt-Jakob disease (CJD), Multiple system atrophy, Tangle-only dementia, and Progressive subcortical gliosis.

Though tauopathies are predominantly associated with tau protein malfunction and aggregation, much like in AD, ApoE is also considered to play a role in the pathogenesis of this group of diseases. ApoE, a cholesterol trafficking molecule, was first suspected to have a role in tauopathy when it was discovered that NFT are also immunoreactive for ApoE. Investigation of the correlations between tau and ApoE in tauopathies have shown contradictory results but suggest a link between ApoE4 and increased NFT load. However, the correlation to cognitive decline has not been shown. Work in this area is still actively being pursued.

Treatments for tauopathies have yet to be identified, though some symptomatic relief may be provided. Delivery of AAV particles of the invention may be used to treat subjects suffering from tauopathy. In some cases, methods of the present invention may be used to treat subjects suspected of developing a tauopathy. Delivery of AAV particles of the invention may result in decreased accumulation of NFT. Further, these decreases in NFT load may or may not be associated with improvements in cognitive, language or behavioral arenas.

In one embodiment, delivery of AAV particles of the invention, comprising ApoE2, ApoE3 or ApoE4 polynucleotides, may be used to treat subjects suffering from tauopathy.

In one embodiment, delivery of AAV particles of the invention comprising modulatory polynucleotides for the silencing of ApoE2, ApoE3 or ApoE4 gene and/or protein expression may be used to treat subjects suffering from tauopathy.

In one embodiment, delivery of AAV particles of the invention comprising modulatory polynucleotides for the silencing of tau gene and/or protein expression may be used to treat subjects suffering from tauopathy.

In one embodiment, the modulatory polynucleotides are siRNA duplexes or nucleic acids encoding siRNA duplexes or encoded dsRNA.

In one embodiment, delivery of AAV particles of the invention comprising a nucleic acid encoding an anti-tau antibody may be used to treat subjects suffering from tauopathy.

In one embodiment, the compositions described herein are used in combination with one or more known or exploratory treatments for tauopathy. Non-limiting examples of such treatments include inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, and/or immunization with tau phospho-epitopes or treatment with anti-tau antibodies.

Alzheimer's Disease

Alzheimer Disease (AD) is a debilitating neurodegenerative disease and the leading cause of dementia in the elderly today, currently afflicting an estimated 5 million people in the United States and more than 35 million people worldwide. AD is largely a disease of extreme forgetfulness, wherein the ability to lead a normal life is incredibly impaired. Clinical manifestations of the disease include progressive declines in memory, executive function (decision making) and language. Individuals with AD often die from secondary illnesses such as cachexia, pneumonia or sepsis.

AD is likely the most well-known tauopathy, though it is often characterized as an amyloid based disorder. The AD brain is characterized by the presence of two forms of pathological aggregates, the extracellular plaques composed of β-amyloid (Aβ) and the intracellular neurofibrillary tangles (NFT) comprised of hyperphosphorylated microtubule associated protein tau. Based on early genetic findings, β-amyloid alterations were thought to initiate disease, with changes in tau considered downstream. For this reason, most clinical trials have been Aβ-centric.

In addition to the traditional hallmarks of the disease (Aβ and tau), apolipoprotein E has proven to be an important risk factor in the pathogenesis of late onset AD (the form of AD that is not genetically linked to alterations in Aβ processing or production and accounts for 99% of the AD population). ApoE, like other apolipoproteins, contributes to the structure of specific lipoprotein particles and directs lipoprotein trafficking to specific cell surface receptors, and is an important cholesterol transporter. ApoE is expressed in a variety of cell types with highest expression levels evident in the liver and brain. In the brain, ApoE is predominantly expressed in astrocytes and microglia, and is thought to contribute to maintenance of synaptic connections and synaptogenesis. ApoE is thought to contribute to AD pathogenesis through its roles in the blood brain barrier, the innate immune system, synaptic function and accumulation of Aβ.

The three most common variants of ApoE are ApoE2, ApoE3 and ApoE4, with ApoE2 and ApoE4 carrying differential risks associated with development of AD. ApoE2 is considered to be a protective allele, decreasing risk of AD and delaying the age of onset, whereas ApoE4 has the opposite effect, significantly increasing risk of developing AD and reducing the age of onset of disease. Further, ApoE2 is associated with a decreased burden of accumulated Aβ, whereas ApoE4 is associated with increased Aβ load.

Early onset forms of AD (before 65 years, which accounts for <5% of AD cases), may be caused by familial mutations in amyloid beta precursor protein (APP), presenilin 1 (PS1 or PSEN1) or presenilin 2 (PS2 or PSEN2). Common symptoms include progressive delcine in memory, executive function, language, and other areas of cognition. These symptoms are often caused by amyloid plaques and/or neurofibrillary tangles in the brain, neuronal loss, synaptic loss, brain atrophy, and/or inflammation.

Symptomatic treatments for AD have been available for many years, but none are able to alter the course of the disease. Delivery of AAV particles of the invention may be used to treat subjects suffering from AD and other tauopathies. In some cases, methods of the present invention may be used to treat subjects suspected of developing AD or other tauopathies. Delivery of AAV particles of the invention may result in decreased Aβ burden both in the brain and in the cardiovascular system of the subject or in decreased accumulation of NFT. Further, these decreases in Aβ or NFT load, may or may not be associated with improvements in cognitive, language or behavioral arenas.

In one embodiment, delivery of AAV particles of the invention, comprising ApoE2, ApoE3 or ApoE4 polynucleotides, may be used to treat subjects suffering from AD and other tauopathies.

In one embodiment, delivery of AAV particles of the invention comprising modulatory polynucleotides for the silencing of the ApoE2, ApoE3 or ApoE4 gene and/or protein may be used to treat subjects suffering from AD and other tauopathies.

In one embodiment, delivery of AAV particles of the invention comprising modulatory polynucleotides for the silencing of the tau gene and/or protein may be used to treat subjects suffering from AD and other tauopathies.

In one embodiment, the modulatory polynucleotides are siRNA duplexes or nucleic acids encoding siRNA duplexes or encoded dsRNA.

In one embodiment, delivery of AAV particles of the invention comprising a nucleic acid encoding an anti-tau antibody may be used to treat subjects suffering from AD and other tauopathies.

In one embodiment, the compositions described herein are used in combination with one or more known or exploratory treatments for AD or tauopathy. Non-limiting examples of such treatments include cholinesterase inhibitors (donepezil, rivastigmine, galantamine), NMDA receptor antagonists such as memantine, anti-psychotics, anti-depressants, anti-convulsants, secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, and/or immunization with Aβ peptides or tau phospho-epitopes or treatment with anti-tau or anti-amyloid antibodies.

In one embodiment, the compositions described herein are evaluated using mammalian models, such as, but not limited to, mouse models of tauopathy and/or Alzheimer's Disease. A great number of mouse models are available that mimic the phenotypes of tauopathies and/or Alzheimer's Disease. However, no existing mouse model exhibits all features of human tauopathies and/or Alzheimer's Disease. Therefore, in some cases, more than one mouse model, or a mouse model cross of one or more of these models, may be used to evaluate the activities of the compositions of the present invention. Exemplary mouse models of tauopathies and/or Alzheimer's Disease include, but are not limited to, 3XTg-AD, 5XFAD, J20, Tg-SwDI, Tg-SwDI/Nos2, Tg2576, R1.40, APPPS1, APP23, PDAPP, APP NL-G-F, TgCRND8, TASD-41, BRI-Aβ42A, PSAPP (Tg2576×PS1), APPswe/PSEN1dE9, 2×KI, TAPP (Tg2576×JNPL3), hTau, PS1M146V, rTg4510, rTg4510×Camk2a-tTA, PS19, rTg4510×Nop-tTA, GFAP-apoE4, Apoe$^{tm3(APOE*4)}$, APP.PS1/TRE4 and ApoE knock-out or knock-in mouse lines. (See Onos et al., Brain Res Bull. 2016; 122:1-11; Hall and Roberson., Brain Res Bull. 2012; 88(1): 3-12; Elder et al., Mt Sinai J Med. 2010; 77(1): 69-81, the contents of which are herein incorporated by reference in their entirety).

Tau transgenic mouse models overexpress wild-type or mutant human tau protein. More than 20 lines have been generated that contain different tau mutations (See Table 2 of Denk and Wade-Martins, Neurobiol Aging. 2009; 30(1): 1-13, the contents of which are herein incorporated by reference in their entirety). These are mutations present in patients with tauopathies and/or Alzheimer's Disease, including G272V, P301L, P301S, N297K, V337M, and R406W. The P301S transgenic mice express the human tau protein containing the P301S mutation. One P301S model (4R/0N tau under the control of the Thy1.2 promoter), created by Allen et al., exhibits similar characteristics to human tauopathies including filament accumulation of hyperphosphorylated tau, neuronal degeneration, and neuroinflammation. In addition, these mice develop a pronounced motor phenotype by 5-6 months of age (Allen et al., J Neurosci. 2002; 22(21):9340-51; Bellucci et al., Am J Pathol. 2004; 165(5):1643-52, the contents of which are herein incorporated by reference in their entirety). Another P301S mouse line (4R/1N tau under the control of the mouse prion promoter), created by Yoshiyama et al., displays hippocampal synapse loss, impaired synaptic function and concomitant microglial activation by 3-6 months of age. The animals also showed pathological hyperphosphorylated tau accumulations, neuronal loss, as well as hippocampal and entorhinal cortical atrophy by 9-12 months of age (Yoshiyama et al., Neuron. 2007; 53(3):337-51, the contents of which are herein incorporated by reference in their entirety).

APOE knock-in mice express human isoforms of APOE. In some cases, the human APOE genes were engineered in to replace the endogenous mouse APOE alleles (targeted replacement). These targeted placement (TR) models of ApoE2, ApoE3 or ApoE4 were developed in the laboratory of Nobuya Maeda (Sullivan et al., J Clin Invest. 1998; 102(1):130-5; Sullivan et al., J Biol Chem. 1997; 272(29): 17972-80; Knouff et al., J Clin Invest. 1999; 103(11):1579-86, the contents of which are herein incorporated by reference in their entirety) and characterized in many studies. The ApoE TR mice differ on spatial memory performance and avoidance behavior. ApoE4-TR mice show cognitive and synaptic plasticity impairment compared to ApoE3-TR mice. In addition, ApoE4-TR mice exhibit anatomical and functional abnormalities in the hippocampus and the amygdala (Grootendorst, Behav Brain Res. 2005; 159(1):1-14; Bour et al., Behav Brain Res. 2008; 193(2):174-82, the contents of which are herein incorporated by reference in their entirety).

In one embodiment, an AAV-ApoE2 particle may be administered to PDAPP or APP.PS1/TRE4 mice as described in Zhao et al 2016 Neurobiol Aging 159-172, the contents of which are herein incorporated by reference in their entirety. Intracerebral or intrathalamic administration of AAV-ApoE2 (AAV9-CAG-APOE2 or AAVrh.10-CAG-APOE2) showed significant decreases in brain Aβ (oligomeric, soluble and insoluble), amyloid deposition and amyloid pathology, as determined by immunohistochemistry, ELISA or Western blot. More specifically, AAV preparations (2 μL, $1.0 \times 10^{10}$ vg) were bilaterally injected by stereotactic surgery into either the hippocampus or the thalamus of adult mice at a rate of 0.2 μL/min and allowed to express for 8 weeks prior to tissue collection for post-mortem analysis.

Lower doses of AAV-ApoE2, or delivery at a late stage of pathology, proved to be less effective.

Frontotemporal Dementia (FTD)

Frontotemporal Dementia (FTD), also known as frontotemporal degenerations or Pick's disease, refers to a group of disorders which are caused by progressive nerve cell loss in the brain. This nerve cell loss can cause a loss of unction in the frontal and/or temporal lobes of the brain. There are about 45,000 people in the United States who have FTD and the majority are between 45 and 65.

There are three subtypes of FTD, behavior variant frontotemporal dementia (bvFTD), primary progressive aphasia (PPA) and disturbances of motor function. Subjects with bvFTD tend to have major changes in personality, interpersonal relationships and conduct and the nerve loss is most prominent in areas that control conduct, empathy, foresight, and judgment. PPA affects language skills, speaking, writing, and comprehension. Both bvFTD and PPA are less common than AD in those over the age of 65, however bvFTD and PPA are nearly as common as AD in those between 45 and 65.

A mutation of tau is genetically associated with those subjects who have FTD.

Amyotrophic Lateral Sclerosis (ALS)

Amyotrophic Lateral Sclerosis (ALS), also known as Lou Gehrig's disease or classical motor neuron disease, is a rapidly progressive and fatal neurological disease. ALS is associated with cell degeneration and death of upper and lower motor neurons, leading to disablement of muscle movement, weakening, wasting and loss of control over voluntary muscle movement. Early symptoms include muscle weakness of hands, legs and swallowing muscles, eventually progressing to inability to breathe due to diaphragm failure. According to Centers for Disease Control and Prevention (CDC), ALS affects an estimated 12,000-15,000 individuals in the US. About 5-10% of cases are familial.

ALS, as other non-infectious neurodegenerative diseases, has been characterized by presence of misfolded proteins, including, but not limited to, tau, amyloid-beta (A beta), alpha-synuclein, HTT (huntingtin) or SOD1 (superoxide dismutase 1 protein), and myelin associated inhibitors and their receptors, (see, e.g., Krishnamurthy and Sigurdsson, 2011, *N Biotechnol.* 28(5):511-7, and Musaro, 2013, FEBS J.; 280(17):4315-22, and references therein) Familial ALS has been associated with mutations of TAR DNA-binding protein 43 (TDP-43) and RNA-binding protein FUS/TLS. Some proteins have been identified to slow down progression of ALS, such as, but not limited to, growth factors, e.g. insulin-like growth factor 1 (IGF-1), glial cell line-derived growth factor, brain-derived growth factor, vascular endothelial growth factor and ciliary neurotrophic factor, or growth factors promoting muscle growth, e.g. myostatin.

As of today, there is no prevention or cure for ALS. FDA approved drug niluzole has been approved to prolong life expectancy, but does not have an effect on symptoms. Additionally, drugs and medical devices are available to tolerate pain and attacks associated with ALS. There remains a need for therapy affecting the underlying pathophysiology.

In some embodiment, methods of the present invention may be used to treat subjects suffering from ALS. In some cases, methods of the present invention may be used to treat subjects suspected of developing ALS.

AAV Particles and methods of using the AAV particles described in the present invention may be used to prevent, manage and/or treat ALS. As non-limiting examples, the AAV particles of the present invention that may be used for the treatment, prevention or management of ALS may comprise modulatory polynucleotides targeting SOD1, HTT and/or Tau.

Huntington's Disease

Huntington's disease (HD) is a rare, inherited disorder causing degeneration of neurons in the motor control region of the brain, as well as other areas. Typical symptoms of the disease include uncontrolled movements (chorea), abnormal postures, impaired coordination, slurred speech and difficulty of feeding and swallowing accompanied by changes in behavior, judgment and cognition. HD is caused by mutations in the gene associated with the huntingtin (HTT) protein. The mutation causes the (CAG) blocks of DNA to repeat abnormally. HD affects approximately 30,000 individuals in the US.

HD is characterized by mutations of the huntingtin (HTT) protein with abnormal expansions of polyglutamine tracts, e.g. expansion of the length of glutamine residues encoded by CAG repeats. The expansion threshold for occurrence of the disease is considered to be approximately 35-40 residues. HD is also associated with beta sheet rich aggregates in striatal neurons formed by N-terminal regions of HTT. The expansions and aggregates lead to gradual loss of neurons as HD progresses. Additionally, the cell death in HD is associated with death receptor 6 (DR6) which is known to induce apoptosis.

As of today, there is no therapy or cure, to prevent the progression of the disease. Drug therapies available are aimed at management of the symptoms. For example, the FDA has approved tetrabenezine to be prescribed for prevention of chorea. Additionally, e.g. antipsychotic drugs may help to control delusions, hallucinations and violent outbursts. There remains a need for therapy affecting the underlying pathophysiology.

In some embodiment, methods of the present invention may be used to treat subjects suffering from HD. In some cases, methods of the present invention may be used to treat subjects suspected of developing HD.

AAV particles and methods of using the AAV particles described in the present invention may be used to prevent, manage and/or treat HD. As a non-limiting example, the AAV particles of the present invention used to treat, prevent and/or manage HD may comprise modulatory polynucleotides targeting HTT, wherein the modulatory polynucleotides are siRNA duplexes or nucleic acids encoding siRNA duplexes or encoded dsRNA.

Parkinson's Disease

Parkinson's Disease (PD) is a progressive disorder of the nervous system affecting especially the substantia nigra of the brain. PD develops as a result of the loss of dopamine producing brain cells. Typical early symptoms of PD include shaking or trembling of a limb, e.g. hands, arms, legs, feet and face. Additional characteristic symptoms are stiffness of the limbs and torso, slow movement or an inability to move, impaired balance and coordination, cognitive changes, and psychiatric conditions e.g. depression and visual hallucinations. PD has both familial and idiopathic forms and it is suggested to be linked to genetic and environmental causes. PD affects more than 4 million people worldwide. In the US, approximately 60,000 cases are identified annually. Generally, PD begins at the age of 50 or older. An early-onset form of the condition begins at age younger than 50, and juvenile-onset PD begins before the age of 20.

Death of dopamine producing brain cells related to PD has been associated with aggregation, deposition and dysfunction of alpha-synuclein protein (see, e.g. Marques and Outeiro, 2012, *Cell Death Dis.* 3:e350, Jenner, 1989, J Neurol Neurosurg Psychiatry. Special Supplement, 22-28, and references therein). Studies have suggested that alpha-synuclein has a role in presynaptic signaling, membrane trafficking and regulation of dopamine release and transport. Alpha-synuclein aggregates, e.g. in forms of oligomers, have been suggested to be species responsible for neuronal dysfunction and death. Mutations of the alpha-synuclein gene (SNCA) have been identified in the familial forms of PD, but also environmental factors, e.g. neurotoxin affect alpha-synuclein aggregation. Other suggested causes of brain cell death in PD are dysfunction of proteosomal and lysosomal systems, reduced mitochondrial activity.

PD is related to other diseases related to alpha-synuclein aggregation, referred to as "synucleinopathies." Such diseases include, but are not limited to, Parkinson's Disease Dementia (PDD), multiple system atrophy (MSA), dementia with Lewy bodies, juvenile-onset, generalized neuroaxonal dystrophy (Hallervorden-Spatz disease), pure autonomic failure (PAF), neurodegeneration with brain iron accumulation type-1 (NBIA-1) and combined Alzheimer's and Parkinson's disease.

As of today, no cure or preventative therapy for PD has been identified. A variety of drug therapies available provide symptomatic relief. Non-limiting examples of symptomatic medical treatments include carbidopa and levodopa combination reducing stiffness and slow movement, and anticholinergics to reduce trembling and stiffness. Other optional therapies include e.g. deep brain stimulation and surgery. There remains a need for therapy affecting the underlying pathophysiology.

In some embodiment, methods of the present invention may be used to treat subjects suffering from PD and other synucleinopathies. In some cases, methods of the present invention may be used to treat subjects suspected of developing PD and other synucleinopathies.

Friedreich's Ataxia

Friedreich's Ataxia (FA) is an autosomal recessive inherited disease that causes progressive damage to the nervous system. See, Parkinson et al., *Journal of Neurochemistry*, 2013, 126 (Suppl. 1), 103-117, the contents of which are herein incorporated by reference in their entirety. Onset usually occurs at puberty, and always by age 25. See, Campuzano, et al., Science, 271.5254 (Mar. 8, 1996): 1423, the contents of which are herein incorporated by reference in their entirety. FA results from the degeneration of nervous tissue in the spinal cord due to reduced expression of the mitochondrial protein frataxin (FXN) in sensory neurons that are essential (through connections with the cerebellum) for directing muscle movement of the arms and legs. See, Koeppen, Arnulf; *J Neurol Sci.*, 2011, April 15; 303(1-2): 1-12, the contents of which are herein incorporated by reference in their entirety. Initial symptoms include poor coordination such as gait disturbance, poor balance, leg weakness, decreased walking, impaired coordination, dysarthria, nystagmus, impaired sensation, kyphoscoliosis, and foot deformities. See, Parkinson et al., *Journal of Neurochemistry*, 2013, 126 (Suppl. 1), 103-117. The disease generally progresses until a wheelchair is required for mobility. Incidence of FA among the Caucasian populations is between about 1 in 20,000 and about 1 in 50,000, with a deduced carrier frequency of about 1 in 120 in European populations. See, Nageshwaran and Festenstein, *Frontiers in Neurology*, Vol. 6, Art. 262 (2015); Campuzano, et al., Science, 271.5254 (Mar. 8, 1996): 1423, the contents of each of which are herein incorporated by reference in their entirety.

The expansion of an intronic GAA triplet repeat in the FXN gene is the genetic cause of reduced expression of frataxin resulting in FA. See, Parkinson et al., *Journal of Neurochemistry*, 2013, 126 (Suppl. 1), 103-117. Over time the deficiency causes the aforementioned symptoms, as well as frequent fatigue due to effects on cellular metabolism.

Currently, no effective treatments exist for FA and patients are most often simply monitored for symptom management. Consequently, there remains a long felt need in the art to develop pharmaceutical compositions and methods for the treatment of FXN related disorders and to ameliorate deficiencies of the protein in patients afflicted with FA.

Delivery of AAV particles of the invention may be used to treat subjects suffering from Friedreich's Ataxia. In some cases, methods of the present invention may be used to treat subjects suspected of developing Friedreich's Ataxia. Delivery of AAV particles of the invention may result in increased frataxin protein. Further, this increase in frataxin protein may or may not be associated with improvements in mobility.

In one embodiment, delivery of AAV particles of the invention, comprising frataxin polynucleotides, may be used to treat subjects suffering from Friedreich's Ataxia.

In one embodiment, the AAV particles of the invention, comprising frataxin polynucleotides, may be delivered to the dentate nucleus of the cerebellum, brainstem nuclei and/or Clarke's column of the spinal cord. Delivery to one or more of these regions may treat and/or reduce the effects of Friedreich's Ataxia in a subject.

In one embodiment, the AAV particles of the invention, comprising frataxin polynucleotides, may be delivered by intravenous administration to the central nervous system, peripheral nervous system, and/or peripheral organs for the treatment of Friedreich's Ataxia in a subject.

Cardiovascular Disease

Cardiovascular disease, also called heart disease or heart and blood vessel disease, is a general term describing many diseases or disorders of the heart and/or blood vessels. Many of the diseases or disorders in cardiovascular disease are related to atherosclerosis where plaque builds up in the walls of the arteries. This buildup narrows the arteries making it harder for blood to flow through. Non-limiting examples of cardiovascular disease include, heart failure (when the heart is not pumping blood as well as it should be), arrhythmia (abnormal rhythm of the heart, e.g., bradycardia (heart rate of less than 60 beats per minute) or tachycardia (heart rate of more than 100 beats per minute)), heart valve problems (e.g., stenosis (valves don't open enough to allow blood to flow through as it should), regurgitation (valves do not close properly), and prolapse (valve leaflets bulge or prolapse back into the upper chamber)), stroke (e.g., an ischemic stroke when there is a blockage of the blood vessel that feeds to the brain), and heart attack (when the blood flow is blocked to the heart).

The AAV particles of the invention may be used to treat subjects suffering from cardiovascular disease.

Heart Failure

Heart failure is the leading cause of mortality in the United States with approximately 5.8 million patients and 300,000 deaths per year. Heart failure is the common endpoint of cardiac disease caused by various factors including, but not limited to, diet, smoking, hypertension or genetics. Heart failure may be cause by the dysregulation of calcium handling which leads to impaired heart muscle contractility. Current treatments for heart failure include, but are not limited to, symptomatic therapy (e.g., diuretics, β-adrenergic blockers, and/or angiotensin-converting enzyme (ACE) inhibitors), and device or surgery therapy (e.g., left ventricular assist device (LVAD), valve replacement, and/or angioplasty). These currently therapies do not directly correct heart contractility but provide only a short term solution to the disease. A long term therapeutic option to treat heart failure is gene therapy using AAV delivery.

A majority of cardiac AAV gene therapeutic approaches have focused on the β-adrenergic system (βARKct, Adenylyl Cyclase 6) or calcium handling proteins (SERCA2a, PP1, S100A1) to rescue cardiac contractility. See e.g., Hulot et al., 2016 and Zouein & Booz 2013, the contents of each of which are incorporated by reference in their entireties. However, increased transduction of cardiomyocytes by systemic or targeted delivery of the AAV capsids described herein, provides the best opportunity for the treatment of heart failure.

The New York Heart Association (NYHA) created a functional classification system to categorize subjects with heart failure. NYHA provides 4 classes of patient symptom assessment and 4 classes of objective assessments based on how much a subject is limited during physical activity. Class I patient symptom assessment means a subject has no limit of physical activity as ordinary physical activity does not cause a subject undue fatigue, palpitation, or shortness of breath. Class II patient symptom assessment means a subject has a slight limitation of physical activity as they are comfortable at rest but ordinary physical activity results in fatigue, palpitation, and shortness of breath. Class III patient symptom assessment means a subject has a limitation of physical activity as the subject is comfortable at rest but activity other than normal activity causes fatigue, palpitation, or shortness of breath. Class IV patient symptom assessment means a subject is unable to carry on any physical activity without discomfort. An objective assessment means that a subject has no objective evidence of cardiovascular disease and there are no symptoms nor limitation to ordinary physical activity. A Class B objective assessment means that there is objective evidence of minimal cardiovascular disease with mild symptoms and a slight limitation during ordinary activity but the subject is comfortable at rest. A Class C objective assessment means that there is objective evidence of moderately severe cardiovascular disease, the subject is only comfortable at rest and has marked limitation activity due to symptoms even during activity which is less than ordinary. A Class D objective assessment means that there is objective evidence of severe cardiovascular disease, the subject has symptoms even at rest, and has severe activity limitations.

In one embodiment, delivery of the AAV particles of the invention may be used to treat subjects who has heart failure.

In one embodiment, delivery of the AAV particles of the present invention occurs after a myocardial injury. In one embodiment, delivery of the AAV particles of the present invention occurs after a subject has depressed ventricular performance In one embodiment, delivery of the AAV particles of the present invention occurs after administration of digoxin to a subject. In one embodiment, delivery of the AAV particles of the present invention occurs at the same time as administration of digoxin to a subject. In one embodiment, delivery of the AAV particles of the present invention occurs after a subject has depressed ventricular performance but prior to a subject having reduced cardiac output. In one embodiment, delivery of the AAV particles of the present invention occurs prior to administration of beta-blockers to a subject.

In one embodiment, the AAV particles of the present invention are administered in combination with digoxin, beta-blockers, ACE1, aRB, spironolactone, diuretics, and/or vasodilators.

In one embodiment, the AAV particles of the present invention, comprising ATP2A2 (also called SERCA2a) polynucleotides, are administered to treat a subject who has heart failure. While not wishing to be bound by theory, ATPase Sarcoplasmic/Endoplasmic Reticulum Ca2+ Transporting 2 (also called Sarcoplasmic Reticulum Ca2+ ATPase (SERCA2a) is a component of calcium cycling in cardiomyocytes. Decreased function of proteins responsible for calcium transport (Ca2+) in the sarcoplasmic reticulum (SR) may cause the contraction/relaxation defect seen after heart failure. Decreased expression and activity of ATP2A2 has been observed in human tissue after heart failure (see Arai et al. Circulation Research 72(2) February 2013; the contents of which are herein incorporated by reference in their entirety). The calcium cycle and contractility may be restored by ATP2A2 overexpression in a subject.

In one embodiment, delivery of the AAV particles of the present invention comprising ATP2A2 polynucleotides increases the expression of ATP2A2 in a subject. The expression may be increased in a cell, tissue and/or organ of interest. As a non-limiting example, the expression of ATP2A2 is increased in the heart. As a non-limiting example, the expression of ATP2A2 is increased in cardiomyocytes.

In one embodiment, the AAV particles of the present invention, comprising S100A1 polynucleotides, are administered to treat a subject who has heart failure. While not wishing to be bound by theory, S100 Calcium Binding Protein A1 enhances the activity of ATP2A2, RyR, mitochondrial ATP production and/or titin-mediated contraction. Increased activity of ATP2A2, protein responsible for calcium transport (Ca2+) in the sarcoplasmic reticulum (SR), may correct the contraction/relaxation defect seen after heart failure.

In one embodiment, delivery of the AAV particles of the present invention comprising S100A1 polynucleotides increases the expression of S100A1 in a subject. The expression may be increased in a cell, tissue and/or organ of interest. As a non-limiting example, the expression of S100A1 is increased in the heart. As a non-limiting example, the expression of S100A1 is increased in cardiomyocytes.

In one embodiment, delivery of the AAV particles of the present invention comprising S100A1 polynucleotides increases the expression of ATP2A2in a subject. The expression may be increased in a cell, tissue and/or organ of interest. As a non-limiting example, the expression of ATP2A2 is increased in the heart. As a non-limiting example, the expression of ATP2A2 is increased in cardiomyocytes.

Methods of Treatment of Neurological Disease

AAV Particles Encoding Protein Payloads

Provided in the present invention are methods for introducing the AAV particles of the present invention into cells, the method comprising introducing into said cells any of the vectors in an amount sufficient for an increase in the production of target mRNA and protein to occur. In some aspects, the cells may be muscle cells, stem cells, neurons such as but not limited to, motor, hippocampal, entorhinal, thalamic or cortical neurons, and glial cells such as astrocytes or microglia.

Disclosed in the present invention are methods for treating neurological disease associated with insufficient function/presence of a target protein (e.g., ApoE, FXN) in a subject in need of treatment. The method optionally comprises administering to the subject a therapeutically effective amount of a composition comprising AAV particles of the present invention. As a non-limiting example, the AAV particles can increase target gene expression, increase target protein production, and thus reduce one or more symptoms of neurological disease in the subject such that the subject is therapeutically treated.

In some embodiments, the AAV particle of the present invention comprising a nucleic acid encoding a protein payload comprise an AAV capsid that allows for transmission across the blood brain barrier after intravenous administration. In one example, the AAV capsid is VOY101 and in another example, the AAV capsid is VOY201.

In one embodiment, the composition comprising the AAV particles of the present invention is administered to the central nervous system of the subject via systemic administration. In one embodiment, the systemic administration is intravenous injection.

In some embodiments, the composition comprising the AAV particles of the present invention is administered to the central nervous system of the subject. In other embodiments, the composition comprising the AAV particles of the present invention is administered to a tissue of a subject (e.g., brain of the subject).

In one embodiment, the composition comprising the AAV particles of the present invention is administered to the central nervous system of the subject via intraparenchymal injection. Non-limiting examples of intraparenchymal injections include intrathalamic, intrastriatal, intrahippocampal or targeting the entorhinal cortex.

In one embodiment, the composition comprising the AAV particles of the present invention is administered to the central nervous system of the subject via intraparenchymal injection and intrathecal injection.

In one embodiment, the AAV particles of the present invention may be delivered into specific types of targeted cells, including, but not limited to, hippocampal, cortical, motor or entorhinal neurons; glial cells including oligodendrocytes, astrocytes and microglia; and/or other cells surrounding neurons such as T cells.

In one embodiment, the AAV particles of the present invention may be delivered to neurons in the striatum and/or cortex.

In some embodiments, the AAV particles of the present invention may be used as a therapy for neurological disease.

In some embodiments, the AAV particles of the present invention may be used as a therapy for tauopathies.

In some embodiments, the AAV particles of the present invention may be used as a therapy for Alzheimer's Disease.

In some embodiments, the AAV particles of the present invention may be used as a therapy for Amyotrophic Lateral Sclerosis.

In some embodiments, the AAV particles of the present invention may be used as a therapy for Huntington's Disease.

In some embodiments, the AAV particles of the present invention may be used as a therapy for Parkinson's Disease.

In some embodiments, the AAV particles of the present invention may be used as a therapy for Friedreich's Ataxia.

In some embodiments, the AAV particles of the present invention may be used to increase target protein expression in astrocytes in order to treat a neurological disease. Target protein in astrocytes may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles may be used to increase target protein in microglia. The increase of target protein in microglia may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles may be used to increase target protein in cortical neurons. The increase of target protein in the cortical neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles may be used to increase target protein in hippocampal neurons. The increase of target protein in the hippocampal neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles may be used to increase target protein in DRG and/or sympathetic neurons. The increase of target protein in the DRG and/or sympathetic neurons may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein in sensory neurons in order to treat neurological disease. Target protein in sensory neurons may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein and reduce symptoms of neurological disease in a subject. The increase of target protein and/or the reduction of symptoms of neurological disease may be, independently, altered (increased for the production of target protein and reduced for the symptoms of neurological disease) by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the AAV particles of the present invention may be used to reduce the decline of functional capacity and activities of daily living as measured by a standard evaluation system such as, but not limited to, the total functional capacity (TFC) scale.

In one embodiment, the AAV particles of the present invention may be used to improve performance on any assessment used to measure symptoms of neurological disease. Such assessments include, but are not limited to ADAS-cog (Alzheimer Disease Assessment Scale-cognitive), MMSE (Mini-Mental State Examination), GDS (Geriatric Depression Scale), FAQ (Functional Activities Questionnaire), ADL (Activities of Daily Living), GPCOG (General Practitioner Assessment of Cognition), Mini-Cog, AMTS (Abbreviated Mental Test Score), Clock-drawing test, 6-CIT (6-item Cognitive Impairment Test), TYM (Test Your Memory), MoCa (Montreal Cognitive Assessment), ACE-R (Addenbrookes Cognitive Assessment), MIS (Memory Impairment Screen), BADLS (Bristol Activities of Daily Living Scale), Barthel Index, Functional Independence Measure, Instrumental Activities of Daily Living, IQCODE (Informant Questionnaire on Cognitive Decline in the Elderly), Neuropsychiatric Inventory, The Cohen-Mansfield Agitation Inventory, BEHAVE-AD, EuroQol, Short Form-36 and/or MBR Caregiver Strain Instrument, or any of the other tests as described in Sheehan B (Ther Adv Neurol Disord. 5(6):349-358 (2012)), the contents of which are herein incorporated by reference in their entirety.

In some embodiments, the present composition is administered as a solo therapeutic or as combination therapeutic for the treatment of neurological disease.

The AAV particles encoding the target protein may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles of the present invention can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation. As a non-limiting example, the combination therapy may be in combination with one or more neuroprotective agents such as small molecule compounds, growth factors and hormones which have been tested for their neuroprotective effect on motor neuron degeneration.

Compounds tested for treating neurological disease which may be used in combination with the AAV particles described herein include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetycholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the AAV particles of the present invention for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV particle described herein may be co-administered with AAV particles expressing neurotrophic factors such as AAV-IGF-I (See e.g., Vincent et al., *Neuromolecular medicine,* 2004, 6, 79-85; the contents of which are incorporated herein by reference in their entirety) and AAV-GDNF (See e.g., Wang et al., *J Neurosci.,* 2002, 22, 6920-6928; the contents of which are incorporated herein by reference in their entirety).

In some embodiments, the composition of the present invention for treating neurological disease is administered to the subject in need intravenously, intramuscularly, subcutaneously, intraperitoneally, intraparenchymally, intrathecally and/or intraventricularly, allowing the AAV particles to pass through one or both the blood-brain barrier and the blood spinal cord barrier. In some aspects, the method includes administering (e.g., intraparenchymal administration, intraventricular administration and/or intrathecally administration) directly to the central nervous system (CNS) of a subject (using, e.g., an infusion pump and/or a delivery scaffold) a therapeutically effective amount of a composition comprising AAV particles of the present invention. The vectors may be used to increase target gene expression, and/or reducing one or more symptoms of neurological disease in the subject such that the subject is therapeutically treated.

In one embodiment, administration of the AAV particles described herein to a subject may increase target protein levels in a subject. The target protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may increase the protein levels of a target protein by at least 50%. As a non-limiting example, the AAV particles may increase the proteins levels of a target protein by at least 40%. As a non-limiting example, a subject may have an increase of 10% of target protein. As a non-limiting example, the AAV particles may increase the protein levels of a target protein by fold increases over baseline. In one embodiment, AAV particles lead to 5-6 times higher levels of a target protein.

In one embodiment, administration of the AAV particles described herein to a subject may increase the expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may increase the expression of a target protein by at least 50%. As a non-limiting example, the AAV particles may increase the expression of a target protein by at least 40%.

In one embodiment, intravenous administration of the AAV particles described herein to a subject may increase the CNS expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may increase the expression of a target protein in the CNS by at least 50%. As a non-limiting example, the AAV particles may increase the expression of a target protein in the CNS by at least 40%.

In one embodiment, administration of the AAV particles to a subject will increase the expression of a target protein in a subject and the increase of the expression of the target protein will reduce the effects and/or symptoms of neurological disease in a subject.

AAV Particles Comprising Modulatory Polynucleotides

Provided in the present invention are methods for introducing the AAV particles, comprising a nucleic acid sequence encoding the siRNA molecules of the present invention into cells, the method comprising introducing into said cells any of the vectors in an amount sufficient for degradation of a target mRNA to occur, thereby activating target-specific RNAi in the cells. In some aspects, the cells may be muscle cells, stem cells, neurons such as but not limited to, motor, hippocampal, entorhinal, thalamic or cortical neurons, and glial cells such as astrocytes or microglia.

Disclosed in the present invention are methods for treating neurological diseases associated with dysfunction of a target protein in a subject in need of treatment. The method optionally comprises administering to the subject a therapeutically effective amount of a composition comprising AAV particles comprising a nucleic acid sequence encoding the siRNA molecules of the present invention. As a non-limiting example, the siRNA molecules can silence target gene expression, inhibit target protein production, and reduce one or more symptoms of neurological disease in the subject such that the subject is therapeutically treated.

In some embodiments, the composition comprising the AAV particles of the present invention comprising a nucleic acid sequence encoding siRNA molecules comprise an AAV capsid that allows for transmission across the blood brain barrier after intravenous administration.

In some embodiments, the composition comprising the AAV particles comprising a nucleic acid sequence encoding the siRNA molecules of the present invention is administered to the central nervous system of the subject. In other embodiments, the composition comprising the AAV particles comprising a nucleic acid sequence encoding the siRNA molecules of the present invention is administered to a tissue of a subject (e.g., brain of the subject).

In one embodiment, the composition comprising the AAV particles comprising a nucleic acid sequence encoding the siRNA molecules of the present invention is administered to the central nervous system of the subject via systemic administration. In one embodiment, the systemic administration is intravenous injection.

In one embodiment, the composition comprising the AAV particles comprising a nucleic acid sequence encoding the siRNA molecules of the present invention is administered to the central nervous system of the subject via intraparenchymal injection. Non-limiting examples of intraparenchymal injections include intrathalamic, intrastriatal, intrahippocampal or targeting the entorhinal cortex.

In one embodiment, the composition comprising the AAV particles comprising a nucleic acid sequence encoding the siRNA molecules of the present invention is administered to the central nervous system of the subject via intraparenchymal injection and intrathecal injection.

In one embodiment, the AAV particles comprising a nucleic acid sequence encoding the siRNA molecules of the present invention may be delivered into specific types of targeted cells, including, but not limited to, hippocampal, cortical, motor or entorhinal neurons; glial cells including oligodendrocytes, astrocytes and microglia; and/or other cells surrounding neurons such as T cells.

In one embodiment, the AAV particles comprising a nucleic acid sequence encoding the siRNA molecules of the present invention may be delivered to neurons in the striatum and/or cortex.

In some embodiments, the AAV particles comprising a nucleic acid sequence encoding the siRNA molecules of the present invention may be used as a therapy for neurological disease.

In some embodiments, the AAV particles comprising a nucleic acid sequence encoding the siRNA molecules of the present invention may be used as a therapy for tauopathies.

In some embodiments, the AAV particles comprising a nucleic acid sequence encoding the siRNA molecules of the present invention may be used as a therapy for Alzheimer's Disease.

In some embodiments, the AAV particles comprising a nucleic acid sequence encoding the siRNA molecules of the present invention may be used as a therapy for Amyotrophic Lateral Sclerosis.

In some embodiments, the AAV particles comprising a nucleic acid sequence encoding the siRNA molecules of the present invention may be used as a therapy for Huntington's Disease.

In some embodiments, the AAV particles comprising a nucleic acid sequence encoding the siRNA molecules of the present invention may be used as a therapy for Parkinson's Disease.

In some embodiments, the AAV particles comprising a nucleic acid sequence encoding the siRNA molecules of the present invention may be used as a therapy for Friedreich's Ataxia.

In some embodiments, the AAV particles comprising a nucleic acid sequence encoding the siRNA molecules of the present invention may be used to suppress a target protein in astrocytes in order to treat neurological disease. Target protein in astrocytes may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in astrocytes may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress a target protein in microglia. The suppression of the target protein in microglia may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress target protein in cortical neurons. The suppression of a target protein in cortical neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress a target protein in hippocampal neurons. The suppression of a target protein in the hippocampal neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress a target protein in DRG and/or sympathetic neurons. The suppression of a target protein in the DRG and/or sympathetic neurons may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress a target protein in sensory neurons in order to treat neurological disease. Target protein in sensory neurons may be suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. Target protein in the sensory neurons may be reduced may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles comprising a nucleic acid sequence encoding the siRNA molecules of the present invention may be used to suppress a target protein and reduce symptoms of neurological disease in a subject. The suppression of target protein and/or the reduction of symptoms of neurological disease may be, independently, reduced or suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the AAV particles comprising a nucleic acid sequence encoding the siRNA molecules of the present invention may be used to reduce the decline of functional capacity and activities of daily living as measured by a standard evaluation system such as, but not limited to, the total functional capacity (TFC) scale.

In some embodiments, the present composition is administered as a solo therapeutic or as combination therapeutic for the treatment of neurological disease.

The AAV particles encoding siRNA duplexes targeting the gene of interest may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles encoding the nucleic acid sequence for the siRNA molecules of the present invention can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation.

Compounds tested for treating neurological disease which may be used in combination with the AAV particles comprising a nucleic acid sequence encoding the siRNA molecules of the present invention include, but are not limited to, cholinesterase inhibitors (donepezil, rivastigmine, galantamine), NMDA receptor antagonists such as memantine, anti-psychotics, anti-depressants, anti-convulsants (e.g., sodium valproate and levetiracetam for myoclonus), secretase inhibitors, amyloid aggregation inhibitors, copper or zinc modulators, BACE inhibitors, inhibitors of tau aggregation, such as Methylene blue, phenothiazines, anthraquinones, n-phenylamines or rhodamines, microtubule stabilizers such as NAP, taxol or paclitaxel, kinase or phosphatase inhibitors such as those targeting GSK3β (lithium) or PP2A, immunization with Aβ peptides or tau phospho-epitopes, anti-tau or anti-amyloid antibodies, dopamine-depleting agents (e.g., tetrabenazine for chorea), benzodiazepines (e.g., clonazepam for myoclonus, chorea, dystonia, rigidity, and/or spasticity), amino acid precursors of dopamine (e.g., levodopa for rigidity), skeletal muscle relaxants (e.g., baclofen, tizanidine for rigidity and/or spasticity), inhibitors for acetycholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the AAV particles encoding the nucleic acid sequence for the siRNA molecules of the present invention for treating neurological disease. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV particle encoding the nucleic acid sequence for the at least one siRNA duplex targeting the gene of interest may be co-administered with AAV particles expressing neurotrophic factors such as AAV-IGF-I (See e.g., Vincent et al., *Neuromolecular medicine,* 2004, 6, 79-85; the content of which is incorporated herein by reference in its entirety) and AAV-GDNF (See e.g., Wang et al., *J Neurosci.,* 2002, 22, 6920-6928; the contents of which are incorporated herein by reference in their entirety).

In some embodiments, the composition of the present invention for treating neurological disease is administered to the subject in need intravenously, intramuscularly, subcutaneously, intraperitoneally, intraparenchymally, intrathecally and/or intraventricularly, allowing the siRNA molecules or vectors comprising the siRNA molecules to pass through one or both the blood-brain barrier and the blood spinal cord barrier. In some aspects, the method includes administering (e.g., intraparenchymal administration, intraventricular administration and/or intrathecally administration) directly to the central nervous system (CNS) of a subject (using, e.g., an infusion pump and/or a delivery scaffold) a therapeutically effective amount of a composition comprising AAV particles encoding the nucleic acid sequence for the siRNA molecules of the present invention. The vectors may be used to silence or suppress target gene expression, and/or reducing one or more symptoms of neurological disease in the subject such that the subject is therapeutically treated.

In one embodiment, administration of the AAV particles encoding a siRNA of the invention, to a subject may lower target protein levels in a subject. The target protein levels may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may lower the protein levels of a target protein by at least 50%. As a non-limiting example, the AAV particles may lower the proteins levels of a target protein by at least 40%.

In one embodiment, administration of the AAV particles encoding a siRNA of the invention, to a subject may lower the expression of a target protein in a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may lower the expression of a target protein by at least 50%. As a non-limiting example, the AAV particles may lower the expression of a target protein by at least 40%.

In one embodiment, intravenous administration of the AAV particles encoding a siRNA of the invention, to a subject may lower the expression of a target protein in the CNS of a subject. The expression of a target protein may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the AAV particles may lower the expression of a target protein by at least 50%. As a non-limiting example, the AAV particles may lower the expression of a target protein by at least 40%.

In one embodiment, administration of the AAV particles to a subject will reduce the expression of a target protein in a subject and the reduction of expression of the target protein will reduce the effects and/or symptoms of neurological disease in a subject.

In one embodiment, the AAV particles may be used to decrease target protein in a subject. The decrease may independently be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. As a non-limiting example, a subject may have a decrease of 70% of target protein. As a non-limiting example, a subject may have a 50% decrease of target protein. As a non-limiting example, a subject may have a 40% decrease of target protein. As a non-limiting example, a subject may have a decrease of 10% of target protein.

Methods of Treatment of Cardiovascular Disease

Provided in the present invention are methods for introducing the AAV particles of the present invention into cells, the method comprising introducing into said cells any of the vectors in an amount sufficient for an increase in the production of target mRNA and protein to occur. In some aspects, the cells may be muscle cells such as but not limited to, cardiomyocytes.

Disclosed in the present invention are methods for treating cardiovascular disease associated with insufficient function/presence of a target protein (e.g., ATP2A2) in a subject in need of treatment. The method optionally comprises administering to the subject a therapeutically effective amount of a composition comprising AAV particles of the present invention. As a non-limiting example, the AAV particles can increase target gene expression, increase target protein production, and thus reduce one or more symptoms of cardiovascular disease in the subject such that the subject is therapeutically treated.

In some embodiments, the AAV particle of the present invention comprising a nucleic acid encoding a protein payload comprise an AAV capsid that allows for distribution to cardiomyocytes after intravenous administration.

In one embodiment, the composition comprising the AAV particles of the present invention is administered to a subject via systemic administration. In one embodiment, the systemic administration is intravenous injection.

In some embodiments, the composition comprising the AAV particles of the present invention is administered directly to the cardiovascular system of the subject. In other embodiments, the composition comprising the AAV particles of the present invention is administered to a tissue of a subject (e.g., heart of the subject).

In one embodiment, the composition comprising the AAV particles of the present invention is administered to the cardiovascular system of the subject via intrathecal injection.

In one embodiment, the AAV particles of the present invention may be delivered into specific types of targeted cells, including, but not limited to, cardiomyocytes.

In one embodiment, the AAV particles of the present invention may be delivered to cardiomyocytes.

In some embodiments, the AAV particles of the present invention may be used as a therapy for cardiovascular disease.

In some embodiments, the AAV particles of the present invention may be used as a therapy for dilated cardiomyopathy (DCM). DCM affects the heart's ventricles and atria, where the heart muscle begins to dilate causing the heart muscle to contract abnormally resulting in the heart not pumping blood efficiently.

In some embodiments, the AAV particles of the present invention may be used as a therapy for hypertrophic cardiomyopathy. Hypertrophic cardiomyopathy is where a portion of the heart muscle is enlarged making it difficult for the heart to pump blood.

In some embodiments, the AAV particles may be used to increase target protein in cardiac tissue. The increase of target protein in cardiac tissue may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein expression in cardiomyocytes in order to treat a cardiovascular disease. Target protein in cardiomyocytes may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein and reduce symptoms of cardiovascular disease in a subject. The increase of target protein and/or the reduction of symptoms of cardiovascular disease may be, independently, altered (increased for the production of target protein and reduced for the symptoms of cardiovascular disease) by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the present composition is administered as a solo therapeutic or as combination therapeutic for the treatment of cardiovascular disease.

The AAV particles encoding the target protein may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles of the present invention can be small molecule compounds which are antioxidants, anti-inflammatory agents, anti-apoptosis agents, calcium regulators, antiglutamatergic agents, structural protein inhibitors, compounds involved in muscle function, diuretics, ACE inhibitors, β-adrenergic blockers, and compounds involved in metal ion regulation.

In some embodiments, the composition of the present invention for treating cardiovascular disease is administered to the subject in need intravenously, intramuscularly, subcutaneously, intrathecally, anterograde coronary injection, and/or intraventricularly, allowing the AAV particles to be delivered to the desired cell, tissue, and/or organ. In some aspects, the method includes administering (e.g., intraparenchymal administration, intraventricular administration and/or intrathecally administration) directly to the cardiovascular system of a subject (using, e.g., an infusion pump and/or a delivery scaffold) a therapeutically effective amount of a composition comprising AAV particles of the present invention. The vectors may be used to increase target gene expression, and/or reducing one or more symptoms of cardiovascular disease in the subject such that the subject is therapeutically treated.

In one embodiment, administration of the AAV particles described herein to a subject may increase target protein levels in a subject. The target protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular of a subject. As a non-limiting example, the AAV particles may increase the protein levels of a target protein by at least 50%. As a non-limiting example, the AAV particles may increase the proteins levels of a target protein by at least 40%. As a non-limiting example, a subject may have an increase of 10% of target protein. As a non-limiting example, the AAV particles may increase the protein levels of a target protein by fold increases over baseline. In one embodiment, AAV particles lead to 5-6 times higher levels of a target protein.

In one embodiment, administration of the AAV particles described herein to a subject may increase the expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular system of a subject. As a non-limiting example, the AAV particles may increase the expression of a target protein by at least 50%. As a non-limiting example, the AAV particles may increase the expression of a target protein by at least 40%.

In one embodiment, intravenous administration of the AAV particles described herein to a subject may increase the cardiovascular system expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular system of a subject. As a non-limiting example, the AAV particles may increase the expression of a target protein in the cardiovascular system by at least 50%. As a non-limiting example, the AAV particles may increase the expression of a target protein in the cardiovascular system by at least 40%.

In one embodiment, administration of the AAV particles to a subject will increase the expression of a target protein in a subject and the increase of the expression of the target protein will reduce the effects and/or symptoms of cardiovascular disease in a subject.

Methods of Treatment of Heart Failure

Provided in the present invention are methods for introducing the AAV particles of the present invention into cells, the method comprising introducing into said cells any of the vectors in an amount sufficient for an increase in the production of target mRNA and protein to occur. In some aspects, the cells may be muscle cells such as but not limited to, cardiomyocytes.

Disclosed in the present invention are methods for treating heart failure associated with insufficient function/presence of a target protein (e.g., ATP2A2) in a subject in need of treatment. The method optionally comprises administering to the subject a therapeutically effective amount of a composition comprising AAV particles of the present invention. As a non-limiting example, the AAV particles can increase target gene expression, increase target protein production, and thus reduce one or more symptoms of heart failure in the subject such that the subject is therapeutically treated.

In some embodiments, the AAV particle of the present invention comprising a nucleic acid encoding a protein payload comprise an AAV capsid that allows for distribution to cardiomyocytes after intravenous administration.

In one embodiment, the composition comprising the AAV particles of the present invention is administered to a subject via systemic administration. In one embodiment, the systemic administration is intravenous injection.

In some embodiments, the composition comprising the AAV particles of the present invention is administered directly to the cardiovascular system of the subject. In other embodiments, the composition comprising the AAV particles of the present invention is administered to a tissue of a subject (e.g., heart of the subject).

In one embodiment, the composition comprising the AAV particles of the present invention is administered to the cardiovascular system of the subject via intrathecal injection.

In one embodiment, the AAV particles of the present invention may be delivered into specific types of targeted cells, including, but not limited to, cardiomyocytes.

In one embodiment, the AAV particles of the present invention may be delivered to cardiomyocytes.

In one embodiment, the AAV particles of the present invention may be used as a therapy for heart failure.

In one embodiment, the AAV particles of the present invention may be used to reduce the number of hospitalization of a subject.

In one embodiment, the AAV particles of the present invention may be used to prolong survival of a subject In some embodiments, the AAV particles may be used to increase target protein in cardiac tissue. The increase of target protein in cardiac tissue may be, independently, increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein expression in cardiomyocytes in order to treat heart failure. Target protein in cardiomyocytes may be increased by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the AAV particles of the present invention may be used to increase target protein and reduce symptoms of heart failure in a subject. The increase of target protein and/or the reduction of symptoms of heart failure may be, independently, altered (increased for the production of target protein and reduced for the symptoms of heart failure) by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In some embodiments, the present composition is administered as a solo therapeutic or as combination therapeutic for the treatment of heart failure.

The AAV particles encoding the target protein may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the AAV particles of the present invention can be small molecule compounds which are antioxidants, anti-inflammatory agents, anti-apoptosis agents, calcium regulators, antiglutamatergic agents, structural protein inhibitors, compounds involved in muscle function, diuretics, ACE inhibitors, β-adrenergic blockers, and compounds involved in metal ion regulation.

In some embodiments, the composition of the present invention for treating cardiovascular disease is administered to the subject in need intravenously, intramuscularly, subcutaneously, intrathecally, anterograde coronary injection, and/or intraventricularly, allowing the AAV particles to be delivered to the desired cell, tissue, and/or organ. In some aspects, the method includes administering (e.g., intraparenchymal administration, intraventricular administration and/or intrathecally administration) directly to the cardiovascular system of a subject (using, e.g., an infusion pump and/or a delivery scaffold) a therapeutically effective amount of a composition comprising AAV particles of the present invention. The vectors may be used to increase target gene expression, and/or reducing one or more symptoms of heart failure in the subject such that the subject is therapeutically treated.

In one embodiment, administration of the AAV particles described herein to a subject may increase target protein levels in a subject. The target protein levels may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular of a subject. As a non-limiting example, the AAV particles may increase the protein levels of a target protein by at least 50%. As a non-limiting example, the AAV particles may increase the proteins levels of a target protein by at least 40%. As a non-limiting example, a subject may have an increase of 10% of target protein. As a non-limiting example, the AAV particles may increase the protein levels of a target protein by fold increases over baseline. In one embodiment, AAV particles lead to 5-6 times higher levels of a target protein.

In one embodiment, administration of the AAV particles described herein to a subject may increase the expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular system of a subject. As a non-limiting example, the AAV particles may increase the expression of a target protein by at least 50%. As a non-limiting example, the AAV particles may increase the expression of a target protein by at least 40%.

In one embodiment, intravenous administration of the AAV particles described herein to a subject may increase the cardiovascular system expression of a target protein in a subject. The expression of the target protein may be increased by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the cardiovascular system, a region of the cardiovascular system, or a specific cell of the cardiovascular system of a subject. As a non-limiting example, the AAV particles may increase the expression of a target protein in the cardiovascular system by at least 50%. As a non-limiting example, the AAV particles may increase the expression of a target protein in the cardiovascular system by at least 40%.

In one embodiment, administration of the AAV particles described herein to a subject may increase the expression of a target protein in cardiomyocytes of a subject. The expression of the target protein may be increased by about 20%, 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, administration of the AAV particles described herein to a subject may express ATP2A2 in cardiomyocytes of a subject. The expression of ATP2A2 in cardiomyocytes may be 20%, 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. In one embodiment, the expression of ATP2A2 may be seen in 30% of cardiomyocytes. In one embodiment, the expression of ATP2A2 may be seen in 30-40% of cardiomyocytes. In one embodiment, the expression of ATP2A2 may be seen in 30-50% of cardiomyocytes. In one embodiment, the expression of ATP2A2 may be seen in 30% of cardiomyocytes. In one embodiment, the expression of ATP2A2 may be seen in 30-60% of cardiomyocytes. In one embodiment, the expression of ATP2A2 may be seen in 30-70% of cardiomyocytes. In one embodiment, the expression of ATP2A2 may be seen in 30-80% of cardiomyocytes. In one embodiment, the expression of ATP2A2 may be seen in 30-90% of cardiomyocytes. In one embodiment, the expression of ATP2A2 may be seen in 20% of cardiomyocytes. In one embodiment, the expression of ATP2A2 may be seen in 20-40% of cardiomyocytes. In one embodiment, the expression of ATP2A2 may be seen in 20-50% of cardiomyocytes. In one embodiment, the expression of ATP2A2 may be seen in 20% of cardiomyocytes. In one embodiment, the expression of ATP2A2 may be seen in 20-60% of cardiomyocytes. In one embodiment, the expression of ATP2A2 may be seen in 20-70% of cardiomyocytes. In one embodiment, the expression of ATP2A2 may be seen in 20-80% of cardiomyocytes. In one embodiment, the expression of ATP2A2 may be seen in 20-90% of cardiomyocytes.

In one embodiment, administration of the AAV particles described herein to a subject may express S100A1 in cardiomyocytes of a subject. The expression of S100A1 in cardiomyocytes may be 20%, 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. In one embodiment, the expression of S100A1 may be seen in 30% of cardiomyocytes. In one embodiment, the expression of S100A1 may be seen in 30-40% of cardiomyocytes. In one embodiment, the expression of S100A1 may be seen in 30-50% of cardiomyocytes. In one embodiment, the expression of S100A1 may be seen in 30% of cardiomyocytes. In one embodiment, the expression of S100A1 may be seen in 30-60% of cardiomyocytes. In one embodiment, the expression of S100A1 may be seen in 30-70% of cardiomyocytes. In one embodiment, the expression of S100A1 may be seen in 30-80% of cardiomyocytes. In one embodiment, the expression of S100A1 may be seen in 30-90% of cardiomyocytes. In one embodiment, the expression of S100A1 may be seen in 20% of cardiomyocytes. In one embodiment, the expression of S100A1 may be seen in 20-40% of cardiomyocytes. In one embodiment, the expression of S100A1 may be seen in 20-50% of cardiomyocytes. In one embodiment, the expression of S100A1 may be seen in 20% of cardiomyocytes. In one embodiment, the expression of S100A1 may be seen in 20-60% of cardiomyocytes. In one embodiment, the expression of S100A1 may be seen in 20-70% of cardiomyocytes. In one embodiment, the expression of S100A1 may be seen in 20-80% of cardiomyocytes. In one embodiment, the expression of S100A1 may be seen in 20-90% of cardiomyocytes.

In one embodiment, administration of the AAV particles to a subject will increase the expression of a target protein in a subject and the increase of the expression of the target protein will reduce the effects and/or symptoms of heart failure in a subject.

In one embodiment, a subject is administered a dose of $1 \times 10^{13}$ VG of the AAV particles of the present invention to treat heart failure. As a non-limiting example, the subject is administered the dose of AAV particles by percutaneous intracoronary administration.

In one embodiment, a subject is administered a dose of $1 \times 10^{13}$ VG of the AAV particles of the present invention to treat heart failure. As a non-limiting example, the subject is administered the dose of AAV particles by intravenous administration.

In one embodiment, a subject is administered a dose of $2 \times 10^{13}$ VG of the AAV particles of the present invention to treat heart failure. As a non-limiting example, the subject is administered the dose of AAV particles by percutaneous intracoronary administration.

In one embodiment, a subject is administered a dose of $2 \times 10^{13}$ VG of the AAV particles of the present invention to treat heart failure. As a non-limiting example, the subject is administered the dose of AAV particles by intravenous administration.

In one embodiment, a subject is administered a dose of $3 \times 10^{13}$ VG of the AAV particles of the present invention to treat heart failure. As a non-limiting example, the subject is administered the dose of AAV particles by percutaneous intracoronary administration.

In one embodiment, a subject is administered a dose of $3 \times 10^{13}$ VG of the AAV particles of the present invention to treat heart failure. As a non-limiting example, the subject is administered the dose of AAV particles by intravenous administration.

In one embodiment, a subject is administered a dose of $3 \times 10^{11}$ VG of the AAV particles of the present invention to treat heart failure. As a non-limiting example, the subject is administered the dose of AAV particles by percutaneous intracoronary administration.

In one embodiment, a subject is administered a dose of $3 \times 10^{11}$ VG of the AAV particles of the present invention to treat heart failure. As a non-limiting example, the subject is administered the dose of AAV particles by intravenous administration.

In one embodiment, a subject is administered a dose of $3 \times 10^{12}$ VG of the AAV particles of the present invention to treat heart failure. As a non-limiting example, the subject is administered the dose of AAV particles by percutaneous intracoronary administration.

In one embodiment, a subject is administered a dose of $3 \times 10^{12}$ VG of the AAV particles of the present invention to treat heart failure. As a non-limiting example, the subject is administered the dose of AAV particles by intravenous administration.

V. Kits and Devices

Kits

In one embodiment, the invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

Any of the AAV particles of the present invention may be comprised in a kit. In some embodiments, kits may further include reagents and/or instructions for creating and/or synthesizing compounds and/or compositions of the present invention. In some embodiments, kits may also include one or more buffers. In some embodiments, kits of the invention may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably aliquoted. Where there is more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present invention may also typically include means for containing compounds and/or compositions of the present invention, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In one embodiment, the AAV particles may delivered to a subject using a device to deliver the AAV particles and a head fixation assembly. The head fixation assembly may be, but is not limited to, any of the head fixation assemblies sold by MRI interventions. As a non-limiting example, the head fixation assembly may be any of the assemblies described in U.S. Pat. Nos. 8,099,150, 8,548,569 and 9,031,636 and International Patent Publication Nos. WO201108495 and WO2014014585, the contents of each of which are incorporated by reference in their entireties. A head fixation assembly may be used in combination with an MRI compatible drill such as, but not limited to, the MRI compatible drills described in International Patent Publication No. WO2013181008 and US Patent Publication No. US20130325012, the contents of which are herein incorporated by reference in its entirety.

In one embodiment, the AAV particles may be delivered using a method, system and/or computer program for positioning apparatus to a target point on a subject to deliver the AAV particles. As a non-limiting example, the method, system and/or computer program may be the methods, systems and/or computer programs described in U.S. Pat. No. 8,340,743, the contents of which are herein incorporated by reference in their entirety. The method may include: determining a target point in the body and a reference point, wherein the target point and the reference point define a planned trajectory line (PTL) extending through each; determining a visualization plane, wherein the PTL intersects the visualization plane at a sighting point; mounting the guide device relative to the body to move with respect to the PTL, wherein the guide device does not intersect the visualization plane; determining a point of intersection (GPP) between the guide axis and the visualization plane; and aligning the GPP with the sighting point in the visualization plane.

In one embodiment, the AAV particles may be delivered to a subject using a convention-enhanced delivery device. Non-limiting examples of targeted delivery of drugs using convection are described in US Patent Application Publication Nos. US20100217228, US20130035574 and US20130035660 and International Patent Publication No. WO2013019830 and WO2008144585, the contents of each of which are herein incorporated by reference in their entirety.

In one embodiment, a subject may be imaged prior to, during and/or after delivery of the AAV particles. The imaging method may be a method known in the art and/or described herein, such as but not limited to, magnetic resonance imaging (MRI). As a non-limiting example, imaging may be used to assess therapeutic effect. As another non-limiting example, imaging may be used for assisted delivery of AAV particles.

In one embodiment, the AAV particles may be delivered using an MRI-guided device. Non-limiting examples of MRI-guided devices are described in U.S. Pat. Nos. 9,055,884, 9,042,958, 8,886,288, 8,768,433, 8,396,532, 8,369,930, 8,374,677 and 8,175,677 and US Patent Application Publication No. US20140024927 the contents of each of which are herein incorporated by reference in their entirety. As a non-limiting example, the MRI-guided device may be able to provide data in real time such as those described in U.S. Pat. Nos. 8,886,288 and 8,768,433, the contents of each of which are herein incorporated by reference in their entirety. As another non-limiting example, the MRI-guided device or system may be used with a targeting cannula such as the systems described in U.S. Pat. Nos. 8,175,677 and 8,374,677, the contents of each of which are herein incorporated by reference in their entireties. As yet another non-limiting example, the MRI-guided device includes a trajectory guide frame for guiding an interventional device as described, for example, in U.S. Pat. No. 9,055,884 and US Patent Application No. US20140024927, the contents of each of which are herein incorporated by reference in their entirety.

In one embodiment, the AAV particles may be delivered using an MRI-compatible tip assembly. Non-limiting examples of MRI-compatible tip assemblies are described in US Patent Publication No. US20140275980, the contents of which are herein incorporated by reference in their entirety.

In one embodiment, the AAV particles may be delivered using a cannula which is MRI-compatible. Non-limiting examples of MRI-compatible cannulas include those taught in International Patent Publication No. WO2011130107, the contents of which are herein incorporated by reference in their entirety.

In one embodiment, the AAV particles may be delivered using a catheter which is MRI-compatible. Non-limiting examples of MRI-compatible catheters include those taught in International Patent Publication No. WO2012116265, U.S. Pat. No. 8,825,133 and US Patent Publication No. US20140024909, the contents of each of which are herein incorporated by reference in their entireties.

In one embodiment, the AAV particles may be delivered using a device with an elongated tubular body and a diaphragm as described in US Patent Publication Nos. US20140276582 and US20140276614, the contents of each of which are herein incorporated by reference in their entireties.

In one embodiment, the AAV particles may be delivered using an MRI compatible localization and/or guidance system such as, but not limited to, those described in US Patent Application Publication Nos. US20150223905 and US20150230871, the contents of each of which are herein incorporated by reference in their entirety. As a non-limiting example, the MRI compatible localization and/or guidance systems may comprise a mount adapted for fixation to a patient, a targeting cannula with a lumen configured to attach to the mount so as to be able to controllably translate in at least three dimensions, and an elongate probe configured to snugly advance via slide and retract in the targeting cannula lumen, the elongate probe comprising at least one of a stimulation or recording electrode.

In one embodiment, the AAV particles may be delivered to a subject using a trajectory frame as described in US Patent Application Publication Nos. US20150031982 and US20140066750 and International Patent Publication Nos. WO2015057807 and WO2014039481, the contents of each of which are herein incorporated by reference in their entirety.

In one embodiment, the AAV particles may be delivered to a subject using a gene gun.

VI. Definitions

At various places in the present specification, substituents of compounds of the present disclosure are disclosed in groups or in ranges. It is specifically intended that the present disclosure include each and every individual sub-combination of the members of such groups and ranges.

Unless stated otherwise, the following terms and phrases have the meanings described below. The definitions are not meant to be limiting in nature and serve to provide a clearer understanding of certain aspects of the present invention.

About: As used herein, the term "about" means+/−10% of the recited value.

Adeno-associated virus: The term "adeno-associated virus" or "AAV" as used herein refers to members of the dependovirus genus comprising any particle, sequence, gene, protein, or component derived therefrom.

AAV Particle: As used herein, an "AAV particle" is a virus which comprises a capsid and a viral genome with at least one payload region and at least one ITR region. AAV particles of the present disclosure may be produced recombinantly and may be based on adeno-associated virus (AAV) parent or reference sequences. AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Activity: As used herein, the term "activity" refers to the condition in which things are happening or being done. Compositions of the invention may have activity and this activity may involve one or more biological events.

Administering: As used herein, the term "administering" refers to providing a pharmaceutical agent or composition to a subject.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, an AAV particle of the present invention may be considered biologically active if even a portion of the encoded payload is biologically active or mimics an activity considered biologically relevant.

Capsid: As used herein, the term "capsid" refers to the protein shell of a virus particle.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Compound: Compounds of the present disclosure include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conditionally active: As used herein, the term "conditionally active" refers to a mutant or variant of a wild-type polypeptide, wherein the mutant or variant is more or less active at physiological conditions than the parent polypeptide. Further, the conditionally active polypeptide may have increased or decreased activity at aberrant conditions as compared to the parent polypeptide. A conditionally active polypeptide may be reversibly or irreversibly inactivated at normal physiological conditions or aberrant conditions.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an polynucleotide or polypeptide or may apply to a portion, region or feature thereof.

Control Elements: As used herein, "control elements", "regulatory control elements" or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Controlled Release: As used herein, the term "controlled release" refers to a pharmaceutical composition or compound release profile that conforms to a particular pattern of release to effect a therapeutic outcome.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering an AAV particle, a compound, substance, entity, moiety, cargo or payload.

Delivery Agent: As used herein, "delivery agent" refers to any substance which facilitates, at least in part, the in vivo delivery of an AAV particle to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least one AAV particle and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Heterologous Region: As used herein the term "heterologous region" refers to a region which would not be considered a homologous region.

Homologous Region: As used herein the term "homologous region" refers to a region which is similar in position, structure, evolution origin, character, form or function.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that a substance is substantially separated from the environment in which it was formed or detected. Partial separation can include, for example, a composition enriched in the substance or AAV particles of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein "linker" refers to a molecule or group of molecules which connects two molecules. A linker may be a nucleic acid sequence connecting two nucleic acid sequences encoding two different polypeptides. The linker may or may not be translated. The linker may be a cleavable linker.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the invention. Molecules may be modified in many ways including chemically, structurally, and functionally.

Mutation: As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

Naturally Occurring: As used herein, "naturally occurring" or "wild-type" means existing in nature without artificial aid, or involvement of the hand of man.

Non-human vertebrate: As used herein, a "non-human vertebrate" includes all vertebrates except Homo sapiens, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition.

Payload: As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" or "prevention" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may there for comprise the N- and/or C-termini as well as surrounding amino acids. In some embodiments, N- and/or C-terminal regions comprise from about 3 amino acid to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and 3' termini. 5' termini refer to the end of a polynucleotide comprising a nucleic acid with a free phosphate group. 3' termini refer to the end of a polynucleotide comprising a nucleic acid with a free hydroxyl group. 5' and 3' regions may there for comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interfering or RNAi: As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Self-complementary viral particle: As used herein, a "self-complementary viral particle" is a particle comprised of at least two components, a protein capsid and a polynucleotide sequence encoding a self-complementary genome enclosed within the capsid.

Sense Strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

Short interfering RNA or siRNA: As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hour period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Vector: As used herein, a "vector" is any molecule or moiety which transports, transduces or otherwise acts as a carrier of a heterologous molecule. Vectors of the present invention may be produced recombinantly and may be based on and/or may comprise adeno-associated virus (AAV) parent or reference sequence. Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral genome: As used herein, a "viral genome" or "vector genome" is a polynucleotide comprising at least one inverted terminal repeat (ITR) and at least one encoded payload. A viral genome encodes at least one copy of the payload.

VII. EXAMPLES

Example 1. Production and Purification of AAV Particles

AAV particles described herein may be produced using methods known in the art, such as, for example, triple transfection or baculovirus mediated virus production. Any suitable permissive or packaging cell known in the art may be employed to produce the vectors. Mammalian cells are often preferred. Also preferred are trans-complementing packaging cell lines that provide functions deleted from a replication-defective helper virus, e.g., 293 cells or other Ela trans-complementing cells.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes Recombinant AAV virus particles are, in some cases, produced and purified from culture supernatants according to the procedure as described in US20160032254, the contents of which are incorporated by reference. Production may also involve methods known in the art including those using 293T cell, sf9 insect cells, triple transfection or any suitable production method.

In some cases, 293 cells are transfected with CaPO4 with plasmids required for production of AAV, i.e., AAV2 rep, an adenoviral helper construct and a ITR flanked transgene cassette. The AAV2 rep plasmid also contains the cap sequence of the particular virus being studied. Twenty-four hours after transfection, which occurs in serum containing DMEM, the medium is replaced with fresh medium with or without serum. Three (3) days after transfection, a sample is taken from the culture medium of the 293 adherent cells. Subsequently cells are scraped and transferred into a receptacle. After centrifugation to remove cellular pellet, a second sample is taken from the supernatant after scraping. Next, cell lysis is achieved by three consecutive freeze-thaw cycles (−80C to 37C). Cellular debris is removed and sample 3 is taken from the medium. The samples are quantified for AAV particles by DNase resistant genome titration by Taqman.™ PCR. The total production yield from such a transfection is equal to the particle concentration from sample 3.

AAV particle titers are measured according to genome copy number (genome particles per milliliter). Genome particle concentrations are based on Taqman.® PCR of the vector DNA as previously reported (Clark et al. (1999) Hum. Gene Ther., 10:1031-1039; Veldwijk et al. (2002) Mol. Ther., 6:272-278).

Example 2. Tissue Specific Expression

To evaluate the expression of various encoded payloads in tissues, a series of AAV particles carrying the encoded sequences driven by a panel of ubiquitous and tissue-specific promoters are made. These particles are administered to the specific tissue, e.g., systemically, via an appropriate route, e.g., a single intravenous injection and expression is monitored to determine the relative expression potential of the payload as well as of each promoter in this target tissue. Measurement of payload production is performed using standard techniques, for example by ELISA.

In some cases, the cytomegalovirus immediate early promoter (CMV), chimeric chicken-beta-actin (CAG), and ubiquitin C (UBC), CBA, H1, αMHC, cTnT, and CMV-MLC2k promoters provide robust expression.

Example 3. In Vivo Mouse Biodistribution and Expression Levels Following Intravenous Treatment with VOY101-GFP Vector An adeno-associated capsid variant (VOY101) was engineered for widespread gene transfer into the brain and heart. A viral genome comprising AAV2 wild-type inverted terminal repeats (ITR), a synthetic promoter composed of CMV enhancer and chicken beta-actin promoter (CBA), an enhanced green fluorescent protein variant (eGFP) and a rabbit globin polyadenylation sequence was used to generate AAV particles, having a capsid serotype of either VOY101 or AAV9, by triple transfection into HEK293T cells. The ITR to ITR sequence of the viral genome is provided as SEQ ID NO: 1799.

The single-stranded AAV particles were purified and formulated in phosphate buffered saline (PBS) with 0.001% F-68, and then administered to adult C57B1/6J mice at 6-7 weeks of age via lateral tail vein injection at ∼4 ml/kg, with a vector concentration of $5.0 \times 10^{12}$ vg/mL. The total dose was $2.0 \times 10^{13}$ VG/kg. A control group was treated with vehicle (PBS with 0.001% F-68).

Approximately 28 days following administration, several tissue samples were collected. Tissue samples allocated for GFP protein quantification or vector genome quantification were flash-frozen in liquid nitrogen. Tissue samples allocated for anti-GFP immunohistochemistry were post-fixed in 4% paraformaldehyde overnight. Analysis of the tissue samples by immuno-histochemical staining with an anti-GFP antibody and subsequent DAB substrate development showed that systemic injection with VOY101-GFP particles resulted in increased GFP levels throughout the brain and spinal cord as compared to the administered AAV9-GFP particles.

GFP protein levels were measured by ELISA and reported in ng GFP/mg of total protein and the results are shown in Table 13. Vector genome digital PCR quantification was performed using a probe set against the CMV enhancer region of the CBA promoter, normalized to host TFRC (transferrin receptor protein 1) and expressed in vector genome per diploid cell (VG/DC) and the results are shown in Tables 14 and 15. In Tables 13, 14 and 15, "BLLQ" means below lower limit of quantification.

TABLE 13

GFP Expression in Mouse after Intravenous Injection

| AAV Serotype (Protein SEQ ID NO; Nucleotide SEQ ID NO) | GFP Expression (ng GFP/mg of total protein) | | | | |
|---|---|---|---|---|---|
| | Striatum | Lumbar Spinal Cord | Lumbar Dorsal Root Ganglia | Heart | Liver |
| VOY101 (SEQ ID NO: 1; SEQ ID NO: 1800) | 30.4 ± 3.7 | 111.2 ± 18.2 | 4.2 ± 2.3 | 261.8 ± 127.8 | 428.2 ± 239.2 |
| AAV9 (SEQ ID NO: 136; SEQ ID NO: 135) | 0.5 ± 0.1 | 1.5 ± 0.4 | 14.3 ± 9.2 | 453.2 ± 138.1 | 2115.9 ± 951.0 |
| Vehicle | BLLQ | BLLQ | 0.2 ± 0.5 | BLLQ | BLLQ |

TABLE 14

Vector Genome Distribution in Mouse after Intravenous Injection

| AAV Serotype (Protein SEQ ID NO; Nucleotide SEQ ID NO) | VG Distribution (VG/DC) | | | |
|---|---|---|---|---|
| | Striatum | Cortex | Brainstem | Cerebellum cortex |
| VOY101 (SEQ ID NO: 1; SEQ ID NO: 1800) | 27.8 ± 6.2 | 31.7 ± 8.2 | 33.5 ± 7.1 | 4.0 ± 1.2 |
| AAV9 (SEQ ID NO: 136; SEQ ID NO: 135) | 0.3 ± 0.1 | 0.2 ± 0.1 | 0.5 ± 0.6 | 0.1 ± 0.1 |
| Vehicle | BLLQ | BLLQ | BLLQ | BLLQ |

TABLE 15

Vector Genome Distribution in Mouse after Intravenous Injection

| AAV Serotype (Protein SEQ ID NO; Nucleotide SEQ ID NO) | GFP Expression (ng GFP/mg of total protein) | | | | |
|---|---|---|---|---|---|
| | Dentate nucleus | Thoracic Spinal Cord | Thoracic Dorsal Root Ganglia | Heart | Liver |
| VOY101 (SEQ ID NO: 1; SEQ ID NO: 1800) | 34.0 ± 11.6 | 20.8 ± 2.4 | 2.1 ± 3.0 | 1.1 ± 0.6 | 17.7 ± 7.2 |
| AAV9 (SEQ ID NO: 136; SEQ ID NO: 135) | 0.2 ± 0.1 | 0.2 ± 0.1 | 0.1 ± 0.02 | 1.0 ± 0.2 | 95.8 ± 19.7 |
| Vehicle | BLLQ | BLLQ | BLLQ | BLLQ | BLLQ |

In mouse striatum, 28 days after intravenous injection of $2.0 \times 10^{13}$ VG/kg, VOY101-GFP resulted in GFP levels 58-fold higher and vector genome distribution 101-fold higher than AAV9-GFP. In mouse spinal cord, 28 days after intravenous injection of $2.0 \times 10^{13}$ VG/kg, VOY101-GFP resulted in GFP levels 74-fold higher and vector genome distribution 104-fold higher than AAV9-GFP. In mouse liver, 28 days after intravenous injection of $2.0 \times 10^{13}$ VG/kg, VOY101-GFP resulted in GFP levels 4.9-fold lower and vector genome distribution 5.4-fold lower than AAV9-GFP.

Example 4. Intravenous Delivery of VOY101-FXN AAV Particles

A. In Vivo Mouse Biodistribution and Expression Levels Following Intravenous Treatment with VOY101-FXN AAV Particles Widespread gene transfer into the brain and heart was also observed when using a viral genome with *Macaca fascicularis* (cynomolgus monkey) frataxin (cFXN) transgene. A viral genome comprising AAV2 wild-type ITRs, a synthetic promoter composed of CMV enhancer and chicken beta-actin promoter (CBA), *Macaca fascicularis* frataxin (cFXN) and a human growth hormone polyadenylation sequence was used to generate AAV particles, having a capsid serotype of either VOY101 or AAV9, by triple transfection into HEK293T cells. The ITR to ITR sequence of the viral genome is provided as SEQ ID NO: 1801.

The single-stranded AAV particles were purified and formulated in phosphate buffered saline (PBS) with 0.001% F-68, and then administered to adult C57B1/6J mice at 9 weeks of age via lateral tail vein injection ~4 ml/kg, with a vector concentration of $1.0 \times 10^{12}$ vg/mL. The total dose was $4.2 \times 10^{12}$ VG/kg. A control group was treated with vehicle (PBS with 0.001% F-68).

Seven days following AAV particle or vehicle administration, several tissue samples were collected. Tissue samples were flash-frozen in liquid nitrogen. Vector genome digital PCR quantification was performed using a probe set against the CMV enhancer region of the CBA promoter, normalized to host TFRC, and expressed in vector genome per diploid cell (VG/DC). cFXN protein levels were measured by ELISA and reported in ng cFXN/mg of total protein. cFXN protein levels and vector genome distribution are shown in Tables 16 and 17. In Tables 16 and 17, "BLLQ" means below lower limit of quantification.

TABLE 16 cFXN Expression in Mouse after Intravenous Injection

| AAV Serotype (Protein SEQ ID NO; Nucleotide SEQ ID NO) | cFXN Expression (ng cFXN/mg of total protein) | | | | | |
|---|---|---|---|---|---|---|
| | Cortex | Lumbar Spinal Cord | Lumbar Dorsal Root Ganglia | Heart | Liver | Trigeminal ganglion |
| VOY101 (SEQ ID NO: 1; SEQ ID NO: 1800) | 23.4 ± 13.8 | 64.1 ± 10.2 | 11.2 ± 2.4 | 17.8 ± 17.1 | 69.2 ± 51.1 | 6.0 ± 3.1 |
| AAV9 (SEQ ID NO: 136; SEQ ID NO: 135) | BLLQ | BLLQ | BLLQ | 1.9 ± 3.1 | 327.8 ± 171.5 | 0.4 ± 0.5 |
| Vehicle | BLLQ | BLLQ | BLLQ | BLLQ | BLLQ | BLLQ |

TABLE 17

Vector Genome Distribution in Mouse after Intravenous Injection

| AAV Serotype (Protein SEQ ID NO; Nucleotide SEQ ID NO) | VG Distribution (VG/DC) | | | | | |
|---|---|---|---|---|---|---|
| | Cortex | Lumbar Spinal Cord | Thoracic Dorsal Root Ganglia | Heart | Liver | Trigeminal ganglion |
| VOY101 (SEQ ID NO: 1; SEQ ID NO: 1800) | 14.85 ± 3.58 | 23.51 ± 1.96 | 6.49 ± 3.19 | 0.46 ± 0.13 | 8.74 ± 5.98 | 2.45 ± 1.27 |
| AAV9 (SEQ ID NO: 136; SEQ ID NO: 135) | 0.09 ± 0.01 | 0.07 ± 0.02 | 0.55 ± 0.40 | 0.17 ± 0.05 | 56.74 ± 30.60 | 0.04 ± 0.02 |
| Vehicle | BLLQ | BLLQ | BLLQ | BLLQ | BLLQ | BLLQ |

In mouse cortex, seven days after intravenous injection of $4.2 \times 10^{12}$ vg/kg, VOY101-cFXN resulted in 165-fold higher vector genome than AAV9-cFXN and at least 234-fold higher cFXN protein expression than AAV9-cFXN. In mouse lumbar spinal cord, seven days after intravenous injection of $4.2 \times 10^{12}$ vg/kg, VOY101-cFXN resulted in 336-fold higher vector genome and at least 640-fold higher cFXN protein expression than AAV9-cFXN.

In dorsal root ganglia, seven days after intravenous injection of $4.2 \times 10^{12}$ vg/kg, VOY101-cFXN resulted in 11.8-fold higher vector genome and 112-fold higher cFXN protein expression than AAV9-cFXN. In trigeminal ganglion, seven days after intravenous injection of $4.2 \times 10^{12}$ vg/kg, VOY101-cFXN resulted in 61-fold higher vector genome and at least 16-fold higher cFXN protein expression than AAV9-cFXN.

In heart, seven days after intravenous injection of $4.2 \times 10^{12}$ VG/Kg, VOY101-cFXN resulted in 2.7-fold higher vector genome and 9.4-fold higher cFXN protein expression than AAV9-cFXN, indicating significantly higher expression as compared to AAV9.

B. In Vivo Study in Non-Human Primate of cFXN Expression after Treatment with VOY101-FXN-HA AAV Particles A study in cynomolgus monkeys (Macaca fascicularis) was conducted to evaluate cFXN expression within the CNS after IV dosing of VOY101-cFXN-HA.

A viral genome comprising HA-tagged cynomolgus frataxin (cFXN-HA) was engineered into a single stranded expression vector. A viral genome comprising AAV2 wild-type ITRs, a synthetic promoter composed of CMV enhancer and chicken beta-actin promoter (CBA), Macaca fascicularis frataxin (cFXN) with 3' sequence for HA-tag and a human growth hormone polyadenylation sequence was used to generate AAV particles, having a capsid serotype of VOY101, by triple transfection into HEK293T cells. The ITR to ITR sequence of the viral genome is provided as SEQ ID NO: 1801.

The single-stranded AAV particles (VOY101-cFXN-HA) were purified and formulated in phosphate buffered saline (PBS) with 0.001% F-68, and then administered to non-human primate (Macaca fascicularis) via saphenous vein injection at 5 ml/kg, with a vector concentration of $1.34 \times 10^{12}$ vg/mL and a total dose of $6.7 \times 10^{12}$ VG/kg. In addition, a single-stranded AAV9 with a CBA promoter and a viral genome comprising cFXN-HA (AAV9-cFXN-HA) was tested by intravenous injection at a dose of $2 \times 10^{13}$ VG/kg.

Approximately 28 days following AAV particle administration, several tissue samples were collected. Tissue samples allocated for cFXN-HA protein quantification or vector genome quantification were snap-frozen. Tissue samples allocated for anti-HA immunohistochemistry were post-fixed in 4% paraformaldehyde for 12 to 72 hours at 2-8° C. Tissue sections (20 μm thickness) were stained with a rabbit monoclonal antibody to HA tag (1:1000 or 1:2000), followed by a goat-anti-rabbit IgG biotinylated secondary antibody (1:1000), and then developed with DAB plus nickel. cFXN-HA staining was observed in multiple CNS regions after IV dosing of VOY101-cFXN. These regions include but are not limited to, the spinal cord (cervical, thoracic and lumbar segments), brainstem nuclei, cerebellum (including cerebellar dentate nucleus), thalamus, caudate nucleus, and cerebral cortex. Homogeneous HA staining was observed along the entire rostral-caudal extent of the spinal cord, particularly in ventral horn motor neurons, after IV dosing of VOY101-cFXN-HA at $6.7 \times 10^{12}$ VG/kg. The spinal cord and especially ventral horn motor neurons were labeled to a much greater degree with VOY101-cFXN-HA than with AAV9-cFXN-HA, despite the 3-fold lower dose of VOY101-cFXN-HA. Vehicle-treated control non-human primates exhibited essentially no detectable background staining.

HA staining in the lumbar ventral horn, including motor neurons, was similar after IV VOY101-cFXN-HA ($6.7 \times 10^{12}$ VG/kg) compared with IT administration of a similar dose of a single-stranded rh10 vector and a viral genome comprising cFXN-HA (AAVrh10-FXN-HA).

Vector genome digital PCR quantification was performed using a probe set against the CMV enhancer region of the CBA promoter, normalized to host RnaseP and expressed in vector genome per diploid cell (VG/DC). cFXN-HA protein levels were measured by ELISA. cFXN-HA protein levels (in ng cFXN-HA/mg of total protein) and vector genome distribution (VG/DC) are shown in Table 18. In Table 18, "BLLQ" means below lower limit of quantification and "NA" means not analyzed.

TABLE 18 cFXN-HA Expression in NHP after Intravenous Injection

|  | NHP2001 | |
| --- | --- | --- |
| Tissue | cFXN-HA (ng/mg prot.) | VG (VG/DC) |
| Frontal Cortex | BLLQ | 0.24 |
| Striatum | BLLQ | 0.04 |
| Brainstem | 112.9 | 0.50 |
| Cerebellum | BLLQ | 0.02 |
| Cervical Spinal Cord | 49.2 | 0.14 |
| Thoracic Spinal Cord | 14.1 | 0.15 |
| Lumbar Spinal Cord | 32.4 | NA |
| Cervical Dorsal Root Ganglia | 195.4 | 0.71 |
| Thoracic Dorsal Root Ganglia | 88.2 | 1.18 |
| Lumbar/Sacral Dorsal Root Ganglia | 87.4 | 1.86 |
| Heart Ventricle | 212.4 | 9.1 |
| Heart Atrium | 358.0 | 7.23 |
| Liver | 4.48 | 224.83 |
| Kidney | BLLQ | 0.93 |
| Lung | BLLQ | 0.58 |
| Soleus | 1.1 | 0.44 |
| Jejunum | 2.0 | 1.86 |
| Spleen | BLLQ | 14.65 |

These results show that in non-human primates (NHPs) 28 days after intravenous injection of $6.7 \times 10^{12}$ VG/kg, VOY101-cFXN-HA resulted in brain transduction. Significant levels of cFXN-HA protein were detected in many CNS regions including the spinal cord (cervical, thoracic and lumbar segments) and brainstem. Significant levels of vector genomes were detected in many CNS regions including the spinal cord (cervical and thoracic segments), brainstem, and cortex, after IV dosing.

C. In Vivo Biodistribution and Expression Levels of cFXN Expression in Non-Human Primates after Treatment with PHP.B-FXN-HA AAV Particles A dose-response study in cynomolgus monkeys (*Macaca fascicularis*) was conducted to evaluate cFXN expression within the CNS after IV dosing of PHP.B-cFXN-HA.

A viral genome comprising HA-tagged cynomolgus frataxin (cFXN-HA) was engineered into a single stranded expression vector. A viral genome comprising AAV2 wild-type ITRs, a synthetic promoter composed of CMV enhancer and chicken beta-actin promoter (CBA), *Macaca fascicularis* frataxin (cFXN) with 3' sequence for HA-tag, triple repeat of a miR-122 target sequence (to reduce transgene liver expression), and a human growth hormone polyadenylation sequence was used to generate AAV particles, having a capsid serotype of PHP.B, by triple transfection into HEK293T cells. The ITR to ITR sequence of the viral genome is provided as SEQ ID NO: 1802.

The single-stranded AAV particles were purified and formulated in phosphate buffered saline (PBS) with 0.001% F-68, and then administered to non-human primate (*Macaca fascicularis*) via saphenous vein injection at 5 ml/kg, with a vector concentration of $1.54 \times 10^{11}$ to $4.75 \times 10^{12}$ vg/mL. Animals were dosed at $6.32 \times 10^{11}$, $2.0 \times 10^{12}$, or $2.0 \times 10^{13}$, VG/kg.

Approximately 28 days following AAV particle administration, several tissue samples were collected. Tissue samples allocated for cFXN-HA protein quantification or vector genome quantification were snap frozen. Tissue samples allocated for anti-HA immunohistochemistry were post-fixed in 4% paraformaldehyde for 12 to 72 hours at 2-8° C. For single labeling, tissue sections (20 μm thickness) were stained with a rabbit monoclonal antibody to HA tag (1:1000 or 1:2000), followed by a goat-anti-rabbit IgG biotinylated secondary antibody (1:1000), and then developed with DAB plus nickel. HA staining was observed in multiple CNS regions after IV dosing of PHP.B-cFXN-HA at $2 \times 10^{13}$ vg/kg. These regions include but are not limited to, the spinal cord (cervical, thoracic and lumbar segments), cerebellum (including dentate nucleus), thalamus, striatum, substantia nigra, and sensory and motor cortex. Furthermore, HA staining showed transduction of large numbers of neurons in multiple CNS regions, including those of neuronal morphology in the substantia nigra, dentate nucleus and thalamus. In addition, cells of neuronal morphology in the spinal cord, motor and sensory cortices, and striatum were HA-immunoreactive.

Double labeling for the HA tag and the neuronal marker NeuN was carried out using a chromogenic method. Tissue sections (20 μm thickness) were stained with a rabbit monoclonal antibody to HA tag (1:1000), followed by a goat-anti-rabbit IgG biotinylated secondary antibody (1:1000), and then developed with DAB (without nickel). The sections were then stained with a mouse monoclonal to NeuN second primary antibody, followed by a goat-anti-mouse IgG biotinylated secondary antibody. The NeuN signal was then detected with a green chromogen. Multiple HA+ cells were double-labeled with the neuronal marker NeuN. These results demonstrate that neurons of the cerebellar dentate nucleus were labeled for the HA tag after intravenous injection of PHP.B-cFXN-HA at $2 \times 10^{13}$ VG/kg. Therefore, after an intravenous dose of $2 \times 10^{13}$ vg/kg in cynomolgus monkeys, neurons of the cerebellar dentate nucleus are transduced and express the transgene.

Expression of the HA tag in lumbar dorsal root ganglia was present in both large (>40 um) and small sensory neurons, with the labeling increasing in a dose-dependent manner with IV injection of PHP.B-cFXN-HA at $6.32 \times 10^{11}$, $2.0 \times 10^{12}$, or $2.0 \times 10^{13}$, VG/kg.

Vector genome digital PCR quantification was performed using a probe set against the CMV enhancer region of the CBA promoter, normalized to host RnaseP and expressed in vector genome per diploid cell (VG/DC). cFXN-HA protein levels were measured by ELISA. cFXN-HA protein levels (in ng cFXN-HA/mg of total protein) and vector genome distribution (VG/DC) for the PHP.B capsid serotype are shown in Table 19. In Table 19, "BLLQ" means below lower limit of quantification and "NA" means not analyzed.

TABLE 19 cFXN-HA Expression in NHP after Intravenous Injection of PHP.B-cFXN-HA

| Tissue | $6.3 \times 10^{11}$ VG/kg NHP003 NHP004 | | $2 \times 10^{12}$ VG/kg NHP005 NHP009 | | $2 \times 10^{13}$ VG/kg NHP007 NHP008 | |
|---|---|---|---|---|---|---|
| | cFXN-HA (ng/mg prot.) | VG (VG/DC) | cFXN-HA (ng/mg prot.) | VG (VG/DC) | cFXN-HA (ng/mg prot.) | VG (VG/DC) |
| Frontal Cortex | NA | 0.03 | NA | 0.06 | NA | 0.27 |
| | NA | 0.05 | NA | 0.03 | NA | 0.54 |
| Striatum | BLLQ | BLLQ | BLLQ | BLLQ | BLLQ | 0.27 |
| | BLLQ | BLLQ | BLLQ | BLLQ | BLLQ | 0.81 |
| Brainstem | BLLQ | BLLQ | BLLQ | BLLQ | 29.4 | 0.73 |
| | BLLQ | BLLQ | BLLQ | 0.03 | BLLQ | 0.96 |
| Cerebellum | BLLQ | BLLQ | BLLQ | BLLQ | BLLQ | 0.03 |
| | 5.1 | BLLQ | BLLQ | BLLQ | 5.1 | 0.22 |
| Cervical Spinal Cord | BLLQ | BLLQ | BLLQ | BLLQ | 63.7 | 0.36 |
| | BLLQ | 0.02 | BLLQ | BLLQ | 85.0 | 0.12 |
| Thoracic Spinal Cord | BLLQ | BLLQ | BLLQ | 0.02 | 41.2 | 0.32 |
| | BLLQ | 0.06 | BLLQ | BLLQ | 44.5 | 0.32 |
| Lumbar Spinal Cord | BLLQ | 0.01 | BLLQ | 0.01 | 43.9 | 0.37 |
| | BLLQ | BLLQ | BLLQ | 0.01 | 49.2 | 0.53 |
| Cervical Dorsal Root Ganglia | BLLQ | BLLQ | 9.29 | 0.07 | 421.5 | 2.41 |
| | 2.8 | 0.03 | BLLQ | 0.06 | 509.9 | 1.87 |
| Thoracic Dorsal Root Ganglia | BLLQ | BLLQ | 6.1 | 0.05 | 227.2 | 2.92 |
| | BLLQ | 0.01 | BLLQ | 0.02 | 866.4 | 2.52 |
| Lumbar/Sacral Dorsal Root Ganglia | BLLQ | BLLQ | 4.9 | 0.04 | 122.2 | 3.68 |
| | BLLQ | 0.03 | BLLQ | 0.04 | 138.1 | 1.63 |
| Heart Ventricle | BLLQ | BLLQ | 22.9 | 0.5 | 1034.5 | 15.3 |
| | 6.0 | 0.2 | BLLQ | 0.4 | 185.6 | 7.7 |
| Heart Atrium | 7.3 | 0.03 | 60.5 | 0.97 | 650.5 | 26.3 |
| | 5.2 | 0.08 | BLLQ | 0.13 | 810.0 | 26.6 |
| Liver | BLLQ | 0.4 | BLLQ | 30.4 | BLLQ | 444.1 |
| | BLLQ | 7.9 | BLLQ | 74.8 | BLLQ | 284.4 |
| Kidney | BLLQ | BLLQ | BLLQ | 0.3 | 6.4 | 6.3 |
| | BLLQ | 0.1 | BLLQ | 0.1 | 2.8 | 2.5 |
| Lung | BLLQ | NA | BLLQ | NA | 0.9 | 3.3 |
| | BLLQ | NA | BLLQ | NA | BLLQ | 3.6 |
| Soleus | BLLQ | NA | BLLQ | NA | 69.9 | 13.4 |
| | BLLQ | NA | BLLQ | NA | 12.6 | 6.7 |
| Jejunum | BLLQ | NA | BLLQ | NA | BLLQ | 0.6 |
| | BLLQ | NA | BLLQ | NA | BLLQ | 0.3 |
| Spleen | BLLQ | 1.3 | BLLQ | 4.3 | BLLQ | 4.4 |
| | BLLQ | 1.2 | BLLQ | 4.6 | 2.1 | 2.3 |

In summary, in non-human primates (NHPs) 28 days after intravenous injection of PHP.B-cFXN-HA, all three dose levels resulted in brain transduction. Significant levels of cFXN-HA protein were detected in many CNS regions including the spinal cord (cervical, thoracic and lumbar segments), brainstem, and cerebellum. Significant levels of vector genome were detected in many CNS regions including the spinal cord (cervical, thoracic and lumbar segments), striatum, brainstem, cerebellum and frontal cortex after IV dosing. Substantial gene transfer to the NHP CNS was observed, including regions such as spinal cord, brain stem, sensory cortex, motor cortex, cerebellum, thalamus, and substantia nigra, with cells of neuronal morphology in these regions exhibiting transgene expression. In addition, the dorsal root ganglia and the heart showed dose-dependent transgene expression, with sensory neurons of the dorsal root ganglia exhibiting transduction.

D. In Vivo Dose Dependent Study in Non-Human Primate of cFXN Expression after Treatment with VOY101-FXN-HA AAV Particles A study in cynomolgus monkeys (*Macaca fascicularis*) was conducted to evaluate cFXN expression within the CNS after two different IV dose levels of single stranded VOY101-cFXN-HA.

A viral genome comprising HA-tagged cynomolgus frataxin (cFXN-HA) was engineered into a single stranded expression vector. A viral genome comprising AAV2 wild-type ITRs, a synthetic promoter composed of CMV enhancer and chicken beta-actin promoter (CBA), *Macaca fascicularis* frataxin (cFXN) with 3' sequence for HA-tag and a human growth hormone polyadenylation sequence was used to generate AAV particles, having a capsid serotype of VOY101. The ITR to ITR sequence of the viral genome is provided as SEQ ID NO: 1801.

The single-stranded AAV particles were purified and formulated in phosphate buffered saline (PBS) with 0.001% F-68, and then administered to non-human primate (*Macaca fascicularis*) via saphenous vein injection at 5 ml/kg, with a total dose of $6.7 \times 10^{12}$ VG/kg or $4.9 \times 10^{13}$ VG/kg VOY101-cFXN-HA. A vehicle negative control group was also evaluated.

Approximately 28 days following AAV particle administration, several tissue samples were collected. Tissue samples allocated for cFXN-HA protein quantification or vector genome quantification were snap-frozen. Tissue samples allocated for anti-HA immunohistochemistry were post-fixed in 4% paraformaldehyde for 12 to 72 hours at 2-8° C. Tissue sections (20 μm thickness) were stained with a rabbit monoclonal antibody to HA tag (1:1000 or 1:2000), followed by a goat-anti-rabbit IgG biotinylated secondary antibody (1:1000), and then developed with DAB plus nickel.

Vector genome digital PCR quantification was performed using a probe set against the CMV enhancer region of the CBA promoter, normalized to host TFRC, and expressed in vector genome per cell (VG/Cell). Vector genome distribution (mean±standard deviation) is shown in Table 20 for VOY101-cFXN-HA. In Table 20, SC-C is the cervical spinal cord and SC-L is the lumbar spinal cord.

TABLE 20

Vector Genome Distribution in NHP after Intravenous Injection of VOY101-cFXN-HA

| | | VG Distribution (VG/Cell) | | | |
|---|---|---|---|---|---|
| Dose | N | SC-C | SC-L | Brainstem | Motor Cortex |
| $6.7 \times 10^{12}$ VG/kg | 3 | 0.14 ± 0.14 | 0.17 ± 0.12 | 0.11 ± 0.09 | 0.14 ± 0.13 |
| $4.9 \times 10^{13}$ VG/kg | 3 | 1.44 ± 0.37 | 1.15 ± 0.44 | 1.32 ± 0.9 | 1.87 ± 0.41 |

Homogeneous HA staining was observed along the entire rostral-caudal extent of the spinal cord, particularly in ventral horn motor neurons after IV dosing of VOY101-cFXN-HA. HA staining in the cervical (C5), thoracic (T12) and lumbar (L4) spinal cord of animals receiving a dose of $4.9 \times 10^{13}$ VG/kg of VOY101-cFXN-HA revealed robust HA staining at all rostral-caudal levels of the spinal cord, particularly in ventral horn motor neurons (FIG. 5). Numerous HA+ cells were observed in animals receiving a dose of $4.9 \times 10^{13}$ VG/kg of VOY101-cFXN-HA including those of neuronal morphology in the motor cortex, the brainstem including the olivary nucleus, hippocampus, the substantia nigra and lateral geniculate nucleus, and the deep cerebellar nuclei including the dentate nucleus. Vehicle-treated control exhibited essentially no detectable or very low background staining.

Example 5. VOY101-FXN for the Treatment of Friedreich's Ataxia

A. In Vivo Distribution, Expression and Efficacy Study with Intravenous Dosing of VOY101-FXN in a Mouse Model of Friedreich's Ataxia Selected viral genomes comprising a nucleic acid encoding human frataxin are designed and packaged into a single stranded VOY101 capsid.

The viral genome from ITR to ITR, recited 5' to 3', comprises a wild type ITR, a promoter (which includes a CMVie enhancer, a CBA, or a CMV, or a frataxin promoter, or a truncated CBA or a truncated CMV promoter, and a human beta globin intron), hFXN cDNA sequence, a human growth hormone polyA sequence, a fragment of human albumin as a stuffer sequence, and wild type ITR. The viral genomes are packaged into VOY101 capsids, purified and formulated in phosphate buffered saline (PBS) with 0.001% F-68.

Six groups of approximately 10 mice/group, at 7 weeks of age, and balanced for gender and litter, receive vehicle (PBS with 0.001% F-68; two groups), or VOY101-FXN vector at either low (2 groups) or high dose (2 groups) levels (approximately $6.3 \times 10^{12}$ vg/kg–$2 \times 10^{13}$ vg/kg body weight) via intravenous injection.

To test the efficacy, distribution and expression of VOY101-FXN in mice, any test known in the art may be utilized. Non-limiting examples include limb electromyography, notched bar walking test, string hanging test, rotarod test, body weight, and/or survival. Other readouts include FXN protein and mRNA expression in tissues (e.g. dorsal root ganglia, heart, cerebellum, spinal cord) by ELISA, PCR, immunohistochemistry and in situ hybridization, and in situ assessment of mitochondrial enzyme function in tissue (dorsal root ganglia) sections. Vector genome levels in different tissues are determined by PCR and ISH.

Three groups of animals (vehicle, low dose, high dose) are euthanized by 18 weeks. Three remaining groups of animals (vehicle, low dose, high dose) are maintained for 6 months or longer to assess effect on survival. Control groups (n=10/group) include wild type mice and disease model mice dosed with a reference vector.

The distribution and expression of human frataxin (hFXN) and vector genome distribution in target tissues such as, but not limited to, DRGs, cerebellum, spinal cord and heart in animals receiving the hFXN vector, is measured by ELISA, PCR, ISH, IHC for hFXN expression and PCR and ISH for vector genome analysis. Human frataxin analysis (by ELISA, PCR, ISH, IHC) demonstrate that upon the delivery of the hFXN vector, expression in target tissues e.g., DRGs, cerebellum, spinal cord and heart occurs with distribution to target tissues. In situ assessment of mitochondrial enzyme activity shows that upon delivery of the hFXN vector, increased activity in slices of DRG occurs. Electromyography, notched bar, string hanging and rotarod tests demonstrate improved performance over vehicle control animals.

B. In Vivo Distribution and Expression Study with Intravenous Dosing of VOY101-FXN in Non-Human Primates mSelected viral genomes comprising a nucleic acid sequence encoding human frataxin are designed and packaged in a single stranded (ss) VOY101 capsid.

The single stranded viral genome from ITR to ITR, recited 5' to 3', comprises a wild type ITR, a prooter (which includes a CMVie enhancer, a CBA, or a CMV, or a frataxin promoter, or a truncated CBA or a truncated CMV promoter, and a human beta globin intron), hFXN cDNA sequence, a human growth hormone polyA sequence, a fragment of human albumin as a stuffer sequence, and wild type ITR. The viral genomes are packaged into VOY101 capsids, purified and formulated in phosphate buffered saline (PBS) with 0.001% F-68.

Eight groups of approximately 3 cynomolgus monkeys/group, approximately 3 years of age or older, with at least one animal of each gender per group, receive vehicle (PBS with 0.001% F-68; two groups), or VOY101-FXN vector at either low (2 groups) or high dose (2 groups) levels (approximately $6.7 \times 10^{12}$ vg/kg–$6 \times 10^{13}$ vg/kg body weight) via intravenous injection.

To test the efficacy, distribution and expression of VOY101-FXN in NHP, any test known in the art may be utilized. Non-limiting examples include measurement of body weight over time, clinical monitoring, histopathology and blood safety panel testing. Other readouts include FXN protein and mRNA expression in tissues (e.g. dorsal root ganglia, heart, cerebellum, spinal cord) as assessed by ELISA, PCR, immunohistochemistry and in situ hybridization. Vector genome levels in different tissues are determined by PCR and ISH.

Three groups of animals (vehicle, low dose, high dose) are euthanized by 4 weeks. Three remaining groups of animals (vehicle, low dose, high dose) are maintained for 12 weeks to assess long term gene expression.

The distribution and expression of human frataxin (hFXN) and vector genome distribution in target tissues such as, but not limited to, DRGs, cerebellum, spinal cord and heart in animals receiving the hFXN vector, are measured by ELISA, PCR, ISH, IHC for hFXN expression and PCR and ISH for vector genome analysis. The primate frataxin expression data are compared to the frataxin expression level which resulted in rescue of the FA disease phenotype in a genetic mouse model of Friedreich's Ataxia. Based on these results, efficacious doses for human trials are calculated.

Example 6. VOY101-APOE miRNA for the Treatment of Alzheimer's Disease

A. In Vivo Distribution, Expression, and Efficacy Study of Intravenous Dosing of scVOY101-APOE miRNA in Mouse Model of Alzheimer's Disease Selected viral genomes comprising pri-miRNA cassettes containing guide strands targeting APOE and passenger strands are engineered into self-complementary (sc) VOY101-miRNA expression vectors.

The scAAV-miRNA viral genome from ITR to ITR, recited 5' to 3', comprises a wild type ITR, a promoter, the pri-miRNA cassette containing a guide sequence targeting ApoE and a passenger sequence, a polyA sequence, a stuffer sequence, and a wild type ITR.

The viral genomes are packaged into VOY101 capsids, purified and formulated in phosphate buffered saline (PBS) with 0.001% F-68.

Three groups of P301S mutant tau mice, approximately 20 mice/group, at 2 months of age, are administered vehicle (PBS with 0.001% F-68), or VOY101-APOE miRNA at either high or low dose levels (approximately $4 \times 10^{12}$ vg/kg–$4 \times 10^{13}$ vg/kg) via intravenous tail vein injection.

Any test known in the art may be utilized to test the efficacy, distribution and expression of VOY101-APOE miRNA in mice. Non-limiting examples include the measurement of body weight, expression of APOE mRNA as measured by qRT-PCR, expression of APOE protein as assessed by immunohistochemistry and enzyme-linked immunosorbent assay, levels of amyloid-beta pathology as assessed by immunohistochemistry and enzyme-linked immunosorbent assay, levels of neurodegeneration as assessed by immunohistochemistry, and vector genome levels as measured by digital droplet PCR.

All animals are evaluated for body weight and survival. Animals are euthanized at approximately 11 months of age for evaluation of brain, spinal cord, and liver samples for APOE mRNA expression, tau and/or amyloid pathology, and neurodegeneration.

PCR data will demonstrate the delivery of vector genome throughout the brain in animals receiving intravenous VOY101-APOE miRNA vector. Expression data should indicate widespread reduction of APOE protein and mRNA throughout the brain in animals receiving vector. Brain regions demonstrating significant APOE reduction should be those important for tauopathy related disease, including the entorhinal cortex, hippocampus, and cortex. Groups receiving the vector would likely show strong reductions in pathological amyloid-beta and neurodegeneration.

B. In Vivo Distribution and Expression Study of APOE in Non-Human Primates Following Intravenous Dosing of scVOY101-APOE miRNA Selected viral genomes comprising pri-miRNA cassettes containing guide strands targeting APOE and passenger strands are engineered into self-complementary (sc) VOY101-miRNA expression vectors.

The scAAV-miRNA viral genome from ITR to ITR, recited 5' to 3', comprises a wild type ITR, a promoter, the pri-miRNA cassette containing a guide sequence targeting ApoE and a passenger sequence, a polyA sequence, a stuffer sequence, and a wild type ITR.

The viral genomes are packaged into VOY101 capsid, purified and formulated in phosphate buffered saline (PBS) with 0.001% F-68.

Non-human primates (NHPs) (Cynomolgus macaques, adult male, prescreened for AAV neutralizing antibodies) in three groups are administered scVOY101-ApoE miRNA vector with one group a vehicle only control. The NHPs are administered either high or low dose levels (approximately $4 \times 10^{12}$ vg/kg–$4 \times 10^{13}$ vg/kg) using intravenous delivery. 4 weeks post-administration, a saline perfusion is performed and the brain sectioned into 3 mm coronal blocks and snap-frozen.

To test the efficacy, distribution and expression of VOY101-APOE miRNA in NHP, any test known in the art may be utilized. Non-limiting examples include measurement of expression of APOE mRNA by qRT-PCR, expression of tau protein as assessed by immunohistochemistry and enzyme-linked immunosorbent assay, and vector genome levels as assessed by digital droplet PCR.

Brain regions demonstrating significant APOE reduction would be expected to cover areas important for tauopathy related disease, including the entorhinal cortex, hippocampus, and cortex. Consistent with the expression data, PCR would likely demonstrate widespread distribution of vector genome through the brain.

Example 7. VOY101-APOE2 for the Treatment of Alzheimer Disease and Other Tauopathies A. In Vivo Distribution, Expression, and Efficacy Study of Intravenous Dosing of VOY101-APOE2 in Mouse Model of Alzheimer's Disease and Other Tauopathies A nucleic acid encoding human APOE2 (apolipoprotein E2 allele) is engineered into an AAV viral genome and packaged in the VOY101 capsid.

The AAV-APOE2 viral genome, recited 5' to 3' from ITR to ITR, comprises a wild type ITR, a promoter, the nucleic acid encoding human APOE2, a polyA sequence, and a wild type ITR. The viral genomes are packaged into VOY101 capsids, purified and formulated. The VOY101-APOE2 particles are formulated in phosphate buffered saline (PBS) with 0.001% F-68.

Three groups of APP.PS1-21/TRE4 mice, approximately 20 mice/group, at 9 months of age, are administered vehicle (PBS with 0.001% F-68), or VOY101-APOE2 at either high or low dose levels (approximately $4 \times 10^{12}$ vg/kg–$4 \times 10^{13}$ vg/kg) via intravenous tail vein injection.

To test the efficacy, distribution and expression of VOY101-APOE2 in mice, any test known in the art may be utilized. Non-limiting examples include measurements of body weight, expression of APOE2 as assessed by immunohistochemistry and enzyme-linked immunosorbent assay, levels of amyloid-beta pathology as assessed by immunohistochemistry and enzyme-linked immunosorbent assay, levels of neurodegeneration as assessed by immunohistochemistry, and vector genome levels as measured by digital droplet PCR.

All animals are evaluated for body weight and survival. Animals are euthanized at approximately 11 months of age for evaluation of brain, spinal cord, and liver samples for APOE2 expression, amyloid and/or tau pathology, and neurodegeneration.

Distribution of the vector genome through the brain in animals receiving intravenous VOY101-APOE2 is analyzed by PCR. Expression data will likely show widespread expression of APOE2 throughout the brain in animals receiving VOY101-APOE2 vector. Brain regions demonstrating significant APOE2 expression would likely cover areas important for tauopathy related disease, including the entorhinal cortex, hippocampus, and cortex. Groups receiving VOY101-APOE2 vector should show strong reductions in pathological amyloid-beta and/or tau and neurodegeneration.

B. In Vivo Distribution and Expression Study of Intravenous Dosing of VOY101-APOE2 in Non-Human Primates A nucleic acid sequence encoding human APOE2 (apolipoprotein E 2 allele) is engineered into an AAV viral genome and packaged in the VOY101 capsid.

The AAV-APOE2 viral genome, recited 5' to 3' from ITR to ITR, comprises a wild type ITR, a promoter, the nucleic acid encoding human APOE2, a polyA sequence, and a wild type ITR. The viral genomes are packaged into VOY101 capsids, purified and formulated. The VOY101-APOE2 particles are formulated in phosphate buffered saline (PBS) with 0.001% F-68.

Non-human primates (NHPs) (Cynomolgus macaques, adult male, prescreened for AAV neutralizing antibodies) in three groups are administered, by intravenous injection, the VOY101-APOE2 vector with one group a vehicle only control (PBS with 0.001% F-68). The NHPs are administered either high or low dose levels (approximately $4 \times 10^{12}$ vg/kg–$4 \times 10^{13}$ vg/kg) using intravenous delivery. 4 weeks post-administration, a saline perfusion is performed and the brain sectioned into 3 mm coronal blocks and snap-frozen.

Any test known in the art may be utilized to test the efficacy, distribution and expression of VOY101-APOE2 in NHP. Non-limiting examples include measurement of expression of APOE2 as assessed by immunohistochemistry and enzyme-linked immunosorbent assay and vector genome levels as assessed by digital droplet PCR.

Expression data will likely show widespread expression of APOE2 throughout the brain in animals receiving VOY101-APOE2 vector. Brain regions demonstrating significant APOE2 levels would likely cover areas important for tauopathy related disease, including the entorhinal cortex, hippocampus, and cortex. Consistent with the expression data, PCR would likely demonstrate widespread distribution of vector genome through the brain.

Example 8. VOY101-HTT miRNA for the Treatment of Huntington's Disease

A. In Vivo Efficacy Study of VOY101-miRNA in Mouse Model of Huntington's Disease Selected pri-miRNA cassettes containing guide strands targeting HTT and passenger strands are engineered into scAAV-miRNA viral genomes and packaged into VOY101 capsid.

The viral genome from ITR to ITR, recited 5' to 3', comprises a wild type ITR, a CBA promoter (which includes a CMVie enhancer, a CBA promoter and an SV40 intron), the pri-miRNA cassette containing a guide sequence targeting HTT and a passenger sequence, a rabbit globin polyA sequence, a fragment of human alpha-1 antitrypsin as a stuffer sequence, and a wild type ITR. The viral genomes are packaged into VOY101 capsids, purified and formulated. The VOY101-HTT miRNA particles are formulated in phosphate buffered saline (PBS) with 0.001% F-68.

Bilateral intrastriatal dosing will be used. Three groups of approximately 12 mice/group, approximately 2 months of age and balanced for sex, will receive vehicle (PBS and 0.001% F-68), or VOY101-HTT miRNA vector at either high or low dose levels (approximately $3 \times 10^9$ vg–$5 \times 10^{10}$ vg per striatum).

To test the efficacy of VOY101-HTT miRNA in mice, any test known in the art may be utilized. Non-limiting examples include measurement of body weight, rotarod, Porsolt swim test, as well as measurement of HTT protein aggregates as assessed by immunohistochemistry.

All animals will be evaluated for body weight, rotarod, Porsolt swim test and survival. Some animals will be euthanized at 5 months of age (3 months after dosing) for evaluation of striatum tissue samples for HTT mRNA suppression (by RT-qPCR) and HTT protein level by western blot or MSD assay, whereas others will be euthanized at approximately 8 months of age (6 months after dosing) for evaluation of aggregates (by immunohistochemistry).

HTT measurement data should show widespread reduction of human HTT protein and mRNA throughout the brain in animals receiving HTT miRNA vectors including in primary target areas (striatum and cortex). Groups receiving HTT miRNA vectors would also show reductions in pathological HTT aggregates, and demonstrate significant improvements in lifespan and motor activities.

B. In Vivo Pharmacology and Distribution Study in Non-Human Primates Following Intravenous Dosing of scVOY101-HTT miRNA Selected pri-miRNA cassettes containing guide strands targeting HTT and passenger strands are engineered into scAAV-miRNA viral genomes and packaged into VOY101 capsid.

The scAAV-miRNA viral genome from ITR to ITR, recited 5' to 3', comprises a wild type ITR, a promoter, the pri-miRNA cassette containing a guide sequence targeting HTT and a passenger sequence, a polyA sequence, a stuffer sequence, and a wild type ITR. The viral genomes are packaged into VOY101 capsids, purified and formulated. The VOY101-HTT miRNA particles are formulated in phosphate buffered saline (PBS) with 0.001% F-68.

Non-human primates (NHPs) (rhesus macaque, adult male, prescreened for AAV neutralizing antibodies) in three groups are administered scVOY101-HTT miRNA particles. The NHPs are administered either high, middle or low dose levels (approximately $5 \times 10^{12}$ vg/kg, $1.5 \times 10^{13}$ vg/kg and $4.5 \times 10^{13}$ vg/kg) using intravenous or intracarotid arterial delivery. 4 weeks post-administration, a saline perfusion is performed and part of the spinal cord, brain sections and selected peripheral tissues will be harvested. A subset of tissue will be snap-frozen in liquid nitrogen and a subset will be post-fixed in 4% PFA.

To test the efficacy of VOY101-HTT miRNA in NHP, any test known in the art may be utilized. Non-limiting examples include measurement of expression of HTT mRNA as measured by bDNA assay and/or qRT-PCR, expression of HTT protein as assessed by western blot and by immunohistochemistry, and vector genome levels as assessed by digital droplet PCR. In addition, clinical observation, serum and CSF clinical pathology, CSF biomarkers and histopathology of CNS and peripheral tissues will be analyzed.

Example 9. VOY101-SOD1 miRNA for Treatment of Amyotrophic Lateral Sclerosis

A. In Vivo Pharmacology Study of VOY101-SOD1 miRNA in a Mouse Model of ALS

Selected pri-miRNA cassettes containing guide strands targeting SOD1 and passenger strands are engineered into scAAV-miRNA viral genomes and packaged into a VOY101 capsid.

The viral genome from ITR to ITR, recited 5' to 3', comprises a wild type ITR, a H1 promoter, the pri-miRNA cassette containing a guide sequence targeting SOD1 and a passenger sequence, a rabbit globin polyA sequence, and a wild type ITR. The viral genomes are packaged into VOY101 capsids, purified, and formulated. The VOY101-SOD1 miRNA particles are formulated in phosphate buffered saline (PBS) with 0.001% F-68.

Three groups of approximately 10 mice/group, approximately 40-50 days of age and balanced for sex, age and littermates, will receive vehicle (PBS with 0.001% F-68), or VOY101-SOD1 miRNA vector at either high or low dose levels (approximately $5\times10^{11}$ vg/mouse or $2\times10^{12}$ vg/mouse). All the animals will be dosed intravenously. All the animals will be euthanized at approximately 4 weeks after intravenous administration.

Analytical methods known in the art may be used to assess pharmacological profile, primary readouts will include hSOD1 mRNA and protein expression and vector genome biodistribution in multiple CNS regions and selected peripheral tissues. Secondary readouts will include body weights, immunohistochemistry and cage side observations.

B. In Vivo Efficacy Study of VOY101-SOD1 miRNA in a Mouse Model of ALS

Selected pri-miRNA cassettes containing guide strands targeting SOD1 and passenger strands are engineered into scAAV-miRNA viral genomes and packaged into a VOY101 capsid.

The scAAV-miRNA viral genome from ITR to ITR, recited 5' to 3', comprises a wild type ITR, a H1 promoter, the pri-miRNA cassette containing a guide sequence targeting SOD1 and a passenger sequence, a rabbit globin polyA, and a wild type ITR. The viral genomes are packaged into VOY101 capsids, purified and formulated. The VOY101-SOD1 miRNA particles are formulated in phosphate buffered saline (PBS) with 0.001% F-68.

Three groups of approximately 36 mice/group, approximately 40-50 days of age and balanced for sex, age and littermates, will receive vehicle, or the vector at either high or low dose levels (approximately $5\times10^{11}$ vg/mouse or $2\times10^{12}$ vg/mouse). All the animals will be dosed intravenously.

To assess efficacy of VOY101-SOD1 miRNA in mice, analytical methods known in the art may be used to obtain primary readouts and may include body weight, behavioral NeuroScore, survival and disease onset and duration. Neurological score will be measured daily. Animals will be euthanized when the NeuroScore for that animal reaches 4. Secondary readouts include hSOD1 mRNA/protein expression, vector genome biodistribution and IHC (skeletal muscle and NMJ imaging, spinal cord).

The data demonstrate that upon delivery of the intravenous VOY101-SOD1 miRNA vector to the motor neurons, brainstem and motor cortex widespread reduction of SOD1 protein and mRNA occurs.

C. In Vivo Efficacy Study of VOY101-SOD1 miRNA in Canine Degenerative Myelopathy as a Disease Model for ALS Selected pri-miRNA cassettes containing guide strands targeting SOD1 and passenger strands are engineered into scAAV-miRNA viral genomes designed and packaged in a VOY101 capsid.

The scAAV-miRNA viral genome from ITR to ITR, recited 5' to 3', comprises a wild type ITR, a H1 promoter, the pri-miRNA cassette containing a guide sequence targeting SOD1 and a passenger sequence, a rabbit globin polyA sequence, a stuffer sequence, and a wild type ITR. The viral genomes are packaged into VOY101 capsids, purified, and formulated. The VOY101-SOD1 miRNA particles are formulated in phosphate buffered saline (PBS) with 0.001% F-68.

Companion DM dogs will be screened for pre-existing immunity to the VOY101 capsid by evaluating serum samples in an in vitro neutralizing antibody assay. Dogs with negative nAb will be candidates for the study. Dogs will be divided into two treatment groups and administered either VOY101-SOD1 miRNA or vehicle (PBS with 0.001% F-68) using intravenous dosing.

To assess efficacy of VOY101-SOD1 miRNA in dog, any test known in the art may be utilized. Non-limiting examples include longitudinal monitoring of gait and neurologic outcome, DTI and MRS, electrodiagnostic testing, MUNE and electrical Impedance Myography (EIM) at the specified time points.

Serum and CSF samples will be collected at designated times and at the time of euthanasia for evaluating pNF-H and NFL level in dogs. At the time of euthanasia, CNS and peripheral tissues will be collected for SOD1 mRNA quantification and vector genome biodistribution analysis.

The data demonstrate that upon delivery of the intravenous VOY101-SOD1 miRNA vector to the motor neurons, brainstem and motor cortex reduction of SOD1 protein and mRNA occurs.

D. In Vivo Pharmacology and Distribution Study in Non-Human Primates Following Intravenous Dosing of scVOY101-SOD1 miRNA Selected pri-miRNA cassettes containing guide strands targeting SOD1 and passenger strands are engineered into scAAV-miRNA viral genomes and packaged into a VOY101 capsid.

The scAAV-miRNA viral genomes from ITR to ITR, recited 5' to 3', comprise a wild type ITR, a promoter, the pri-miRNA cassette containing a guide sequence targeting SOD1 and a passenger sequence, a polyA sequence, a stuffer sequence, and wild type ITR. The viral genomes are packaged into VOY101 capsids, purified, and formulated. The VOY101-SOD1 miRNA particles are formulated in phosphate buffered saline (PBS) with 0.001% F-68.

Non-human primates (NHPs) (Cynomolgus macaques, adult male, prescreened for AAV neutralizing antibodies) in three groups are administered sc VOY101-SOD1 miRNA vector. The NHPs are administered either high, middle or low dose levels (approximately $5\times10^{12}$ vg/kg, $1.5\times10^{13}$ vg/kg and $4.5\times10^{13}$ vg/kg) using intravenous delivery. 4 weeks post-administration, a saline perfusion is performed and part of the spinal cord, brain sections and selected peripheral tissues will be harvested. A subset of the collected tissues will be snap-frozen in liquid nitrogen and another subset will be post-fixed in 4% PFA.

To determine efficacy and distribution in NHP, any test known in the art may be utilized. Non-limiting examples include measurement of expression of SOD1 mRNA by qRT-PCR, expression of SOD1 protein as assessed by WB and by immunohistochemistry, and vector genome levels as assessed by digital droplet PCR. In addition, clinical observation, serum and CSF clinical pathology, CSF biomarkers and histopathology of CNS and peripheral tissues will be analyzed.

The data demonstrate that upon intravenous delivery of the VOY101-SOD1 miRNA vector to the spinal cord motor neurons, brainstem and motor cortex, reduction of SOD1 protein and mRNA occurs.

Example 10. Anti-Tau Antibody Delivery for the Treatment of Alzheimer's Disease and Other Tauopathies A. In Vivo Distribution, Expression and Efficacy Study of Intravenous Dosing of VOY101-Anti-Tau Antibody in a Mouse Model of Alzheimer's Disease and Other Tauopathies A nucleic acid encoding a monoclonal antibody targeting tau is engineered into an AAV viral genome and produced in the VOY101 capsid.

The viral genome, recited 5' to 3' from ITR to ITR, comprises a wild type ITR, a promoter, the nucleic acid encoding a monoclonal antibody targeting tau, a polyA sequence, and a wild type ITR. The viral genomes are packaged into VOY101 capsids, purified and formulated. The VOY101-anti Tau antibody particles are formulated in phosphate buffered saline (PBS) with 0.001% F-68.

Three groups of P301S mice, approximately 20 mice/group, at 2 months of age, are administered vehicle (PBS with 0.001% F-68), or VOY101-anti Tau antibody vector at either high or low dose levels (approximately $4\times10^{12}$ vg/kg–$4\times10^{13}$ vg/kg) via intravenous tail vein injection.

To test the efficacy, distribution and expression of VOY101-anti Tau antibody in mice, any test known in the art may be utilized. Non-limiting examples include measurement of body weight, rotarod, expression of anti-Tau antibody as assessed by immunohistochemistry and enzyme-linked immunosorbent assay, levels of pathogenic tau as assessed by immunohistochemistry and enzyme-linked immunosorbent assay, levels of neurodegeneration as assessed by immunohistochemistry, and vector genome levels as measured by digital droplet PCR. All animals are evaluated for body weight and survival Animals are euthanized at approximately 5 months of age for evaluation of brain, spinal cord, and liver samples for antibody expression, tau pathology, and neurodegeneration.

In the case that VOY101-anti Tau antibody delivery for the treatment of Alzheimer Disease and tauopathy is successful, one might anticipate PCR data to demonstrate delivery of vector genome throughout the brain in animals receiving intravenous VOY101-anti-Tau antibody vector. Expression data will also likely show widespread expression of anti-Tau antibody throughout the brain in animals receiving vector, at levels equal to or exceeding that following passive immunization. Brain regions expected to demonstrate significant antibody levels include areas important for tauopathy related disease, including the entorhinal cortex, hippocampus, and cortex. Groups receiving VOY101-anti Tau antibody vector are expected to show strong reductions in pathological tau and neurodegeneration, and demonstrate significant improvements in lifespan and rotarod performance.

B. In Vivo Distribution and Expression Study of Intravenous Dosing of VOY101-Anti-Tau Antibody in Non-Human Primates A nucleic acid encoding a monoclonal antibody targeting tau is engineered into an AAV viral genome and produced in the VOY101 capsid.

The viral genome, recited 5' to 3' from ITR to ITR, comprises a wild type ITR, a promoter, the nucleic acid encoding a monoclonal antibody targeting tau, a polyA sequence, and a wild type ITR. The viral genomes are packaged into VOY101 capsids, purified and formulated. The VOY101-anti Tau particles are formulated in phosphate buffered saline (PBS) with 0.001% F-68.

Non-human primates (NHPs) (Cynomolgus macaques, adult male, prescreened for AAV neutralizing antibodies) in three groups are administered the VOY101-anti-Tau vector with one group a vehicle only control (PBS with 0.001% F-68). The NHPs are administered either high or low dose levels (approximately $4\times10^{12}$ vg/kg–$4\times10^{13}$ vg/kg) using intravenous delivery. 4 weeks post-administration, a saline perfusion is performed and the brain sectioned into 3 mm coronal blocks and snap-frozen.

To test the efficacy, distribution and expression of VOY101-anti Tau antibody in NHP, any test known in the art may be utilized. Non-limiting examples include measurement of expression of anti-Tau antibody as assessed by immunohistochemistry and enzyme-linked immunosorbent assay and vector genome levels as assessed by digital droplet PCR.

One might anticipate expression data to show that anti-Tau antibody is expressed widely in the NHP brain at levels exceeding that following passive immunization. Brain regions expected to demonstrate significant antibody levels include areas important for tauopathy related disease, including the entorhinal cortex, hippocampus, and cortex. Consistent with the expression data, PCR would likely demonstrate widespread distribution of vector genome through the brain.

Example 11. VOY101-Tau miRNA for Treatment of Tauopathy

A. In Vivo Distribution, Expression, and Efficacy Study of Intravenous Dosing of scVOY101-Tau miRNA in a Mouse Model of Tauopathy Selected pri-miRNA cassettes containing guide strands targeting Tau and passenger strands are engineered into scAAV-miRNA viral genomes and packaged into a VOY101 capsid.

The scAAV-miRNA viral genome from ITR to ITR, recited 5' to 3', comprises a wild type ITR, a promoter, the pri-miRNA cassette containing a guide sequence targeting Tau and a passenger sequence, a polyA sequence, a stuffer sequence, and a wild type ITR. The viral genomes are packaged into VOY101 capsids, purified and formulated.

The VOY101-Tau miRNA particles are formulated in phosphate buffered saline (PBS) with 0.001% F-68.

Three groups of P301S mice, approximately 20 mice/group, at 2 months of age, are administered vehicle (PBS with 0.001% F-68), or VOY101-Tau miRNA vector at either high or low dose levels (approximately $4 \times 10^{12}$ vg/kg–$4 \times 10^{13}$ vg/kg) via intravenous tail vein injection.

To test the efficacy, distribution and expression of VOY101-Tau miRNA in mice, any test known in the art may be utilized. Non-limiting examples include measurement of body weight, rotarod, expression of tau mRNA as measured by qRT-PCR, expression of total human tau as assessed by immunohistochemistry and enzyme-linked immunosorbent assay, levels of pathogenic tau as assessed by immunohistochemistry and enzyme-linked immunosorbent assay, levels of neurodegeneration as assessed by immunohistochemistry, and vector genome levels as measured by digital droplet PCR.

All animals are evaluated for body weight and survival. Animals are euthanized at approximately 5 months of age for evaluation of brain, spinal cord, and liver samples for Tau mRNA expression, tau pathology, and neurodegeneration.

In the case that VOY101-Tau miRNA delivery for the treatment of tauopathy is successful, one might anticipate PCR data to demonstrate delivery of vector genome throughout the brain in animals receiving intravenous VOY101-Tau miRNA vector. Expression data would also be expected to show widespread reduction of human tau protein and mRNA throughout the brain in animals receiving VOY101-Tau miRNA vector. Brain regions likely to demonstrate significant tau reduction include areas important for tauopathy related disease, including the entorhinal cortex, hippocampus, and cortex. Groups receiving VOY101-Tau miRNA vector would likely show strong reductions in pathological tau and neurodegeneration, and demonstrate significant improvements in lifespan and rotarod performance.

B. In Vivo Distribution and Expression Study of Tau in Non-Human Primates Following Intravenous Dosing of scVOY101-Tau miRNA Selected pri-miRNA cassettes containing guide strands targeting Tau and passenger strands are engineered into scAAV-miRNA viral genomes and packaged into a VOY101 capsid.

The viral genome from ITR to ITR, recited 5' to 3', comprises a wild type ITR, a promoter, the pri-miRNA cassette containing guide sequence targeting Tau and passenger sequence, a polyA sequence, a stuffer sequence, and a wild type ITR. The viral genomes are packaged into VOY101 capsids, purified and formulated. The VOY101-Tau miRNA particles are formulated in phosphate buffered saline (PBS) with 0.001% F-68.

Non-human primates (NHPs) (Cynomolgus macaques, adult male, prescreened for AAV neutralizing antibodies) in three groups are administered the scVOY101-Tau miRNA with one group a vehicle only control (PBS with 0.001% F-68). The NHPs are administered either high or low dose levels of VOY101-Tau miRNA (approximately $4 \times 10^{12}$ vg/kg–$4 \times 10^{13}$ vg/kg) using intravenous delivery. 4 weeks post-administration, a saline perfusion is performed and the brain sectioned into 3 mm coronal blocks and snap-frozen.

To test the distribution and expression of VOY101-Tau miRNA in NHP, any test known in the art may be utilized. Non-limiting examples include measurement of expression of tau mRNA by qRT-PCR, expression of tau protein as assessed by immunohistochemistry and enzyme-linked immunosorbent assay, and vector genome levels as assessed by digital droplet PCR.

One might expect expression data to show that tau protein and mRNA is reduced widely in the brain. Brain regions likely to demonstrate significant tau reduction include areas important for tauopathy related disease, including the entorhinal cortex, hippocampus, and cortex. Consistent with the expression data, PCR would likely demonstrate widespread distribution of vector genome through the brain.

Example 12. VOY101-ATP2A2 for the Treatment of Cardiovascular Disease (e.g., Heart Failure)

A. In Vivo Distribution, Expression and Efficacy Study with Intravenous Dosing of VOY101-ATP2A2 in a Mouse Model of Cardiovascular Disease Selected viral genomes comprising a nucleic acid encoding human ATP2A2 are designed and packaged into a single stranded VOY101 capsid.

The viral genome from ITR to ITR, recited 5' to 3', comprises a wild type ITR, a promoter, hATP2A2 cDNA sequence, a human growth hormone polyA sequence, a fragment of human albumin as a stuffer sequence, and a wild type ITR. The viral genomes are packaged into VOY101 capsids, purified and formulated in phosphate buffered saline (PBS) with 0.001% F-68.

Six groups of approximately 10 mice/group, at 7 weeks of age, and balanced for gender and litter, receive vehicle (PBS with 0.001% F-68; two groups), or VOY101-ATP2A2 vector at either low (2 groups) or high dose (2 groups) levels (approximately $6.3 \times 10^{12}$ vg/kg–$2 \times 10^{13}$ vg/kg body weight) via intravenous injection.

To test the efficacy, distribution and expression of VOY101-ATP2A2 in mice, any test known in the art may be utilized. Non-limiting examples include limb electromyography, notched bar walking test, string hanging test, rotarod test, body weight, and/or survival. Other readouts include ATP2A2 protein and mRNA expression in tissues (e.g. dorsal root ganglia, heart (e.g., cardiomyocytes), cerebellum, spinal cord) by ELISA, PCR, immunohistochemistry and in situ hybridization, and in situ assessment of mitochondrial enzyme function in tissue (dorsal root ganglia) sections. Vector genome levels in different tissues are determined by PCR and ISH.

Three groups of animals (vehicle, low dose, high dose) are euthanized by 18 weeks. Three remaining groups of animals (vehicle, low dose, high dose) are maintained for 6 months or longer to assess effect on survival. Control groups (n=10/group) include wild type mice and disease model mice dosed with a reference vector.

The distribution and expression of human ATP2A2 and vector genome distribution in target tissues such as, but not limited to, DRGs, cerebellum, spinal cord and heart in animals receiving the hATP2A2 vector, is measured by ELISA, PCR, ISH, IHC for hATP2A2 expression and PCR and ISH for vector genome analysis. Human ATP2A2 analysis (by ELISA, PCR, ISH, IHC) demonstrate that upon the delivery of the hATP2A2 vector, expression in target tissues e.g., heart occurs with distribution of the viral genome to target tissues. In situ assessment of mitochondrial enzyme activity shows that upon delivery of the hATP2A2 vector, increased activity in slices of heart occurs. Electromyography, notched bar, string hanging and rotarod tests demonstrate improved performance over vehicle control animals.

B. In Vivo Distribution and Expression Study with Intravenous Dosing of VOY101-ATP2A2 in Non-Human Primates Selected viral genomes comprising a nucleic acid sequence encoding human ATP2A2 are designed and packaged in a single stranded (ss) VOY101 capsid.

The single stranded viral genome from ITR to ITR, recited 5' to 3', comprises a wild type ITR, a promoter, hATP2A2 cDNA sequence, a human growth hormone polyA sequence, a fragment of human albumin as a stuffer sequence, and a wild type ITR. The viral genomes are packaged into VOY101 capsids, purified and formulated in phosphate buffered saline (PBS) with 0.001% F-68.

Eight groups of approximately 3 cynomolgus monkeys/group, approximately 3 years of age or older, with at least one animal of each gender per group, receive vehicle (PBS with 0.001% F-68; two groups), or VOY101-ATP2A2 vector at either low (2 groups) or high dose (2 groups) levels (approximately $6.7 \times 10^{12}$ vg/kg–$6 \times 10^{13}$ vg/kg body weight) via intravenous injection.

To test the efficacy, distribution and expression of VOY101-ATP2A2 in NHP, any test known in the art may be utilized. Non-limiting examples include measurement of body weight over time, clinical monitoring, histopathology and blood safety panel testing. Other readouts include ATP2A2 protein and mRNA expression in tissues (e.g. heart) as assessed by ELISA, PCR, immunohistochemistry and in situ hybridization. Vector genome levels in different tissues are determined by PCR and ISH.

Three groups of animals (vehicle, low dose, high dose) are euthanized by 4 weeks. Three remaining groups of animals (vehicle, low dose, high dose) are maintained for 12 weeks to assess long term gene expression.

The distribution and expression of human ATP2A2 (hATP2A2) and vector genome distribution in target tissues such as, but not limited to, heart in animals receiving the hATP2A2 vector, is measured by ELISA, PCR, ISH, IHC for hATP2A2 expression and PCR and ISH for vector genome analysis. The primate ATP2A2 expression data are compared to the ATP2A2 expression level which resulted in rescue of the cardiovascular disease phenotype in a genetic mouse model of cardiovascular disease. Based on these results, efficacious doses for human trials are calculated.

Example 13. VOY101-S100A1 for the Treatment of Cardiovascular Disease (e.g., Heart Failure)

A. In Vivo Distribution, Expression and Efficacy Study with Intravenous Dosing of VOY101-S100A1 in a Mouse Model of Cardiovascular Disease Selected viral genomes comprising a nucleic acid encoding human S100A1 are designed and packaged into a single stranded VOY101 capsid.

The viral genome from ITR to ITR, recited 5' to 3', comprises a wild type ITR, a promoter, hS100A1 cDNA sequence, a human growth hormone polyA sequence, a fragment of human albumin as a stuffer sequence, and a wild type ITR. The viral genomes are packaged into VOY101 capsids, purified and formulated in phosphate buffered saline (PBS) with 0.001% F-68.

Six groups of approximately 10 mice/group, at 7 weeks of age, and balanced for gender and litter, receive vehicle (PBS with 0.001% F-68; two groups), or VOY101-S100A1 vector at either low (2 groups) or high dose (2 groups) levels (approximately $6.3 \times 10^{12}$ vg/kg–$2 \times 10^{13}$ vg/kg body weight) via intravenous injection.

To test the efficacy, distribution and expression of VOY101-S100A1 in mice, any test known in the art may be utilized. Non-limiting examples include limb electromyography, notched bar walking test, string hanging test, rotarod test, body weight, and/or survival. Other readouts include S100A1 protein and mRNA expression in tissues (e.g. dorsal root ganglia, heart (e.g., cardiomyocytes), cerebellum, spinal cord) by ELISA, PCR, immunohistochemistry and in situ hybridization, and in situ assessment of mitochondrial enzyme function in tissue (dorsal root ganglia) sections. Vector genome levels in different tissues are determined by PCR and ISH.

Three groups of animals (vehicle, low dose, high dose) are euthanized by 18 weeks. Three remaining groups of animals (vehicle, low dose, high dose) are maintained for 6 months or longer to assess effect on survival. Control groups (n=10/group) include wild type mice and disease model mice dosed with a reference vector.

The distribution and expression of human S100A1 and vector genome distribution in target tissues such as, but not limited to, DRGs, cerebellum, spinal cord and heart in animals receiving the hS100A1 vector, are measured by ELISA, PCR, ISH, IHC for hS100A1 expression and PCR and ISH for vector genome analysis. Human S100A1 analysis (by ELISA, PCR, ISH, IHC) demonstrate that upon the delivery of the hS100A1 vector, expression in target tissues e.g., heart occurs with distribution of the viral genome to target tissues. In situ assessment of mitochondrial enzyme activity shows that upon delivery of the hS100A1 vector, increased activity in slices of heart occurs. Electromyography, notched bar, string hanging and rotarod tests demonstrate improved performance over vehicle control animals.

B. In Vivo Distribution and Expression Study with Intravenous Dosing of VOY101-S100A1 in Non-Human Primates Selected viral genomes comprising a nucleic acid sequence encoding human S100A1 are designed and packaged in a single stranded (ss) VOY101 capsid.

The single stranded viral genome from ITR to ITR, recited 5' to 3', comprises a wild type ITR, a promoter, hS100A1 cDNA sequence, a human growth hormone polyA sequence, a fragment of human albumin as a stuffer sequence, and a wild type ITR. The viral genomes are packaged into VOY101 capsids, purified and formulated in phosphate buffered saline (PBS) with 0.001% F-68.

Eight groups of approximately 3 cynomolgus monkeys/group, approximately 3 years of age or older, with at least one animal of each gender per group, receive vehicle (PBS with 0.001% F-68; two groups), or VOY101-S100A1 vector at either low (2 groups) or high dose (2 groups) levels (approximately $6.7 \times 10^{12}$ vg/kg–$6 \times 10^{13}$ vg/kg body weight) via intravenous injection.

To test the efficacy, distribution and expression of VOY101-S100A1 in NHP, any test known in the art may be utilized. Non-limiting examples include measurement of body weight over time, clinical monitoring, histopathology and blood safety panel testing. Other readouts include S100A1 protein and mRNA expression in tissues (e.g. heart) as assessed by ELISA, PCR, immunohistochemistry and in situ hybridization. Vector genome levels in different tissues are determined by PCR and ISH.

Three groups of animals (vehicle, low dose, high dose) are euthanized by 4 weeks. Three remaining groups of animals (vehicle, low dose, high dose) are maintained for 12 weeks to assess long term gene expression.

The distribution and expression of human S100A1 (hS100A1) and vector genome distribution in target tissues such as, but not limited to, heart in animals receiving the hS100A1 vector, are measured by ELISA, PCR, ISH, IHC for hS100A1 expression and PCR and ISH for vector genome analysis. The primate S100A1 expression data are compared to the S100A1 expression level which resulted in rescue of the cardiovascular disease phenotype in a genetic mouse model of cardiovascular disease. Based on these results, efficacious doses for human trials are calculated.

Example 14. Anti-Tau Antibody Delivery for the Treatment of Alzheimer's Disease and Other Tauopathies A. In Vivo Distribution, Expression and Efficacy Study of Intravenous Dosing of VOY101 or VOY201-Anti-Tau Antibody A nucleic acid encoding the monoclonal antibody PHF-1 targeting tau was engineered into an AAV viral genome and produced in the VOY101 capsid (capsid sequence provided as SEQ ID NO: 1809) or VOY201 capsid (capsid sequence provided as SEQ ID NO: 1810).

The viral genome, recited 5' to 3' from ITR to ITR, comprised a wild type ITR, a promoter, the nucleic acid encoding the monoclonal antibody PHF-1 targeting tau (kozak, heavy chain, linker region, light chain and stop codon provided as SEQ ID NO: 1816), a polyA sequence, and a wild type ITR. The viral genomes were packaged into VOY101 or VOY201 capsids, purified and formulated. The VOY101 or VOY201-anti Tau antibody particles were formulated in phosphate buffered saline (PBS) with 0.001% F-68.

Three groups of wild type (WT) mice, approximately 5 mice/group, at 2 months of age, were administered vehicle (PBS with 0.001% F-68), VOY101-anti Tau antibody vector at $1.4 \times 10^{13}$ vg/kg, or VOY201-anti Tau antibody vector at $1.4 \times 10^{13}$ vg/kg via intravenous tail vein injection.

Approximately 28 days following AAV particle administration, several tissue samples were collected. Vector genome digital PCR quantification was performed using a probe set against the CMV enhancer region of the CBA promoter, normalized to host TFRC, and expressed in vector genome per cell (VG/Cell). Vector genome distribution is shown in Table 21 for VOY101.PHF-1 and VOY201.PHF-1. In Table 21, Hp is the hippocampus, SC-C is the cervical spinal cord, SC-T is the thoracic spinal cord, and SC-L is the lumbar spinal cord.

TABLE 21

Viral Genome Distribution in WT Mice after Intravenous Injection

| Vector (Dose: 1.4 × $10^{13}$ VG/kg) | VG/Cell Distribution (Standard Dev. in Parenthesis) | | | | |
|---|---|---|---|---|---|
| | Hp | SC-C | SC-T | SC-L | Brainstem |
| Vehicle | 0.06 (0.54) | 0.01 (0.13) | 0.01 (0.14) | 0.003 (0.002) | 0.02 (0.19) |
| VOY101.PHF-1 | 11.01 (6.22) | 15.45 (8.20) | 17.82 (9.67) | 18.59 (9.49) | 29.80 (14.68) |
| VOY201.PHF-1 | 4.68 (1.48) | 9.30 (2.42) | 7.42 (2.6) | 9.52 (2.2) | 16.16 (4.76) |

The expression levels of PHF-1, present in the soluble fraction of tissue lysates, were also measured in collected tissues by detecting the interaction with PHF tau coated on an ELISA plate. The antibody-antigen complex was visualized and quantified using HRP labeled anti-mouse IgG and its substrate TMB, followed by reading at OD450 on a plate reader and normalized to input tissue protein quantity. PHF1 expression from AAV transduced cells is shown in Table 22 for VOY101.PHF-1 and VOY201.PHF-1. In Table 22, Hp is the hippocampus and SC spinal cord.

TABLE 22

PHF-1 Expression Distribution in WT Mice after Intravenous Injection

| Vector (Dose: 1.4 × $10^{13}$ VG/kg) | PHF-1 Expression (ng/mg protein, Standard Dev. in Parenthesis) | | | |
|---|---|---|---|---|
| | Hp | Cortex | SC | Brainstem |
| Vehicle | 0 (0) | 0 (0) | 0 (0) | 0 (0) |
| VOY101.PHF-1 | 82 (36.4) | 94 (35.6) | 718 (440.8) | 394.0 (301.3) |
| VOY201.PHF-1 | 96 (35.1) | 66 (19.6) | 361 (147.4) | 207.0 (116.3) |

IV dosing of PHF-1 in VOY201 resulted in up to 15-fold higher anti-tau antibody levels in mouse CNS as compared to passive immunization. The passive immunization level of antibody in brain is 20-40 ng/mg of protein, and VOY201 provided 2-5× fold above passive in the hippocampus, 5-10× fold above passive in the brain stem, and 8-16× fold above passive in the spinal cord. IV dosing of VOY101 and VOY201 resulted in widespread CNS biodistribution and transduction of vectorized antibodies.

Mouse brains were hemisected and tissue samples allocated for antibody immunohistochemistry then post-fixed in 4% paraformaldehyde overnight. PHF-1 antibody was detected by immunohistochemistry using anti-mouse IgG1 antibody (PHF-1 is a mouse IgG1 antibody). In animals dosed with $1.4 \times 10^{13}$ vg/kg via intravenous tail vein injection of VOY101.PHF-1 or VOY201.PHF-1, staining was observed throughout the brain, including in the hippocampus, cortex, striatum, and thalamus. Numerous PHF1+ cells were observed, including those with neuronal and astroglial morphology. Vehicle-treated control exhibited essentially no detectable background staining B. In Vivo Distribution, Expression and Efficacy Study of Intravenous Dosing of VOY101 or VOY201-Anti-Tau Antibody in a Mouse Model Three groups of P301S mice, approximately 20 mice/group, at 2 months of age, were administered vehicle (PBS with 0.001% F-68), VOY101-anti Tau antibody vector (VOY101.PHF-1) at $1.4 \times 10^{13}$ vg/kg, or VOY201-anti Tau antibody vector (VOY201.PHF-1) at $5.0 \times 10^{13}$ vg/kg via intravenous tail vein injection.

Approximately 3 months following AAV particle administration, several tissue samples were collected. Vector genome digital PCR quantification was performed using a probe set against the CMV enhancer region of the CBA promoter, normalized to host TFRC, and expressed in vector genome per cell (VG/Cell). Vector genome distribution is shown in Table 23 for VOY101.PHF-1 and VOY201.PHF-1. In Table 23, Hp is the hippocampus and SC is the spinal cord.

TABLE 23

Vector Genome Distribution in P301S Mice after Intravenous Injection

| Vector | VG/Cell Distribution (Standard Dev. in Parenthesis) | | | | |
|---|---|---|---|---|---|
| | Hp | Cortex | Thalamus | SC | Brainstem |
| Vehicle | 0.09 (0.17) | 0.06 (0.07) | 0.03 (0.04) | 0.07 (0.11) | 0.06 (0.06) |
| VOY101.PHF-1 (Dose: $1.4 \times 10^{13}$ VG/kg) | 26.17 (10.01) | 32.13 (11.8) | 55.16 (20.75) | 49.82 (29.57) | 59.9 (24.85) |
| VOY201.PHF-1 (Dose: $5.0 \times 10^{13}$ VG/kg) | 16.2 (8.28) | 22.29 (11.1) | 30.92 (17.9) | 27.46 (20.51) | 45.86 (30.53) |

PHF-1 expression within the CNS after administration of $1.4 \times 10^{13}$ vg/kg via intravenous tail vein injection of VOY101.PHF-1 or VOY201.PHF-1 was evaluated by mouse anti-IgG1 and anti-NeuN double labeling immunofluorescent staining. PHF-1 is a mouse IgG1 antibody, and is therefore detected by anti-IgG1 antibody staining. Colocalization studies showed multiple PHF1+ cells including those double-labeled with the neuronal marker (NeuN).

PHF-1 expression within the CNS after administration of $1.4 \times 10^{13}$ vg/kg via intravenous tail vein injection of VOY101.PHF-1 was evaluated by mouse anti-IgG1 and anti-GFAP (glial fibrillary acidic protein) double labeling immunofluorescent staining. PHF-1 is a mouse IgG1 antibody, and is therefore detected by anti-IgG1 antibody staining. Colocalization studies showed multiple PHF1+ cells including those double-labeled with the astrocytic marker (GFAP).

The expression levels of PHF1, present in the soluble fraction of tissue lysates, were also measured in collected tissues by detecting the interaction with PHF tau coated on an ELISA plate. The antibody-antigen complex was visualized and quantified using HRP labeled anti-mouse IgG and its substrate TMB, followed by reading at OD450 on a plate reader and normalized to input tissue protein quantity. PHF1 expression from AAV transduced cells is shown in Table 24 for VOY101.PHF-1 and VOY201.PHF-1. In Table 24, Hp is the hippocampus and SC spinal cord.

TABLE 24

PHF1 Expression in P301S Mice after Intravenous Injection

| Vector | PHF1 Expression (ng/mg protein, Standard Dev. in Parenthesis) | | | | |
|---|---|---|---|---|---|
| | Hp | Cortex | Thalamus | SC | Brainstem |
| Vehicle | 0.96 (4.07) | 0 (0) | 0.79 (3.33) | 0 (0) | 0 (0) |
| VOY101.PHF-1 (Dose: $1.4 \times 10^{13}$ VG/kg) | 193.8 (115.3) | 338.1 (176.9) | 220.3 (100.9) | 1103 (404.8) | 1152 (630.3) |
| VOY201.PHF-1 (Dose: $5.0 \times 10^{13}$ VG/kg) | 140.8 (87.45) | 238.6 (120.5) | 210.6 (103.8) | 902.5 (317) | 619.3 (386.8) |

IV dosing of VOY101 and VOY201 resulted in high levels of antibody to the CNS of P301 tauopathy mice. AT8 immunoreactivity (IR) is significantly reduced in the PHF1-treated mice. IV dosing using VOY101 and VOY201 resulted in widespread CNS biodistribution and transduction of vectorized antibodies in P301S tauopathy mice.

Example 15. Anti-Tau Antibody Delivery for Treatment of Tauopathies Including Alzheimer's Disease A. In Vivo Distribution, Expression and Efficacy Study of Intravenous Dosing of VOY101 or VOY201-Anti-Tau Antibody A nucleic acid encoding the monoclonal antibody PHF-1 targeting tau is engineered into an AAV viral genome and produced in the VOY101 capsid (capsid sequence provided as SEQ ID NO: 1809) or VOY201 capsid (capsid sequence provided as SEQ ID NO: 1810).

The viral genome, recited 5' to 3' from ITR to ITR, comprises a wild type ITR, a promoter, the nucleic acid encoding the monoclonal antibody PHF-1 targeting tau (light chain (SEQ ID NO: 1819), linker region, heavy chain (SEQ ID NO: 1814) and stop codon), a polyA sequence, and a wild type ITR. The viral genomes are packaged into VOY101 or VOY201 capsids, purified and formulated. The VOY101 or VOY201-anti Tau antibody particles are formulated in phosphate buffered saline (PBS) with 0.001% F-68.

Three groups of wild type (WT) mice, approximately 5 mice/group, at 2 months of age, are administered vehicle (PBS with 0.001% F-68), VOY101-anti Tau antibody vector at $1.4 \times 10^{13}$ vg/kg, or VOY201-anti Tau antibody vector at $1.4 \times 10^{13}$ vg/kg via intravenous tail vein injection.

Approximately 28 days following AAV particle administration, several tissue samples are collected. Vector genome digital PCR quantification is performed using a probe set against the CMV enhancer region of the CBA promoter, normalized to host TFRC, and expressed in vector genome per cell (VG/Cell).

The expression levels of PHF1, present in the soluble fraction of tissue lysates, are also measured in collected tissues by detecting the interaction with PHF tau coated on an ELISA plate. The antibody-antigen complex is visualized and quantified using HRP labeled anti-mouse IgG and its substrate TMB, followed by reading at OD450 on a plate reader and normalized to input tissue protein quantity.

Mouse brains are hemisected and tissue samples allocated for antibody immunohistochemistry. The samples are post-fixed in 4% paraformaldehyde overnight. PHF-1 antibody is detected by immunohistochemistry using anti-mouse IgG1 antibody (PHF-1 is a mouse IgG1 antibody).

PHF-1 expression within the CNS after administration of $1.4 \times 10^{13}$ vg/kg via intravenous tail vein injection of VOY101.PHF1 or VOY201.PHF-1 is evaluated by mouse anti-IgG1 and anti-NeuN or GFAP (glial fibrillary acidic protein) double labeling immunofluorescent staining. PHF-1 is a mouse IgG1 antibody, and is therefore detected by anti-IgG1 antibody staining B. In Vivo Distribution, Expression and Efficacy Study of Intravenous Dosing of VOY101 or VOY201-anti-Tau antibody in a Mouse Model Three groups of P301S mice, approximately 20 mice/group, at 2 months of age, are administered vehicle (PBS with 0.001% F-68), VOY101-anti Tau antibody vector (VOY101.PHF-1) at $1.4 \times 10^{13}$ vg/kg, or VOY201-anti Tau antibody vector (VOY201.PHF-1) at $5.0 \times 10^{13}$ vg/kg via intravenous tail vein injection.

Approximately 3 months following AAV particle administration, several tissue samples are collected. Vector genome digital PCR quantification is performed using a probe set against the promoter, normalized to host TFRC, and expressed in vector genome per cell (VG/Cell).

The expression levels of PHF1, present in the soluble fraction of tissue lysates, are also measured in collected tissues by detecting the interaction with paired helical filamentous tau coated on an ELISA plate. The antibody-antigen complex is visualized and quantified using HRP labeled anti-mouse IgG and its substrate TMB, followed by reading at OD450 on a plate reader and normalized to input tissue protein quantity.

VIII. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCE LISTING

The patent contains a lengthy sequence listing. A copy of the sequence listing is available in electronic form from the USPTO web site (https://seqdata.uspto.gov/?pageRequest=docDetail&DocID=US12305189B2). An electronic copy of the sequence listing will also be available from the USPTO upon request and payment of the fee set forth in 37 CFR 1.19(b)(3).

We claim:

1. A method for decreasing expression of a gene of interest associated with a muscular dystrophy in a cell in a subject, comprising administering to the subject an effective amount of an AAV particle comprising an engineered AAV capsid and a viral genome encoding an RNAi payload comprising an siRNA, wherein the engineered AAV capsid comprises the amino acid sequence of SEQ ID NO: 1 and the siRNA targets an mRNA of the gene of interest.

2. The method of claim 1, wherein the engineered AAV capsid is encoded by the nucleic acid sequence of SEQ ID NO: 1809.

3. The method of claim 1, wherein the AAV particle transduces a muscle cell, a heart cell, or a brain cell.

4. The method of claim 3, wherein the AAV particle transduces a muscle cell.

5. The method of claim 4, wherein the muscle cell is a skeletal muscle cell or a cardiomyocyte.

6. The method of claim 1, wherein the method comprises administering the AAV particle to the subject by intramuscular delivery or intravenous delivery.

* * * * *